US010413755B1

(12) United States Patent
Sahadevan

(10) Patent No.: US 10,413,755 B1
(45) Date of Patent: Sep. 17, 2019

(54) DEVICE AND METHODS FOR ADAPTIVE RESISTANCE INHIBITING PROTON AND CARBON ION MICROBEAMS AND NANOBEAMS RADIOSURGERY

(71) Applicant: Velayudhan Sahadevan, Beckley, WV (US)

(72) Inventor: Velayudhan Sahadevan, Beckley, WV (US)

( * ) Notice: Subject to any disclaimer, the term of this patent is extended or adjusted under 35 U.S.C. 154(b) by 753 days.

(21) Appl. No.: 13/658,843

(22) Filed: Oct. 24, 2012

Related U.S. Application Data

(63) Continuation-in-part of application No. 13/507,829, filed on Aug. 1, 2012, now abandoned.

(51) Int. Cl.
*A61N 5/00* (2006.01)
*A61N 5/10* (2006.01)

(52) U.S. Cl.
CPC .................. *A61N 5/1084* (2013.01)

(58) Field of Classification Search
CPC ............. A61N 5/10; A61N 5/1042; A61N 2005/1087; A61N 2005/1095; A61N 2005/1091; A61N 5/1069; A61N 5/1077; A61N 1/36021; A61N 1/406; A61N 2005/1061; A61N 2005/1098; A61N 2/002; A61N 5/00; A61N 5/062; A61N 5/103; A61N 2005/1055; A61N 2005/1076; A61N 2005/1085; A61N 2005/1097; A61N 5/025; A61N 5/1043; A61N 5/1049;

(Continued)

(56) References Cited

U.S. PATENT DOCUMENTS 5,339,347 A    8/1994    Slatkin
5,547,454 A    8/1996    Horn et al.
(Continued)

OTHER PUBLICATIONS

S Bellucci, VM Biryukov, YA Chesnokov, V Guidi, and W Scandale "Making microbeams and nanobeams by channeling in microstructures and nanostructures." Physical Review Special Topics—Accelerators and Beams, vol. 6, 033502 (2003).*

(Continued)

*Primary Examiner* — Christine H Matthews
*Assistant Examiner* — Joshua D Lannu

(57) ABSTRACT

This invention relates to adaptive resistance inhibiting 100 to 10,000 Gy, single fraction proton and carbon ion microbeam and nanobeam radiosurgery, proton spray chemotherapy and proton spray gadolinium and boron neutron capture therapy with least normal tissue toxicity. Secondary neutrons, protons, ions and radiation from the accelerator and the patient specific collimator are removed with tissue equivalent collimator that also generates proton and carbon ion microbeam and nanobeam. Laser interaction with micrometer and nanometer thick metallic and diamond like carbon targets are also used for proton and carbon ion beam generation. Polyenergetic proton beam is spatially separated. Ion beam and Laser ion beam is accelerated in a hybrid RF accelerator. It is split into microbeam and nanobeam. Secondary neutrons, protons and gamma radiation are removed with tissue equivalent collimators that also generate microbeams and nanobeams. Adaptive resistance to cancer treatment is inhibited by dual target radiation, DNA strands break and enzymes inactivation.

22 Claims, 39 Drawing Sheets

(58) Field of Classification Search
CPC .. A61N 5/1065; A61N 5/1068; A61N 5/1078; A61N 5/1084
USPC .......................................................... 600/1
See application file for complete search history.

(56) References Cited

U.S. PATENT DOCUMENTS

| | | | |
|---|---|---|---|
| 7,554,094 B2 | 6/2009 | Knippelmeyer et al. | |
| 7,714,624 B2 | 5/2010 | Takasu et al. | |
| 7,755,068 B2 | 7/2010 | Ma et al. | |
| 7,835,492 B1 | 11/2010 | Sahadevan | |
| 7,902,530 B1 | 3/2011 | Sahadevan | |
| 8,076,657 B2 | 12/2011 | Mackie et al. | |
| 2008/0122390 A1 | 5/2008 | Lidestri | |
| 2009/0093863 A1* | 4/2009 | Dilmanian | 607/88 |
| 2011/0273115 A1 | 11/2011 | Liu et al. | |

OTHER PUBLICATIONS

Bellucci, S.,Nanotubes for particle channeling, radiation and electron sources, Nuclear Instruments and Methods in Physics Research B 234 (2005) 57-77: Abstract, p. 57.
Chung-Jong Yu. et al., Physical and Magnetic Characteristics of Carbon Nanotubes Radiated by Proton Beams, Journal of the Korean Physical Society, vol. 50, No. 5, May 2007.
Krasheninnikov, A.V., et alChanneling of heavy ions through multi-walled carbon nanotubes Nuclear Instruments and Methods in Physics Research B 228 (2005) 21-25, p. 25, col.
Zhen Zhou Z. et al., A first-principles study of lithium absorption in boron or nitrogen-doped single-walled carbon nanotubes Carbon 42 (2004) 2677-2682, p. 2677, col. 1.
Shimoda H. et al., Lithium Intercalation into Opened Single-Wall Carbon Nanotubes: Storage Capacity and Electronic Properties, Physical review letters, vol. 88, No. 1, January.
Lao, J. Y. et al.Boron carbide nanolumps on carbon nanotubes, Applied Physics Letters, vol. 80. No. 3, Jan. 21, 2002, 500-502, Abstract, p. 501.
Matsudaira1, M. et al., Meissner effect in films of ropes of boron-doped single-walled carbon nanotubes;—Journal ofPhysics:ConferenceSeries 153 (2009) 012070, Astract p. 1.
Bhride, A. A. et al. Distribution and clearance of PEG-single-walled carbon—Nanomedicine (Lond). 2010 Dece ; 5(10): 1535-1546. doi:10.2217/nnm.10.90., p. 2, para3, line 4-6.
Bhride, A. A. et al. Distribution and clearance of PEG-single-walled carbon—Nanomedicine (Lond). 2010 Dece ; 5(10): 1535-1546. doi:10.2217/nnm.10.90., p. 7, para3, line 1-6.
Wang, L. et al.Synergistic enhancement of cancer therapy using a combination of docetaxel and photo—International J. of Nanomedicine, 2011:6 2641-2652, Abstract, p. 2641.
Steinman, D.A. et al,Fabrication of a new type of double-shell target having a PVA inner layer, General Atomic Report GA-A24455, p. 1, Abstract and Fig. 1.
Tayyebi, P et al,Design and Construction of Deuterium Target for Fast Neutron Production,IEEE NPSS (Toronto), UOIT, Oshawa, ON, Jun. 25-26, 2010 Intern Works. p. 2-1, abstrac.
Horn et al, The use of Low Energy, Ion Induced Nuclear Reactions for Proton Radiation Therapy Applications; , 1995, p. 4, paragraph 3, lines 1-4.
Horn et al, The use of Low Energy, Ion Induced Nuclear Reactions for Proton Radiation Therapy Applications; , 1995, p. 6, paragraph 1, lines 1-5.
Horn et al, The use of Low Energy, Ion Induced Nuclear Reactions for Proton Radiation Therapy Applications; , 1995,p. 7, paragraph 3, lines 1-10.
Coupier , B. et al,Inela intera of prot and elect with biologi relev molec, The Europ PhysiJournal DEDP Sciences, Societ'a Italiana di Fisica,2002, p. 2 col. 2, par 2, lin 2-6.
Coupier , B. et al,Inela intera of protons and electrons with biologi relev molec, The European Physical Journal DEDP Sciences, Societ'a Italiana di Fisica,2002, p. 1, Abstr.
Wikipedia, Neutron capture therapy of cancer, Mitchell HJ et al.
Coupier , B. et al,Inela intera of prot and elect with biologi relev molec, The Europ PhysiJournal DEDP Sciences, Socie'a Italiana di Fisica,2002, p. 5 col. 2, Fig.4.
Coupier , B. et al,Inela intera of prot and elect with biologi relev molec, The Europ PhysiJournal DEDP Sciences, Societ'a Italiana di Fisica,2002, p. 7 col. 2, Fig.6.
Hoffman, I.Collec and focu of laser acce—Physical Review Special Topics Accelerators and Beams, vol. 14, 031304-031311, (2011), p. 031304-9 ,col. 2, par 3, lin 1-4,pa 4, lin 7-12.
Hoffman, I.Collec and focu of laser acce—Physical Review Special Topics Accelerators and Beams, vol. 14, 031304-031311, (2011), p. 031304-1 ,col. 1, par 3, Summary, lin 9.
Hoffman, I.Collec and focu of laser acce—Physical Review Special Topics Accelerators and Beams, vol. 14, 031304-031311, (2011), p. 031304-10,col. 1, par 2, lin 1-10.
Hoffman, I.Collec and focu of laser acce—Physical Review Special Topics Accelerators and Beams, vol. 14, 031304-031311, (2011), p. 031304-2 ,col. 1, par 5, lin 1-3.
Case M. B.,Thesis, Borosilicate Polycapillary lens for collimation of X-rays, Naval Postgraduate School 1997; p. v, Abstract.
Case M. B.,.,Thesis, Borosilicate Polycapillary lens for collimation of X-rays, Naval Postgrad School 1997; p. 18, para 2, lin 1-6 and FIG. 4, p. 19 and par3, lin 1-5, Fig 5, p. 19.
Milosavljevic, A.R. et al; Guiding of Electrons by Al2O3 Nanocapillaries, XVII Symposium on Condensed Matter Physics—SFKM 2007, Vršac—Serbia, p. 1, Abstract.
Nebiki, T et al,In Air PIXIE Analysis by Means of Glass Capillary Optics, Nuclear Instruments and Methods in Physics and Research Section B, Beam Interaction with Materials a.
Lagutin, A. et al.,Experi Results of the Beam Dynamics by using Glass Capillaries for the ESA-2, Proceedings of RuPAC 2008,—Parti Dyna in ANew Methods of Accel Abst, p. 12.
Kowarik, G. et al,Temperature Control of Ion Guiding Through Insulating Capillaries, arXiV: 1109.3953 v1 [cond-mater.other] Sep. 19, 2011; p. 1, Abstract.
Allen, F. I. et al,Transpo multi and highl charg ions thr nanoscale apertures in silicon nitride membranes , Nuclear Instruments and Methods in Physics ReseB244(2006)323—Abst.
Allen, F. I. et al,Trans multi and highl charg ions thr nanosc apertures in silicon nitride membra , Nuclear Instrumen and Methods in Physics ReseB244(2006)p. 324—prg2,lin 5-11.
Pedroni, E. et al, The 200-MeV proton therapy project at the Paul Scherrer Institute Concep desi and practi realization,Med. Phys. 22,1995, p. 39 col. 2, pa3.
Smith, A.R.,Vision 20/20: Proton therapy, Med. Phys. 36 Feb. 2, 2009, p. 558, Fig. 3.
DeNardo, S.J. et al Enhancement of Clinical Radioimmunotherapy for Cancer—, Journal of the National Cancer Institute, vol. 84,1992, p. 375, paragraph 2, lines 10-11.
Stickney, et al, Enhancement of monoclonal antibody binding to melanoma—NCI Monographs: a Publication of the National Cancer Institute [1987(3):47-52 p. 49, Abstract.
Alessandra di Pietro et al, Heat shock protein peptide complex 96-based vaccines in melanoma,—Human Vaccines 5:11, 727-737; Nov. 2009;, p. 727, abstract.
Testori a A et al, Phase III Vitespen, an Autologus Tumor—Derived Heat Shock Protein gp96 Peptide Vaccine, Melanoma:—J Clin Oncol 26:955-962, 2008, p. 955, Abstract.
Vuillez, J. P., Radioimmunodetection in oncology, La Revue de Médecine Interne, vol. 16, Issue 11, 1995, pp. 833-842, p. 833, Summary.
Castro R et al,Particle Radiation Therapy, p. 1548, in Text book of Radiation Oncology; Leibel & Phillips ed. 2nd Edition, 2004, Saunders, Philadelphia, Figures 69-1, A & B.
Westerly D. C., Scanning Aperture Ion Beam Modulator, U.S. Pat. No. 7,977,648 2011, p. 1, Abstract.
Grime, G., Nuclear micro and nanobeams focusing MeV ions to micron and submicron dimensions, University of Surrey, Ion Beam Center, Guildford, UK; slides 14 and 15, Internet.

(56) References Cited

OTHER PUBLICATIONS

Matusuzaki, Y, et al, Nuclear collision processes around the Bragg peak in proton therapy, Radiol Phys Technol. Jan. 2010;3(1):84-92. Epub Dec. 29, 2009 Abstract, lines 10-20.
Bee-Wang, J. et al, Simulation of Proton Therapy Treatment Verification via PET imaging of Induced Positron-EmittersC-A/AP # 122, Nov. 2003; Abstract.
Biryukov,V.M.,Creating microbeam and nanob by channeling in micro- and nano struc, V.M., Proceedings of the 2003 Particle Accel Conf, 0-7803-7739-9 ©2003 IEE, p. 986, Abstrac.
Biryukov,V.M.,Channeling as a method of making nano beams of particles,Intern workshop, Nanotubes and Nanostr 2004 (Frascati, Oct. 14-20, 2004) PACS: 61.85.+p; 02. 40.-k,Abstr.
Moghe A,. K, et al,Co-axial Electrospinning for Nanofiber Structures: Preparation and Applications, Polymer Reviews, 48:353-377, 2008, p. 367-368, FIG. 16, p. 368.
Abdurizzagh, Production of hollow fibers by co-elctrospinning of cellulose acetate, Thesis, Master of Science in Engineering, In—at the University of Stellenbosch, p. 3, Abst.
Biryukov,V.M.,,Creating micro and nanobeams by channel in micro- and nano structu, Proce of the 2003 Particle Accel Confer, 0-7803-7739-9 ©2003 IEE, p. 987, par 2, lines 1-4.
Vajatai, R.,Building carbon nanotubes and their smart architectures, Smart Mater. Struct. 11 (2002) 691-698 PII: Fig. 6, p. 695.
Larson, A,Nano-Scale Convective Heat Transfer of Verti Alig Carb Nanotube Arrays,Worcester Polytechnic Institute, Thesis BSc, 2010, Fig. 18,p. 22.
FEI Company,Focused ion beam technology, capabilities and applications,Hillsboro, Oregon 97124-5793 USATechnology, 030-PB00113 Jun. 2005, p. 8, Fig 8.
Bigelow, A. W et al,Single-Particl/Singl-Cell Ion Microb as Prob of Biol Mech, IEEE Transactions on Plasma Science, 36, No. 4, Aug. 2008, p. 1425, col. 2, parg 3, lin 1-3.
Volkov, H.B. et al, Intraoperative Radiation therapy, in Text book of Radiation Oncology; Leibel & Phillips ed. 2004, Saunders, Philadelphia, p. 352.
Swaby, S.F., Circulating tumor cells in breast cancer: A tool whose time has come of age, BMC Medicine 2011, p. 9:43, Abstract, lines 1-5.
Fehm, T., Detection of disseminated tumor cells in patients with gynecological cancers Gynecological Oncology (2006) vol. 103, p. 942-947, p. 943m Conclusion, lines 1-4.
Luttgen, M.S., Circulating tumor cells monitored over time in lung cancer patients, ASCO Poster Abstract 11025, 2009.
Loberg, R.D. et. al, Detection and Isolation of Circulating Tumor Cells in Urologic Cancers: A Review, , Neoplasia (2004) 6, 302-309, p. 302, lines 12-15.
Fadlonl, E. J. et al, Detection of circulating prostate-specific antigen-positive cells—prostate cancer—, B. J. of Cancer (1996) 74, 400-405, p. 400, Abstract, li 1-10.
Karl EGAN1, et al, Platelet Adhesion and Degranulation Induce Pro-Survival—Ovarian Cancer Cells, PLoS One | www.plosone.org 1, 2011 | vol. 6, e26125, p. 1, Abstr, li 11-12.
Lawler K. et al., stress—platelet-secret matrix proteins—tumor cells—Am J Physiol Cell Physiol 287: 2004, doi:10.1152/ ajpcell. 00159.2004, p. C1320, col. 1, par 1, li 2-3.
Zaki, M.M.,Parasite Platelet Interactions, Review Article, PUJ, 2011, 4 (2):127-136, p. 127, col. 1, paragraph 2, lines 1-4.
Zaki, M.M.,Parasite Platelet Interactions,Review Article, PUJ, 2011, 4 (2):127-136, p. 127, col. 2, paragraph 1, lines 2-8.
Zaki, M.M.,Parasite Platelet Interactions,Review Article, PUJ, 2011, 4(2): p. 128, col. 2, par 2, p. 138, col. 1, par 4, p. 130, col. 2, par 3, LI 1-11.
Grozingrr, S.O.,Volume Conformal Irradiation of Moving Target Volumes with Scanned IonBeams,Active Methods—Intensity Controlled Magnetic Raster Scanning,pra2,lin 3-6, par3.
Weber U, et al,Depth scanning for a conformal ion beam treatment of deep seated tumours,Phys. Med. Biol. 45 (2000) 3627-3, p. 3629, paragraph 6, 2.1.1.
Harbi, N.A. et al,Design of a compact synchrotron for medical applications, Review of Scientific Instruments, 4 (4), 2003: p. 2541, col. 1, paragraph 1, lines 6-18.
Brenner D.J. et al, Reduction of the secondary neutron dose—Phys. Med. Biol. 54 (2009) 6065-6078, p. 6071, paragraph 2, lines 1-3 and Table 2.
Brenner D.J. et al, Reduction of the secondary neutron dose—Phys. Med. Biol. 54 (2009) 6065-6078, p. 6066, paragraph 4, lines 1-8.
Brenner D.J. et al, Reduction of the secondary neutron dose—Phys. Med. Biol. 54 (2009) 6065-6078, p. 6066, paragraph 5, lines 1-12.
Belluccia, S et al., Channeling of high-energy particles in a multi-wall Nanotube,arXiv Physics 0501006v1 [Physics acc-ph] Jan. 3, 2005, p. 2, paragraph 1, lines 1-11.
Krasheninnikov, A.V., et al.,Multiwalled carbon nanotubes as apertures and conduits for energetic ions, Physical Review B 71, 245408 s2005d, Abstract, p. 245408-1.
Da-Peng Zhou et al., Dynamic Polarization Effects in Ion Channeling Through Single-Well Carbon Nanotubs, (2005). Physics and Computer Science Faculty Publications. Paper 81.
Teli.Cki, I et al.,Axial channeling of high energy protons in carbon nanotubes, Publ. Astron. Obs. Belgrade No. 84 (2008), 173-176: Abstract, p. 173.
Serduc, R. I. et al High-Precision Radiosurgical Dose Delivery by Interlaced Microbeam Arrays of High-Flux Low-Energy Synchrotron X-Rays, , PLoS One, vol. 5 | Issue 2, e90.
Serduc, R. I. et al High-Precision Radiosurgical Dose Delivery by Interlaced Microbeam Arrays of High-Flux Low-Energy Synchrotron X-Rays, PLoS One, vol. 5 | Issue 2, e902.
J.A. Laissue et al Microbeam radiation therapy (MRT): Milestones—Clinical Prospects, , New prospects for brain tumour radiotherapy: Synchrotron—p. 1, paragraph 3, line 7-8.
M Miura et al—murine SCCVII squamous cell carcinomas using synchrotron-generated X-ray microbeams , The B.J. of Radiology, 79: (2006), 71-75, p. 71, abstract, line 1-9.
NF-kB Mediated HER2 Overexpression in Radiation-Adaptive Resistance, Radiat Res. Jan. 2009; 171(1): 9-21, Abstract lines 7-8 and p. 7, paragraph 3.
Adaptive Response and the Bystander Effect Induced by Radiation in C3H 10T½ Cells in Culture, Radiat. Res. 156, 177-180 (2001), abstract lines 7-8.
Yi Qing et al, Microarray analysis of DNA damage repair gene expression profiles in cervical cancer cells radioresistant to 252Cf neutron and X-rays, BMC Cancer 2010, 10:71.
U.S. Appl. No. 12/655,825, filed Jan. 7, 2010, Sahadevan, V.
U.S. Appl. No. 12/658,205, filed Feb. 2, 2010, Sahadevan, V.
U.S. Appl. No. 12/459,120, filed Jun. 25, 2009, Sahadevan, V.
U.S. Appl. No. 12/799,949, filed Jun. 5, 2010, Sahadevan, V.
U.S. Appl. No. 12/929,770, filed Feb. 15, 2011, Sahadevan, V.
Ming Fan et al, Nuclear Factor—KB and Manganese Superoxide Dismutase—Adaptive Radioresistance—, Cancer Res 2007; 67: (7). Apr. 1, 2007, 3220-3228, Abstract lines 5-20.
Kuwahar, Y et al, Enhancement of autophagy—refractory to radiotherapy, Cell Death and Disease (2011) 2, e177; doi:10.1038/cddis.2011.56; Jun. 30, 2011, Abstract. li 3-5.
Minsky B. et al., Cancer of the Stomach, p. 826, in Text book of Radiation Oncology; Leibel & Phillips ed. 2nd Edition, 2004, Saunders, Philadelphia.
Harless W., Cancer treatments transform residual cancer cell phenotype, Cancer Cell International 2011, 11:1, p. 2, paragraph 3-4, lines 1-20.
Savona M et al, Getting to the stem of chronic myeloid leukaemia, Nature Reviews Cancer 8, 341-350 (May 2008), Abstract, lines 3-6.
Xu Qing-Yong et al, Identification—radioresistant lung cancer cell line—radiation in vitro, Chin Med J 2008;121(18):1830-1837, Abstract, paragraph 3, lines 1-7.
Lammering, G et al, EGFRvIII-mediated radioresistance through a strong cytoprotective response, Oncogenic (2003) 22, 5545-5553, Abstract, col. 1, lines 1-18.
Bipasha Muk Herjee, EGFRvIII and DNA Double-Strand Break Repair: A Molecular—in Glioblastoma Cancer Res 2009; 69: (10). May 15, 2009, p. 4252-4259.

(56) References Cited

OTHER PUBLICATIONS

Hui-Fang Li, Radiation-induced Akt activation modulates radioresistance in human glioblastoma cells, Radiation Oncology 2009, 4:43, p. 1 Abstract-conclusion, lines 1-4.
Thariat J et. al, Intg,—Radiotherapy with EGFR antagonists—head and neck cancer, Int J Radiat Oncol Biol Phys. 2007: 15; 69(4): 974-984, p. 3, EGFR—Radiotherapy, lin 1-9.
Horn K.M et al, Ion-Induced Nuclear Radiotherapy, U.S. Pat. No. 5,547,454, issued Aug. 20, 1996, p. 21, col. 16, paragraph 2, lines 9-13.
Hall, E.J., 15, Radiation Protection , Radiation Weighing Factors, Equivalent Dose, p. 236, in Radiobiology for the Radiologist, Fifth Edition, Lippencott,Will and Wilk 2000.
Castro J.R. et. al,Particle Radiation Therapy, in Text book of Radiation Oncology; Leibel & Phillips ed. 1998, Saunders, Philadelphia, p. 1552.
Gustafsson, B.,Optimizati of material in proton-therapy collimators with resp to neutron production,Univ of Uppsala, Thesis, Teknisknaturvetens fak Jan. 2009 p. 26,par3,Tab 4.
Moskvin, V et al,Pitfalls of tungsten multileaf collimator in proton beam therapy, Med. Phys. 38 (12), Dec. 2011, p. 6395, Abstract.
Gustafsson, B.,Opti of mate in proton-therapy collim with resp to neutron produc,Univ of Uppsala, Thesis, Teknisk-natury fak Jan. 2009 p. 23-24, Fig 11.1, 11.2, 11.3, 11.4 11.4.
Hall E.J.Intensity-modulated radiation therapy, protons, and the risk of second cancers, , Int. J. Radiation Oncology Biol. Phys., vol. 65, No. 1, pp. 1-7, 2006, p. 1, Abstra.
Newhauser, W.D. et al, The risk of developing a second cancer after receiving craniospinal proton irradiation , Phys. Med. Biol. 54 (2009) 2277-2291 Abstract, p. 2277.
Brenner, D.J. et al,Reduction of the secondary neutron dose in passiv scatte proton radioth, an optim pre-collim/coll, Phys. Med. Biol. 54 (2009) 6065-6078, Abst p. 6065.
Brenner, D.J. et al,Redu of the seco neutron dose in passiv scatte proton radioth, an optimi pre-colli/collim, Phys. Med. Biol. 54 (2009) 6065-6078, p. 6067 par 3, line 3-13.
Yu D et al Redundancy of Radioresistant—Insulin-like Growth Factor I Receptor, J of Biological Chemistry, vol. 278, No. 9, p. 6702, Abstract, lines 1-27.
B C. Turner et al, Insulin-like Growth Factor-I Receptor-Radioresistance—Breast Cancer Recurrence, Cancer Research, 56, 1997J, p. 3079, Abstract, lines 1-21.
Knowlden, J. M. et al,erbB3—insulin receptor substrate-1—estrogen receptor positive breast cancer cell lines, Breast Cancer Research 2011, 13:R93, p. 2, lines 1-6.
D Sachdev et al The IGF system and breast cancer,—Cancer (2001) 8 197-209, p. 201, col. 1, lines 1-7, p. 202, lines 1-2 and 16-19.
C Garofalo et al,—resistance to anti-IGF-1R therapies in Ewing's sarcoma insulin receptor—Oncogene 30, 2730-2740, Abstract, col. 1, lines 17-46.
Nguyen G.H et al, Cancer Stem Cell Radioresistance and—:—Radiation Therapy May Fail in Lung andEsophageal Cancers, Cancers 2011, 3, 1232-1252, p. 8, para 5, line-1.
Nguyen G.H et al, Cancer Stem Cell Radioresistance and—:—Radiation Therapy May Fail in Lung andEsophageal Cancers, Cancers 2011, 3, 1232-1252, p. 7, para 1, line-1-3.
Rich J.N, Cancer Stem Cells in Radiation Resistance, Cancer Res 2007; 67:8980-8984. Published online Oct. 1, 2007, p. 8981, col. 2, paragraph 1, lines 1-2.
Rich J.N, Cancer Stem Cells in Radiation Resistance, Cancer Res 2007; 67:8980-8984. Published online Oct. 1, 2007, p. 8981, paragraph 1, col. 1, lines 3-16.
Rich J.N, Cancer Stem Cells in Radiation Resistance, Cancer Res 2007; 67:8980-8984. Published online Oct. 1, 2007, p. 8981, col. 1, and paragraph 2, lines 9-13.
Zaki, M.M, Parasite Platelet Interactions,., Review Article, Puj, 2011, 4(2):127-136, p. 128, col. 2, par 2, p. 138, col. 1, para 4, p. 131, col. 2, par 1, p. 133, col. 1, para 3.

Zaki, M.M., Parasite Platelet Interactions, Review Article, Puj, 2011, 4 (2):127-136, p. 130, col. 1, para 3, p. 138, col. 1, par 4, p. 131, col. 2, li 1-6.
Erpenbeck, L., et a Deadly allies: the fatal interplay between platelets-metastasizing cancer cells, Prepub online Mar. 1, 2010; doi:10.1182/blood-2009-10-247296, Abstract.
Nierodzik, M. L. et al Thrombin Stimulates Tumor-Platelet Adhesion in Vitro and Metastasis in Vivo,., J. Clin. Invest. vol. 87, 1991, 229-236, Abstract, Abstract lines 4-8.
Lawler K. et al., stre-platelet-secret matrix proteins—tumor cells—Am J Physiol Cell Physiol 287: 2004, doi:10.1152/ ajpcell. 00159. 2004, p. C1320, col. 1, par 1, li 1-4.
Gastpar, H., S.A Inhibition of Cancer Cell Stickiness by the Blocking of Platelet Aggregation,. Medical Journal, 1974, p. 621, summary, paragraph 2, lines 1-3.
Karl EGAN1, et al, Platelet Signalling in Ovarian Cancer Cells,PLoS One 2011 | vol. 6 | e26125, p. 1, par 2, li 1-3.
Effects of ionizing radiation on blood and blood components: A survey, IAEA-TECDOC-934, 2007, p. 22, lines 3-7.
Metha P. et al, Effect of Human Tumor Cells on Platelet Aggregation:—Metastasis, Cancer Res 1987;47:3115-3117, Abstract, p. 3115, col. 1, paragraph 1, lines 1-7.
Karpatkin, S et al, Role of Adhesive Proteins in Platelet Tumor Interaction—Metastasis—J. Clin. Invest, vol. 81, 1988, 1012-1019, p. 1012, Abstract, col. 1, lines 1-6.
Courier , B. et al,Inela intera of prot and elect with biologi relev molec, The Europ PhysiJournal DEDP Sciences, Societ'a Italiana di Fisica,2002,p. 7 col. 2, Fig.6.
Coupier , B. et al,Inela intera of prot and elect with biologi relev molec, The Europ PhysiJournal DEDP Sciences, Societ'a Italiana di Fisica,2002, p. 4 col. 4, lin 1-9.
Crotti, S. et al,Review, Some thoughts on electrospray ionization mechanisms: European Journal of Mass Spectrometry, 17: p. 85-100, (2001), Abstract, p. 85.
Sahoo, S. et al;Bio-Electrospraying: A Potentially Safe Technique for Delivering Progenitor Cells: Biotechnology and Bioengineering, vol. 106, No. 4, Jul. 1, 2010, p. 690-.
Kempski, H et al,Pilot study to invest the possib of cytoge and physiological changes in bio-electrosprayed human lymphocyte cells, Regen. Med. (2008) p. 345, col. 2, lin 31-35.
Kempski, H et al,Pilot study to invest the possib of cytoge and physiological changes in bio-electrosprayed human lymphocyte cells, Regen. Med. (2008) p. 345, col. 2, lin 18-22.
Kempski, H et al,Pilot study to invest the possib of cytoge and physiological changes in bio-electrosprayed human lymphocyte cells, Regen. Med. (2008) p. 343, concl lin 1-6.
Kempski, H et al,Pilot study to invest the possib of cytoge and physiological changes in bio-electrosprayed human lymphocyte cells, Regen. Med. (2008) p. 343, concl lin 30-32.
Hofmann, B, et. al, Gadolinium neutron capture therapy (Gd NCT) of melanoma cells and solid tumors with the magn reso—: Invest RadiolFeb. 1999;34(2):126-33, Abstract p. 126.
Coderre, J.A.Boron neutron capture therapy, in Text book of Radiation Oncology; Leibel & Phillips ed. 1998, Saunders, p. 1264, Figure 66-1, p. 165, Fig 66-2;66-3.
Rich J.N, Cancer Stem Cells in Radiation Resistance, Cancer Res 2007; 67:8980-8984. Published online Oct. 1, 2007, p. 8981, col. 1, and paragraph 3, lines 1-11.
Fukes Z et al Engaging the vascular component of the tumor response, Cancer Cell. Aug. 2005; 8(2):89-9, Abstract, lines 3-6.
Yeom, C.J. et al, Strategies to Assess Hypoxic/HIF-1-Active Cancer Cells for Innovative Radiation Therapy Cancers 2011, 3, 3610-3631, p. 3614, paragraph 5, lines 2-6.
Yeom, C.J. et al, Strategies to Assess Hypoxic/HIF-1-Active Cancer Cells for Innovative Radiation Therapy Cancers 2011, 3, 3610-3631, p. 3616, lines 7-10.
Glazer, P.M. et al, Radiation Resistance-Cancer Therapy:—Summary—NCI Workshop—Sep. 1-3, 2010, Radiation Research 176, p. e0016, col. 1, line 6 and col. 2, lines 1-6.
Onishi, A.C. et al, Surmounting Chemotherapy and Radioresistance-Chondrosarcoma:—Molecular—Sarcoma, vol. 2011, article ID 381564, doi 10.1155/2011/381564, p. 3, Table.

(56) References Cited

OTHER PUBLICATIONS

Shalini Nair et al. Adaptive Copy Number Evolution in Malaria Parasites, PLoS Genetics | www.plosgenetics.org, 2008, vol. 4 | e1000243, Abstract, p. 1, lines 1-17.
Noel J. G., Protection—Cerebral Malaria—Single Dose, Radiation-Attenuated, Pl berghei—, PLoS One | www.plosone.org, 2011 | vol. 6| e24398, p. 2, col. 2, par 5, lines 1-5;.
Postlethwalt J.H Development in genetic mosaics of Aristapedia, Genetics 76: 767-774 Apr. 1974., p. 678, col. 1, paragraph 2, lines 3.
Pacheoco N. D. et. al.,—vaccination with irradiated sporozoites of Pl, berghei Bulletin—WHO, 57 (Suppl. 1), 159-163 (1979)p. 159, col. 2, paragraph 2, lines 2-4.
Jurasz, P. et al., Review, Platelet-cancer interactions:—British Journal of Pharmacology (2004) 143,819-826, p. 820, col. 2, paragraph 3, lines 1-4.
Jurasz, P. et al., Review, Platelet-cancer interactions:—British Journal of Pharmacology (2004) 143,819-826, p. 821, col. 2, paragraph 1, li 1-17.
Hilf, N. et al, Human platelets express heat shock protein receptors and regulate dendritic, cell maturation, Blood, 2002 vol. 99, 3676-3682, p. 3677, Abstract.
Nierodzik, M.L. et al., Thrombin Stimulates Tumor-Platelet Adhesion in Vitro and Metastasis in Vivo, J. Clin. Invest.vol. 87, Jan. 1991, 229-236, p. 229, Abstract,.
Karl EGAN1, et al, Platelet Signalling in Ovarian Cancer Cells,PLoS ONE 2011 | vol. 6 | e26125, p. 2, col. 1, li 10-14.
Chakravarty, P.K. et al, Dendritic Cells—Irradiated Prostate Tumor Cells—Immune Response, Journal of Cancer Molecules 3(2): 55-60, 2007, p. 59, col. 1, par.5, li 1-11.
Liu B. et al. Minireview, Overcoming Immune Tolerance to Cancer by Heat Shock Protein Vaccines1, Molecular Cancer Therapeutics, vol. 1, 1147-1151, 2002, Abstract p. 1147.
Singh-Jasuja H. et al. The heat shock protein gp96: a receptor-targeted cross—activator of dendritic cells, Cell Stress & Chaperones (2000) 5 (5), 462-470, Abstract, p. 462.
Yang Lin, T. et al.,Proteomics—in head and Neck Cancer: Gp96—Marker—Target-Radiotherapy, 2010, Int. J. Radiation Oncology Biol. Phys., vol. 78, No. 1, Abstr, p. 246.
Kalofonos, et al., Enhancement of Monoclonal Antibody Uptake in Human Colon Tumor Xenografts following Irradiation, Cancer Res 1990;50:159-163, Abstract, p. 159.
Simulation of Proton Therapy Treatment Verification via PET imaging of Induced Positron-Emitters: J. Beebe-Wang, et al, C-A/AP # 122, Nov. 2003; p. 1, Table I.
Bee-Wang, J., et al,Simulation of Proton Therapy Treatment Verifi via PET imaging of Induced Positron-Emitters:C-A/AP # 122, Nov. 2003; p. 1, col. 2, parg.3, Table II,line 2-4.
Bee-Wang, J., et al,Simulation of Proton Therapy PET ima of Indu Positron-Emitters: C-A/AP # 122, Nov. 2003; p. 1, col. 2, parg.3, Table II,line 2-4,li 2-4, p. 3, col. 1, Tab.II.
Ulmer, W. et al,Foundation of an analytical proton beamlet model-MPI of Biophysical Chemistry, Gottingen and Klinikun Frankfurt/Oder. Germany, ET Zurich, p. 5, line 23-24.
Ulmer, W. et al,Foundation of an analytical proton beamlet model-MPI of Biophysical Chemistry, Gottingen and Klinikun Frankfurt/Oder. Germany, ET Zurich, p. 8, line 23-25.
Ulmer, W. et al,Foundation of an analytical proton beamlet model-MPI of Biophysical Chemistry, Gottingen and Klinikun Frankfurt/Oder. Germany, ET Zurich, p. 9, line 17-18.
Ulmer, W. et al,Foundation of an analytical proton beamlet model-MPI of Biophysical Chemistry, Gottingen and Klinikun Frankfurt/Oder. Germany, ET Zurich, p. 10, line 10-14.
Inokuti, M.Interactions of antiprotons with atoms and—, Nucl Tracks Radial. Meas., vol. 16, No. 2/3, pp. 115-123, 1989 Inl. J. Radial. Appl . . . Ins/rum., Part D, p. 120, Fig 3.
Horn, et al, The use of Low Energy, Ion Induced Nuclear Reactions for Proton Radiation Therapy Applications; 1995, p. 1, Abstract.
Horn, etal, The use of Low Energy, Ion Induced Nuclear Reactions for Proton Radiation Therapy Applications;, 1995, p. 11, paragraph 3, lines 1-6.
Orjig A. U. et al, Immunization rodent malaria—irradiated sporozoites of pl. berghei, Am. J. Trop. Med. Hyg., 29 (3), 1980, pp. 343-347, , p. 344, col. 1, para 2,line 7-8.
Hoffman S.L. et al, Protection—Malaria by Immunization with Radiation-Attenuated PI. falciparum Sporozoites, Journal of Infectious Diseases 2002;185:1155-64, p. 1157.
Noel J. G., Protection—Cerebral Malaria—Single Dose, Radiation-Attenuated, Pl berghei—, PLoS One | www.plosone.org, 2011 | vol. 6, e24398, p. 2, col. 2, par 4, li 6-20, p.
Schaue, D et al, Links between Innate Immunity and Normal Tissue Radiobiology, Radiat Res. Apr. 2010 ; 173(4): 406-417, p. 408, paragraph 3, lines 1-18.
Chakraborty, M et al, Irradiation-Tumor Cells Up-Regulates Fas—CTL Adoptive Immunotherapy, J Immunol 2003;170;6338-6347, p. 6341, par 3, lines 21-23, col. 2, li 1-3.
Chakravarty, P.K. et al, Dendritic Cells—Irradiated Prostate Tumor Cells—Immune Response, Journal of Cancer Molecules 3(2): 55-60, 2007, Abstract, page lines 1-14.
Chakravarty, P.K.Dendritic Cells—Irradiated Prostate Tumor Cells—Tumor Specific Immune Response, Chakravarty, J. Cancer Molecules 3(2): 55-60, 2007, Abstract, lines 1-14.
Frelinger, M, et al, Radiation-Induced IFN-g Production—Tumor Microenvironment—Antitumor Immunity, J Immunol 2008;180;3132-3139, p. 3138, col. 2, par 3, li 1-22.
Frelinger, M, et al, Radiation-Induced IFN-g Production—Tumor Microenvironment—Antitumor Immunity, J Immunol 2008;180;3132-3139, p. 3134, col. 1, paragraph 3, lines 1-17.
Moret-Tatay, I et al Complete tumor prevention—tumor cell vaccines employing nonviral vectors Cancer Gene Therapy (2003) 10,887-897, p. 887, Abstract, li 1-4.
Horn, etal, The use of Low Energy, Ion Induced Nuclear Reactions for Proton Radiation Therapy Applications;, 1995, p. 4, paragraph 2, lines 8-10.
Horn, etal, The use of Low Energy, Ion Induced Nuclear Reactions for Proton Radiation Therapy Applications;, 1995, p. 6, paragraph 5, lines 6-7.
Horn, etal, The use of Low Energy, Ion Induced Nuclear Reactions for Proton Radiation Therapy Applications;, 1995,Fig. 2, μINRT, p. 21.
Horn, etal, The use of Low Energy, Ion Induced Nuclear Reactions for Proton Radiation Therapy Applications;, 1995, Fig. 2, Topical INRT, p. 22.
Horn, etal, The use of Low Energy, Ion Induced Nuclear Reactions for Proton Radiation Therapy Applications;, 1995,p. 8, paragraph 4, lines 3-5.
Horn, etal, The use of Low Energy, Ion Induced Nuclear Reactions for Proton Radiation Therapy Applications;, 1995, p. 13, paragraph 1, lines 1-7 and paragraph 2, lines 5-9.
Beley A.S. et al; An alternating phase focusing channel for low energy proton therapy: Proceedings of EPAC 2000, Vienna, Austria, p. 1478-1479; Abstract, p. 1477.
Beasely P., et al.,Prog towa a novel compact high voltage Proceedings of 2011 particle accelerator Conference, New York, NY, USA IPAC 10, Kyoto, Japan, MOPDO18, Abs, p. 1876.
Adler R. J., et al, High Voltage high power nested—, 0-7803.0135. 8/91$01.00 @IEEE 3201-3203, PAC 1991, p. 3203, col. 2, paragraph 3, in Tandem NHVNHVG accel.lines 1-7.
Horon, K.M et al,Ion-Induced Nuclear Radiotherapy, U.S. Pat. No. 5,547,454, issued Aug. 20, 1996, col. 8, paragraph 3 lines 17-41.
Liu, Z. et al.,Drug Delivery with Carbon Nanotubes for in vivo Cancer Treatment, Cancer Res 2008;68: (16). Aug. 15, 2008, 6652-6660, Abstract, p. 6652.
Felix Zwicker et al,Biological in-vivo measurement of dose distribution—by gamma-H2AX—IMRT prostate—IMRT of the prost gland, Radiation Oncology 2011, 6:62: p. 1,Abstract.
Ronsivalle. C et al,Hybrid Schemes for the Post-Acceleration of Laser Ge—, Proceedings of IPAC'10, Kyoto, Japan, THPD038, 03 Linear Colliders, Lepton Accelerator Abst p. 4363.

(56) References Cited

OTHER PUBLICATIONS

Hoffman, I.Collection and focusing of laser accel—, Physical Review Special Topics-Accelerators and Beams, vol. 14, 031304-031311, (2011), p. 031304-3,col. 2, par 5, lin 1-15.

Hoffman, I.Collection and focusing of laser accel—, Physical Review Special Topics-Accelerators and Beams, vol. 14, 031304-031311, (2011), p. 031304-4,col. 1, par 2, lin 1-28.

Hoffman, I.Collection and focusing of laser accel—, Physical Review Special Topics-Accelerators and Beams, vol. 14, 031304-031311, (2011), p. 031304-5 ,col. 1, par 1, lin 1-7.

Ness G. C. et al., Target size analysis by radiation inactivation: The use of free radical scav-Experimental Biology and Medicine 2005, 230:455-463, p. 459, Figures 4 and 5.

Bernstein, S. L. et al; Radiation target analysis of RNA: Proc. Natl. Acad. Sci. USA, vol. 93, pp. 6410-6414, Jun. 1996 Biophysic, p. 6413, Fig. 3.

Hoffman, I.Collection and focusing of laser accel—, Physical Review Special Topics-Accelerators and Beams, vol. 14, 031304-031311, (2011), p. 031304-3 ,col. 1, par 2, lin 1-2.

Hoffman, I.Collec and focu of laser acce-Physical Review Special Topics Accelerators and Beams, vol. 14, 031304-031311, (2011), p. 031304-3 ,col. 2, par 1, lin 1-8,pa 3, lin 2-6.

\* cited by examiner

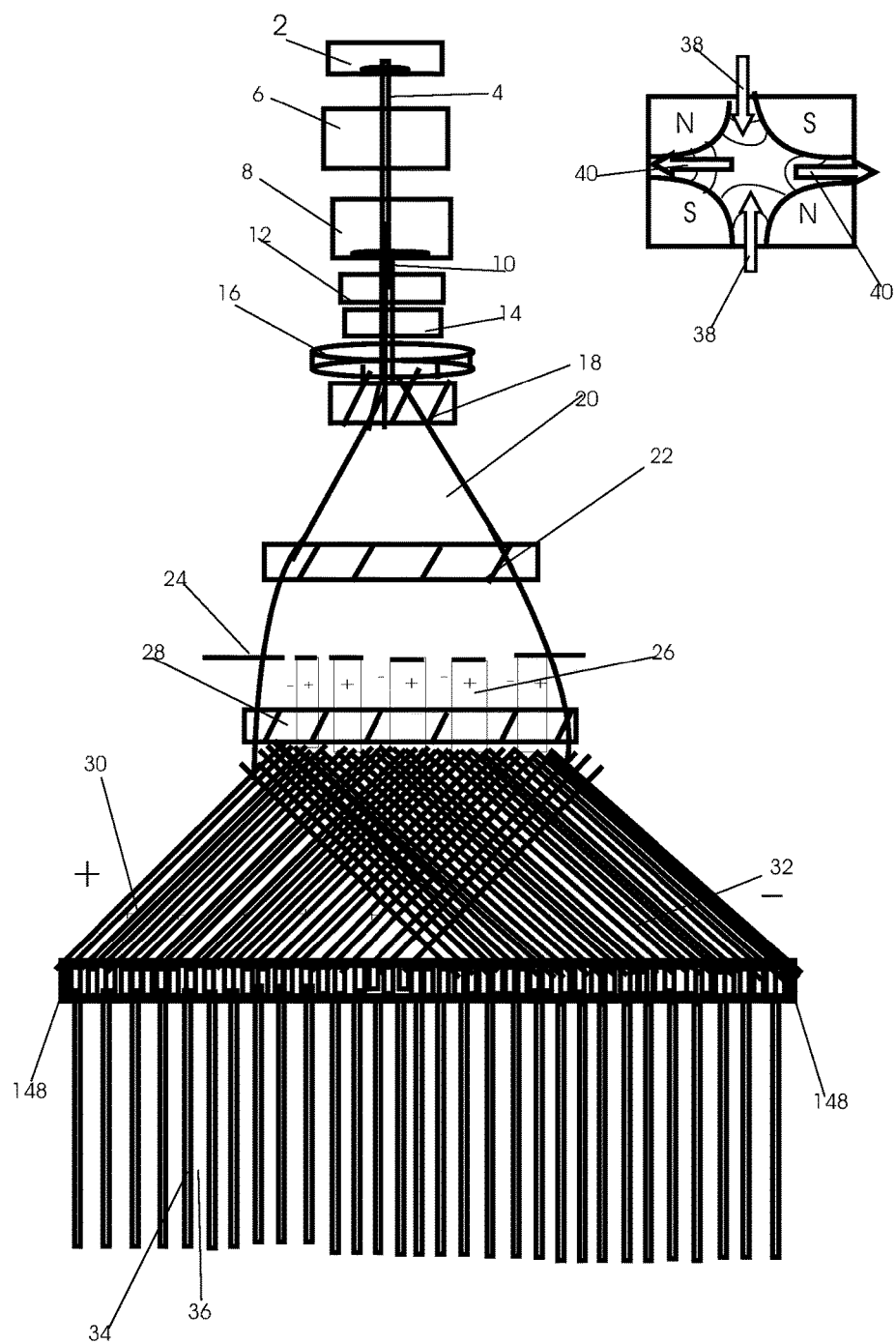

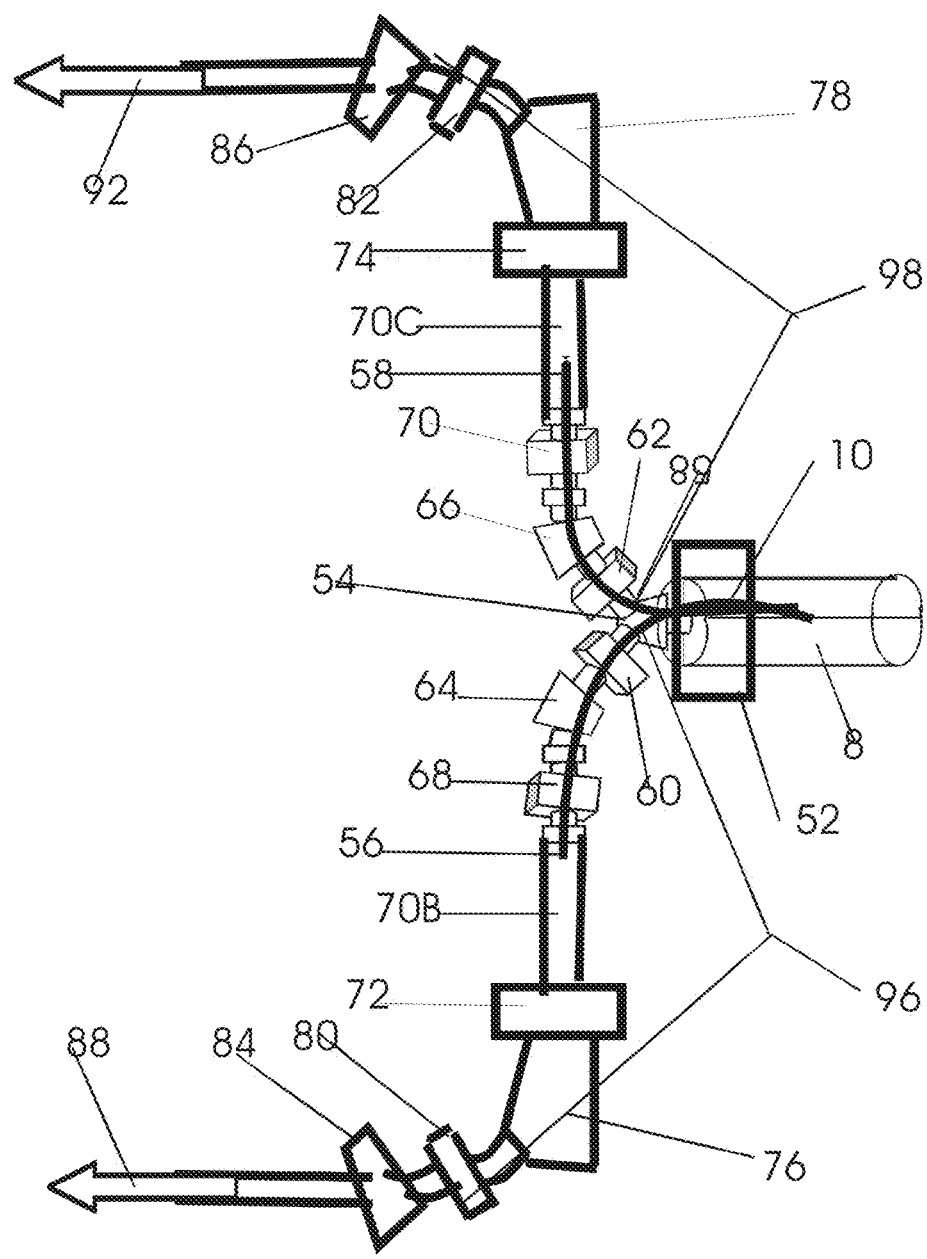

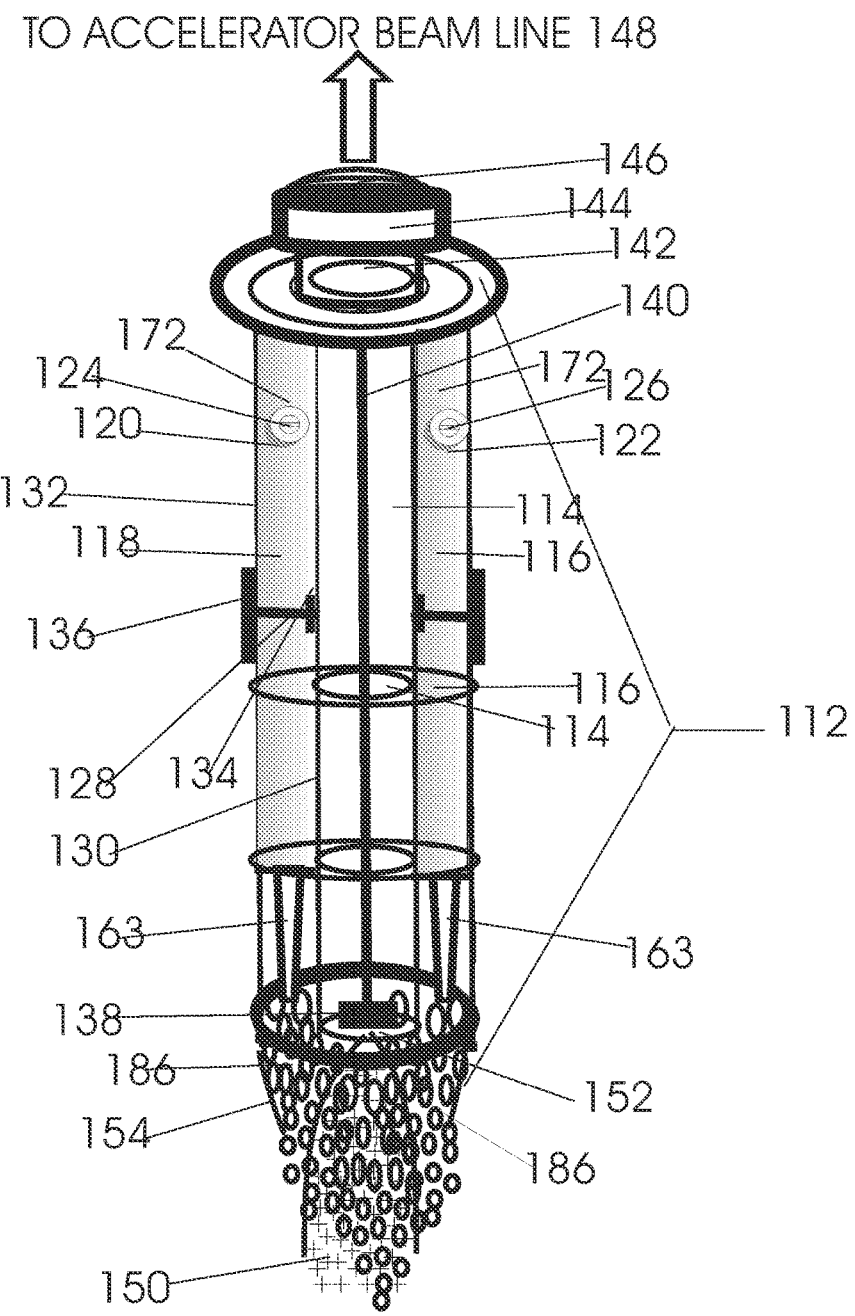

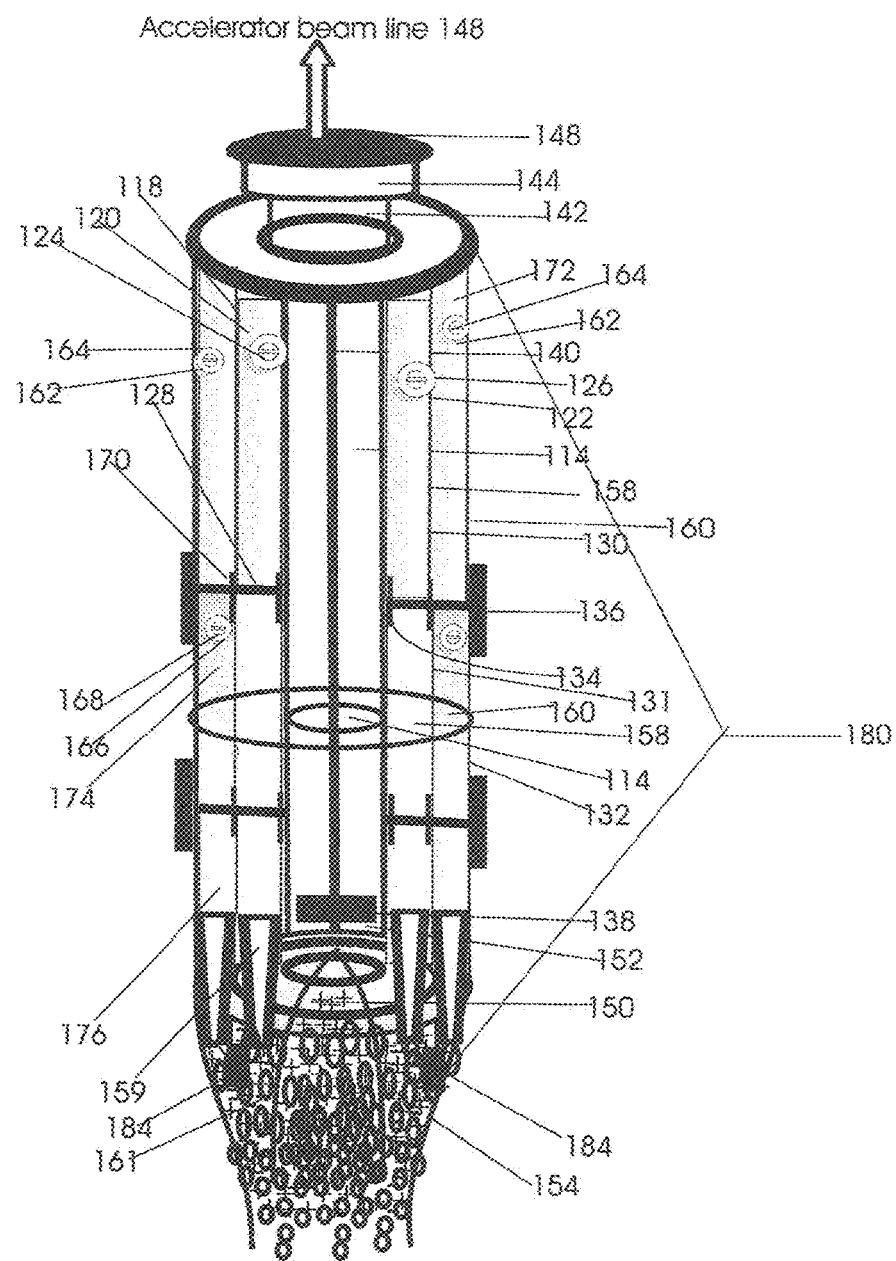

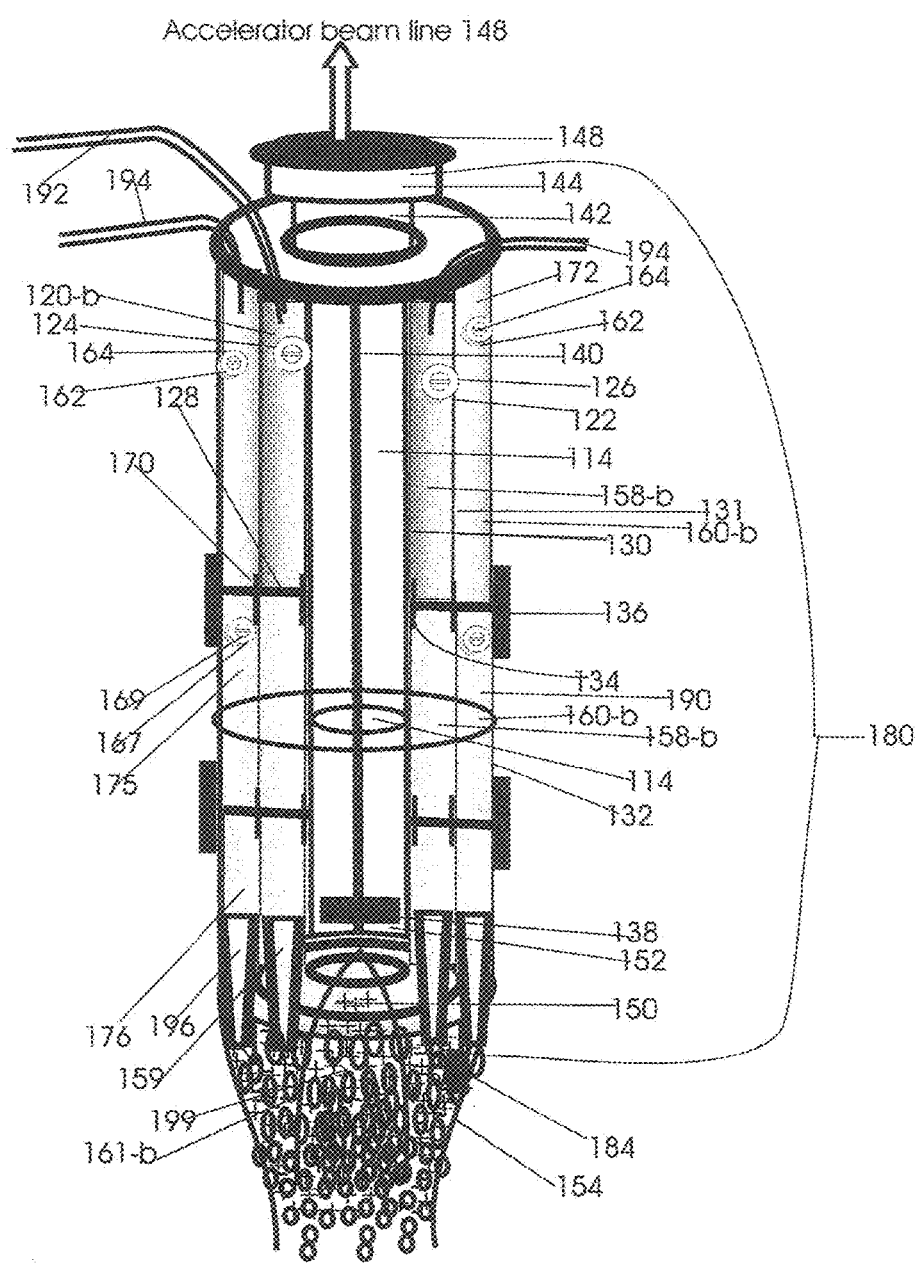

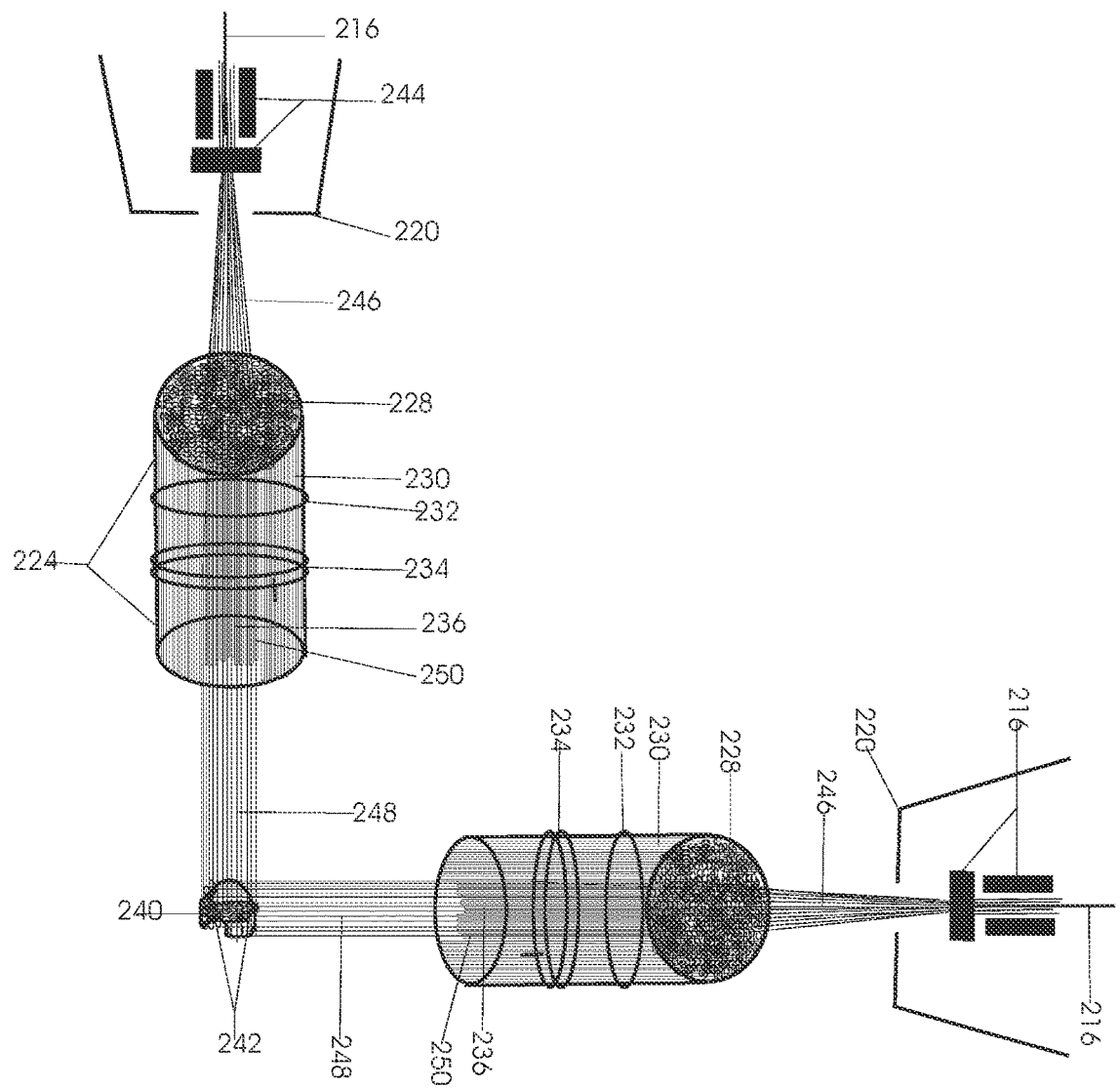

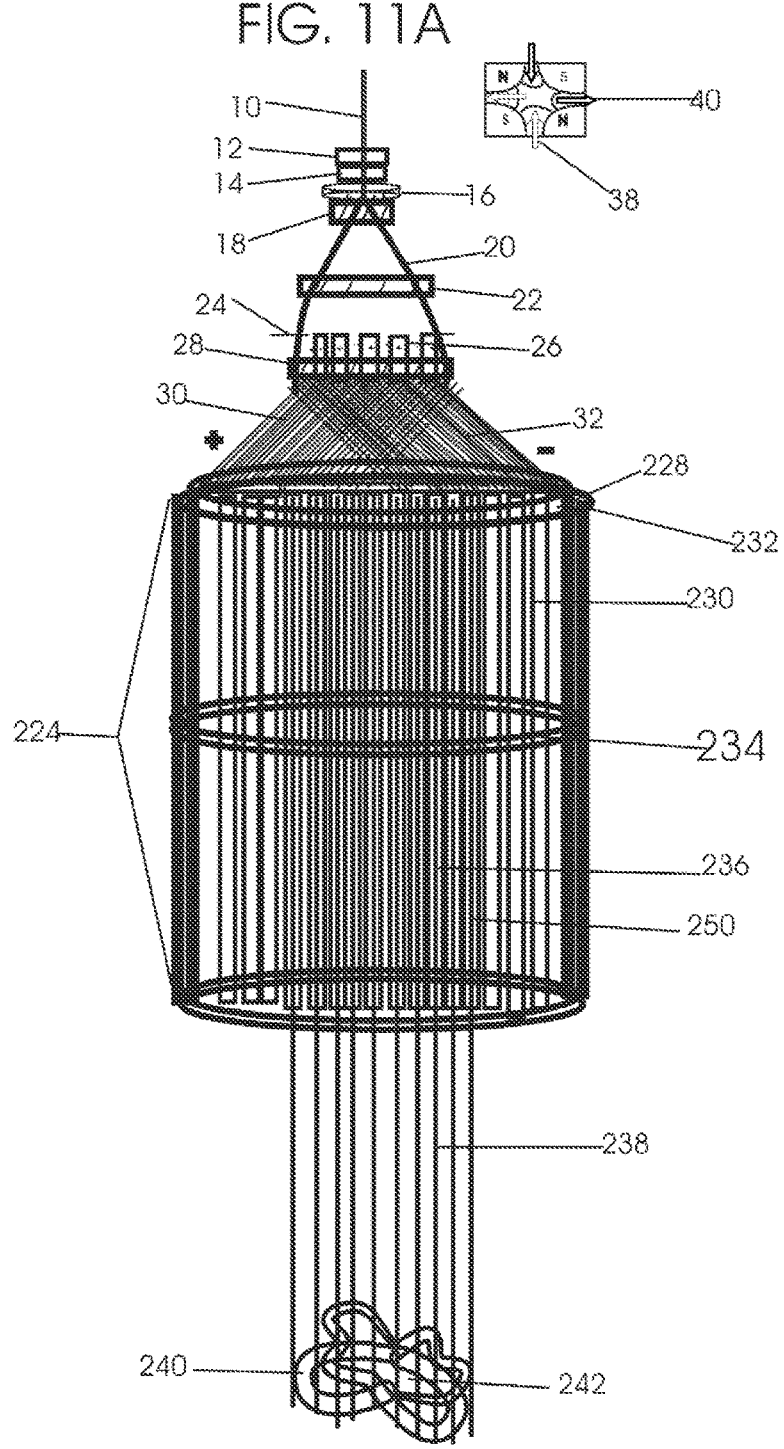

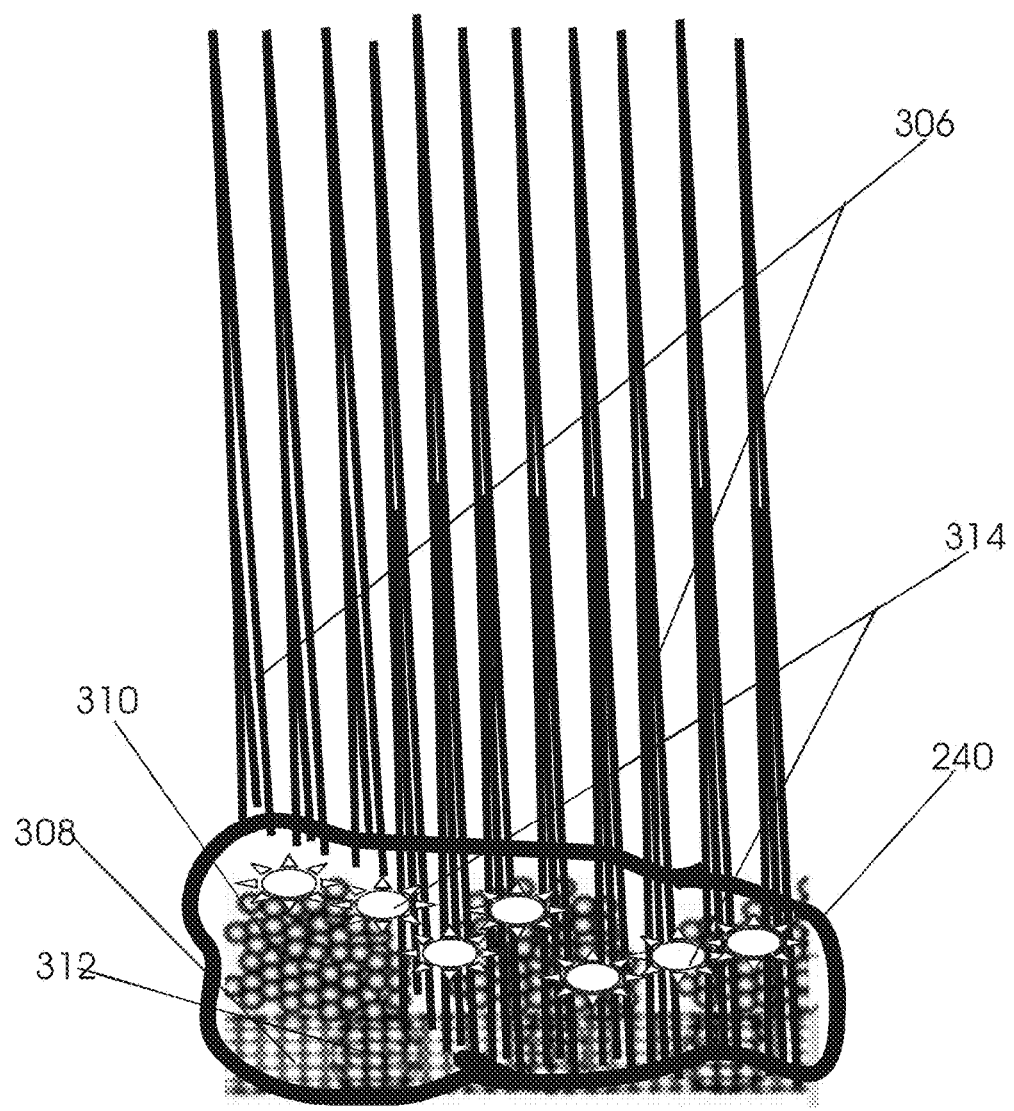
FIG. 11-D

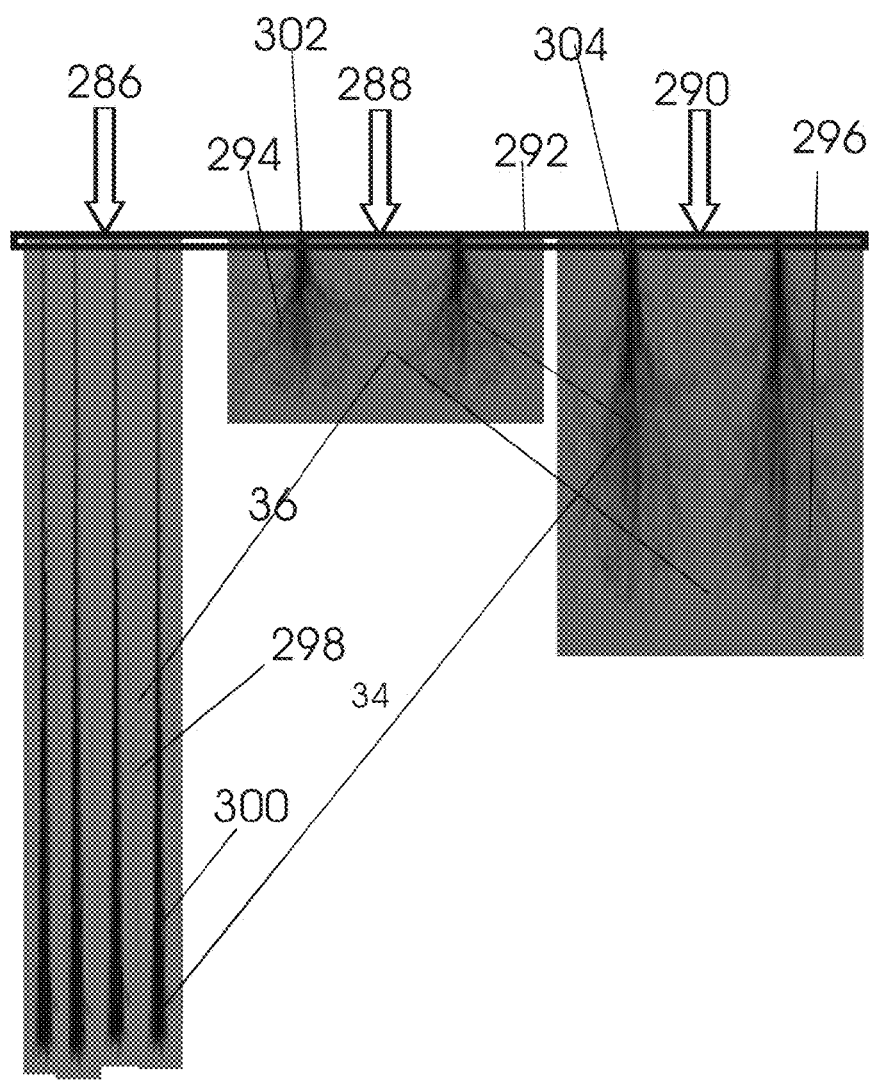

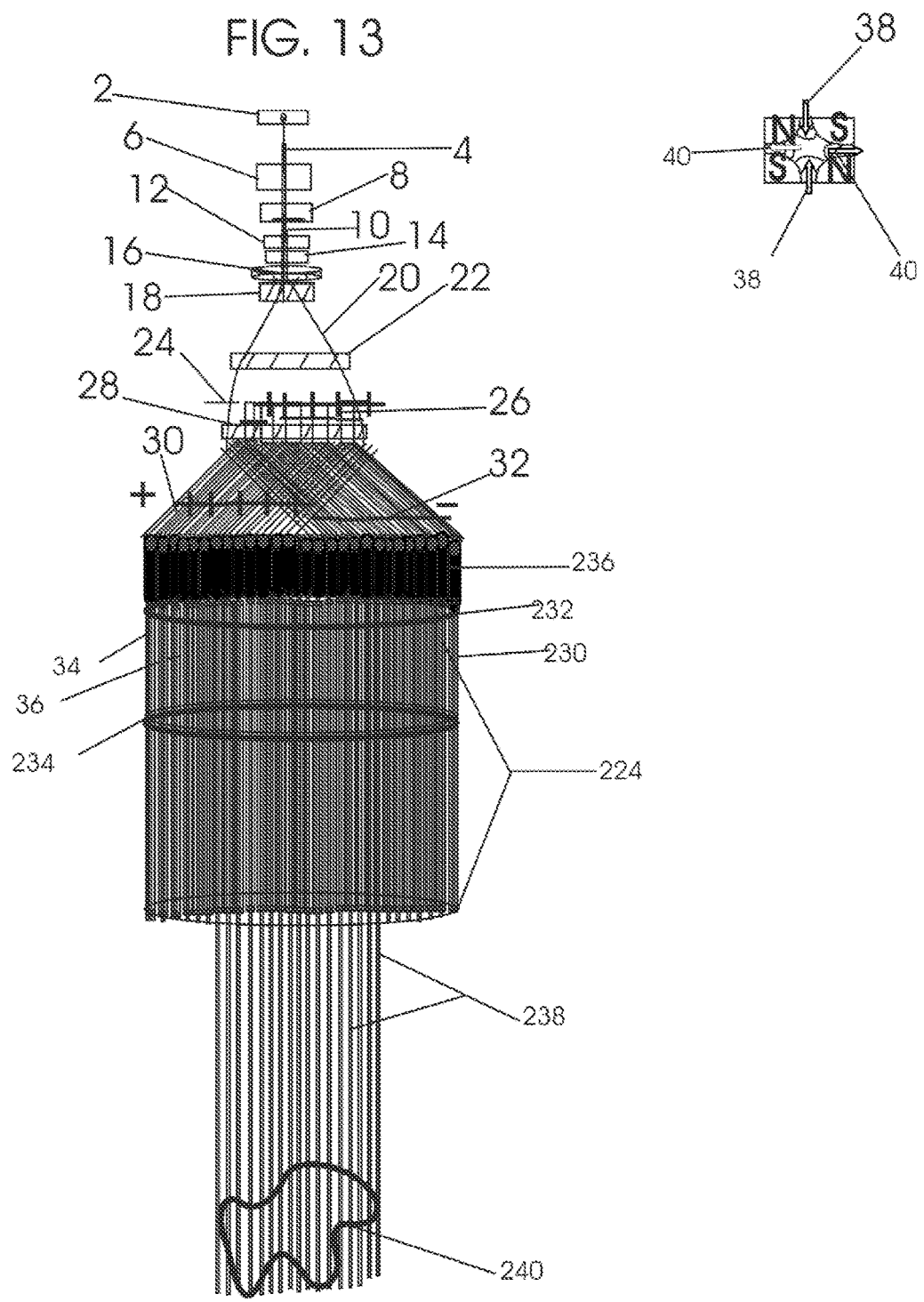

DEVICE AND METHODS FOR ADAPTIVE RESISTANCE INHIBITING PROTON AND CARBON ION MICROBEAMS AND NANOBEAMS RADIOSURGERY

This is a continuation-in-part Application of previously filed application Ser. No. 13/507,829 filed on Aug. 1, 2012.

FIELD OF INVENTION

X-Ray Beam Therapy, Class 378, 424, 530

FEDERALLY SPONSORED RESEARCH

None;

SEQUENCE LISTING

Table of Contents attached

1. BACKGROUND OF THE INVENTION

Two hundred to five hundred Gy high dose and dose rate radiation therapy with Synchrotron generated microbeam is curative even for most radiation resistant tumors like glioblastoma multiforme (1). Its dose rate is in the range of 20 Gy/sec. This invention is aimed at very high dose and absorbed dose rate radiosurgery with compact RFQ accelerators and RFQ-drift tube combination accelerators and proton microbeam and nanobeam generation by accelerated proton beam splitting into multiple parallel microbeams and nanobeams for high dose and dose rate radiosurgery and with ion induced nuclear reaction radiotherapy (I-INRRT).

In general, curative surgery removes the entire visible tumor but leaves residual microscopic tumor cells behind that may proliferate and metastasize. Conventional radiation and chemotherapy destroys most of the residual tumor cells. However by the present methods of conventional radiation therapy, the maximum dose that can be administered to a tumor is limited to about 70 to 80 Gy. This dose is delivered by divergent, broad beam fractionated radiation therapy at daily dose of 1.8 to 2 Gy. Its dose rate per second is about 5-10 cGy. It is a relatively lower dose radiation. It does not cause significant oxidative direct and indirect damage to DNA and to proteins, especially to proteins that controls cell cycles and cell proliferation. Tumor cells that acquire radiation resistance are not controlled fractionated, 5-10 cGy per second radiation therapy.

Very high dose chemotherapy that cause DNA and protein damage without severe normal tissue damage is not available. Most tumor cells acquire resistance to conventional radiation and chemotherapy. Tumor stem cells with metastatic potentials are usually resistant to 70 to 80 Gy fractionated 5-10 cGy/sec accelerator dose rate broad beam radiotherapy.

In summary, the present surgery, radiation and chemotherapy are only partially effective to cure and control most tumors. Hence after surgery, tumors with residual radiation and chemotherapy resistant cancer stem cells and cells with metastatic potentials will continue to proliferate even after completion of the present fractionated 70 to 80 Gy radiations and conventional chemotherapy. It culminates in our inability to cure and control most cancers.

The advantages of simultaneous multiple field radiation therapy with super high additive absorbed dose rate at isocenter from multiple simultaneous beams are described by this applicant. They include U.S. Pat. Nos. 7,714,624 (2), 7,835,492 (3) and 7,902,530 (4), none-provisional patent application Ser. Nos. 12/655,825 (5), 12/658,205 (6), 12/459,120 (7), 12/799,949 (8) and 12/929,770 (9). In this invention, the same principles of simultaneous multiple beam radiation therapy is implemented for proton spray radiation therapy. It increases the dose and dose rate of low energy proton beam. It also generates high LET radiation with low energy proton beam by proton beam-beam collision reactions that produce locally absorbed secondary protons, neutrons, α-particles, ions and gamma rays.

2. PRESENT RADIATION THERAPY'S LOW DOSE AND DOSE RATE ASSOCIATED RADIORESISTANCE

In the present practice of daily fractionated radiation therapy, the radiation is administered as 1.8 to 2 Gy at dose rate of 5 or 10 cGy (0.05 to 0.1 Gy) in about 10 to 15 min. The prolonged treatment time is due to low dose rate radiation which is usually administered through multiple fields, 6 or eight fields. To treat each field, the patient setup needs to be checked and the accelerator needs to be rotated to bring both the patient and the tumor in alignment with the accelerator's beam's eye view. Hence the daily treatment dose of say 1.8 Gy is further subfractionated as 6 to 8 fractions, namely to 30 or 25 cGy (0.3 to 0.25 Gy) per treatment field. If the dose rate of the accelerator were 300 cGy (3 Gy)/min and if the tumor is located at about 10 cm depth from the skin and the percent isodose were 70 at the isocentric tumor, an entrance dose of 43 cGy (0.43 Gy) is administered to each of the 6 fields of a six field setup in 8.6 seconds. Likewise, if the dose rate of the accelerator were 600 cGy (6 Gy)/min and if the tumor is located at about 10 cm depth from the skin and the percent isodose were 70 at the isocentric tumor, an entrance dose of 43 cGy (0.43 Gy) is administered to each of the 6 fields of a six field setup in 4.3 sec. Most of the present medical accelerator's dose rate is in the range of 300 to 600 cGy. Furthermore, such treatment's daily total dose of say 1.8 Gy is given as interrupted due to patient and the accelerator setup and re-setup to treat each filed in about 10 to 15 minutes. Such interrupted very low dose at dose rate of 5 or 10 cGy (0.05 or 0.1 Gy) per sec in 4 or 8 seconds will generate very poor oxidative reaction of radiation in the tumor tissue. Hence there will be very few DNA double and single strand breaks and oxidation of the protein, the hall marks of radiation reactions in the tissue.

3. MICROBEAM RADIOSURGERY

Microbeam radiosurgery (MRS) at doses ranging from 200 to 4,000 Gy and at dose rate of 16,000 Gy per second is shown to be safe to destroy the caudate nucleus in rat without damaging the normal tissue (10). For safe administration of such high dose radiation, the microbeam width is kept at 50 μm and the center to center distances of the microbeams are kept 200 to 400 μm. Its peak dose is confined within the 50 μm width microbeam and the valley dose is confined within the 200-400 μm separation of the microbeams. When the separation is 400 μm, the valley dose drops to about 10 percent of the 100 percent peak dose (11). The X-ray-microbeam generated by the Synchrotron has no penumbra as compared with the α-ray microbeam generated with a $^{60}Co$ source as in the case of a gamma knife (12). With interlaced multiple beams from different angles directed towards an isocentric target tumor and treated sequentially, dose to normal tissue is reduced while the isocentric target tumor is treated with combined dose of all the interlaced beams (13, 14) but each of the interlacing beam is administered sequentially. Hence it has no added advantage of additive high dose and dose rate that is described by this inventor before (2, 3, 4, 5, 6, 7, 8, 9). If it were multiple simultaneous interlaced microbeams from a synchrotron, its dose rate would have been 16,000 Gy× the number of interlacing simultaneous beams. If the interlacing simultaneous beams were 4 and the dose rate at the isocentric tumor were 16,000 Gy per second, then its combined dose rate at the isocenter would be 48,000 Gy. In several laboratory animal experiments, the microbeam radiation therapy has shown its efficacy to treat most radioresistant tumors like the glioblastoma multiforme, transplanted subcutaneous murine mammary carcinoma (15) and aggressive murine SCCVII squamous cell carcinoma (16).

4. ADAPTIVE RESISTANCE TO RADIATION THERAPY AND CHEMOTHERAPY

Low dose and low dose rate daily fractionated radiation therapy induce adaptive response to radiation injury (18, 21). Hela cells exposed to fractionated Neutron and X-Ray radiation from 2 to 10 Gy likewise acquires radioresistance (19). The adaptive response to radiation is evoked by a host of molecular events triggered by the oxidative process of ionizing radiation. Mouse skin pre-exposed to 10 cGy X-rays cause radioresistance to subsequent 200 cGy radiation. This adaptive resistance is mediated by the NF-kB family of proteins, the manganese superoxide dismutase, phosphorylated kinases, Cyclin B 1(20) and a number of other enzymes. Clinically relevant adaptive radioresistance is reported when HepG2-8960-R and HepG2-R cells from HepG2 are exposed to 200 cGy daily for 30 days (21). More frequent HER2 positive invasive recurrent breast tumors occur after radiation as compared to primary tumors (17). Peptic ulcer treated with radiation to a dose of 1500 to 2000 cGy by orthovoltage radiation is known to increase the risk of gastric cancer. When this radiation was combined with surgery, it increased 10 fold. (22). Like the adaptive response to radiation induced stress and its defensive response, wound healing process is an adaptive response by the injured tissue. After surgery, the epithelial mesenchymal transition (EMT) enable the epithelial cell to assume its phenotypic characteristics that enables it to migrate, digest and regeneration through matrix metalloproteinase and to resist apoptosis during such migration and regeneration. Wound healing is such a tissue process with acute inflammatory process, mobilization of molecular factors like TGF, PGF, HGF, PDGF IGF and tissue specific stem cell proliferation (23). Tyrosine kinase inhibitor refractory chronic myeloid leukemia stem cells progress to anaplastic progeny that is independent of myeloid stem cell (24).

5. ADAPTIVE RADIATION RESISTANCE TO FRACTIONATED RADIATION THERAPY

NF-kB activation and radio and chemoresistance are noted in breast cancer. HER2-(Human Epidermal Growth Factor Receptor 2) in breast cancer is known to cause aggressive tumor growth. HER2 expression can be induced by radiation in breast cancer cell lines with low basal level of HER2. The NF-KB is required for HER2 activation by radiation and the HER2 and the NF-KB are co-activated by radiation. NF-kB mediated HER-2 over expression is reported in adaptive radioresistance in breast cancer (17). HER2 mediated radioresistance is inhibited by siRNA (17). The fractionated ionizing radiation therapy at 4 Gy fractions to 60 Gy total dose to human small cell lung cancer lines induced 59 upregulated genes that were associated with DNA damage repair and 43 downregulated genes. The up-regulated genes were associated with DNA damage repair, extracellular matrix, cell adhesion and apoptosis and the 43 downregulated genes were associated with angiogenesis, immune response and calcium signaling pathways (25). The truncated epidermal growth factor receptor EGFRvIII and EGFR wild type (EGFRwt) are coexpressed in human carcinomas and glioblastoma when they are grown as xenografts but not when they are grown in vitro. A single 2 Gy radiation increased the Tyr phosphorylation 2.8 times in EGFRwt (wt—wild type). In EGFRvIII it was increased 4.3 fold. The pro-proliferative mitogen activated protein kinase in EGFRvIII was increased to 8.5 folds. Likewise, the antiapoptotic AKT/phosphatidylinositol-3-kinase pathways in EGFRvIII were increased to 3.2 folds (26). EGFRvIII is known to be a major factor in the radioresistance in glioblastoma multiforme brain tumors (27). Like EGFRvIII, Akt might be an important gene that induces increased radiation resistance in glioblastoma multiforme (28).

6. EGFR AS AN EXAMPLE OF ADAPTIVE RADIORESISTANCE IN CLINICAL PRACTICE

Adaptive radiation resistance is the cellular response to irradiative stress. It is expressed in the cells that survive the very first fraction of the usual total 30 to 40 fractionated radiation therapy. It's EGFR and TGF-α is upregulated. Within 5 to 10 min after the very first dose of 1 to 5 Gy radiations there is a 2-5 fold increase in tyrosine phosphorylation. It returns to base level value within 5-10 min. (29). Such phosphorylation after the very first fractionated dose of radiation is found only in EGFR expressing tumors. Thus it is an adaptive radiation resistance resulting from the first dose of a conventional fractionated radiation therapy regime. Hence it is an acquired or an activated radioresistance. Several EGFR inhibitors are used to overcome this adaptive radioresistance. They include cetuximab, TKIs, antisense nucleotides, other antibodies like hR3 and panitumumab. The radiation therapy combined with these agents increase the tumor response but they also become ineffective (29). Hence, these inhibitors are effective only for a very short time and afterwards the tumor re-grows more aggressively. Hence, they are not effective for cure or control of cancer completely.

Cancer cells have a large number of alternative DNA, cytoplasmic and cellular radiation damage repair oncogenes and mutated of tumor suppression factors such as the mutated p53 and others. They enable the cancer cell to recover from the radiation and chemotherapy damage and become radioresistant. It is not feasible to treat a patient concomitantly with radiation and all the cancer cell proliferation inducing and mutated tumor suppressor genes inhibitors. It is an elusive objective to find any single cancer cell proliferation oncogenes and mutated tumor suppressor growth factors inhibiting drug that will overcome the adaptive resistance to radiation therapy and chemotherapy. On the other hand if a tumor is treated in a single session radiosurgery with high dose and dose rate as in this invention, this adaptive resistance to radiation therapy will not take place and many more cancer will be cured and controlled.

7. INSULIN-LIKE GROWTH FACTOR-I RECEPTOR AND ADAPTIVE RADIATION RESISTANCE

Following ionizing radiation, the Insulin-like growth factor-I receptor (IGF-IR) is known to confer clonogenic radioresistance (30). IGF-IR is known to confer radioresistance directly. Breast cancer specimen containing high levels of IGF-IR have higher incidence of tumor recurrence after lumpectomy and radiation therapy (31). Patients with breast cancer and having elevated levels of IGF-IR in their tumor specimens have early treatment failures. It presents with recurrence and metastasis in less than 4 years (31). Tamoxifen and other hormone resistant, estrogen receptor positive breast cancers are associated with IGF-IR and EGF, a member of erbB receptor family tyrosine kinases (32). It is another example of the adaptive resistance to cancer treatment, in this case, adaptive chemotherapy resistance. Increased IGF-IR can cause resistance to radiation therapy and chemotherapy (33). IGF-IR and estrogen receptor (ER) are coexpressed in some breast cancers. ER regulates transcription of IGF-I, IGF II, IGF-IR and IRS-I (33). The subset of Ewing's sarcoma is highly sensitive to anti-insulin-like growth factor (IGF)-1R therapies. However such treatments induces the Ewing's sarcoma cells to outsmart the IGF-IR inhibiting drugs like the tyrosine kinase inhibitors by switching from IGH-IR1 to its homodimer IGF-IR2 and to continue synthesis AKT and ERK1/2, to maintain its malignant proliferation, migration and metastasis (34).

8. CANCER STEM CELL'S ADAPTIVE RADIATION RESISTANCE

Cancer stem cells are radioresistant and will survive from radiation induced stress more than the differentiated cancer cells (35). The histone H2A phosphorylation, the most readily recognizable marker for DNA double stand breaks is markedly reduced in Cancer Stem cell after radiation than in the differentiated cancer cell (36). Cancer stem cells in solid tumors are resistant to conventional cancer treatments (37), say radiation therapy or chemotherapy. The glioblastoma and colon carcinoma cancer cell surface marker CD 133$^+$ is more enriched than in differentiated cancer cells. In glioblastoma, there is a three to four fold increase in CD 133$^+$ cells immediately after radiation. This indicates that the surviving cancer cells after the radiation injury have relatively higher number of cancer stem cells (38). After radiation, the surviving CD 133$^+$ cells in glioblastoma are capable of proliferation just like the non-radiated glioblastoma cells (39). It is an evidence for stem cell's capacity for repair after radiation injury. In glioblastomas, the degree of DNA damage caused by radiation in CD 133$^-$ and CD 133$^-$ cells are the same but the CD 133$^+$ cells repairs the DNA damage more efficiently than in CD 133$^-$ cells indicating its adaptive radiation resistance (40) and rapid recovery from radiation induced injuries. The cancer stem cells are programmed to withstand the stress caused by radiation. The presence of basal level of activation of DNA damage check point, rad 17, in CD 133$^+$ cells also indicates its adaptive radioresistance. The accelerated repopulation of cancer cells, tumor recurrence and metastasis after radiation all are associated with cancer stem cell recovery after radiation. The present fractionated, 1.8 to 2 Gy per day, 5 treatments per week to a total dose of 70-80 gray is most likely exasperate the efforts to cure and control cancers due to cancer stem cell recovery, its effective survival, proliferation and eventual metastasis after the treatments.

9. HYPOXIA AND HYPOXIA INDUCIBLE FACTOR-1 AND VEGF AND ADAPTIVE RADIATION AND CHEMOTHERAPY RESISTANCE

During the course of the fractionated radiation therapy, the HIF-1 activation initiates multiple adaptive responses in the tumor cell and in the tumor microvasculature network. This pleotropic adaptive response includes both radiosensitizing the tumor cells and tumor radioresistance due to protection of the microvascular endothelium (41)). The hypoxic tumors stimulate tumor microvascular angiogenesis to maintain its nutritional needs and oxygenation. It makes the conventional radiation therapy and chemotherapy mostly ineffective. It stimulates multiple gene expression like the lysyl oxidase, chemokine receptor CXXR4 and osteopoetin (42). Radiation activates HIF-1 and HIF-1 stimulates the vascular endothelial growth factor (VEGF) and the VEGF protects the endothelial cells from radiation (43). It leads to tumor microvascular proliferation, tumor growth and metastasis.

10. "RESISTANCE TO THERAPEUTIC DOSES OF RADIATION REMAINS A CHALLENGE" RADIATION RESISTANCE AND CANCER THERAPY, NATIONAL CANCER INSTITUTE WORKSHOP SUMMARY

The National Cancer Institute's workshop held on Sep. 1-3, 2010 on Radiation Resistance and cancer Therapy, it was concluded that "resistance to therapeutic doses of radiation remains a challenge. Key biological features such as tumor hypoxia, DNA damage response and checkpoint pathways, angiogenesis and vasculogenesis, cancer stem cells, tumor stroma, and immune response pathways all contribute to the complex dynamics governing tumor responses to radiation" (44). These complex features of biology of cancer cell and the difficulty to overcome the resistance to radiation therapy and also to chemotherapy are briefly discussed above. It is not possible to include all the complex defense mechanism that the cancer cell have to overcome the radiation induced stress, some of the other cellular defense against radiation injury that it can call for include the adaptive defense by means of poly(ADP-ribose) polymerase-1 (PARP), the adaptive defense by means of insulin-like growth factor-1-secretory clusterin, the adaptive defense by means of DNA-PK complex and DNA-PK subunit Ku, the adaptive defense by means of protein phosphatases, the adaptive defense by means of gamma secretase, the adaptive defense by means of Wee-1, the adaptive defense by means of small molecule c-Met, the adaptive defense by means of tyrosinekinases, the adaptive defense by means of RcQ helicase, the adaptive defense by means of terminal deoxynucleotidyl transferase (TdT), the adaptive defense by means of DNA-Polymerase X-Family, the adaptive defense by means of shRNA and SiRNA and so many other genomic expressions that are not mentioned here. It shows the complexity of the subject. Therefore, it is obvious that any single or a combination of two, three or say 5 or even 10 anticancer drug combinations and the present methods of daily low dose, fractionated radiation to a total dose of 60 to 80 Gy in about 8 to ten weeks will not sterilize a tumor and its cancer cells, especially the few remaining, usually invisible cancer stem cell from proliferation, recurrence and eventual metastasis.

Examples of such evolving and differing genomic expression are well observed in metastatic breast cancer that contains coexisting estrogen receptor positive and negative components. Treating such a tumor with anti-estrogen will be beneficial to estrogen receptor positive component of the tumor if the tumor growth is solely dependent on estrogen. Unfortunately however, the estrogen receptor negative portion of the tumor will not benefit from the anti-estrogen treatment. Hence the treatment outcome will not be satisfactory. Such is the complexity of attempting to overcome the radioresistance with drugs that will inhibit one element of the cell's or a group of cell's stress defense against radiation while the other elements in the cancer cell or a group of cancer cells will counteract the beneficial effect of a particular radioresistance inhibiting drug. On the other hand, if the anti estrogen were combined with more innovative methods of radiation with super high dose and dose rate than the present "therapeutic doses" then the estrogen receptor positive and negative as well as the many other oncogene controlled tumors will be cured and controlled. Hence the conclusion of the most learned group of experts and scientists gathered at the National Cancer Institute a year ago that the "resistance to therapeutic doses of radiation remains a challenge" is one that we can attempt to overcome with the hope that there is light at the end of the tunnel. This invention is aimed to depart from the present "therapeutic doses of radiation", at daily 1.8 to 2 Gy per fractions and 3 to 6 Gy per min dose rate, five fractions a week, eight to ten weeks treatment to a total dose of 70-80 Gy with seconds to milliseconds duration 100 to 1,000 Gy radiosurgery with minimal or no toxicity to normal tissue.

11. MULTIFACTORIAL COMBINED RADIATION AND CHEMOTHERAPY RESISTANCE, EXAMPLE CHONDROSARCOMA

There are a number of molecular mechanisms acting simultaneously that cause both radiation and chemotherapy resistance. They include p-glycoprotein expression, telomerase activity, angiogenesis, COX-2 expression, melovonate synthesis, tumor suppressor p16, increased expression BcL-2, BcL-xL and XIAP, and hypoxia (45). Their effects within the cell and the therapeutic strategies to overcome them vary (45). There are many more such radiation and chemotherapy resistance causing genes within a single cell that are not included in this list. It is obvious that even if a couple of these radiation and chemotherapy resistance causing molecules are inhibited, the many other remaining ones restore the therapeutic resistance spontaneously. Hence a one, two, or three drugs combination chemotherapy combined with low dose fractionated radiation will not be effective to control the tumor growth, recurrence and metastasis.

12. RADIORESISTANCE, EXAMPLE: ATTENUATED MALARIA PARASITE FOR MALARIA IMMUNITY

Copy number polymorphism (CNP) in malaria parasite is shown to be an effective molecular mechanism that confers the adaptive antifolate biosynthesis through GTP-cyclohydrolase (gch 1) in malaria plasmodium (46). Such gch 1 CNP is shown to be an effective adaptive antifolate drug resistance development evolution in plasmodium malaria (46). It is known that there is a wide variation in CNP in widespread copy number polymorphism in humans, mice, *Drosophila* and other eukaryotes, including its geographical variations and in its contribution in developing geographically variant drug resistance (46). This adaptive evolution is quite developed in malaria parasites.

The plasmodium malaria chromosome 5 carrying the multidrug resistance phenotype differentiates into male and female gametocytes and they fuse in the mosquito midgut that generates the malaria diploid stage ookinete and from its meiosis, the infective haploid malaria sporozoites are formed. The sporozoites are injected into human blood during the mosquito bite for its feeding on human blood (46). These sporozoites are highly radioresistant.

In mouse, over 100 kilorad (1,000 Gy) radiation to malaria sporozoites was required for protection from cerebral malaria caused by plasmodium berghei with attenuated malaria sporozoites (47). Hence it is obvious why the past efforts to immunize against malaria with lower dose and dose rate radiation have failed. Such earlier efforts to immunize against malaria with radiation attenuated malaria sporozoites includes 1,000 rads (10 Gy), (48) (66), 80 Gy at 800 cGy for 10 min (49), 15 k rads (150 Gy) (50, 51) and 100 to 600, 800 and 1,000 Gy (47, 52). There is no effective immunity against cerebral malaria from plasmodium berghei sporozoites when the radiation dose was 100 to 600 Gy. The semilog plot of dose versus percent protective immunity also shows that when the radiation dose was increased to 800 Gy, there was 70% protection and at 1,000 Gy, there was 100% protection (52). Thus, even the adaptive radioresistance of a parasite, in this case the plasmodium berghei sporozoites can be overcome with very high dose, 1,000 Gy which is 500 to 555 times higher than the daily fractionated dose radiation therapy doses of 1.8 to 2 Gy and 12.5 to 16.5 times higher than the 60-80 Gy total dose given in 8 to 10 weeks by IMRT. Thus, this comparison of radioresistance of plasmodium berghei sporozoites and the present daily fractionated radiation dose of 1.8 to 2 Gy illustrates the need for alternative methods for higher dose radiation without much toxicity to normal tissue to treat the radioresistant tumors and to avoid adaptive radioresistance development during the course of radiation therapy.

13. A BRIEF LIST OF ADAPTIVE RADIORESISTANCE CAUSING MOLECULES IN THE CANCER CELL

There is a continuously increasing list of radioresistance and chemotherapy resistance causing molecules in the cancer cell. Because of this rapidly growing number of such molecules, only a brief list can be included here. They include poly (ADP) polymerase-1 (PARP), insulin like growth factors, DNA-PK. WEE-1, terminal deoxynucleotidyl transferase (TdT), DNA polymerase X-family, hypoxia induced HIF-1 α, EGFR, shRNA, NanogP8, H-RAS-, heat-shock protein, NFB family of DNA binding proteins P65/RelA, cRel, p50, p52, and Relb, microRNA-17-92, p53 mutation, Mn-superoxide dismutase, survivin, p-glycoprotein, telomerase, VGF-angiogenesis, COX-2, melovonate, p16, Bcl-2, Bcl-xL and XIAP, selenium, CD 133, CD 47, sphingomyelinase and HER2. It is only a partial list of radiation resistance and chemotherapy resistance causing molecules in the cancer cell; they continue to increase. It is impossible to inhibit all of these molecules simultaneously with their respective chemotherapeutic drugs as part of effective chemotherapy or in combination with radiation as radiation sensitizers. On the other hand, cell shattering microbeam and nanobeam radiation therapy at dose rate of over 10,000 to 20,000 per second and at doses of 100-1,000 Gy (400-4,000 Gy) and given within milliseconds as single exposure radiosurgery overcomes this cellular radioresistance.

14. RADIOIMMUNOTHERAPY WITH TUMOR CELL CYTOKINES AND ANTIGENS

In conventional fractionated radiation therapy, the daily radiation for 8 to 10 weeks wipes out the innate local cancer immunity facilitating mast cells, phagocytes, natural killer cells, γδ T cells, macrophages, neutrophil, dendritic cells, basophils and eosinophils. After each day's radiation, these cells attempts to repopulate the locally irradiated tumor but by the next day's radiation, they are destroyed or damaged making them ineffective to help to establish an effective innate and adaptive immunity against the tumor that is treated. In this case, the daily fractionated localized radiation acts as a local immunosuppressive treatment. If on the other hand, the radiation is given as a single fraction, split second duration normal tissue sparing microbeam and nanobeam radiation as in this invention, its tissue inflammatory reaction induced stress defense is called for. It leads to recovery from the injury and acquiring protection against such future injury through activation of innate and adaptive immunity to tumor that is so treated.

Like the lower dose radioresistant malaria sporozoites, the lower dose radioresistant malignant tumors will also respond to radiation if the dose were increased to higher dose with resultant tumor cure and control. High dose and dose rate microbeam and nanobeam radiation at doses in the range of 100 to 1,000 and 4,000 Gy in seconds to milliseconds to a tumor is capable of curing tumors like that of glioblastoma (14). Such high dose radiation in split seconds without much damage to normal tissue was not possible before. The normal tissue toxicity from radiation is minimized or eliminated by peak and valley dose difference and regeneration of the tissue in the peak dose region by migration of cells from the valley region. In this invention, it is further refined as all fields simultaneous microbeam and nanobeam radiation therapy with additive absorbed dose and dose rate at the isocenter by means of interlaced multiple simultaneous beams. Such high dose localized radiation to a tumor in split seconds causes radiation induced inflammation at the tumor site. It releases a number of cytokines (53) and free radicals. Even the lower dose localized radiation in the range of 5 cGy to 2 Gy evokes localized innate immunity (53). The 100-1,000 Gy radiation in split second obviously evokes much stronger innate immunity and secretion of a number of cytokines. Likewise, radiation evokes adaptive immunity through the FAS pathway (54). In vitro experiments, MC 38 adenocarcinoma cells at 20 Gy dose had increased FAS activity at molecular, phenotypic and functional levels. At this relatively higher dose radiation for an in vitro experiment, radiation sensitized these cells to antigen specific cytotoxic-T-lymphocyte's (CTLs) cell killing by FAS/FAS ligand pathway (55). In vivo experiments, the same MC 38 adenocarcinoma cells growing subcutaneously also showed 8 Gy radiation sensitized CTL adaptive immunity by up regulation of FAS leading to tumor growth arrest and tumor rejection (55). Antigen processing dendritic cells are stimulated by radiated highly malignant prostate cancer cell line RM-1 but with higher dose radiation, in the range of 10-60 Gy. It is a very high single fraction dose for in-vitro experiments. Unirradiated cells had no such immunostimulatory effects (56). Radiation releases several cytokines including IFN-γ which modulates tumor vasculature microenvironment and promotes the cytotoxic T-lymphocytes (CTLs) trafficking and its recognition by the tumor cells (57). The localized radiation dose to the mice in the experiments was 15 Gy (58) which is a large dose to treat a tumor in mice indicating the effectiveness of high dose radiation to modulate tumor microenvironment and tumor immunity. It is increased with high dose and dose rate micro and nanobeam radiation. It also allows personalized dose for radiosurgery and modulation of cancer microenvironment and cancer immunity. Cytokines engineered cells with non-viral lipoplexes and without viral vectors were able to protect mice 100 percent from tumor growth indicating that cytokines can evoke effective long standing tumor immunity (59). The vaccinating tumor cells infected with granulocyte-macrophage colony-stimulating factor (GM-CSF) or IL-4 plasmids bearing cationic lipid were radiated at high dose of 150 Gy (59). In present radiation therapy, such high dose localized radiation is not feasible. The present 2 Gy daily fractionated radiation is weak to cause sufficient cytokine secretion that can cause similar immunoprotection as with the 150 Gy radiations in this case. High dose and dose rate, interlaced multiple simultaneous microbeams and nanobeams radiation to the tumor without much toxicity to normal tissue on the other hand induces very effective immunoprotection. It causes strong inflammatory reaction at the tumor site. The cytokines released from such strong inflammatory reaction thus evokes strong tumor specific immunity.

15. RADIOIMMUNOTHERAPY WITH CIRCULATING PLATELET ADHERENT TUMOR CELL'S CYTOKINES AND ANTIGENS

Circulating tumor cells (CTLs) are generally recognized as circulating nucleated cells lacking CD 45 and with cytokeratin surface markers. Such CTLS are found in breast cancer (60) and in almost all other cancers. It is a general phenomenon even at very early stage of cancers without any manifest metastatic disease, like the cancers of the ovary, cervix and endometrium with the tumor cell homing in the bone marrow (61). Patients with progressive, non-small cell carcinoma of the lung (NSLC) have easily detectable circulating tumor cells (CTCs). As the disease progress and metastasize, the number of CTCs also increases (62). Methods for detection and isolation of circulating cancer cells from prostate cancer, renal cell cancer, testicular cancer and bladder cancer was described as early as in 2004 (63). Flow cytometry and reverse transcription polymerase chain reaction (RT-PCR) was used to identify circulating prostate-specific antigen-positive cancer cells (64). Cancer cell and platelets adherent together and they activate several cytokines that facilitate the tumor cell clumped to platelets to circulate and the cancer to metastasize (65). Platelets interact with tumor cells by shear stress induced protein secretion, the integrin $α_vβ_3$ (66) which enable the tumor cells to clump with the platelets. The platelets adhesion to tumor cells works as a shield against radiation to the tumor cells.

16. PLATELETS AS EFFECTIVE ADAPTIVE IMMUNE RESPONSE INDUCING CELLS

The activated platelet adhesion to its host cell releases a great number of chemokines that activates multitudes of immune receptors on the cell membrane of the platelet (67). In the presence of IGE, IGG, lymphokines or complement factors, the platelets attached to the immunocompetent cells secrets platelet activating factor (PAF), platelet derived growth factor, (PDGF), human platelet factor 4 (PF4), ß-thromboglobulin, IL-1 and leukotrienes (68) that helps to maintain immunological defense against the pathogen like the parasites. This platelet-parasite interaction is a quite efficient anti-inflammatory and host immune reaction to a number of infections, against plasmodium malaria, schistosoma, toxoplasma, and echinococcus (69). Platelets as the most effective immune defense against malaria is described (70). The malaria parasite's Duffy antigen receptor for chemokines (DARC) is very essential for the erythrocyte invasion by plasmodium vivax. It binds to RANATES, a proteome secreted by the platelets. This platelet secreted RANTES is also very effective in suppressing the replication of HIV-1 (70). Thus the platelet is also a first line immune defense against HIV-1 infection.

Platelet adhesion to cancer cells plays an important mechanism in tumor metastasis (72). Thrombin stimulates tumor-platelet adhesion in vitro and metastasis in vivo (73). The interaction of platelet-secreted matrix proteins with tumor cells through the integrin $\alpha_v\beta_3$ is critical in tumor metastasis (74). Cancer cell adhesion to each other can be blocked by platelet aggregation with dipyridamole and its derivatives (75). Interaction of platelets and the circulating cancer cell is thought to be a major cause of metastasis (76). Thus like in the platelet aided malaria sporozoites invasion into red cells, the platelet-cancer cell interaction, their aggregation and circulation that takes them to distant organs from the original tumor helps the cancer cell to invade the distant organs and to metastasize.

Like the high dose radiation, 1,000 Gy to blood containing malaria sporozoites renders immunity from the most aggressive form of malaria, the cerebral plasmodium berghei (46, 52), the high dose radiation in the range of 1,000 Gy to platelet-cancer cell containing blood concentrates and its reinfusion to the patient from whom such platelet-cancer cell concentrate was prepared immunizes the patient against the cancer cell. Such radioimmunotherapy eliminates or minimizes the tumor metastasis in patients who have not yet developed metastasis but have circulating cancer cells and in those who have already developed metastasis.

17. PLATELET'S RESISTANCE TO IONIZING RADIATION

Platelets are very radioresistant. The International Atomic Energy Agency's (IAEA) technical report IAEA-TECDOC-934, "Effects of ionizing radiation on blood and blood components: A survey" describes the tolerance of radiation dose for various cellular elements and other blood components and their safe clinical use. In this technical report, the tolerance of platelets for radiation is described as over 750 Gy; a very high dose for a very small cell (77). Such high dose radiation did not alter the normal functions of the platelet or its survival in patients after transfusion (77). Because of the tumor cell being covered by platelets and platelets being very highly radioresistant, the platelet shielded tumor cells acquires very high tolerance to ionizing radiation.

Like the malaria parasite sporozoites in the red cell, the platelet shielded circulating cancer cell need very high radiation to sterilize it. The malaria sporozoites are inactivated only at about 1,000 Gy (52). Since platelets can absorb ionizing radiation doses of over 750 Gy without any cellular damage (77), the tumor cells shielded by the platelets is sterilized at very high doses, close to as high as 750 Gy. It is closer to the 1,000 Gy radiation required to inactivate the malaria sporozoites in red cells. Like the solid tumors treated with very high dose and dose rate microbeam and nanobeam, such very high dose radiation to circulating tumor cells induces innate immunity from radiation and tumor antigen specific adaptive immunity.

18. TUMOR SPECIFIC RADIOIMMUNOTHERAPY WITH HEAT-SHOCK PROTEIN GP96 BOUND PLATELETS ADHERENT TO IRRADIATED AUTOLOGUS TUMOR-DENDRITIC CELLS

Human cancer cells, like the Osteogenic sarcoma, are known to cause platelet aggregation. It is shown that this platelet aggregation is dependent on the concentration of the tumor cell (78). Monoclonal antibodies 10E5 which inhibits the binding of fibronectin and von Willebrand factor to the platelet membrane glycoprotein GPIIb-GPIIIa complex inhibits the platelet binding to human HC18 colon carcinoma and mouse CT 26 carcinoma (79). Cancer cell is capable of generating its own multiple coagulation factors including those that regulate the fibrin and thrombin (80). By coating the tumor cell with platelets, it shields the tumor cells form tumor immunity and the TNF-x mediated cytotoxicity. The platelets and the platelets coated tumor cell secrete growth factors. They aggregate to vascular endothelium at distant sites and metastasize (81). The platelets are highly radioresistant and they can withstand high dose radiation, doses of over 750 Gy (77), IAEA report) without loosing its functional integrity. Hence the platelet coated tumor cell is shielded from the conventional daily fractionated 2 Gy radiation to a total dose of 60-80 Gy in 8-10 weeks. It makes the present radiation therapy to cancer mostly ineffective to control the metastasis and long for term survival.

Human platelet has receptors for endoplasmic reticulum resident heat-shock protein Gp96 (82). Heat-shock protein Gp96 bound to endoplasmic reticulum causes histocompatibility based specific immunity. In response to inflammatory stimulus, the Gp96 bound to the cell membrane of the antigen processing cells induce major histocompatibility complex (MHC) specific cytokines secretion. Its specificity is derived from histocompatibility class 1 restricted crosspresentation of Gp96 associated peptides. Gp96 stimulates the secretion of proinflammatory cytokines from macrophages and dendritic cells. Gp96 binds to human platelets and it is enhanced by thrombin by ten times (82).

Platelet adhesion to tumor cell is mediated by fibronectin and von Willebrand proteins (83). In vitro, it was fond that thrombin as little as 1-10 mU/ml was sufficient to stimulate the platelet-tumor cell adhesion (83). In vivo, thrombin stimulates metastasis. Thrombin at concentrations of 250-500 mU per animal increased the number of metastasis for CT26 colon carcinoma and 68-413 fold for B16 amelanotic melanoma (83). Platelet adhesion to ovarian cancer cell is shown to have improved tumor cell survival and angiogenesis (84).

Antigen from damaged, proapoptotic and necrotic cells are processed as major histocompatibility complex (MHC) class 1 antigen by the dendritic cells. The activated dendritic cells stimulate the CD8 T-lymphocytes in vitro and in vivo (85). Like the Gp96 binding proinflammatory stimulus from infection and tissue necrosis, radiation cause inflammatory stimulus. Irradiated cancer cells like those from prostate cancer can activate dendritic cells (56). Dendritic cells phagocytosed antigen migrates to lymph nodes and interacts with varying subsets of T-lymphocytes. Dendritic cells capture killed cells containing tumor specific antigens and produce tumor specific immunity. Intact cancer cell like that from prostate cancer is not processed by the dendritic cells (85). On the other hand, radiation damaged cancer cells is captured by the dendritic cells and brought to the lymph nodes to produce tumor specific immunity by the T-lymphocytes in the lymph nodes (85). The immune tolerance to cancer cells is mediated by masked tumor antigen. This masked tumor antigen is unmasked in cancer cells that are severely damaged and unable to replicate; that is in effect they are killed. Unmasked tumor specific antigen and its tumor specific fingerprint peptides is taken up and chaperoned by the heat-shock protein Gp96 and delivered to the dendritic cell. Dendritic cells transport it to the lymph nodes. In the lymph nodes this tumor specific antigen-peptides is taken up and initiates tumor specific immune response in CD4 and CD8 T-lymphocytes (86, 87). In clinical practice, the heat-shock protein Gp96 is associated with radioresistance. For patients with head and neck tumors receiving radiation therapy, it is identified as an adverse prognostic factor (88). During the course of daily low dose, 1.8 to 2 Gy radiotherapy to a total dose of 60-80 Gy in 8-10 week, the tumor acquires adaptive resistance to radiation. In tissue culture experiments with, single fraction doses of as high as 25 Gy was ineffective to suppress the CaSki and H-3 cervical cancer cells proliferation completely while higher single fraction doses of 50 and 100 Gy could completely inhibit the proliferation of both these CaSki and H-3 cervical cancer cells (89). Like the highly radioresistant CaSki and H-3 cervical cancer cell, the radioresistant head and neck tumors also needs very high single fraction dose to stop its proliferation completely. Hence, the daily dose of 1.8 to 2 Gys fractioned radiotherapy to a total dose of 80 Gy in 6 to 8 weeks will not sterilize the entire head and neck tumor cancer cells. Only dead or dying cells are processed by the dendritic cells that elicit immunity against cancer (85). In response to radiation induced inflammatory reaction, Gp96 heat-shock protein is produced. Higher the radiation dose, higher the concentration of Gp96 that is produced in response to radiation. Tumor cells radiated at relatively high dose of 25 Gy still had residual proliferating tumor cells. While this dose of 25 Gy irradiative stresses could produce Gp96, it was ineffective to elicit complete tumor specific immunity. However, tumor cells radiated with single fraction 50 Gy and 100 Gy kills the tumor cells completely. In this instance, there is also a dose dependent increased Gp96 (85). The dead cells are processed in the dendritic cells with the help of Gp96 that leads to cancer specific immunity. With completely killed cancer cells and increased Gp96 with 50 and 100 Gy radiations (85), more efficient tumor specific immunity is achieved.

A number of tissue stress injury can produce Gp96 heat-shock protein. They include heat, viral infections, hypoxia and oxidative stress like that caused by radiation. However, in the absence of complete killing of the cancer cells in a tumor, no efficient Gp96-dendritic cell can take place that could lead to complete immunity against cancer. Viral infection and hypoxia will not kill all the tumor cells in a tumor. Heat can kill the tumor cells but in clinical practice, it is impossible to apply sufficient heat to kill the entire tumor cells. Hence heat therapy alone is inefficient to induce lasting immunity against cancer. Radiation therapy is aimed kill all the tumor cells but the present clinical practice of daily 1.8 to 2 Gy fractionated radiation to a total dose of 60-80 Gy in 8-10 weeks is an inefficient radiation therapy to kill all the tumor cells, especially the cancer cells in a radioresistant tumor. Likewise, fractionated chemotherapy does not kill all the cancer cells. Hence it is also ineffective to induce complete immunity against cancer by the Gp96-dendritic cell interaction. Safe single fraction very high dose radiation therapy, with doses in the range of 100 to 1,000 Gy and higher as described in this invention and those described with the aid of synchrotron based microbeam (14) on the other hand kills all the cancer cells in a tumor. With completely killed cancer cells in a tumor by microbeam radiotherapy, the Gp96-dendritic cell system interacts with the lymph nodes that elicit complete immunity against cancer.

19. ENHANCED MONOCLONAL ANTIBODY BINDING TO TUMOR ANTIGENS AFTER EXTERNAL BEAM RADIATION AS EVIDENCE FOR RADIATION UNMASKED TUMOR ANTIGENS

External beam radiation to a tumor cause several fold increased uptake of tumor antigen specific, radio labeled antibodies by the tumor. A four fold increase in monoclonal antibody uptake by the human xenografts colon carcinoma following 400 to 1,600 cGy external beam radiation is reported (89). Several methods for enhanced monoclonal antibody binding to tumor specific antigens has been tried, they include pre treatment of the tumor with radiation, interlueken-2, interferon and biologically active antibodies (90). Single dose 10 Gy radiation to human melanoma tumors transplanted subcutaneously into nude mice increase the tumor specific uptake of Indium-111 labeled anti-p97 monoclonal antibodies in this tumor (91)). Previously, this increased antibody binding to tumor specific antigens was thought to be due to radiation induced vascular permeability of the tumor. However there are other cellular mechanisms that cause increased antibody binding to tumor after radiation. They include radiation induced cancer cell's adaptive response, apoptosis and cell death and the exposure of the tumor specific antigens, especially through the FAS/FAS adaptive response that leads to increased tumor specific antibody binding to tumor. It seems to be the leading reason for increased antibody uptake by the tumor after radiation; not just due to increased vascular permeability.

20. FAS/FAS LIGAND DEATH PATHWAY TUMOR SPECIFIC ANTIGEN AND CYTOKINES EXPOSURE BY HIGH DOSE RADIATION AND ITS TUMOR SPECIFIC ANTIBODY BINDING

Hundreds to several thousands Gy, high dose localized radiation to a tumor in split seconds cause radiation induced inflammation at the tumor site. It releases a number of cytokines (53) and free radicals. Radiation evokes adaptive immunity through the FAS pathway (54). As described before, in vitro experiments, MC 38 adenocarcinoma cells at 20 Gy dose had increased FAS activity at molecular, phenotypic and functional levels. At this relatively higher dose radiation for an in vitro experiment, radiation sensitized these cells to antigen specific cytotoxic-T-lymphocyte's (CTLs) cell killing by FAS/FAS ligand pathway (55). In vivo experiments, the same MC 38 adenocarcinoma cells growing subcutaneously also showed 8 Gy radiation sensitized CTL adaptive immunity by up regulation of FAS leading to tumor growth arrest and tumor rejection (55). Gp96 mediated antigen-peptide processing with dendritic cells interaction are stimulated by radiated highly malignant prostate cancer cell line RM-1 but with higher dose radiation, in the range of 10-60 Gy which is a relatively high single fraction dose for an in-vitro experiment while unirradiated cells had no such immunostimulatory effects (56). Radiation releases several cytokines including IFN-γ which modulates tumor vasculature microenvironment and promotes the cytotoxic T-lymphocytes (CTLs) trafficking and its recognition by the tumor cells (57). The localized radiation dose to the mice in the experiments was 15 Gy (58) which is a large dose to treat a tumor in mice indicating the effectiveness of high dose radiation to modulate tumor immunity. It is increased with high dose and dose rate nanobeams and microbeams radiation. The interlaced multiple simultaneous microbeam and nanobeam radiation to the tumor as it is in this invention causes strong inflammatory reaction at the tumor site. The cytokines and tumor specific antigens exposed from the tumor and its FAS/FAS death pathways and apoptosis associated molecules effects the increased uptake of tumor specific antibodies after high dose radiation.

21. HEAT-SCHLOCK PROTEIN GP96 IMMUNOTARGETING TUMOR SPECIFIC IMMUNOTHERAPY, IMMUNOSCINTIGRAPHY AND TUMOR VACCINES AFTER NANOBEAM AND MICROBEAM RADIOSURGERY

Heat-shock proteins are produced under stress including radiation. Heat-shock protein peptide complex prepared from tumor is capable of inducing immunity across a number of tumor types. It is an ideal class of tumor and patient specific immunity generating proteins. Thus, without the need for identification of each of the immunogenic peptides in a tumor, Gp96 class of proteins induces immunity across the tumors. Heat-shock protein, Gp96 based vaccine, Vitespen, also known as Oncophage is made from individual patient's tumors. It is active against a number of tumor types including melanoma, pancreatic, gastric and colorectal cancers, myelogenous leukemia and non-Hodgkin's lymphomas (92). In phase III study, the Vitespen vaccine is reported as effective against the most difficult to treat cancer, the malignant melanoma, including its stage IV cases (93). However, the overall results with Gp96 based immunotherapy and cancer vaccines are not very impressive. Only a very few patients have complete or partial response to this immunotherapy and cancer vaccine. Hence it needs to be much improved.

External beam radiation to a tumor cause four fold increased uptake of tumor antigen specific, radio labeled antibodies into the tumor (89). Single dose 10 Gy radiation to human malignant melanoma transplanted into nude mice increase the tumor specific Indium-111 labeled anti-p97 monoclonal antibodies into the tumor (91). The radiation induced cancer cell's adaptive response, apoptosis and cell death, the FAS/FAS adaptive response of the radiated tumor, all leads to increased tumor specific antibody binding to tumor. This adaptive response of the radiated tumor for enhanced tumor uptake of tumor specific antibodies by high dose and dose rate localized nanobeam and microbeam radiation delivered within seconds to milliseconds is described in this invention.

Administration of Gp96 based immunotherapy like that with Vitespen in this case enhances its tumor uptake several folds than when it is given without pre-radiation of the tumor. This uptake is especially very high with very high dose and dose rate radiation with microbeam and nanobeam as it is in this invention. Likewise it facilitates much more efficient diagnostic, tumor specific antigen-antibody bound immunoscintigraphy of the tumor than with conventional immunoscintigraphy without pretreatment of the tumor by high dose and dose rate radiation. Complementary immunoscintigraphy is used for diagnosis and follow up of tumors (94). Complementary immunoscintigraphy (95) with tumor antigen and peptide specific Gp96 leads detection of tumors and helps to guide elective treatment options and follow up like the radioactive iodine is used for the treatment of thyroid cancers. Pretreatment of a tumor with high dose and dose rate radiation leaves the tumor antigens exposed. It helps to perform more efficient Immunoscintigraphy that guides dose, frequency and duration of immunotherapy with Gp96 heat-shock protein vaccine like the Vitespen.

22. HIGH DOSE AND DOSE RATE PARALLEL PROTON MICROBEAM AND NANOBEAM GENERATION

For protons and heavy particles, multiple scattering increases the penumbra width as a function of depth. It increases the depth of maximum dose as the Brag-peak falls. In clinical proton radiation therapy, the Brag peak is spread out to cover the tumor volume with various thickness plastic propellers or with ridges made of metals (96) which can produce small amounts of contaminating neutron and gamma radiation. In this invention, the parallel proton nanobeam and microbeam is generated by proton beam splitting into multiple parallel beams that was described by Joseph Lidestri in US patent application 2008/0122,390 for simultaneous Flurine-18 production with multiple targets (97). It is fully incorporated herein. Proton beam deflection with quadrupole magnet is well known in the art. Similarly deflected proton beam for radiation therapy is described in U.S. Pat. No. 8,076,657 (98) in which proton fan beam is generated by deflecting the proton beam from an accelerator with quadrupole magnets. The quadruple magnets are used in the art to deflect a narrow proton beam in one plane and to focus it in another plane. In U.S. Pat. No. 8,076,657 (98), the edges of the proton fan beam so generated are modulated to conform with the shape of the tumor that is radiated with collimator blocks. In this process, beam attenuating blades that are aligned with separate beamlets are used. Like with a multileaf collimator, multiple arrays of such beam attenuating systems are used. Proton beam's energy absorbing material is placed side by side to span the width of the fan beam. Naturally, it will generate significant level of unwanted radiation, especially the neutron which is very harmful to the patients and to those attending to the patient during the course of treatment. Likewise, in U.S. Pat. No. 7,977,648 (98-b), multiple shutter pairs are used to generate multiple pencil beams to speed up the treatment and to eliminate the need for making custom compensators as in present proton radiation therapy. It also produce significant neutron and thus exposes the patient to unwanted secondary neutron radiation.

Its contribution to developments of second primary tumors in patients who are lucky to survive from the onslaughts of the first primary tumor (149) cannot be underestimated. In present proton radiation therapy, the proton beam is spread out with plastic fans and metallic blades but it is much different in the method described in U.S. Pat. No. 8,076,657 (98). It generates much more neutron and also other unwanted contaminating radiation like the gamma rays from proton beam's energy absorbing metallic plates. Proton beam defocusing and refocusing with quadrupole magnets is also taught by Grime, G. in his presentation titled "Nuclear micro and nanobeams focusing MeV ions to micron and submicron dimensions" (99). In US patent application 2008/0122,390 (97) the positively and negatively charged proton beam from a quadrupole linear accelerator is split into 10 simultaneous beams by magnetic force. First, the proton beam is spread out with a first deflection quadrupole magnet. A second deflection magnet is used to both deflect the beam and to control the split beam's size after the beam is split. It is then passed through a stripper grid that generates positively and negatively charged beam segments. They are charged alternatively as positive and negative ions and they pass through a deflection magnet with DC vertical dipole field. According to the Lawrence law of force, the positively charged beamlets deflects to the left and the negatively charged beamlets deflects to the right with amount of beamlets separation dependent on the strength of dipole field. This principle of high current split proton beam was described to generate a 10 simultaneous beamlets to produce Flurine-18 from 10 targets simultaneously. This concept is modified to generate sets of numerous simultaneous parallel proton microbeams and nanobeams that will cover the entire tumor volume and to treat a tumor with interlaced microbeams or nanobeams from different angles simultaneously.

23. LOW ENERGY PROTON BEAM-BEAM INTERACTIONS IN TISSUE AND GENERATION OF BEAMLETS WITH LOWER ENERGY PROTON AND RADIATION THERAPY

Relatively low energy proton interaction in tissue generates low energy neutrons by nuclear reactions. These relatively low energy neutrons produce recoil protons by elastic collisions with hydrogen atoms. At the Brag peak region, the primary protons are slowed down and the recoil secondary protons become more dominant behind the distal end of the Brag peak (100). At about the Brag peak area, 80-90% of the absorbed dose is from the slowed down primary proton and about 5-20% absorbed dose is from secondary protons. Behind the distal endpoint of the Brag peak, the secondary proton production by $^1$H (n, p) reaction dominates. It contributes 70% of the absorbed dose at this point, behind the distal endpoint of the Brag peak (100). Non-elastic nuclear interactions of proton also produce positron in sufficient quantity that is used for proton dosimetry by positron emission tomography (PET) (101). Such positrons are produced from decay of $^{11}$C, $^{13}$N, and $^{15}$O. They are produced mostly along the path of the proton beam. They diminish near the Brag peak where the primary proton interacts with tissue nuclear elements. They are also used to estimate the depth of the Brag peak. Six major positron emitting proton interaction with O, N and C is summarized in a Table (102) is referred below in its entirety.

| No | Nuclear Reaction | Threshold Energy, (MeV) | Half-life, Time (min) | Positron, maximum energy, (MeV) |
|---|---|---|---|---|
| 1 | $^{16}$O(p, pn)$^{15}$O | 16.79 | 2.037 | 1.72 |
| 2 | $^{16}$O(p, 2p2n)$^{13}$N | 5.66 | 9.965 | 1.19 |
| 3 | $^{14}$N(p, pn)$^{13}$N | 11.44 | 9.965 | 1.19 |
| 4 | $^{12}$C(p, pn)$^{11}$C | 20.61 | 20.39 | 0.96 |
| 5 | $^{14}$N(p, 2p2n)$^{11}$C | 3.22 | 20.39 | 0.96 |
| 6 | $^{16}$O(p, 3p3n)$^{11}$C | 27.50 | 20.39 | 0.96 |

These six major positron emitting proton interactions with $^{16}$O, $^{14}$N and $^{12}$C becomes much more significant with multiple simultaneous, low energy proton bam-beam collision interaction as it is used in this invention for proton beam radiation therapy.

The other fifteen positrons produced by proton beam interaction with lesser abundant $^{13}$C, $^{15}$N, and $^{18}$O in human body are negligible with a single proton beam (103). However, they become more significant with multiple simultaneous, low energy proton bam-beam collision interactions. In this invention, multiple simultaneous low energy proton beam-beam interactions are used for radiation therapy. Hence these other fifteen low abundant positrons production also becomes clinically significant contributors to absorbed dose in low energy proton radiation therapy. These mirror positron emitting proton interaction with $^{13}$C, $^{15}$N, and $^{18}$O is summarized in a Table II (104) is also referred below in its entirety:

| No | Nuclear Reaction | Threshold Energy, (MeV) | Half-life, Time (min) | Positron, maximum energy, (MeV) |
|---|---|---|---|---|
| 1 | $^{12}$C(p, p2n)$^{10}$C | 34.5 | 0.32 | 1.87 |
| 2 | $^{12}$C(p, y)$^{13}$N | 0 | 9.97 | 1.19 |
| 3 | $^{13}$C(p, p2n)$^{11}$C | 25.5 | 20.3 | 0.96 |
| 4 | $^{13}$C(p, n)$^{13}$N | 3.2 | 9.97 | 1.19 |
| 5 | $^{14}$N(p, nα)$^{10}$C | 17.2 | 0.32 | 1.87 |
| 6 | $^{14}$N(p, γ)$^{15}$O | 0 | 2.04 | 1.72 |
| 7 | $^{14}$N(p, n)$^{14}$O | 6.6 | 1.18 | 1.81 |
| 8 | $^{15}$N(p, nα)$^{11}$C | 14.7 | 20.3 | 0.96 |
| 9 | $^{15}$N(p, nd)$^{13}$N | 20.4 | 9.97 | 1.19 |
| 10 | $^{15}$N(p, nt)$^{13}$N | 13.8 | 9.97 | 1.19 |
| 11 | $^{15}$N(p, n)$^{15}$O | 3.8 | 2.04 | 1.72 |
| 12 | $^{16}$O(p, γ)$^{17}$F | 0 | 1.07 | 1.74 |
| 13 | $^{16}$O(p, 3p4n)$^{10}$C | 39.7 | 0.32 | 1.87 |
| 14 | $^{16}$O(p, 2pn)$^{14}$O | 30.7 | 1.18 | 1.81 |
| 15 | $^{18}$O(p, pn)$^{18}$F | 2.6 | 109.8 | 0.64 |

The threshold energy of 7 MeV overcomes the Coulomb repulsion of oxygen nucleus (105). The energy required for the release of a neutron from a proton is in the range of 21 to 27 MeV and to release a secondary proton, the energy has to be in the range of 30 MeV (106). The secondary proton also produces a Brag peak but a broader one than that produced by the primary proton (107). In common proton radiation therapy with a single beam, seven most probable heavy recoil elements are produced. They all produce β$^+$-decay and γ emission with energies in the range of 0.6 to 1 MeV. They are summarized (108) as the followings:

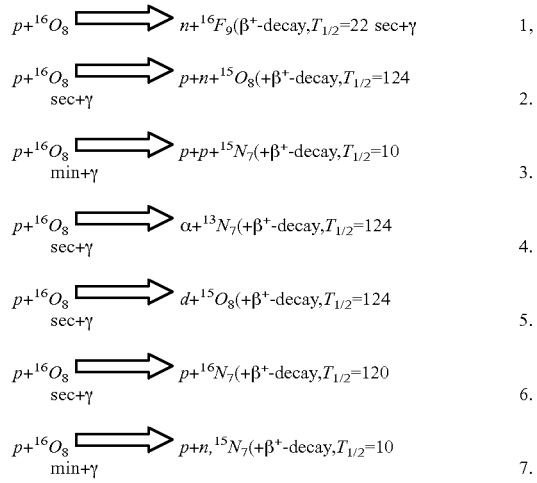

In the case of a low energy, single beam proton radiation therapy, the reaction product β+-decay and γ emission with energies ranging from 0.6 to 1 MeV is the most frequent reaction. The reaction product in tissue generated by lower energy, single proton beam radiation has only sparsely ionizing radiation that reaches the tissue that is a few millimeters away from its source. Hence its dose and dose rate is very low in tissues that is a few millimeters away from the source.

However, with multiple simultaneous proton beams combined with bam-beam elastic interaction, the dose and dose rate of this β+-decay and γ emission increases significantly. With increased beam-beam inelastic collisions in tissue with multiple simultaneous proton beams, more and more nuclear disintegration in tissue is produced. It generates more locally absorbed nuclear fragments and antiprotons. Antiproton adds to the depth of the Brag peak; (109) It enables high dose and dose rate proton radiation therapy even with 7-30 MeV if its Brag peak depth can be brought to correlate with the depth of the tumor site.

24. NEEDLE GUIDED LOW ENERGY PROTON BEAM FROM ION NUCLEAR REACTION

Proton beam guided through hollow needles is described for "Low Energy, Ion Nuclear Reactions for Proton Radiotherapy Applications" (110)). For intraoperative or topical-dermatological- "Ion Induced Nuclear Radiotherapy" INRT with $^3$He/ZrD$_{1.9}$ and similar targets tipped needles were described in a DOE sponsored study (111) and in U.S. Pat. No. 5,547,454 in 1996 (118). In this instance, the ion beam is directed through the evacuated needle. It strikes the target at the needle tip which produces the localized proton beam that is used for radiation therapy (112). Such intraoperatively transported ion beam through an evacuated needle to a tumor site at a depth eliminates the need for higher energy proton beam to enable the Brag peak to coincide with the depth of the tumor site. Needle tip-µINRT is capable of delivering 15 Gy in 20 seconds (113) to about 5 mm tumor volume (114). In topical INRT, this tissue volume is reduced to about 3 mm (115). Such single beam's limited tumor volume treatment capability combined with its poor secondary radiation limits the use of INRT. Hence, although this method of needle guided proton radiation therapy was described over 17 years ago, it is not in clinical practice. To overcome this deficiency of single beam, small tumor volume covering INRT, a new method of INRT is elected in this invention. In this invention, higher intensity of radiation and larger tumor volume coverage is achieved with interlaced, cross firing multiple simultaneous proton beam needle implant INRT. Its beam-beam elastic and none-elastic collision induced, higher secondary radiation including its positron, neutron, secondary protons, nuclear fragments and ions, antiprotons, gamma radiation and ionization of water molecules is a far advanced conformal proton beam radiation therapy with minimal or no toxicities to normal tissue. These principles of interlaced multiple simultaneous proton beam radiation therapy is also adaptable for higher energy proton beam radiation therapy.

The $^3$He ion from a duoplasmatron has small emittance at 1 microampere. Its beam can be focused to 1 mm (116) or to a micrometer wide beam that is to microbeams. With split main proton beam, multiple simultaneous beams are generated in this invention. It generates parallel proton microbeams for proton beam radiosurgery. Proton microbeam radiosurgery with single beam, the µINRT was suggested in 1995 is referred above (117). To treat larger masses by µINRT, repeat, multiple pass INRT was suggested (117). It is a very inefficient method of treating a tumor that is larger than a few mm. Most clinically encountered tumors are larger than a few mm. On the contrary, treating the entire treatment volume with interlaced multiple simultaneous proton beams as in this invention is a more efficient method of conformal radiation therapy. It generates locally confined neutron, secondary protons, γ rays and positron that treats the entire tumor than the few mm tumor volume treatment at any one time with a single proton beam source as with the µINRT (117)

25. HIGHER ENERGY PROTON PENCIL BEAM, MICROBEAM AND NANOBEAM GENERATION FROM GANTRY MOUNTED SYNCHROTRON OR CYCLOTRON WITH SUPERCONDUCTING MAGNET AND WITH REDUCED SECONDARY NEUTRON PRODUCTION FROM PASSIVELY SCATTERED PROTON

The methods of generating split parallel proton beam is described in US patent application 2008/0122, 390 (97). The proton beam generated by gantry mounted synchrotron or cyclotron with superconducting magnet is also split into several parallel microbeams and nanobeams in this invention for large field, very high dose, single or fewer fraction microbeam or nanobeam proton radiation therapy.

26. WATER VAPOR AND VAPORIZED CHEMOTHERAPEUTIC'S INELASTIC INTERACTIONS WITH PROTONS AND ELECTRONS

The collision reaction products of vaporized water molecule and proton includes transformation of the proton as an H$^+$ or as a neutral H after a single electron capture or as a H$^-$ after double electron capture (128). The major principles involved in cancer radiation therapy and chemotherapy is based on inhibition of DNA and RNA synthesis and repair of damaged DNA and RNA by the tumor cells. The water molecules and DNA and RNA are essential elements in biology and cancer treatment. The four bases of the RNA include adenine, guanine, cytosine and uracil. Uracil replaces thymine and both thymine and uracil are known to pair with adenine. No uracil is present in DNA. The collisional interaction of proton with vaporized water and uracil was investigated before (129). It is an important example for the proton spray chemotherapy combined with proton spray microbeam and nanobeam in this invention. The products of proton impact ionization of water includes mostly H$^+$, H$_2$O$^+_2$, and OH$^+$ and to a lesser amounts of H$^+_2$, O$^+_2$, N$^+$, N$^+_2$, O$^+_2$ (131). Similar ions at the same concentration are also produced by monochromatic electron collision with evaporated water molecules (132). There are uracil analogues containing chemotherapeutics. The uracil molecules (C4H4N2O$^+_2$) are fragmented by its collision with proton and monochromatic electron and ionized fragmented larger and smaller uracil molecules (C3H3NO+ and CNO$^+$) with varying energies are produced (133). In this invention proton spray or electron sprays chemotherapy is described. In the case of electron spray, the monochromatic electron source for electron spray is much simpler to make (134). They add to the local cytotoxic effects of both radiation and chemotherapy.

27. PROTON SPRAY IONIZATION RADIATION THERAPY COMPARED WITH ELECTROSPRAY

The monochromatic electron spray (129) has similarities to electrospray (135). Electrosprayed bone marrow stem cells (BMSC) at 7.5 KeV retain its ability to survive and proliferate (136). However, at higher KeV electrospray, the BMSC become less viable (136). Still electrospray is not an efficient cytotoxic cancer treatment. Human lymphocytes electrosprayed at 1-30 KeV (maximum current 4 mA) did not show any cytogenetic or physiological changes (137, 138, 139). In this study, the electrosprayed polydimethylsiloxane (140) did not show cytogenetic or physiological changes in the lymphocytes indicating electrospray with 1-30 KeV, up to 4 mA did not generate ionized fragments of compounds so electrosprayed. Hence there is no ionized radiation cytotoxicity to cells that are electrosprayed. On the contrary, proton sprayed uracil like molecules generates ionized fragments (133). Inelastic interaction of ionized particles causes nuclear fragmentation in the cells.

28. PROTON SPRAY LITHIUM NEUTRON AND GADOLINIUM AND BORON NEUTRON CAPTURE RADIATION THERAPY

Neutron capture radiation therapy with gamma rays and Auger electrons from Gadolinium neutron-capture for Gadolinium neutron-capture therapy (Gd-NCT) was described before (141).

However, like the past attempts to treat a tumor by boron neutron capture, it is not an effective treatment. It is not in clinical use. However, the proton-lithium interaction, 7Li(p, n)7Be, and the neutron interaction with gadolinium; $^{157}Gd$+nth (0.025 eV)→[$^{158}Gd$]→$^{158}Gd$+γ+7.94 MeV releases gamma rays and Auger electrons for Gadolinium neutron-capture therapy (Gd-NCT). Is a very attractive alternative to boron dependent BNCT. Gadolinium compounds are widely used in magnetic resonance imaging (MRI). Gadolinium is also taken up by tumor (141). The proton spray onto the gadolinium compounds also generates ionized fragments of gadolinium compounds which serve as agents for ionized molecular chemotherapy.

The classical nuclear fission reaction used for clinical boron neutron capture treatment (BNCT) is based on the following nuclear fission reaction (142):

$^{4}He$+$^{7}Li$+2.79 MeV (6% of the interaction)

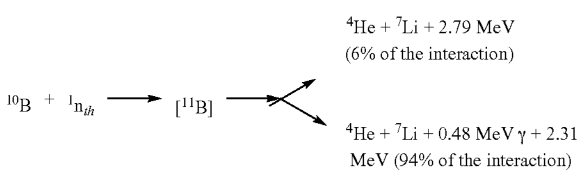

$^{4}He$+$^{7}Li$+0.48 MeV γ+2.31 MeV (94% of the interaction)

Here, both thermal and epithermal neutron fission reaction takes place. Although the BNCT has many attractive features, its clinical efficacy is much limited. One of the primary failures of the past BNCT in clinical practice was due to poor concentration of $^{10}B$ at the tumor site. Intravenously or orally administered $^{10}B$ do not reach in sufficient concentration at the tumor site.

In this invention, multiple lumen needle with a proton beam generating target connected to a RFQ accelerator and lithium-proton reaction, 7Li(p,n)7Be is used to generate neutron. Neutron generation by direct interactions of proton beam spray with lithium target is described in this invention. It is used for ion induced nuclear reactions gadolinium and boron neutron capture radiation therapy. The direct contact proton spray and gadolinium compound or boron compound spray within a tumor eliminates the inefficiency of past BNCT. It improves the prospects for clinical applications of gadolinium based future neutron capture therapy (Gd NCT). It is described further Under FIGS. 9C-3 and 9-C4.

29. PROTON SPRAY CHEMOTHERAPY AND NEUTRON CAPTURE RADIATION THERAPY WITH LITHIUM-BORON AND GADOLINIUM ABSORBED IN CARBON NANOTUBES

Lithium absorption in boron or nitrogen doped single walled carbon nanotubes are used for hydrogen storage and in lithium batteries (186). Lithium diffuses into the interior of single walled carbon nanotubes through the opened ends and side wall defects (187). Multiwalled carbon nanotube interacts with boron and forms boron carbides on the surface of the Multiwalled carbon nanotubes (188). Boron doped Multiwalled carbon nanotube has superconductivity (189). Such lithium-boron carbon nanotubes are ideal for boron-neutron capture therapy. Likewise, gadolinium is an ideal element for neutron capture therapy. It has the highest thermal neutron capture cross-section of any known element and hence it is a highly effective element for neutron capture therapy. It is described above. Single walled carbon nanotubes are used to attach biomolecules such as proteins, DNA, RNAi and thus for drug delivery, for example EGFR and cisplatin (190, 191). Polyethylene glycol (PEG)-coated single walled carbon nanotube (SWNT) is found to be an effective substrate for coating the EGFR on to SWCNT. EGFR coated is on to the outer wall of the SWCNT. EGFR coated SWCNT has tumor specific uptake. Thus, EGFR and cisplatin cogitated SWCNT is a tumor seeking conjugate. The EGFR is taken up by the outer surface of the SWCNT and the cisplatin is taken up in the interior of the SWCNT. Such SWCNT/cisplatin conjugate is effective in tumor growth inhibition. (191). EGFR acts as a receptor for the tumor which facilitates the tumor specific uptake of SWCNT-EGFR-cisplatin. Docetaxel in single walled carbon nanotubes and combined photothermal therapy is used to enhance the effectiveness of cancer therapy (192). Likewise, Paclitaxel conjugated to single walled carbon nanotubes had high efficacy in tumor growth suppression (193).

Proton beam interacts with the water molecules in the CNT. The collision reaction products of vaporized water molecule and proton includes transformation of the proton as an $H^+$ or as a neutral H after a single electron capture or as a $H^-$ after double electron capture (128). The collisional interaction of proton with vaporized water and molecules like uracil (129) is an important link to proton spray chemotherapy combined with proton spray microbeam and nanobeam radiation therapy. The products of proton impact ionization of water includes mostly $H^+$, $H_2O^+{}_2$, and $OH^+$ and to a lesser amounts of $H^+{}_2$, $O^+{}_2$, $N^+$, $N^+{}_2$, $O^+{}_2$ (131). It ionizes the chemotherapeutic compounds attached and absorbed in the carbon nanotubes. Thus when the carbon nanotubes containing the chemotherapeutics is radiated they are ionized. Such proton beam ionization of compounds and chemicals in the SWCNT and MWCNT provides effective chemotherapy even with otherwise non-toxic compounds. In other wards, these pro-drug compounds in the carbon nanotubes become cytotoxic as they are radiated by proton beam.

Proton radiation to a tumor with locally injected carbon nanotube containing absorbed lithium, gadolinium boron, the efficiency of neutron capture therapy improves to several folds than it is possible with conventional neutron capture therapy. Alternatively, the carbon nanotube with lithium, gadolinium and boron is coated with tumor specific EGFR or antibodies. The proton-lithium interaction, 7Li(p,n)7Be, generates neutrons. The neutron interacts with gadolinium by the nuclear reaction $^{157}Gd+nth$ (0.025 eV)→ $[^{158}Gd]$→$^{158}Gd+\gamma+7.94$ MeV. It releases gamma rays and Auger electrons for Gadolinium neutron-capture therapy (Gd-NCT). The classical nuclear fission reaction involved in clinical boron neutron capture treatment (BNCT) is based on the following nuclear fission reaction (142):

$^4He+^7Li+2.79$ MeV (6% of the interaction)

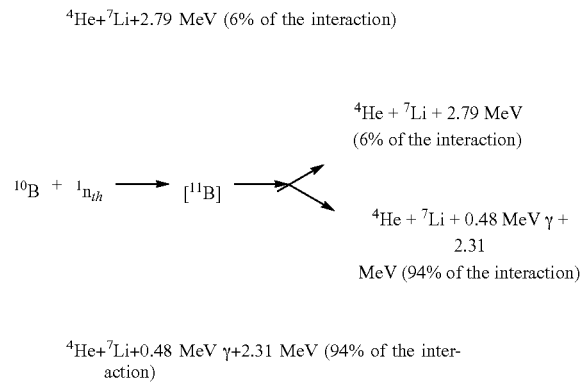

$^4He+^7Li+0.48$ MeV $\gamma+2.31$ MeV (94% of the interaction)

The carbon nanotubes loaded with lithium, gadolinium and boron is injected to the tumor and it is exposed to proton radiation. The nuclear proton interaction with the lithium, gadolinium and boron in carbon nanotubes generates very effective, locally absorbed gadolinium neutron-capture therapy (Gd-NCT) and boron neutron capture treatment (BNCT) in a tumor than it is possible with conventional Gd-NCT or BNCT.

30. LOW ENERGY PROTON BEAM-BEAM INTERACTIONS IN TISSUE AND ITS LINEAR ENERGY TRANSFER (LET) AND RELATIVE BIOLOGICAL EFFECTIVENESS (RBE)

The proton beam on beam collisional interactions and its multiple simultaneous beam on beam interactions in tissue generates low energy secondary protons, low energy neutrons, alpha particles, ionization of water molecules producing $H^+$, $H_2O^+_2$, and $OH^+$ and $O^+_2$, $N^+$, $N^+_2$, $O^+_2$ ions etc, (131) with significantly higher weighing factors than that for the photon beam and for the photon beam's interactions in tissue. The radiation weighing factors for different kind of radiation is taken as representative of relative biological effectiveness (RBE) from which the equivalent dose for various kind of radiation is calculated in units of sieverts (Sv) (144). Neutrons of less than 10 keV have a weighing factor of 5 and neutrons of 100 keV to 2 MeV have a weighing factor of 20. The 2 MeV alpha particles and fission particles of heavy nucleus also has weighing factor of 20 (144). The equivalent dose in sieverts is calculated by multiplying the weighing factor by the absorbed dose in Gy (144). If the average weighing factor for the proton beam-on beam collision in tissue is arbitrarily taken as 10, and if the total dose required for a single fraction such proton beam radiosurgery is taken as 100 Gy, then its Gy equivalent dose for X-ray or gamma ray is 1,000 Gy. If it were 50 Gy such proton dose, then its gamma ray or X-ray equivalent dose is 500 Gy. If such proton dose were 25 Gy, its X-ray or gamma ray equivalent dose is 250 Gy.

The proton dose rate for the past INRT needle was reported as 100 rads per second that is 1 Gy per second (113). With collisions of cross firing two beams, its additive dose rate is rate is 200 rads, 2 Gy/s. Because of the multiple simultaneous proton beams collisions and cross firing as it is used to treat a tumor in this invention, its dose rate per second is much higher than the 2 Gy/s. If four simultaneous beams are used, then the dose rate per second is 4 Gy. In this case, the time to deliver a combined dose of 100 Gy directly to a tumor is 25 seconds. Since its average weighing factor is taken as 10, its photon equivalent dose is 1,000 Gy. Likewise, the time taken to deliver 50 Gy (500 Gy photon equivalent) is 12.5 seconds and to deliver 25 Gy proton dose (250 Gy photon equivalent is 6.25 seconds). It makes it a flash proton beam radiosurgery with dose delivered directly to the tumor without radiating the normal tissue. In this invention, the previously reported INRT needle is replaced with much improved ion-induced nuclear reaction radiation therapy I-INRRT needle with the heat that it generates is conducted away.

31. SECOND PRIMARY TUMORS FROM PROTON RADIATION THERAPY

The present methods of collimation for proton radiation therapy with modulated Brag peak with Lucite propellers, brass ridge propellers, tissue compensators and dynamic raster scanning (145) all produce substantial secondary whole body scattered radiation (100, 101, 102, 103, 104, 105, 106, 107, 108). The scattered radiation from proton nuclear reactions is summarized in the Table below:

| Table of Scattered Radiation from Proton Radiation Therapy | |
|---|---|
| No | Nuclear Reaction |
| 1 | $^{16}O(p, pn)^{15}O$ |
| 2 | $^{16}O(p, 2p2n)^{13}N$ |
| 3 | $^{14}N(p, pn)^{13}N$ |
| 4 | $^{12}C(p, pn)^{11}C$ |
| 5 | $^{14}N(p, 2p2n)^{11}C$ |
| 6 | $^{16}O(p, 3p3n)^{11}C$ |
| 7 | $^{12}C(p, p2n)^{10}C$ |
| 8 | $^{12}C(p, y)^{13}N$ |
| 9 | $^{13}C(p, p2n)^{11}C$ |
| 10 | $^{13}C(p, n)^{13}N$ |
| 11 | $^{14}N(p, n\alpha)^{10}C$ |
| 12 | $^{14}N(p, y)^{15}O$ |
| 13 | $^{14}N(p, n)^{14}O$ |
| 14 | $^{15}N(p, n\alpha)^{11}C$ |
| 15 | $^{15}N(p, nd)^{13}N$ |
| 16 | $^{15}N(p, nt)^{13}N$ |
| 17 | $^{15}N(p, n)^{15}O$ |
| 18 | $^{16}O(p, y)^{17}F$ |
| 19 | $^{16}O(p, 3p4n)^{10}C$ |
| 20 | $^{16}O(p, 2pn)^{14}O$ |
| 21 | $^{18}O(p, pn)^{18}F$ |

There is substantial neutron radiation both from collimations which depends on the material used for collimation. The total deposited neutron dose in the whole phantom from collimators made of nickel, iron, brass or tungsten is 2.45, 2.61, 2.74 and 3.49 mSv/Gy (146). Proton interaction with the collimator material also generates substantial gamma scatter radiation. The collimator material activity, A, for all radioactive isotopes in each collimator material times the mean gamma energy emission, $E\gamma$ of that isotope decay summary (147) is shown in the Table below:

| Material Activities Σ(A* Eγ) [Bq keV] | | | | | |
|---|---|---|---|---|---|
| | 1 Sec, ×10⁹ | 1 Min, ×10⁸ | 1 Hour, ×10⁷ | 1 Day, ×10⁶ | 1 Week, ×10⁵ |
| Cerrobend | 3.7 | 3.6 | 5.7 | 2 | 3.65 |
| Stainless steel | 0.1 | 0.4 | 0.1 | 0.1 | 0.3 |
| Inconel | 0.3 | 0.4 | 0.1 | 0.2 | 0.9 |
| Brass | 0.1 | 0.6 | 0.5 | 0.21 | 0.3 |
| Lead | 1.2 | 2.6 | 4.7 | 2.4 | 2.8 |
| Tungsten | 1.4 | 8.2 | 2.6 | 1.1 | 1.01 |
| Nickel | 0.4 | 0.2 | 0.1 | 0.2 | 1.1 |
| Iron | | 0.3 | 0.1 | 0.11 | 0.15 |

Usually, the tungsten based MLC collimators and brass based treatment field defining collimators are used in proton radiation therapy. The tungsten based MLC collimator causes more neutron and gamma radiation than the brass based collimator. The radiation at the patent's side from the MLC collimation is about 100 mSv/h and it is 27 times higher at the upstream side of the block (148). At 10 cm depth in a water phantom, the H*(10) from a tungsten MLC is about 23.3 mSv/Gy for non collimated 200 MeV proton beam of 20 cm diameter as against 14 mSv for a brass collimator (148). The accumulated radiation dose to the personals treating patients when MLC based collimators are used could easily exceed the permissible 50 mSv maximum in a year (148).

The neutron and scattered radiation from proton radiation therapy is warned as worse than the high scattered radiation from the IMRT. It is especially more harmful to pediatric patients. They live longer than the adult patients. Hence it causes more second primary tumors (149). However, the Mote Carlo method of calculations on the incidence of second primary tumors in pediatric patients when treated with scanning beam proton and passively scattered proton beam is reported as much lesser as compared to IMRT and conventional radiation therapy. The occurrence of second primary tumors when treated by conventional 6 MV radiations is 12 times higher than the scanned proton beam. It is estimated as 7 times higher for passively scattered beam (149-b). Still it is only estimates, not actual clinical data. The scanning proton beam radiation therapy can reduce the incidence of second primary tumors; still it does not spare the normal tissue much from the radiation damage as it is possible with microbeam and nanobeam radiation therapy.

32. SECONDARY PROTONS, NEUTRONS, IONS AND GAMMA RADIATION REDUCING PRIMARY AND SECONDARY COLLIMATORS COMBINED WITH MICROBEAM OR NANOBEAM GENERATING TERTIARY COLLIMATOR

Modulation of the accelerator produced proton pencil beam with Lucite propeller or with magnetic scattering would reduce part of the secondary neutrons than the proton pencil beam modulation with brass ridge filters (145). Still, the secondary neutrons, ions and gamma radiation produced by the nuclear interactions of the proton beam with the beam shaping and patient specific collimator like those with the commonly used brass collimators is a major source of secondary neutrons, ions and gamma radiation (150). To minimize such secondary neutron, combined primary and secondary collimators made of plastic or hybrid plastic-metal combination were proposed (150). High density plastic alone could significantly reduce the neutron contamination but due to such plastic collimator's size associated increase in beam penumbra negates the practical use of such plastic alone collimators in clinical use (151). Nanobeam and microbeam has minimal penumbra. Well separated microbeam and nanobeam can be channeled through crystals and carbon nanotubes (152, 153). Hollow carbon nanotube structures can be prepared by co-axial electrospraying (154, 155). Proton beams of 0.1 to 3 GeV could be transported through carbon nanotubes (156). Methods of building nanotube films with controlled holes are known (157). They can be attached to patient specific collimator. Radiation induced intrinsic ferromagnetism (158) is an added advantage in proton beam transport through carbon nanotubes. It keeps the beam focused which minimizes and or eliminates the penumbra which facilitates using high density plastic alone collimators the neutron contamination in proton radiation therapy. (151). In addition, nanobeam and microbeam has minimal penumbra. However, since there is not sufficient carbon nanotube to make conventional large blocks that are customarily used in clinical radiation therapy, alternative mm sized tubes for electron, proton and ion beam transport and their magnetic focusing to generate micro and nano-beam is also elected in this invention.

33. ELECTRON, PROTON AND ION BEAM TRANSPORT THROUGH SECONDARY NEUTRON ABSORBING CAPILLARY NOZZLE THAT GENERATES MICROBEAM AND NANOBEAM AND BEAM FOCUSING WITH ANODES AND PARALLEL MAGNETIC FORCE

Proton beam transport from the source to a tumor site through hollow steel needle was described in Ion Induced Nuclear Reactions for Proton Radiation Therapy (INRT) (110). In intraoperative electron radiation therapy, 6.4 cm sized applicators made of clear acrylics (Lucite) or aluminum are used (162). Such methods of channeling of electron, proton and ion beams but with millimeter sized channeling tubes is adapted here as part of generating microbeam and nanobeam for radiation therapy.

The transitional X-rays generated from 90 MeV electrons could be focused with polycapillaries consisting of 258 bundles 1387 channels each (163). In this instance, the intensity of the X-ray beam passing through the polycapillaries was reduced by a factor of 0.72 but the X-ray beam's passage through the capillary focused the beam (164).

Guiding of electron beam through anodized aluminum capillaries (165), use of glass capillary for PIXIE analysis with 4 MeV He⁺⁺ ions (166), angular distribution of proton transmitted through glass capillaries and its splitting into a series of equally spaced lines (167), temperature control of highly charged ions guiding through insulating capillaries (168), 100 to 300 nanometer sized hole drilled into silicon nitride membrane for nano-spot sized capillary beam transport (169) all are good examples for capillary transport of microbeam and nanobeam electron, protons and other ions. In this invention, modified versions of such capillary transport of electron, proton and ion beam are adapted for microbeam and nanobeam radiosurgery and radiation therapy.

Magnetic steering and focusing of the capillary beam was reported to make the beam to a spot size (170). The principles of beam steering and focusing as is used in electron microscopy, scanning electron microscopy and ion beam microscopy also makes the diverging beam to a spot sized beam (159). Such magnetic steering is implemented in this invention to make spot sized electron, proton and other ion beam for microbeam and nanobeam radiation therapy. In scanning electron microscopy (SEM) and in focused ion beam (FIB) microscopy, the accelerated electron, proton and other ion beam are focused to microbeam (158, 159). Such focused microbeam is also used for cellular radiation (161). In SEM and in FIB microscopy, the accelerated electron or ion beam is focused by magnetic lenses into very fine point microbeam (159, 161). In this invention, the beam exiting from the primary collimator is transported through millimeter sized tubes like carbon tubes or tubes made of steel, aluminum, titanium and the like is focused to microbeam or nanobeam. The focused microbeam or nanobeam is placed at nanometers and micrometers distance from each other to render the peak and valley dose differential as is used in microbeam radiation therapy. The tissue exposed to the active micro or nanobeam is the peak dose region. The tissue in between the active micro or nanobeam is the valley region tissue which receives no or very little dose. In normal tissue, the radiation damage caused by the microbeam or nanobeam is repaired by the undamaged tissue from the valley region. Such dose differential facilitates high dose microbeam and nanobeam radiation therapy. The microbeams or nanobeam beams arriving at the isocentric tumor from different angels, say from 0-degree and 90-degrees becomes interlaced beams within the tumor. The tumor is sterilized by high dose, interlaced microbeam or nanobeam. It is further described under FIG. 10.

34. MULTIPLE SIMULTANEOUS BEAM SWEEPING SPOT AND RASTER SCANNING

In this instance, a multiple pulse negative polarity proton beam is injected into a defocusing in one plane and focusing in another plane quadrupole magnet which spreads out the proton beam in one plane and focuses it in another plane. Its details are described under FIG. 1. The quadrupole magnet with converging magnetic field in one plane and diverging magnetic field in another plane is arranged symmetrically about the beam axis. The quadrupole magnet with converging magnetic field in one plane focuses the proton beam in that plane and the diverging magnetic field in another plane defocuses the proton beam in another plane. Thus the proton beam is spread out in one plane and focused in another plane. The one plane defocused and in another plane focused multiple pulse negatively charged proton beam is injected into a defocusing, focusing and beam size controlling magnet. The split beam's size and spacing from each other is controlled with this magnet. It is then passed through a stripper grid that generates alternating positively and negatively charged beam segments. They are alternatively charged as positive and negative segments of the beam. Afterwards, they are passed through a deflection magnet with DC vertical dipole field. According to the Lawrence law of force, the positively charged proton beamlets deflects to the left and the negatively charged proton beamlets deflects to the right. The separating distance between each of these beamlets is dependent on the strength of dipole field. It generates sets of numerous simultaneous parallel proton microbeams or nanobeam that covers the entire tumor volume but with beam separating interspaces in between the beams. When these beams strike on the tissue, it generates peak and valley doses in tissue. They are scanned as in proton spot scanning (171, 172) or raster scanning (173) proton beam radiation therapy but with a patient specific, secondary neutron absorbing capillary nozzle. The capillary cylinder to cylinder scanning in this instance is like the 3-D cylinder to cylinder depth scanning for a conformal ion beam radiation therapy to deep seated tumors (174). The portion of the tissue that is radiated by the microbeam or nanobeam is the peak dose regions. The tissue that is separated between the two peak radiation regions in tissue is the low or no dose region, the valley dose 36 region in tissue. Alternatively, the proton beamlets are passed through capillary needles.

35. LASER GENERATED PROTON AND CARBON ION BEAM'S POST ACCELERATION AND MICROBEAM AND NANOBEAM GENERATION

Laser generated proton beam's post acceleration in a conventional radio frequency accelerator is described before in several articles (195). Both the methods of target normal sheath acceleration (TSNA) and radiation pressure acceleration (RPA) are used to generate proton beam from laser. Relatively thicker, $\mu$ meter thick metal foils is radiated with focused laser from a laser source at intensities over $10^{18}$ W/cm$^2$ to produce proton beams of energies up to 60 MeV by TSNA. Micrometer thick metal foils or diamond like carbon (DLC) foils is radiated with focused laser from a laser source at intensities over $10^{18}$ W/cm$^2$. The DLC target mostly generates carbon ions. In TSNA method, the laser interaction with the metal foil first produces relativistic electron at the radiated surface and this electron spreads through the foil and builds up an intense electrostatic filed at the rear surface of the foil. This intense electrostatic field accelerates surface ions, mostly hydrogen contaminants that produce dense polyenergetic proton beams Therapeutic range proton beams of 200-250 MeV is generated by Sub-Peta-Watt intensities by radiation pressure acceleration (RPA) methods (199). Quasimonochromatic therapeutic range, 50 to 250 MeV proton beam with metallic foils or 85-430 MeV/u carbon ion with DLC target is generated by RPA methods (208). In RPA methods of laser-target-ion generation, the radiation pressure pushes the electron inwardly as compared to ions. The pressure caused by radiation compresses the electron in the inside of the target. Such compression of the electron inside the very thin, just a few $\mu$m sized target continues until a balance is reached with the charge separation electric field. The linear and circular polarization differs and the linear polarization acquires twice the laser frequency that cause electron to heat up and to oscillate in longitudinal direction in large amplitudes while the circular polarization produce mostly stationary radiation pressure that pushes the electron in the direction of the laser without heating it. The circular acceleration's phase is stable in terms of longitudinal acceleration. The ions initially stays as coupled with electron in the electrostatic filed and then it accelerates as quasimonochromatic ion beam with ballistic speed and with high laser-to-ion energy conversion efficiency (197). With stable circular acceleration and with laser intensities of about $10^{21}$ W/cm$^2$, proton energies of 200 MeV is generated (198). In US patent application US 2011/0273115 such a RPA based proton accelerator is described. In one embodiment in this invention, the lower energy laser generated proton beam is further accelerated in a RF accelerator. The basic principles of laser generated proton acceleration in a RF accelerator as a hybrids accelerator system were suggested before (195). The laser generated polyenergetic protons beams are spatially separated according to their energies with magnets were described before (200).

35. BRIEF SUMMARY OF THE INVENTION

This invention teaches a systems and methods for adaptive resistance inhibiting proton and carbon ion microbeam and nanobeam radiation therapy and tumor specific radioimmunotherapy. Parallel proton and carbon ion microbeam and nanobeam is generated with hybrid laser proton-RF acceleration or by laser-target-RPA proton and carbon ion and splitting the beam into sets of microbeam and nanobeam. Low energy proton or carbon ion beam generated by laser-target-TSNA method is injected into a RFQ-drift tube accelerator for post acceleration of laser-proton or carbon ions or into a compact proton accelerator or into a compact synchrotron or into a compact synchrotron-cyclotron. The accelerated proton or carbon ion beam split into multiple parallel beams (97). In one embodiment, the split ion beam is directed through evacuated needle with a Ti/D2 target at its tip to generate high dose rate, about 1Gy/sec (113). It is used for intraoperative proton beam radiation therapy. Such intraoperative needle guided proton beam generation at the tumor site eliminates the need for higher energy proton beam for proton radiation therapy. Such a single needle tip-μINRT is capable of treating a 5 mm sized tumor at a dose of 15 Gy in 20 seconds (113, 114).

In this invention, higher intensity of radiation and larger tumor volume coverage is achieved with interlaced, cross firing multiple simultaneous proton beam needle implant I-INRRT. The high LET carbon ion has superior qualities for microbeam and nanobeam radiosurgery. It has hardly any penumbra. Proton and carbon ion's beam-beam elastic and none-elastic collision induced, higher secondary radiation including its positron, neutron, secondary protons, nuclear fragments and ions, antiprotons, gamma radiation and ionization of water molecules and the principles of interlaced multiple simultaneous proton beam radiation therapy to a tumor with minimal or no toxicities to normal tissue and at much lesser costs. If the average weighing factor for the proton beam-on beam collision in tissue is arbitrarily taken as 10, and if the total dose required for a single fraction proton beam radiosurgery is taken as 100 Gy, then its Gy equivalent dose for X-ray or gamma ray is 1,000 Gy. If such proton dose were 50 Gy, then its gamma ray or X-ray equivalent dose is 500 Gy. Likewise, if such proton dose were 25 Gy, its X-ray or gamma ray equivalent dose is 250 Gy. If it were a treatment of a tumor with four simultaneous beams from four I-INRRT needles, then its additive dose rate would be at least 4 Gy/sec. In this case, the time to deliver a combined dose of 100 Gy directly to a tumor is 25 seconds. Since its average weighing factor is taken as 10, its photon equivalent dose is 1,000 Gy. Likewise, the time taken to deliver 50 Gy (500 Gy photon equivalent) is 12.5 seconds and to deliver 25 Gy proton dose (250 Gy photon equivalent is 6.25 seconds). In this instance, conventional IMRT total tumor dose of 70 to 80 Gy is delivered in two seconds or less. It makes the flash proton beam radiosurgery of a tumor without radiating the normal tissue possible.

The I-INRRT needle described in this invention is also adapted for concomitant proton spray chemotherapy. Like collisional interaction of proton with vaporized water and uracil (129) proton spray chemotherapy ionizes the chemotherapeutics. It is also combined with the proton microbeam and nanobeam radiation therapy in this invention. The products of proton impact ionization of water includes mostly $H^+$, $H_2O^+_2$, and $OH^+$ and to a lesser amounts of $H^+_2$, $O^+_2$, $N^+$, $N^+_2$, $O^+_2$ (131). Like the uracil molecule ($C4H4N2O^+_2$) is fragmented into ($C3H3NO+$ and $CNO^+$) into varying energies (133), the proton sprayed chemotherapeutics are ionized and becomes ionized chemotherapeutics carrying both charged particle ion's radiation and the chemotherapeutics. The major principles involved in cancer radiation therapy and chemotherapy is based on inhibition of DNA and RNA synthesis and repair of damaged DNA and RNA by the tumor cells. Proton spray chemotherapy carrying both ionized chemotherapeutics and cytotoxic chemicals inhibits the synthesis of DNA, RNA and repair of damaged DNA and RNA by the cancer cells. It allows no room for the cancer cell to recover from the initial treatment and to develop adaptive resistance to cancer treatment.

The I-INRRT needle is also an ideal source for neutron generation for neutron capture therapy, (NCT) by way of proton-lithium interaction, 7Li(p,n)7Be. Neutron interaction with gadolinium; $^{157}Gd+nth$ (0.025 eV)→$[^{158}Gd]$→$^{158}Gd+\gamma+7.94$ MeV is a powerful reaction for NCT. It releases gamma rays and Auger electrons that are used for Gadolinium neutron-capture therapy (Gd-NCT) in this invention. Gadolinium compounds are widely used in magnetic resonance imaging (MRI) and it is up by the tumor (141). The proton spray onto the gadolinium compounds also generates ionized fragments of gadolinium compounds which serve as agents for ionized molecular chemotherapy.

The I-INRRT needle is also ideal to generate neutron from the proton-lithium-boron interaction (136). Although BNCT has many attractive features, so far its clinical efficacy is much limited. One of the primary failures of the past BNCT in clinical practice was due to poor concentration of $^{10}B$ at the tumor site. Intravenously or orally administered $^{10}B$ do not reach in sufficient concentration at the tumor site. In this invention, multiple lumen needle with a proton beam generating target and proton spray to lithium that generates the lithium-proton reaction, 7Li(p,n)7Be is used to generate neutron. The direct contact proton spray to gadolinium compound or boron compound taking place within a tumor eliminates the inefficiency of past BNCT. It improves the prospects for BNCT and clinical applications of gadolinium based future neutron capture therapy (Gd NCT).

If a tumor is treated with interlacing beams of 10 beams from 0-degree and 10 beams from 90 degree as shown in FIG. 9E, then with the dose rate of 1 Gy per/s per beams, the additive dose rate within the tumor for such a treatment setup will be 20 Gy/s. As discussed before, because of the beam on beam collision reaction products including the secondary protons, low energy neutrons, alpha particles and proton impact ionization products of water $H^+$, $H_2O^+_2$, and $OH^+$ and proton-proton ionization products of tissue, $H^+_2$, $O^+_2$, $N^+$, $N^+_2$, $O^+_2$ and antiprotons, gamma rays etc. its average weighing factor is taken as 10 though it could much higher. Hence its Gy/Eq dose for X-ray or γ-ray is over 200 Gy/sec. Since the I-INRRT needle guided proton beam need not travel through the normal tissue, it spares the toxic effects of radiation to normal tissue. Hence safe, tumor sterilizing doses of 100-1,000 Gy could be administered to a patient.

Its high dose and dose rate single fraction radiation to a localized tumor unmasks the tumor specific antigens for personalized, external beam radioimmunotherapy without systemic toxicity of conventional radioisotope based radioimmunotherapy. Its novelty enables cancer specific radioimmunotherapy that increase the cancer cure and control that were not feasible before.

Its intra operative I-INRRT needle guided radiation therapy eliminates the need for costly, higher energy protons and ions machines. With surgical exposure of the tumor with skin moved away from the path of the radiating beam, the need for skin sparing from radiation is eliminated. It is a very highly efficient method of radiolytic radiosurgery that not only kills all the tumor cells in a tumor but also exposes the tumor antigens and tumor specific peptides that are taken up by the heat-shock protein Gp96 which produce tumor specific immunity. Such tumor ablative radiosurgery combined with tumor specific immunotherapy cures more cancers which is not possible with present radiation therapy systems including with the costly proton and ion beams generating machines.

Because of the adaptive resistance to surgery and to radiation and chemotherapy, they are only partially effective to cure and control most cancers. Hence after surgery, radiation and chemotherapy, the tumors with residual radiation and chemotherapy resistant cells and cancer stem cells with metastatic potentials will continue to proliferate.

High dose and dose rate proton and carbon ion radiation as described in this invention also resolves the National Cancer Institute workshop's conclusion that "resistance to therapeutic doses of radiation remains a challenge. Key biological features such as tumor hypoxia, DNA damage response and checkpoint pathways, angiogenesis and vasculogenesis, cancer stem cells, tumor stroma, and immune response pathways all contribute to the complex dynamics governing tumor responses to radiation" (44). All these adaptive resistances to cancer treatment causing factors due to lower dose and lower dose daily fractionated radiation are eliminated by this inventions' high dose and dose rate, from 100 to 10,000 Gy and higher single fraction radiosurgery. Compact synchrotron for proton radiation therapy is a high dose rate generating system (175). Because of the very high dose and dose rate that could be achieved with multiple accelerators' multiple simultaneous beams, their additive dose and dose rate is sufficient for high dose and dose rate, 100 to 1,000 Gy and higher, interlaced multiple simultaneous microbeam and nanobeam radiosurgery without the interference of organ movement. The laser generated proton and carbon ions have mrad intensities (206) which provide adequate dose for flash radiosurgery. The secondary neutrons, ions and gamma radiation produced by the nuclear interactions of the proton or carbon ion beam during TSNA and RPA methods of ion generation and its collimation is absorbed by a tissue equivalent collimator which also selectively absorbs the low energy protons. The secondary neutrons, ions and gamma radiation produced by the nuclear interactions of the proton beam with the beam shaping collimation as in the conventional proton beam radiation therapy systems is replaced with light and heavy ion beam transporting long capillary tubes containing tissue equivalent collimator. The beam is focused with electrodes and longitudinal magnetic force from focusing magnet. The microbeam and nanobeam travels through long, narrow, millimeter in diameter sized tubes. The secondary neutrons and protons and other nuclear products are absorbed by this tissue equivalent collimator. It protects the patients from second primary tumors. Microbeam and nanobeam channeled through such capillaries and focused with electrodes and parallel magnetic force has practically no penumbra. It is used for well defined simultaneous spot scanning microbeam and nanobeam radiation therapy of the tumor. Passage of the proton beam through carbon nanotubes and its focusing with such electrodes and magnetic force is like etching a substrate with a proton beam; in this instance, the substrate is the tumor tissue.

Hypoxia is known to be a major contributing factor in radioresistance. Hypoxia induced radioresistance is mediated by hypoxia inducible factor-1, (HIF-1) (41, 42). In radioresistant tumor cells, HIF-1 is extremely high and they have high potential for tumor angiogenesis, invasion metastasize and poor prognosis (41). N-Myc downstream regulated gene 2 (NDRG-2) is another HIF-1 target gene and it is associated with hypoxia inducible radioresistance (42).

The proton-proton collisional interaction high LET, high dose ionizing radiation of this invention overcomes the hypoxia inducible radioresistance mediated by HIF-1, NDRG-2 and HR.

The proton-proton interaction, high LET, high dose and dose rate single fraction radiation, 100 to 1,000 Gy/Eq and higher, as it is in this invention also inhibits the adaptive radiation resistance causing insulin-like growth factor-I receptor (IGF-IR) (66). It also inhibit the adaptive radiation resistance causing accelerated repopulation of cancer stem cells and thereby the tumor recurrence and metastasis. The high dose and dose rate single fraction radiation, 100 to 10,000 Gy/Eq and higher as in this invention eliminates the radiation protection to circulating cancer cells rendered by shielding the tumor cells by tumor cell adherent radioresistant platelets. Circulating platelet adherent concentrates of blood from cancer patients radiated with such high dose and dose rate radiation and its infusion back to the patients induces systemic tumor specific immunity.

The high dose and dose rate single fraction radiation, 100 to 10,000 Gy and higher as in this invention also enhance a four fold increase in monoclonal antibody uptake by the human tumor. The cytokines and tumor specific antigens exposed from the tumor and its FAS/FAS death pathways and apoptosis associated molecules effects the increased uptake of tumor specific antibodies after high dose and dose rate radiation.

Pretreatment of a tumor with high dose and dose rate radiation as in this invention leaves the tumor antigens exposed. It helps to perform more efficient tumor specific immunotherapy with Gp96 heat-shock protein vaccines like the Vitespen In summary, this low-cost I-INRRT needle guided multiple simultaneous proton beam-on beam collisional interaction generating high LET radiation and the neutron capture radiation therapy is an advanced affordable high quality cancer treatment system. It facilitates much improved cure and control of cancers including those for which there are no effective treatments. They includes the brain tumor glioblastoma multiforme, advanced malignant melanoma, stage III and IV lung cancers, advanced cancers of the head and neck and of the abdomen. Such high dose and dose rate radiosurgery also evoke more effective, cancer specific, immunity. These were not possible before. This minimally invasive, least toxic and organ preserving radiosurgery with microbeam and nanobeam helps to cure and control many cancers even when they are in their advanced stage.

36. BRIEF DESCRIPTION OF THE DRAWINGS

FIG. 1 is an illustration of generating numerous simultaneous parallel narrow proton beams by splitting the narrow proton beam from a radiofrequency accelerator combined with a drift tube accelerator for narrow proton beam radiation therapy with minimal or no long term toxicity to normal tissue.

FIG. 2A illustrates the interlacing beams from two sets of parallel narrow proton beams and proton beams from two sets of compact radiofrequency accelerators and a drift tube accelerators, one from 0 degree and another from 90 degrees and both converging at the isocenter that generates quasi proton-proton interaction and quasi antiproton for narrow proton beam radiation therapy with minimal or no long term toxicity to normal tissue.

FIG. 3 Illustrates splitting and bending of a low μA proton beam to right (in FIG. 3 the bottom) and to left (in FIG. 3, the upper) and their transport to two numerous simultaneous parallel narrow proton beams generating systems.

Figure 4:
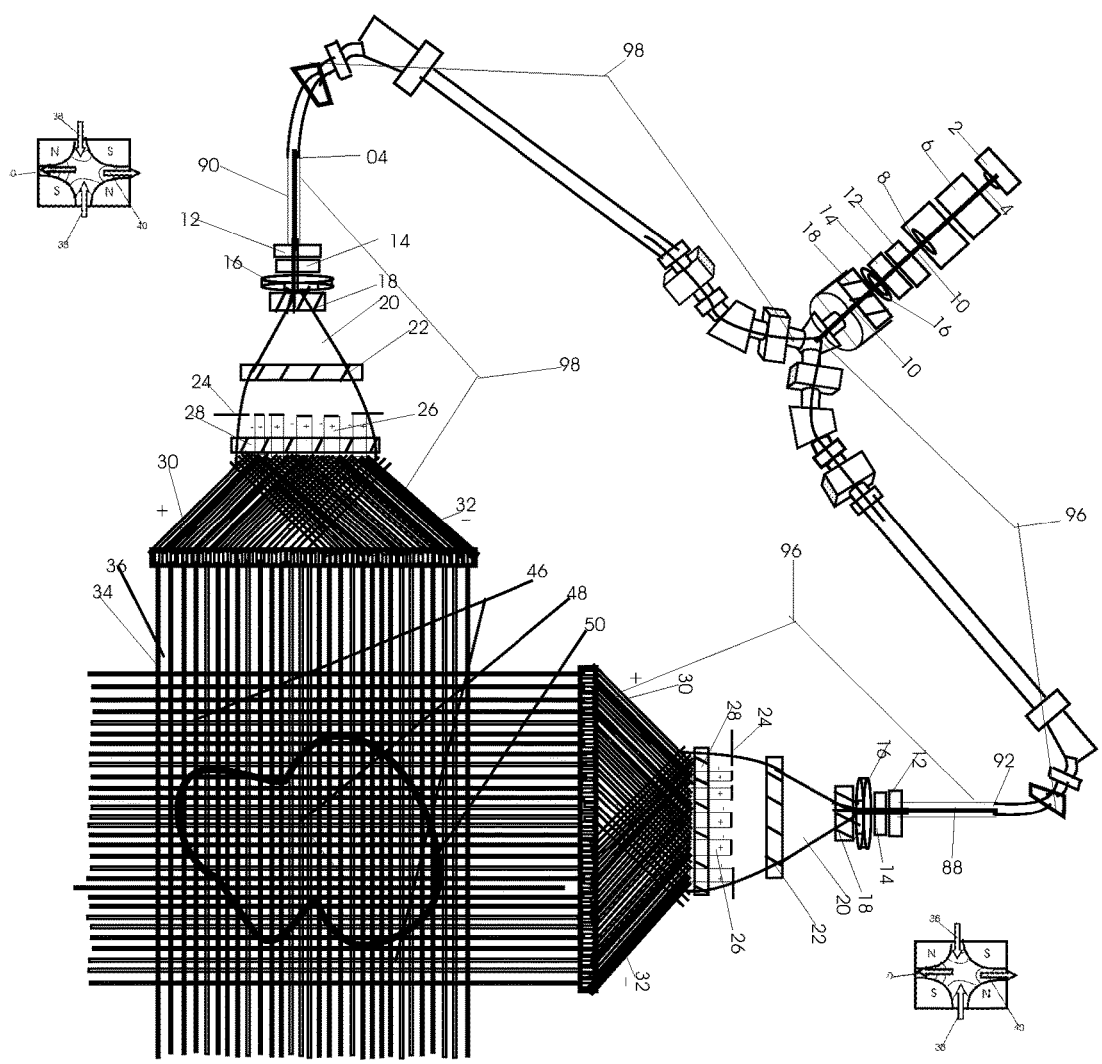
Figure 10A:
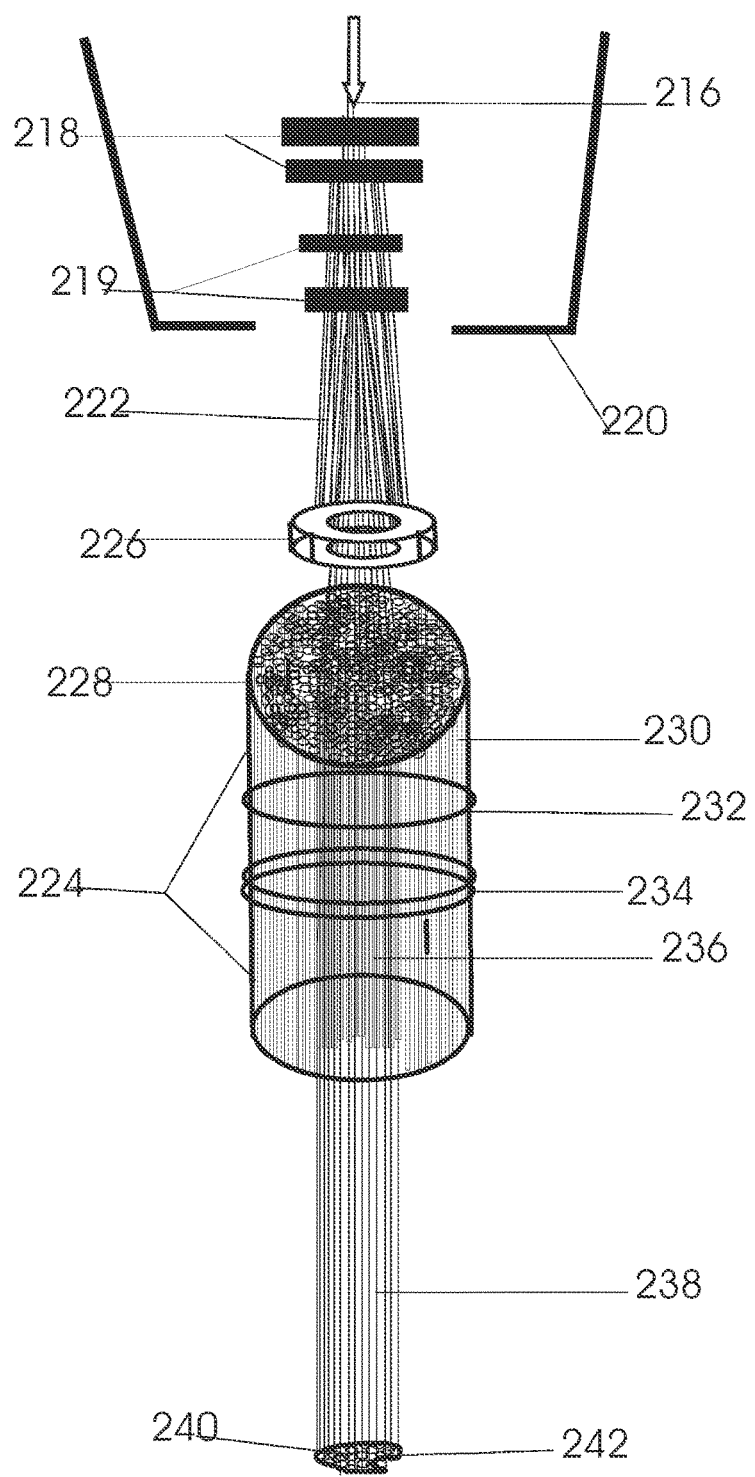
Figures 2, 10A:
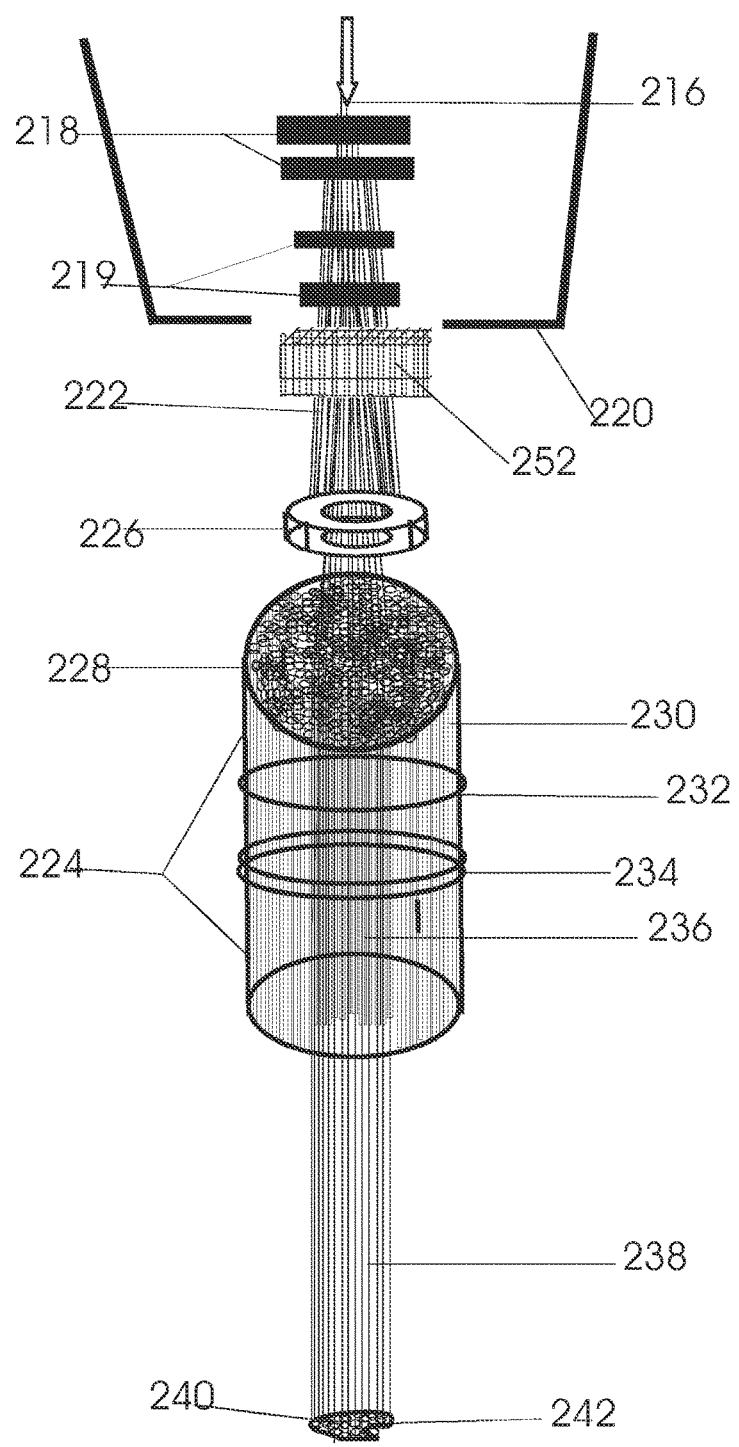

FIG. 4 illustrates a dual narrow proton beam system for radiation therapy as in FIG. 2 but with a single set of radiofrequency accelerator combined with a drift tube accelerator as the proton beam source and its proton beam as split into two and one of the multiple simultaneous parallel narrow proton beam generating system is placed at 0-degree and the other is paced at 90-degree and their parallel narrow beams interlacing at the isocenter that generates quasi proton-proton interaction and quasi antiproton for narrow proton beam radiation therapy with minimal or no long term toxicity to normal tissue.

Figure 5:
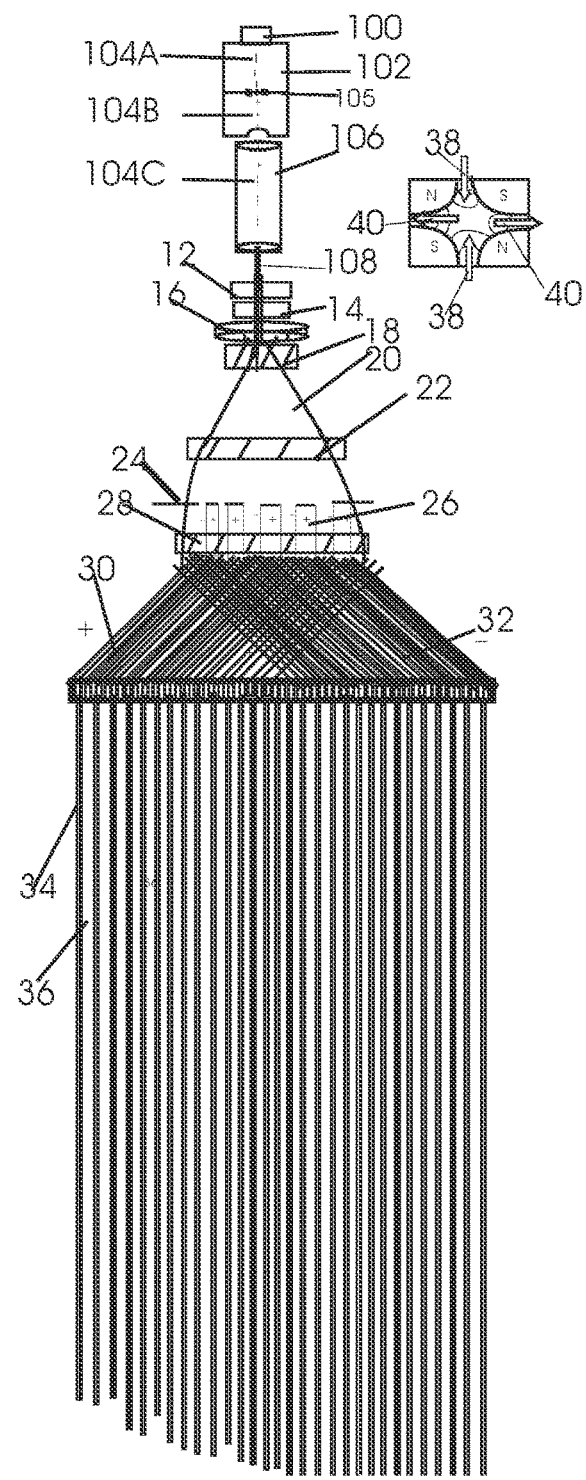

FIG. 5 shows a nested high voltage accelerator combined with a radiofrequency accelerator as the proton beam source and generating numerous simultaneous parallel narrow proton beams for proton radiation therapy with minimal or no long term toxicity to normal tissue.

Figure 6:
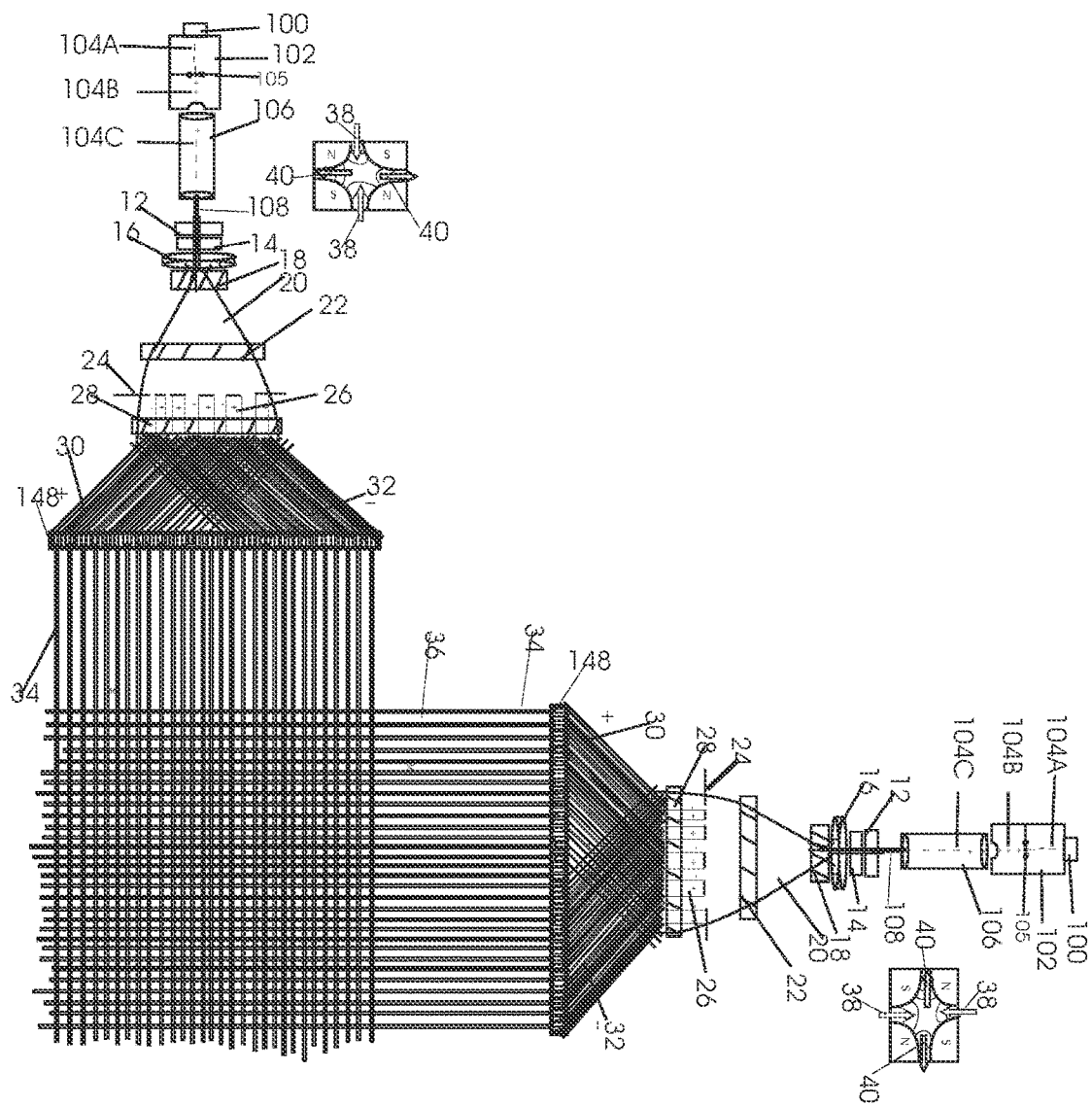

FIG. 6 illustrates interlacing beams from two sets of nested high voltage accelerator combined with a radiofrequency accelerator as the proton beam source and generating numerous simultaneous parallel narrow proton beams and one of the multiple simultaneous parallel narrow proton beam generating system is placed at 0-degree and the other is paced at 90-degree and their parallel narrow beams interlacing at the isocenter that generates quasi proton-proton interaction and quasi antiproton for narrow proton beam radiation therapy with minimal or no long term toxicity to normal tissue.

Figure 7:
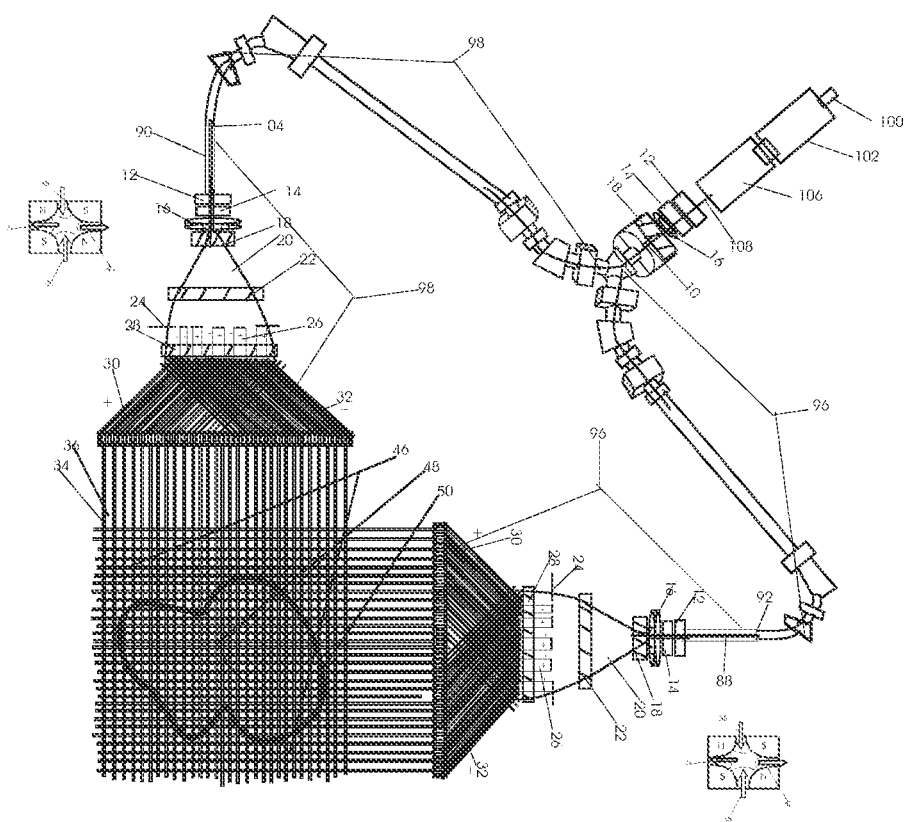

FIG. 7 shows a dual multiple simultaneous narrow proton beam system for radiation therapy as in FIG. 6 but with a single set of nested high voltage accelerator combined with a radiofrequency accelerator as the proton beam source and generating numerous simultaneous parallel narrow proton beams by splitting the accelerator generated proton beam and one such system is placed at 0-degree and the other at 90-degree and their parallel narrow proton beams interlacing at the isocentric tumor that generates quasi proton-proton interaction and quasi antiprotons and treats the tumor with minimal or no long term toxicity to normal tissue.

Figure 8:
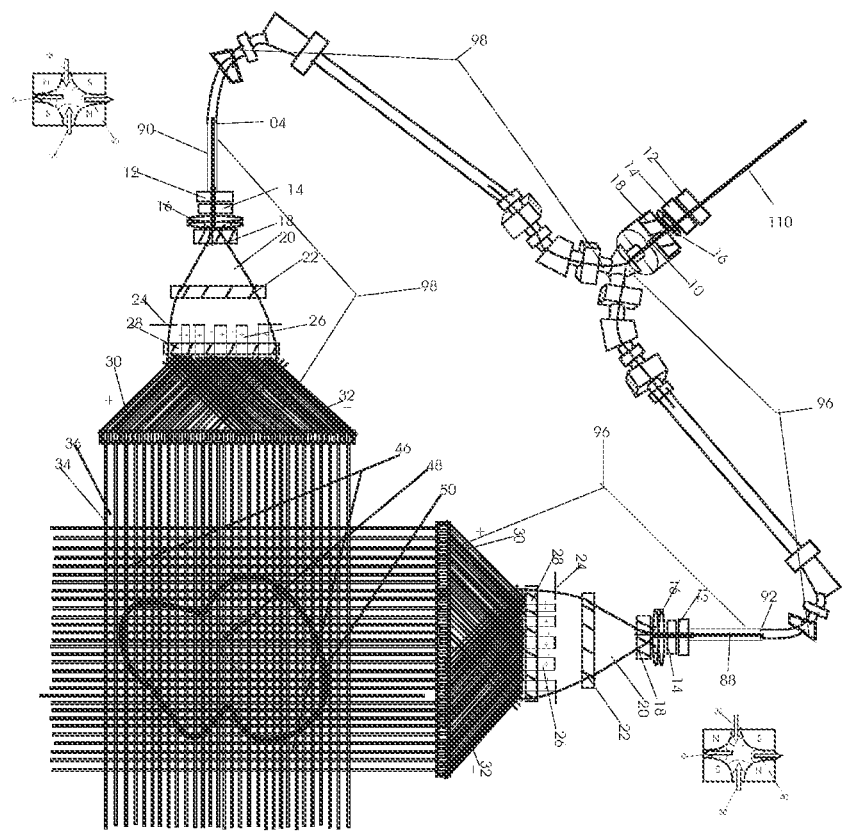

FIG. 8 illustrates a dual proton beam system for radiation therapy as in FIG. 7 but with proton beam from a synchrotron, cyclotron or synchro-cyclotron as the main proton beam source and splitting this proton beam into two and transporting them to two multiple parallel narrow proton beam generating systems and one such system is placed at 0-degree and the other at 90-degree and their interlaced parallel narrow beams exposing an isocenter tumor that generates quasi proton-proton interaction and quasi antiprotons for proton beam radiation therapy with minimal or no long term toxicity to normal tissue.

Figures 1, 9A:
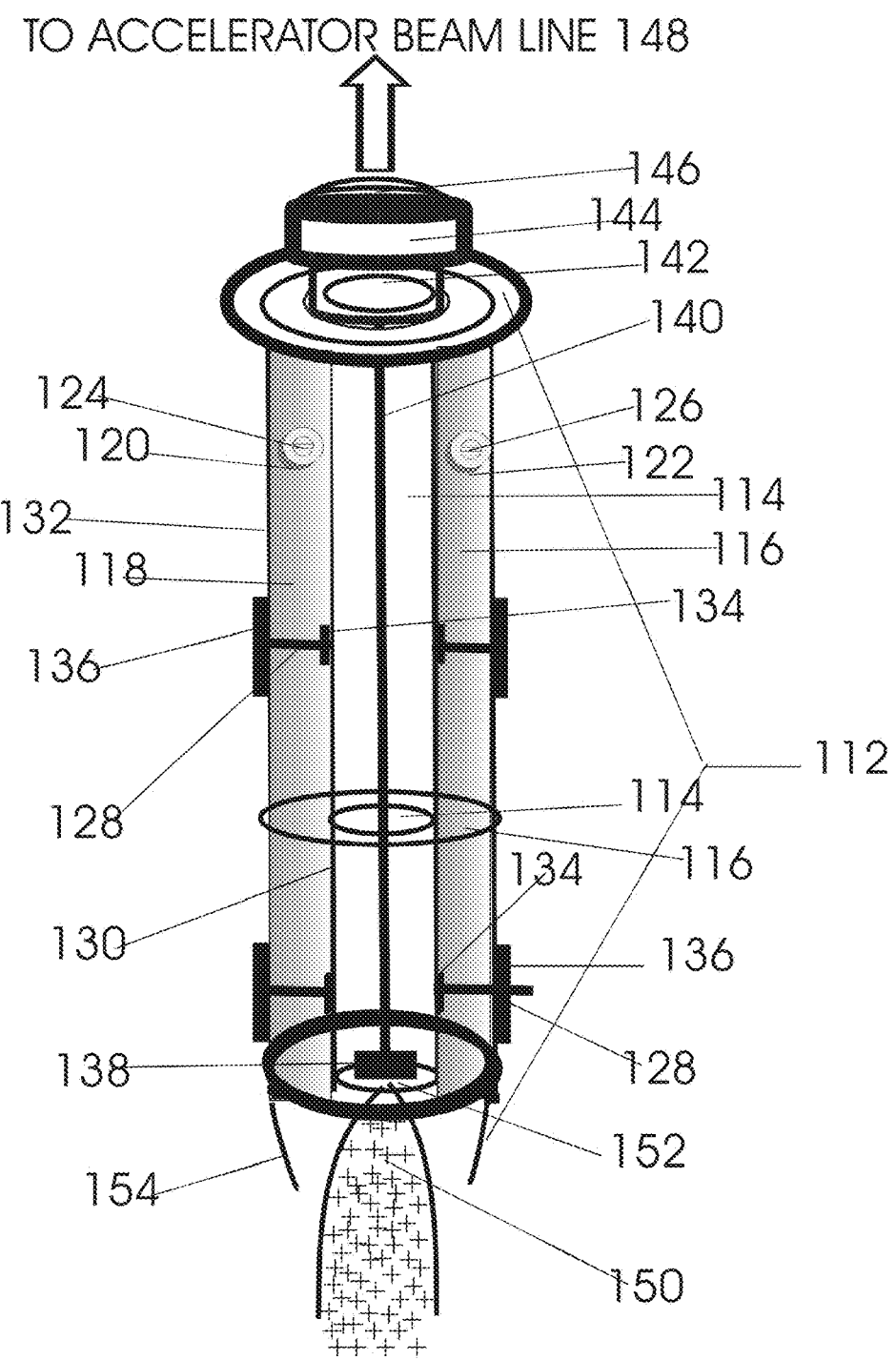

FIG. 9A-1 illustrates an enlarged view of a double lumen needle with titanium/D2 target that is used to generate higher MeV proton beam to transport the proton beam to a desired depth in tissue that is treated.

FIG. 9A-2 illustrates an enlarged view of a double lumen needle with titanium/D2 target that is used to generate higher MeV proton beam to transport the proton beam to a desired depth in tissue that is treated as in FIG. 9A-1 but with added coolant or chemotherapy ionization and protonspray.

Figure 9B:
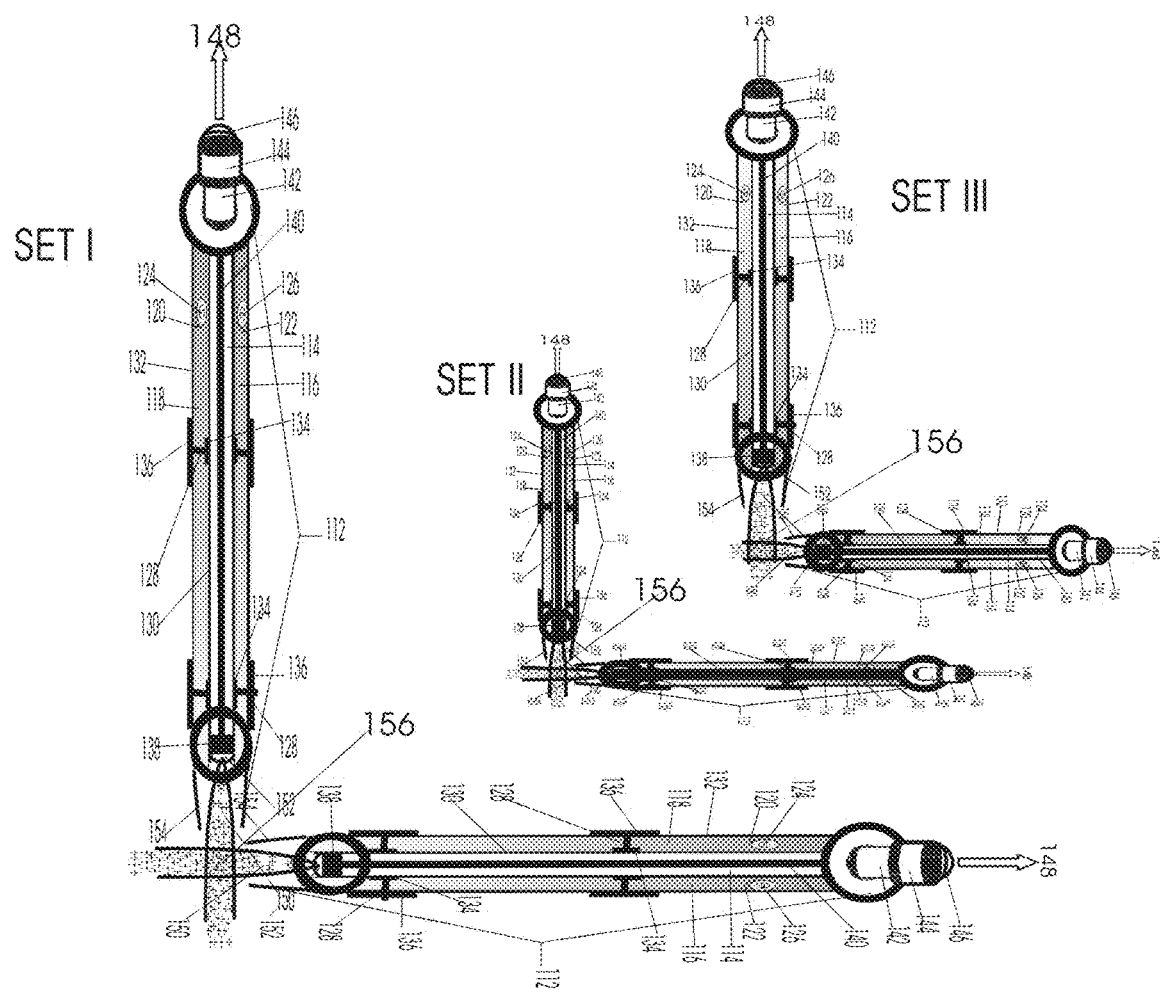

FIG. 9B shows three sets of varying lengths narrow double lumen needle with titanium/D2 target emitting proton-spray beams, in each sets, one from 0-degree and the other from 90 degrees that generates proton-proton-spray beams.

Figures 1, 9C:
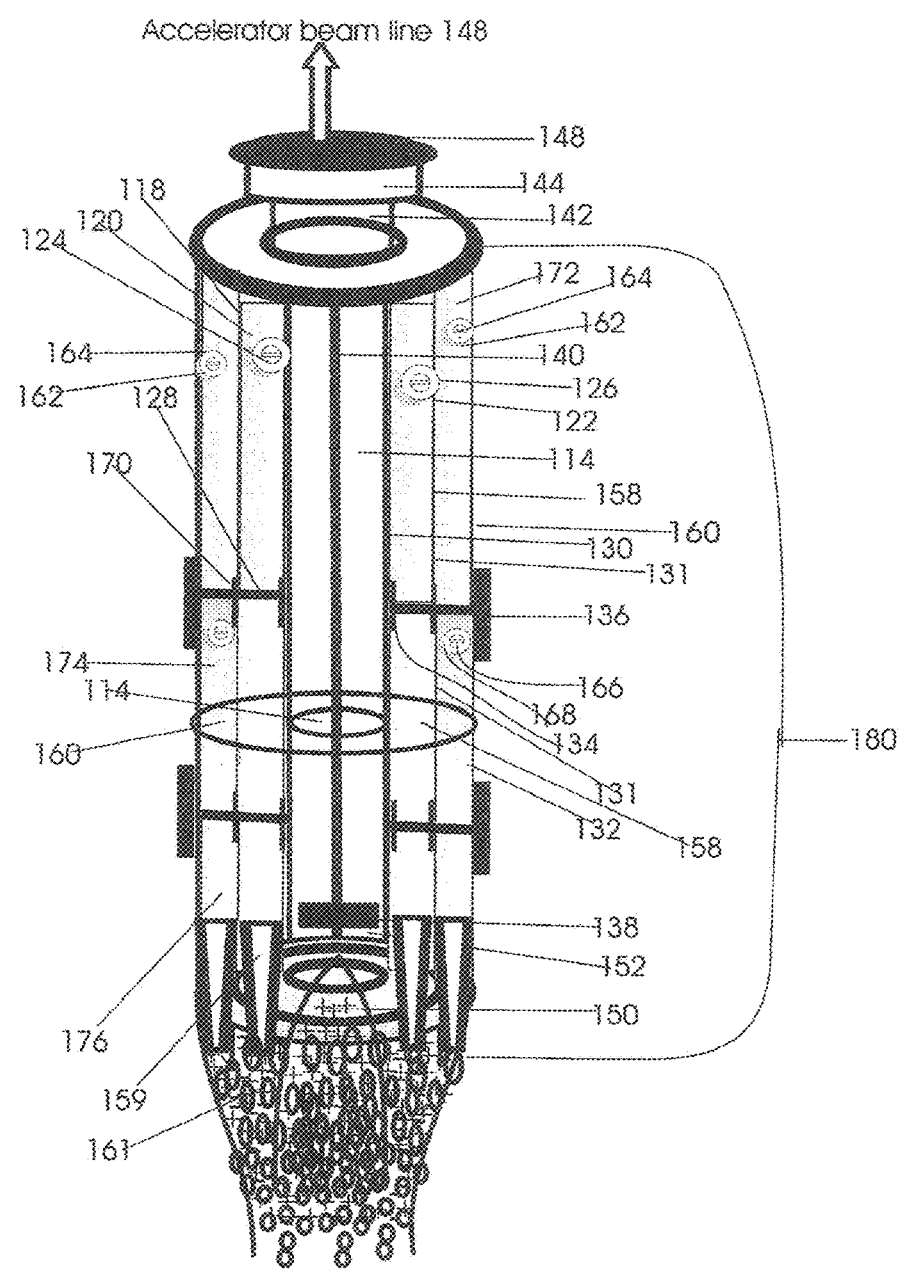
Figures 4, 9C:
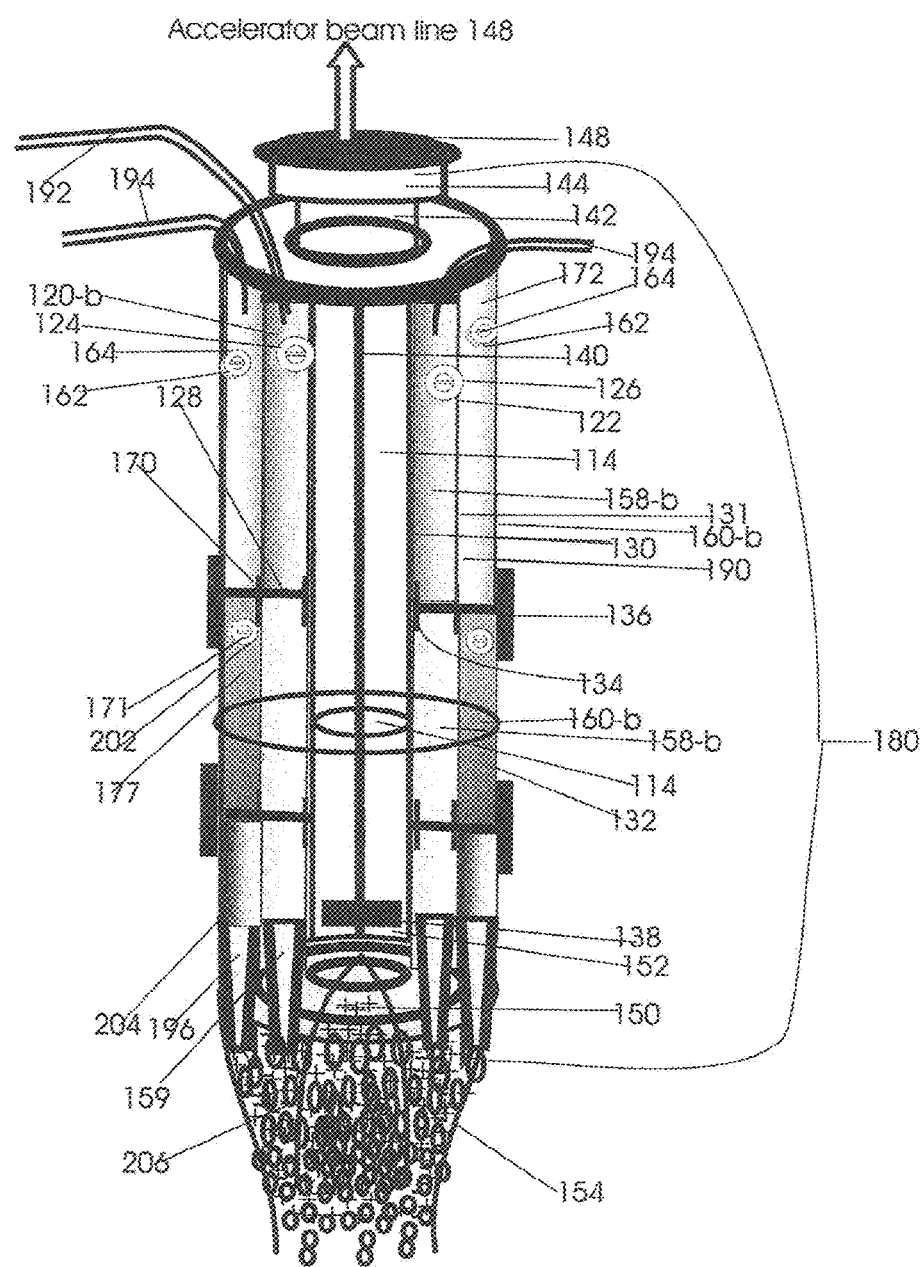

FIG. 9C-1 illustrates an enlarged view of a triple lumen needle with titanium/D2 target that is used for combined ionized proton spay chemotherapy and microbeam-nanobeam proton beam radiation therapy.

FIG. 9C-2 illustrates an enlarged view of a triple lumen needle with titanium/D2 target that is used for combined ionized electrospray plus proton spay chemotherapy and microbeam-nanobeam proton beam radiation therapy.

FIG. 9C-3 illustrates an enlarged view of a triple lumen needle with titanium/D2 target that is used for proton spay neutron capture radiation therapy with gamma rays and Auger electrons from Gadolinium neutron-capture for Gadolinium neutron-capture therapy (Gd-NCT) and chemotherapy with ionized fragments of gadolinium by the proton spray.

Figure 9D:
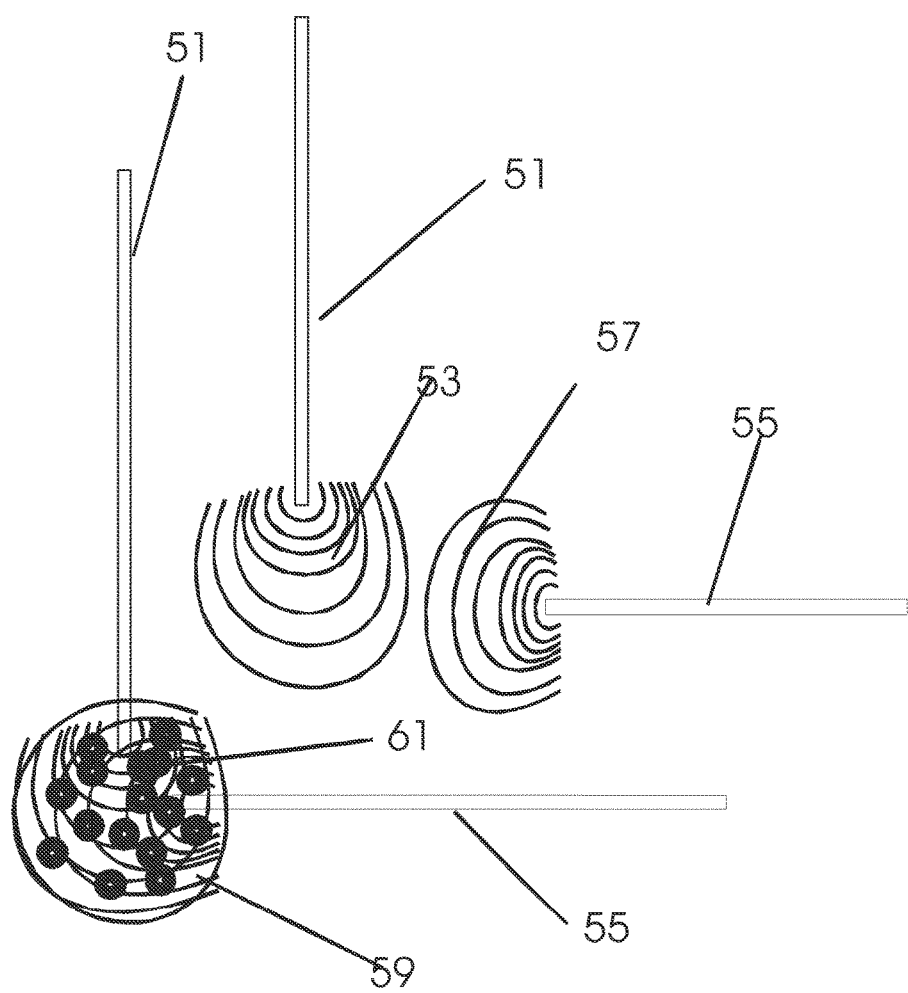

FIG. 9C-4 is another illustration of an enlarged view of a triple lumen needle with titanium/D2 target that is used for proton spay boron neutron capture radiation therapy (psBNCT) with proton beam generated with a triple lumen capillary needle FIG. 9D illustrates an incoming vertical proton microbeam from 0-degree and an incoming horizontal microbeam from 90 degree with their respective isodose before and after beam-beam collision that generates elastic and inelastic proton-proton interaction producing neutron, secondary protons, gamma rays and antiprotons.

Figure 9E:
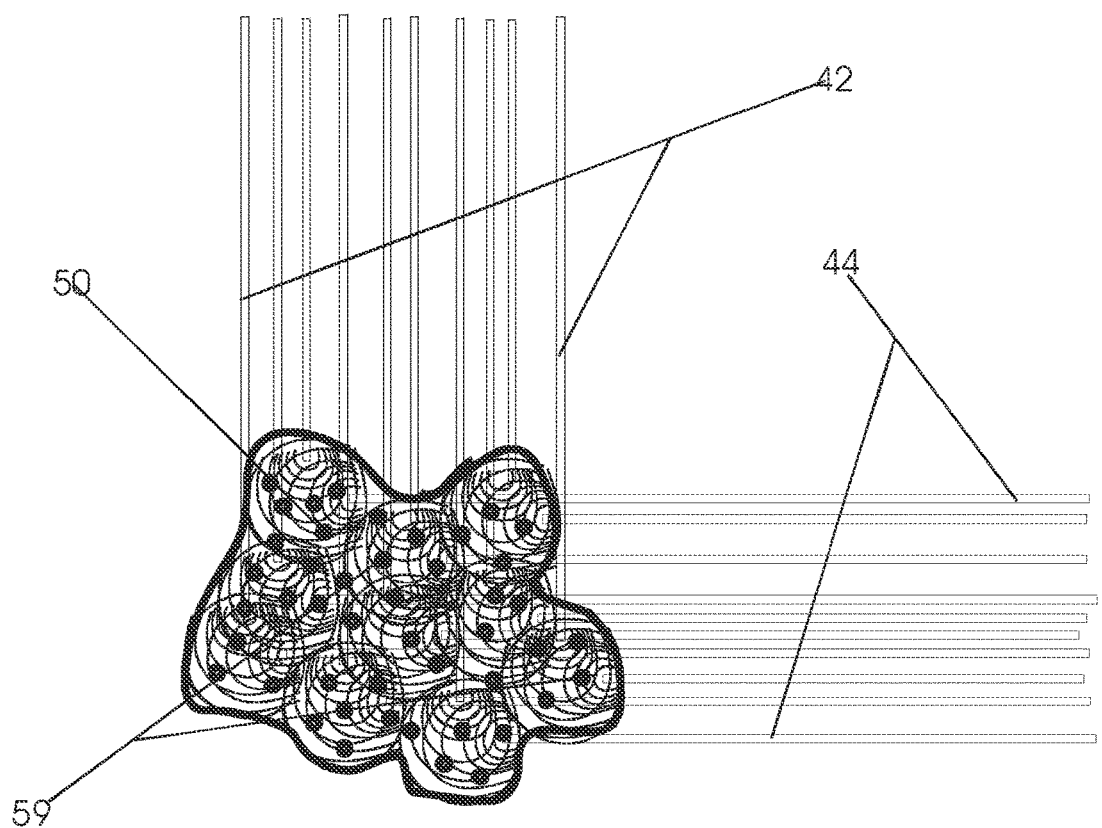

FIG. 9E shows parallel groups of selected microbeam or nanobeams from accelerator-1 at o-degree and with microbeam or nanobeams from accelerator-2 at 90-degree and their bam-beam collision generating ionization, neutron, secondary protons, gamma rays and antiprotons.

Figure 9F:
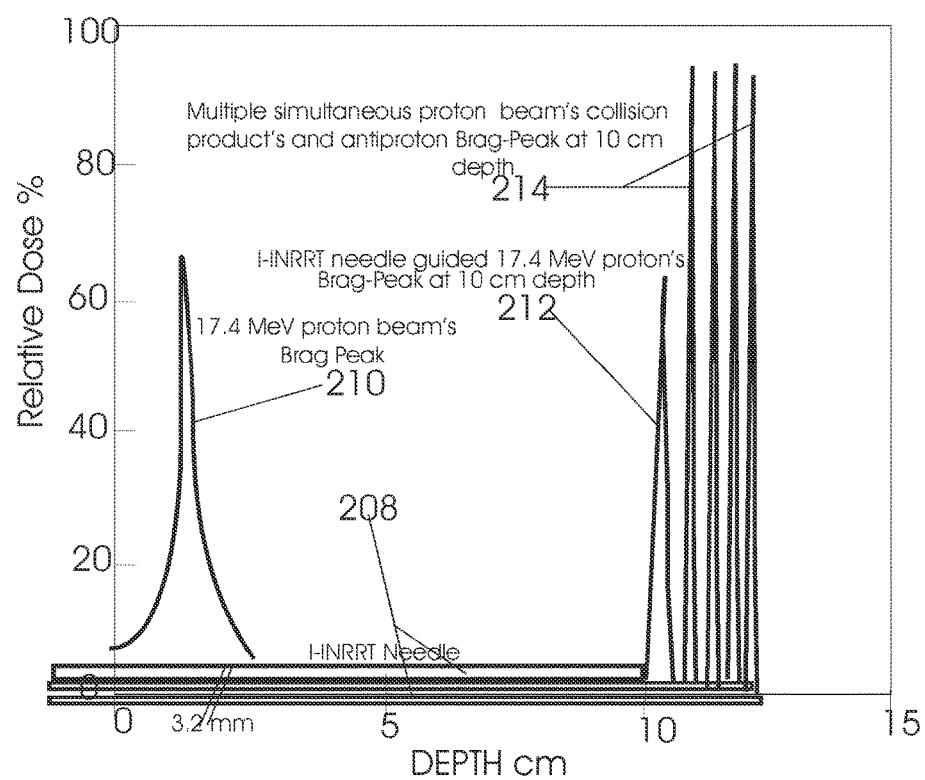

FIG. 9F shows the comparative depth dose and Brag-Peaks of the 17.4 MeV proton beam, its INRT needle guided depth dose and Brag-Peak and the combined Brag Peak of the INRT needle guided multiple simultaneous proton beams and proton spray beam's and their beam-on-beam collision's reaction products and antiprotons.

FIG. 10A illustrates proton microbeam and nanobeam generating and secondary neutron and proton absorbing cylindrical tissue equivalent collimator incorporated with a nozzle and a patient specific collimator through which the spread out proton beam's Bragg-peak travels towards an isocentric tumor in a patient.

FIG. 10A-2 is another illustration of proton microbeam and nanobeam generating and secondary neutron and proton absorbing cylindrical tissue equivalent collimators incorporated with a nozzle and a patient specific collimator through which the spread out proton beam Bragg-peak travels towards an isocentric tumor in a patient as in FIG. 10A but with the proton beam first travels through a semi-patient specific carbon nanotube pre-collimator.

Figures 1, 10B:
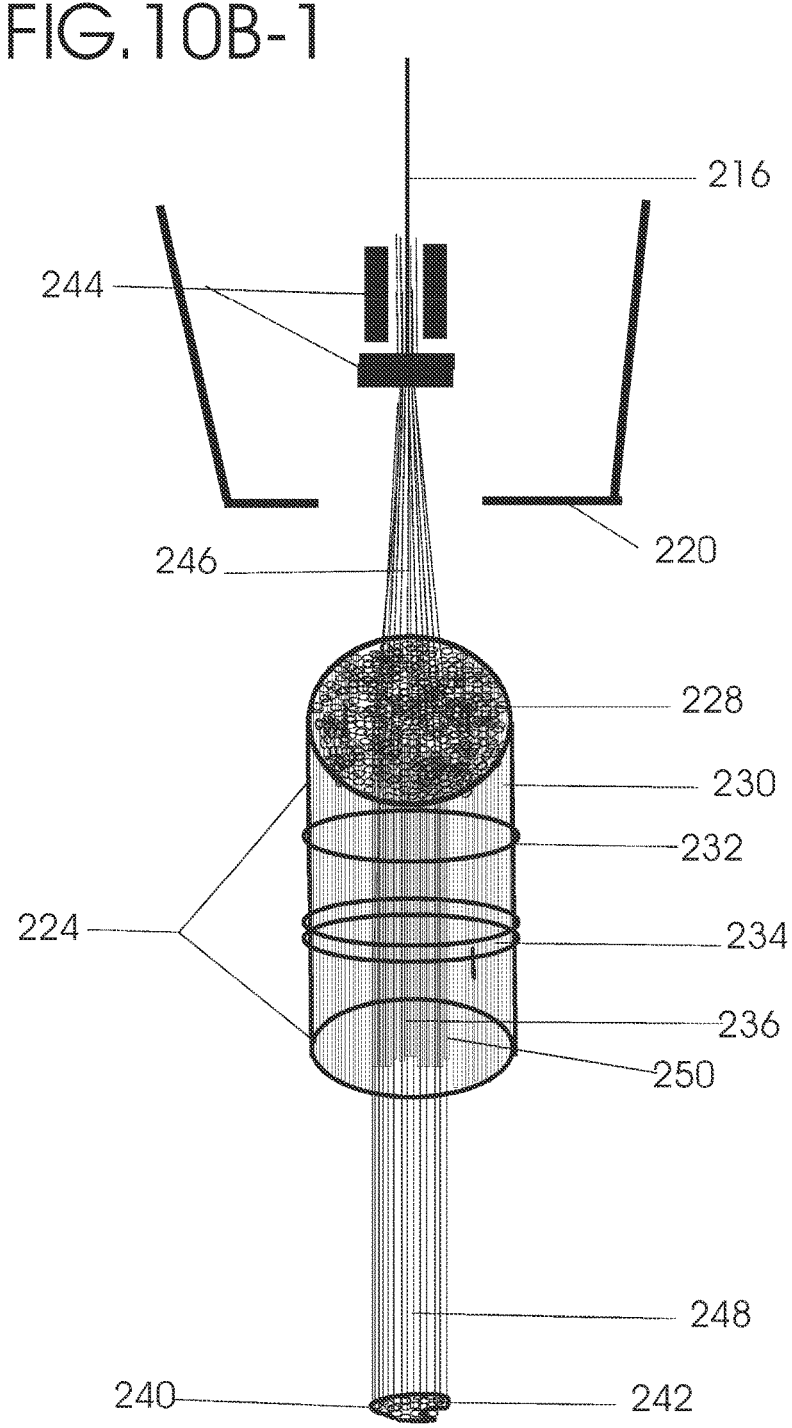
Figures 2, 10B:
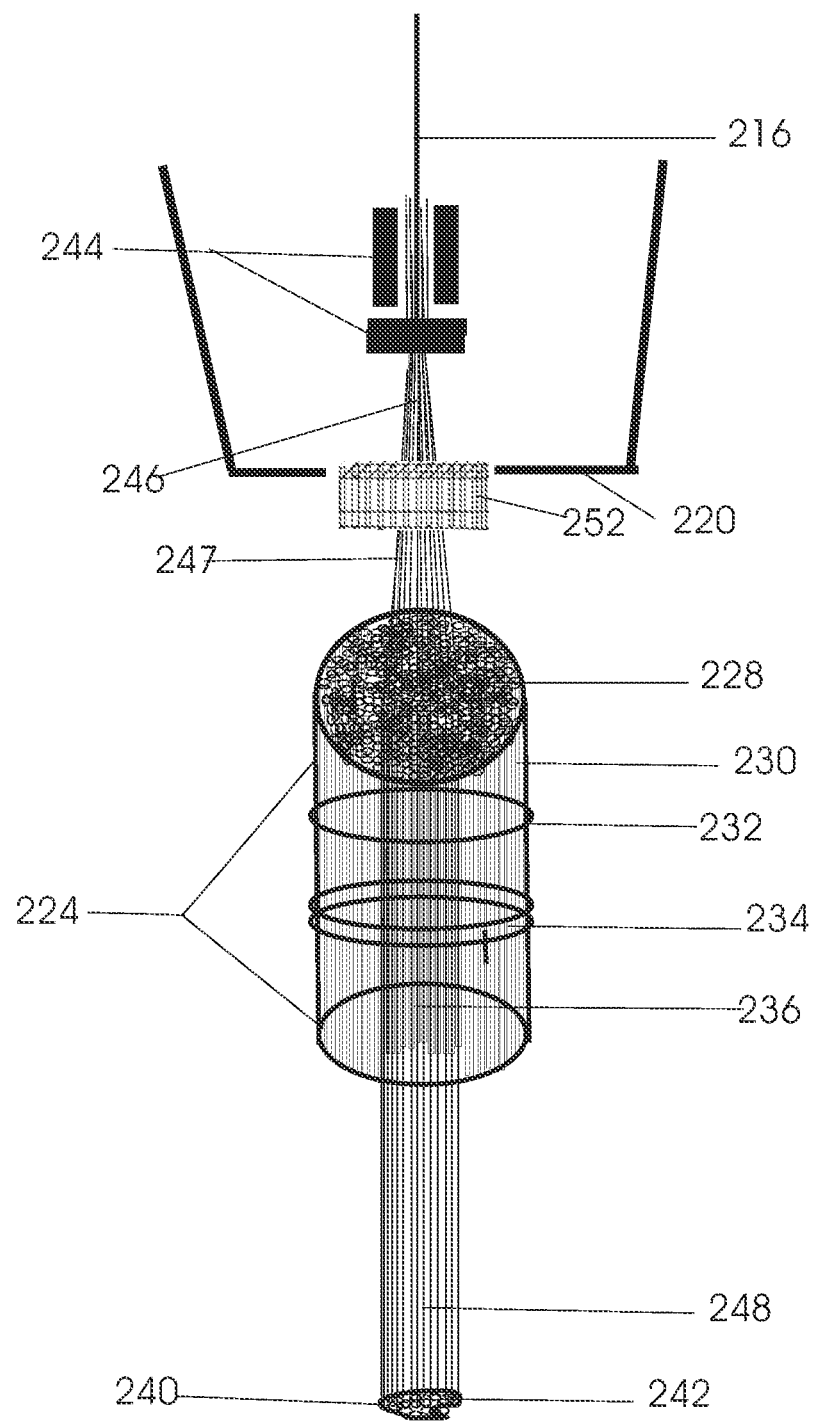

FIG. 10B-1 shows active, pencil proton beam spot scanning with no scattering elements in the nozzle except for the beam monitors, no patient specific collimator and compensators and microbeam and nanobeam generating and secondary neutron and proton absorbing cylindrical tissue equivalent collimator for secondary neutron and proton absorbing proton microbeam and nanobeam radiation therapy.

FIG. 10B-2 illustrates the active, pencil proton beam spot scanning with no scattering elements in the nozzle except for the beam monitors, no patient specific collimator and compensators and microbeam and nanobeam generating and secondary neutron and proton absorbing cylindrical tissue equivalent collimator for secondary neutron and proton absorbing proton microbeam and nanobeam radiation therapy as in FIG. 10B but with the proton beam first travels through a semi-patient specific carbon nanotube pre-collimator.

Figure 10:
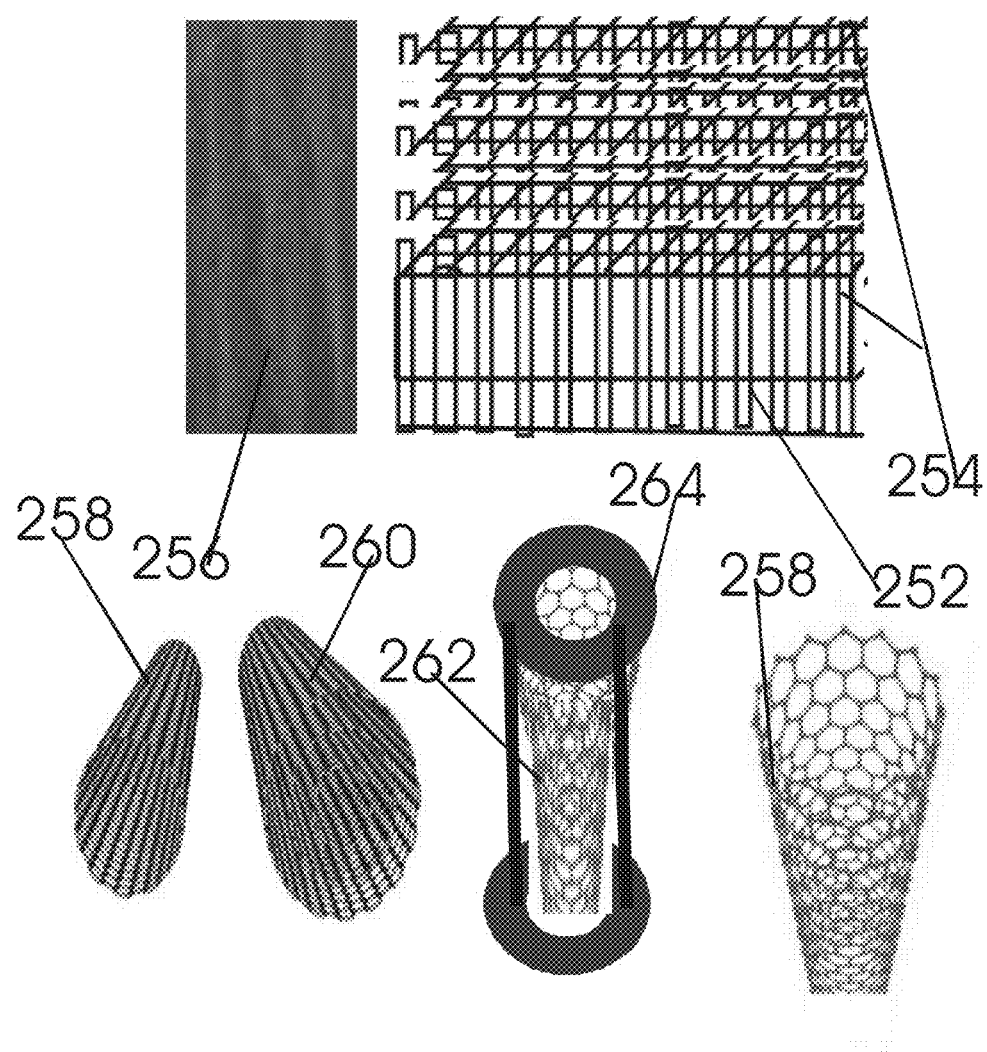
Figure 10:
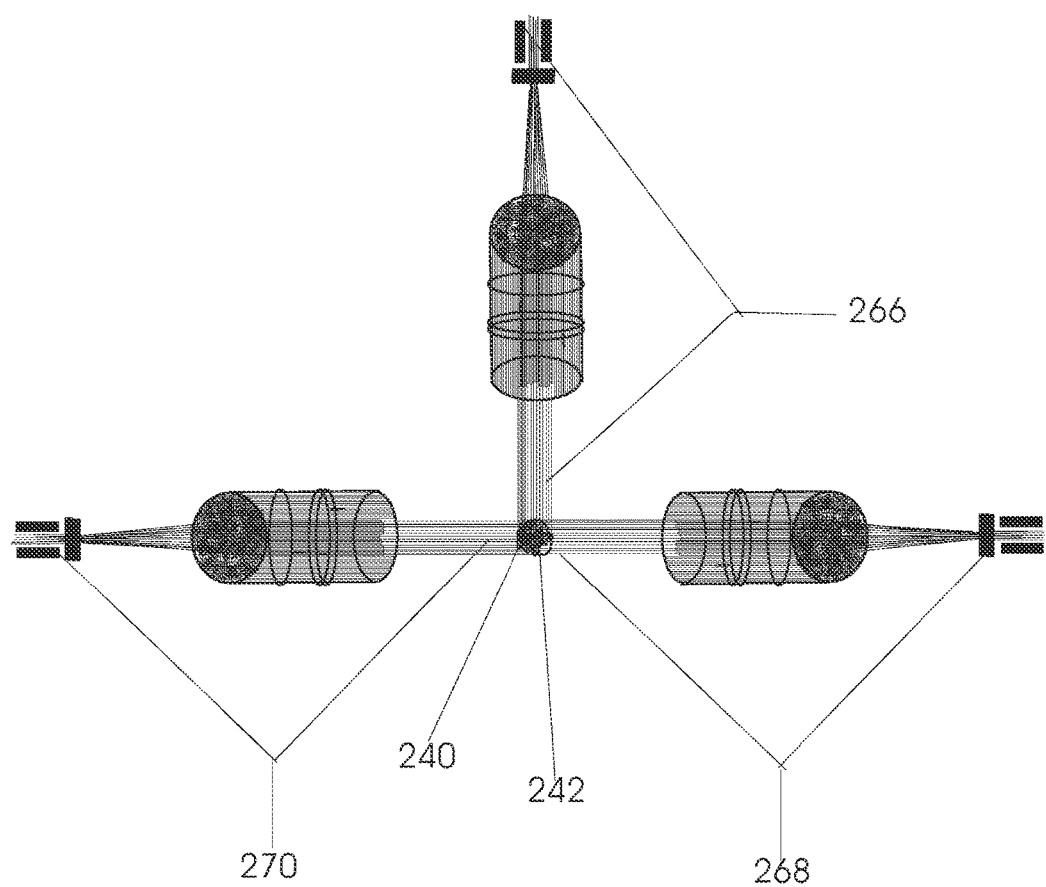

FIG. 10 B-3 shows serial arrays of exposed vertically aligned multi-wall carbon nanotubes that are used as semi-patient specific carbon nanotube pre-collimator to generate focused nanobeams in multi-walled carbon nanotubes and their fine structures.

FIG. 10 B-4 illustrates interlacing scanning beams from two sets of proton accelerators, one at 0-degree and the other at 90-degree and proton beam spot scanning radiation therapy with their cross firing perpendicular and horizontal simultaneous microbeam or nanobeam beam's elastic and none-elastic collisional interaction at the isocentric tumor as they interlace at the isocentric tumor and the nozzles without scattering elements and also without patient specific collimator and compensators and the microbeam and nanobeam generating and secondary neutron and proton absorbing cylindrical tissue equivalent collimator for secondary neutron and proton absorption.

FIG. 10 B-5 shows 3 interlacing scanning beams from three sets of proton accelerators, one at 0-degree, one at 90-degree and other at 270 degree for three sources simultaneous proton beam spot scanning radiation therapy to an isocentric tumor by their cross firing perpendicular and horizontal microbeams or nanobeams as described under FIG. 10 B-4 but with 3 simultaneous beams.

FIG. 11A is an illustration of generating multiple simultaneous sweeping proton parallel microbeams or nanobeams by splitting the proton beam from a gantry mounted compact proton accelerator equipped with microbeam and nanobeam generating and secondary neutron and proton absorbing cylindrical tissue equivalent collimator for secondary neutron and proton absorption.

FIG. 11 B illustrates interlaced, sweeping beam-on-beam collisional scanning with multiple simultaneous proton beams generated by splitting of the initial pencil beam of two gantry mounted compact proton accelerators and microbeam and nanobeam generating and secondary neutron and proton absorbing cylindrical tissue equivalent collimator for conformal microbeam and nanobeam radiation therapy to a tumor.

Figure 11B:
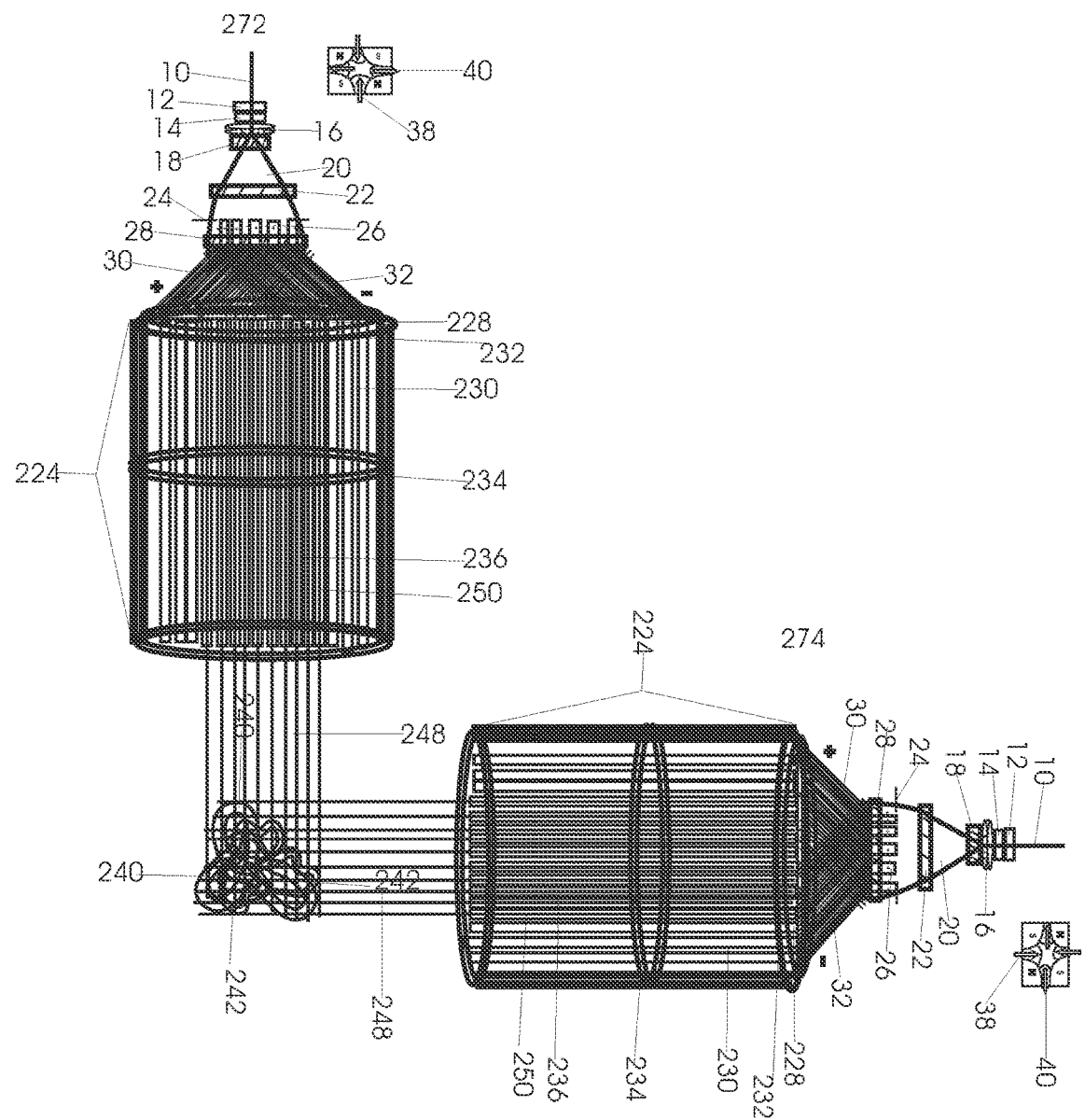

FIG. 11 C shows interlaced, sweeping beam-on-beam collisional scanning with multiple simultaneous proton beams generated by splitting of the initial pencil beam as in FIG. 11B but with five gantry mounted compact proton accelerators and microbeam and nanobeam generating and secondary neutron and proton absorbing cylindrical tissue equivalent collimator for conformal microbeam and nanobeam radiation therapy to a tumor.

FIG. 11-D illustrates proton spray chemotherapy and neutron capture radiation therapy with lithium-boron and gadolinium absorbed in carbon nanotubes.

FIG. 12 is a comparative illustration of proton, electron and high energy photon microbeam and nanobeam's scattering as they travel through tissue and their relative abilities to maintain peak and valley dose differential without much scattered radiation in the valley regions from where the least radiated stem cell regenerates to heal the tissue damage caused by high radiation dose peak regions which is the fundamental principles in high dose, 100 to 1,000 Gy and higher single fraction radiosurgery with least toxicity to normal tissue.

FIG. 13 is an illustration of generating numerous simultaneous parallel narrow proton beams by splitting the narrow proton beam from a radiofrequency accelerator combined with a drift tube accelerator for narrow proton beam radiation therapy with no or minimal long term toxicity to normal tissue.

Figure 14:
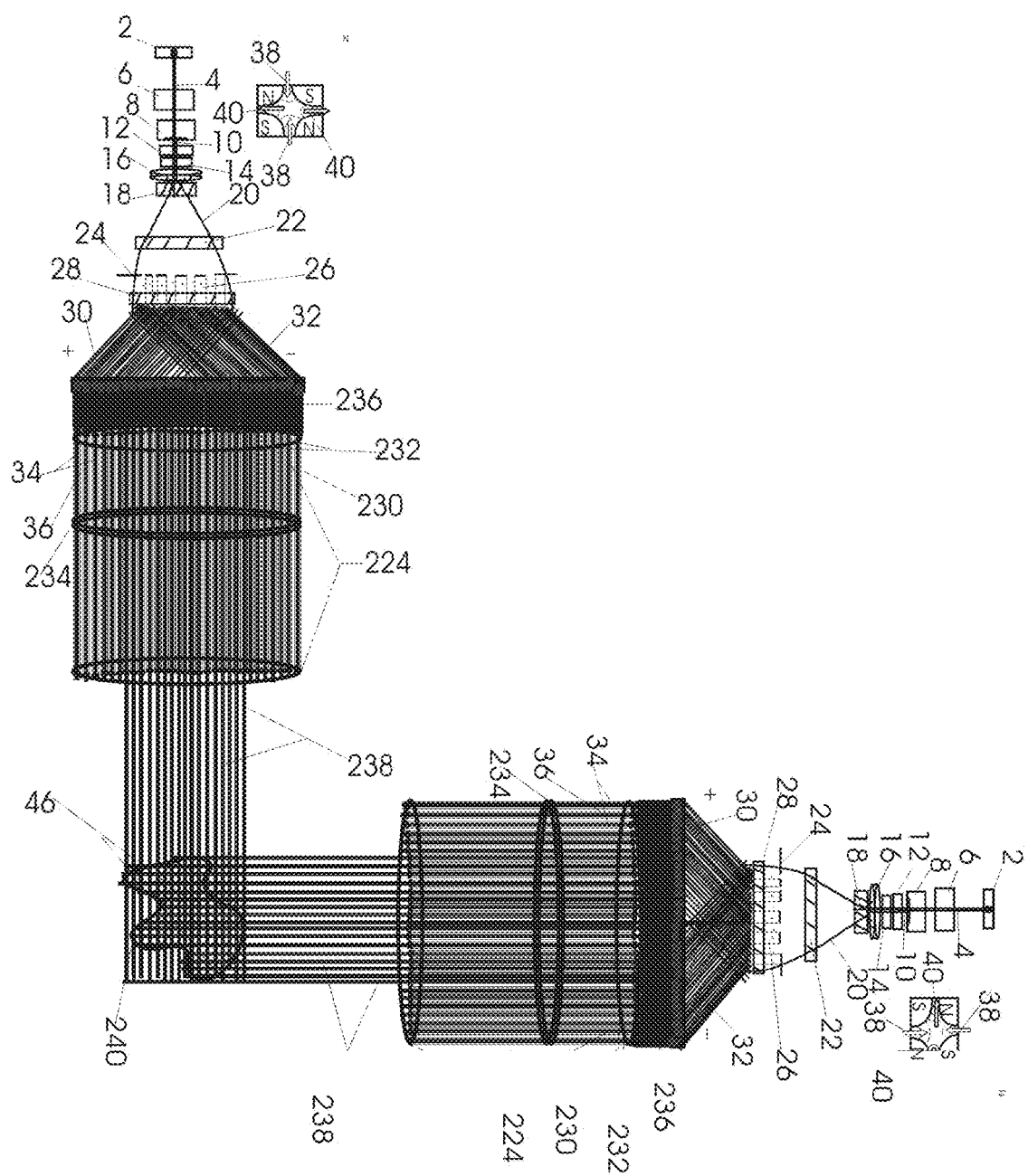

FIG. 14 illustrates the interlacing beams from two sets of parallel narrow proton beams, one from 0 degree and another from 90 degrees and both converging at the isocenter that generates quasi proton-proton interaction and quasi antiproton for narrow proton beam radiation therapy with minimal or no long term toxicity to normal tissue.

Figure 15:
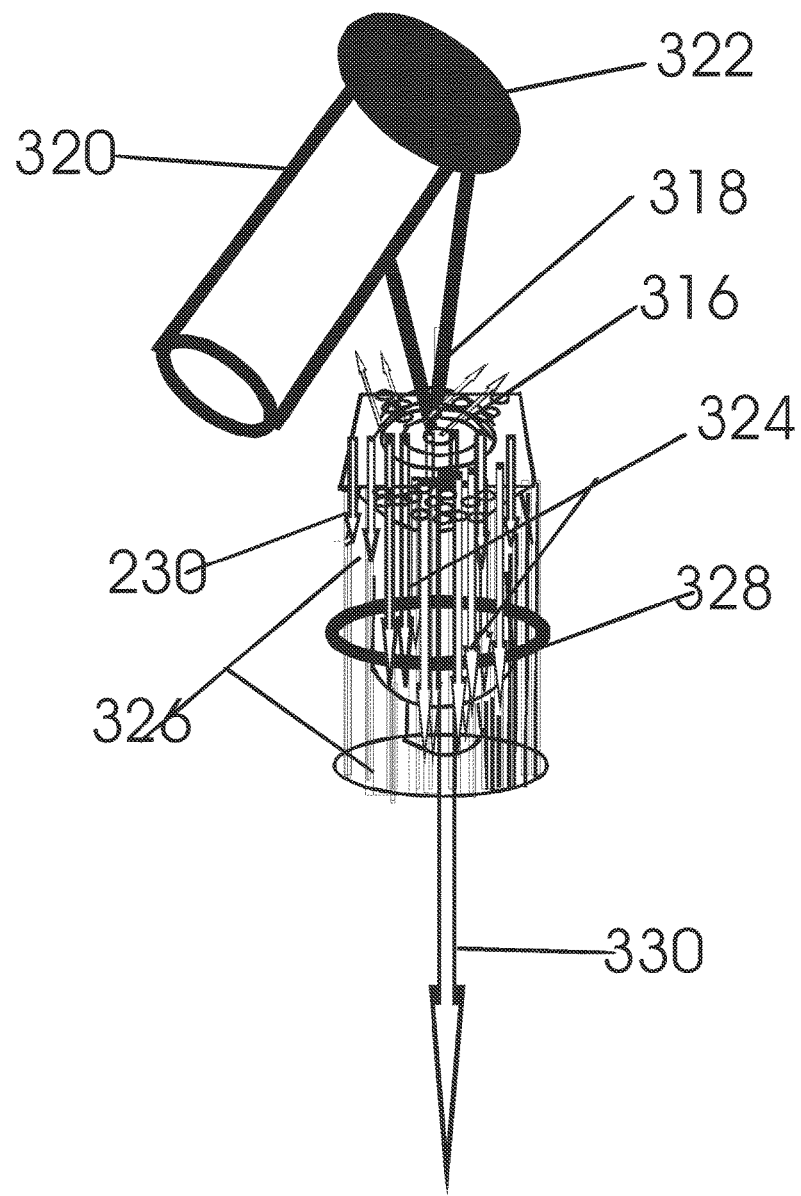

FIG. 15 shows polyenergetic laser-target interaction's proton or monoenergetic carbon ions generation and separation of proton beam's highest energy beam as a monochromatic beam with a tissue equivalent collimator containing microfocus carbon tubes and transport of proton or carbon ion beam for microbeam and nanobeam generation.

Figure 16:
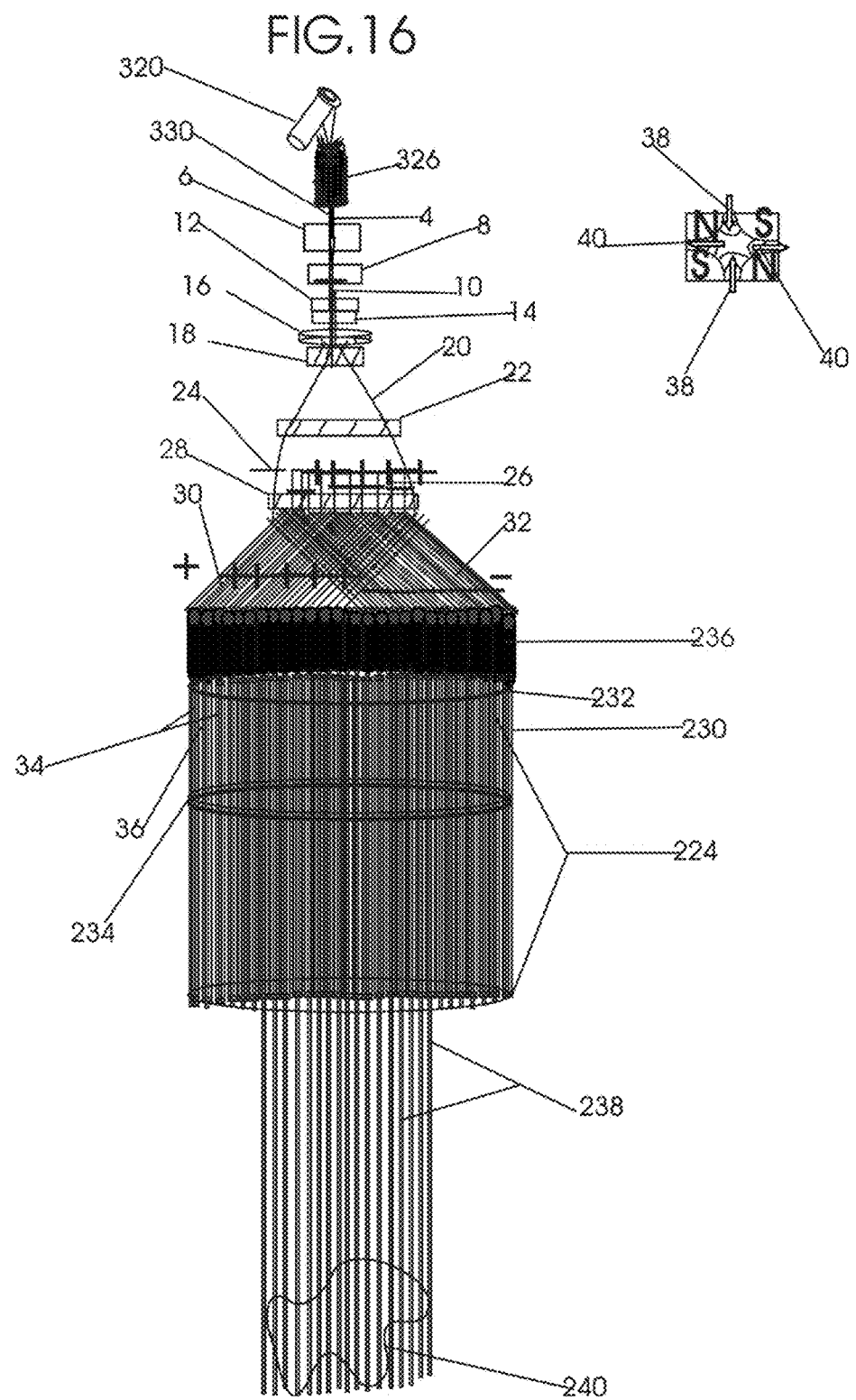

FIG. 16 illustrates an hybrid laser proton or carbon ion-radiofrequency accelerator in which laser generated proton or carbon ion beam's post acceleration is conducted in the hybrid radio frequency accelerator and generating numerous simultaneous parallel narrow proton or carbon ion beams by splitting the accelerated high energy proton or carbon ion beam into microbeams or nanobeams for proton microbeam or nanobeam radiation therapy with no or minimal long term toxicity to normal tissue.

Figure 17:
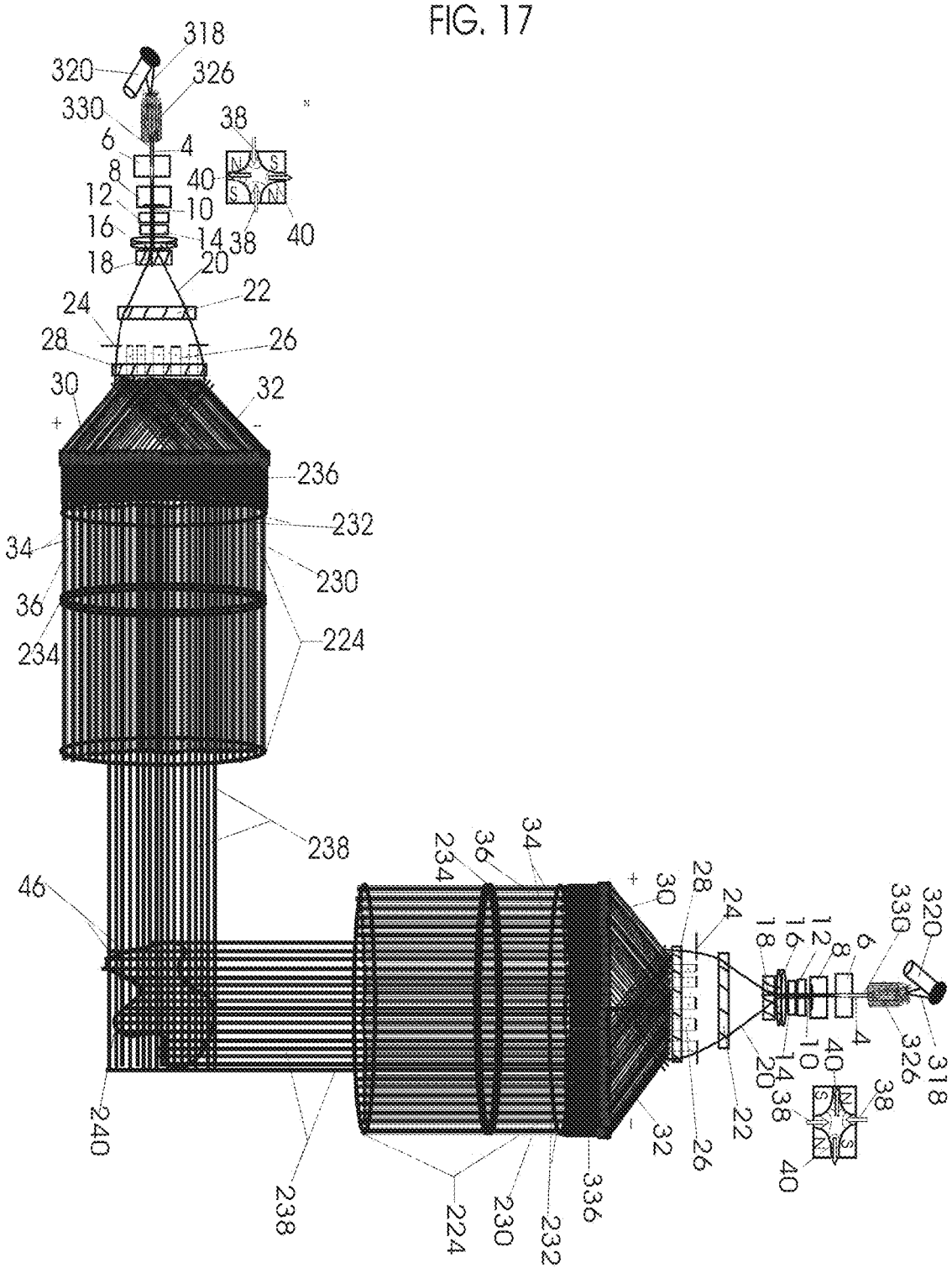

FIG. 17 is another illustration of interlacing beams from two sets of parallel narrow proton or carbon ion beams, one from 0 degree and another from 90 degrees and both converging at the isocenter for narrow proton or carbon ion beam radiation therapy with minimal or no long term toxicity to normal tissue as in FIG. 14 but with two hybrid laser-proton or carbon ion-RF accelerators.

Figure 18:
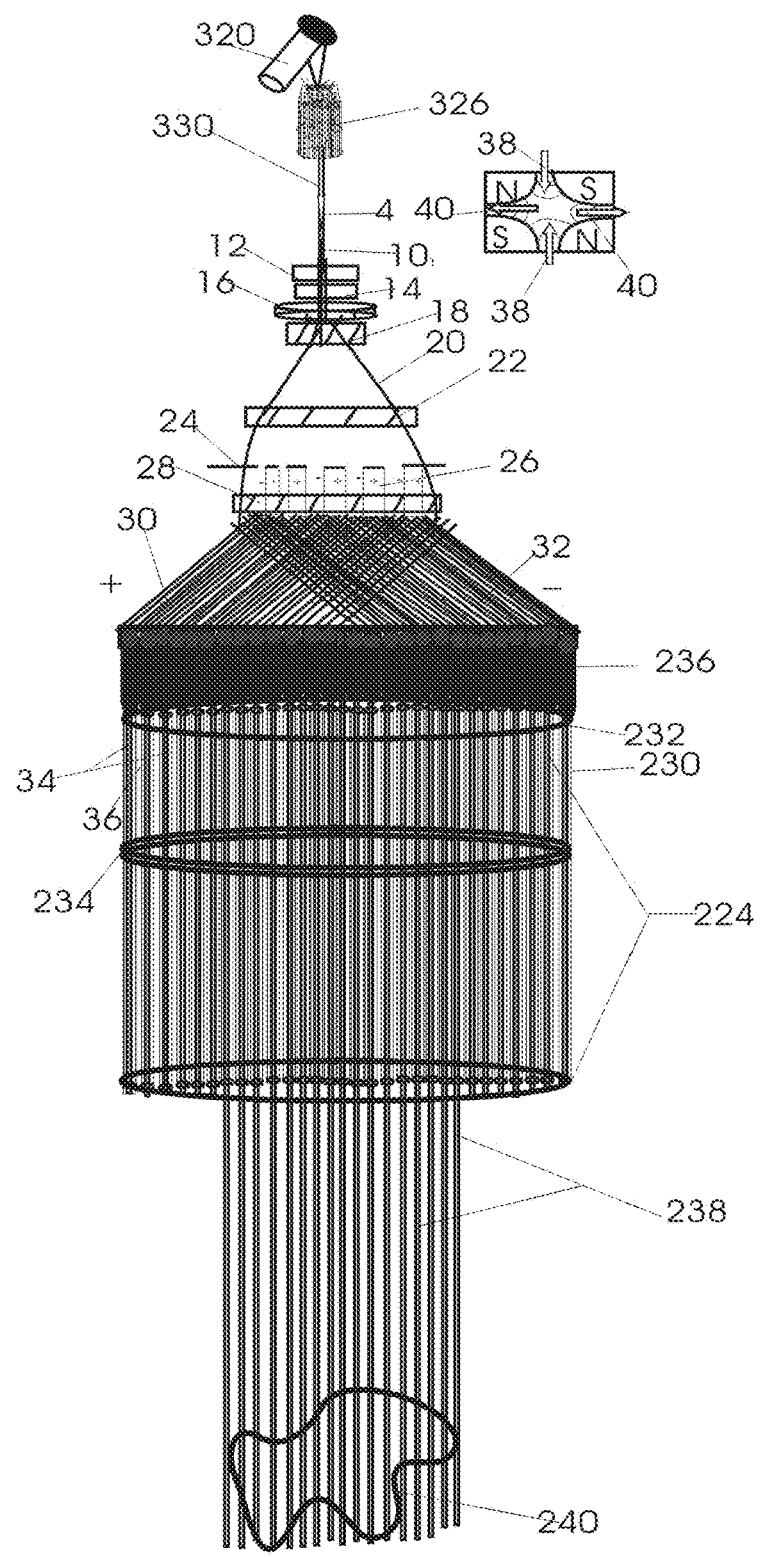

FIG. 18 shows a laser proton or carbon ion generating accelerator in which high 50 to 250 MeV quasimonochromatic proton beam or 85-430 MeV/u carbon ion is generated by the laser-target-radiation pressure acceleration (RPA) methods and also generating numerous simultaneous parallel narrow proton or carbon ion beams by splitting the accelerated high energy proton or carbon ion beam into microbeams or nanobeams for proton or carbon ion microbeam or nanobeam radiation therapy with no or minimal long term toxicity to normal tissue.

Figure 19:
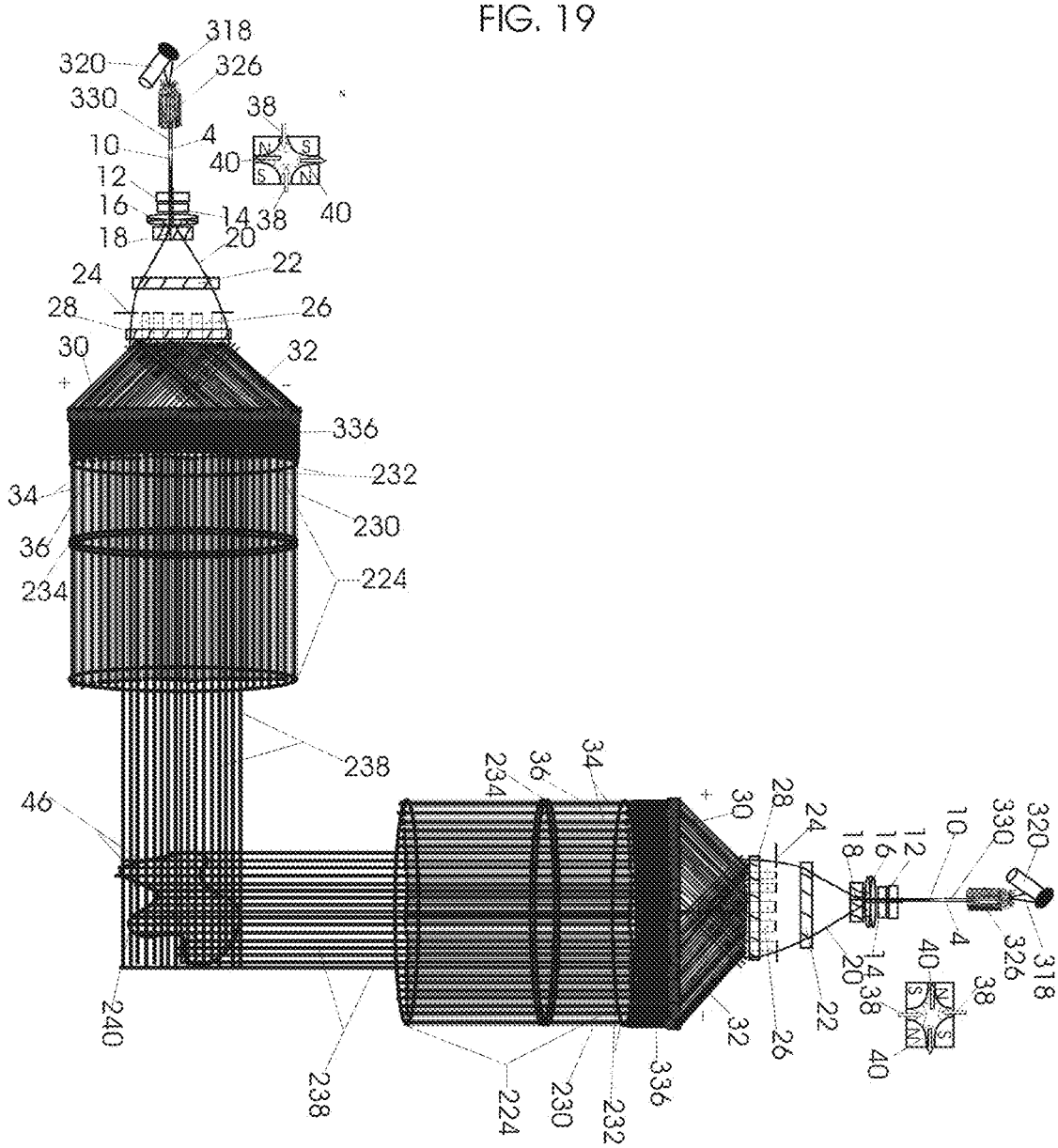

FIG. 19 illustrates two sets of interlacing parallel proton or carbon ion microbeams or nanobeams, one set from 0 degree and another set from 90 degrees and both converging at the isocenter for narrow proton or carbon ion beam radiation therapy with proton or carbon ion accelerator.

Figure 20:
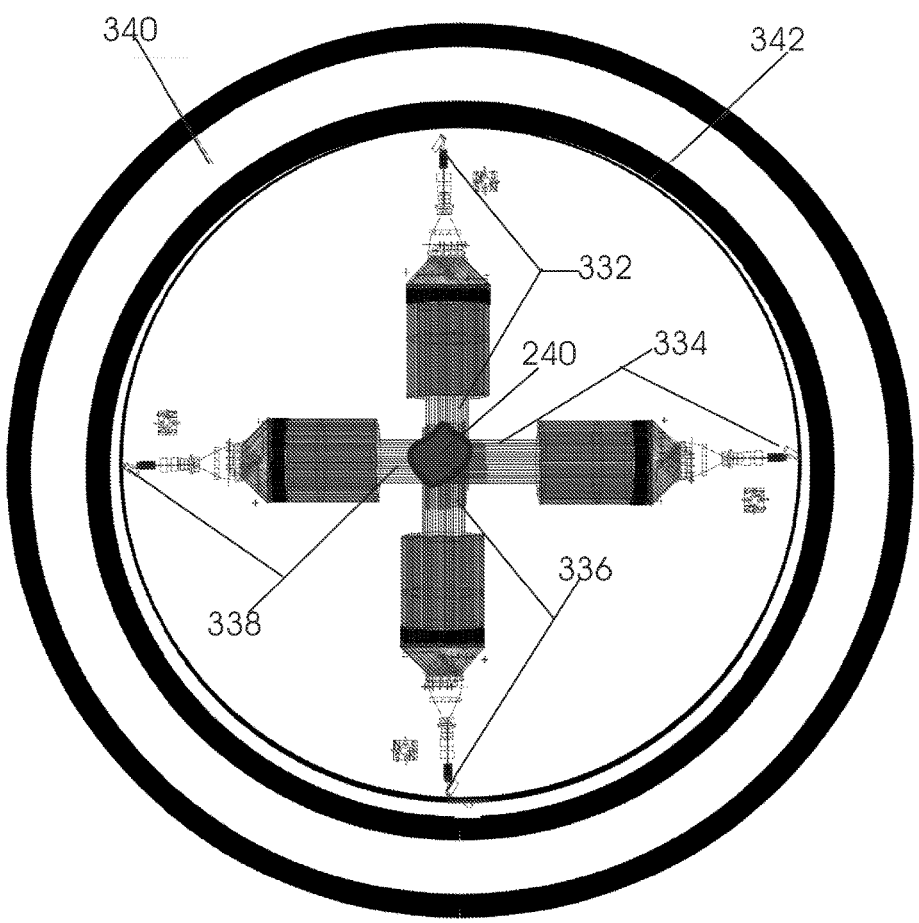

FIG. 20 shows four sets of interlacing parallel proton microbeams or nanobeams generated from a main ring laser from which four split beams are taken for RPA method of high energy proton or carbon ion generation and their interlacing beams. Carbon ion is generated with DLC as the target.

38. REFERENCE NUMERALS

2. Ion source
4. Beam transport
6. Radiofrequency accelerator—RFQ
8. Drift tube accelerator
10 Proton beam
12. Beam stop
14. Dose monitor-1
16. Collimator-1
18. Defocusing quadrupole magnet-1
20. Defocused proton beam 22. Defocusing and beam size controlling quadrupole magnet-2
24. Striper grid
26. Alternating positively and negatively charged proton beam
28. DC vertical deflecting dipole magnet
30. Positive charged proton beam deflected to left
32. Negative charged proton beam deflected to right
34. Parallel narrow beam peak dose
36. Valley dose
38. Quadrupole magnet with converging magnetic field in one field
39. Proton accelerator system-1
40 Quadrupole magnet with diverging magnetic field in another plane
42. Proton accelerator-1 with segments of microbeam or nanobeam
43. Proton accelerator system-2
44. Proton accelerator-2 with segments of microbeam or nanobeam
45. Narrow proton beam
46. High dose interlaced beams
47. Isocentric interlaced beams
48. Isocenter
50. Isocentric tumor
51. A vertical beam from 0 degree
52. Beam splitting quadrupole magnet
53. Isodose of a vertical proton beamlet from 0 degree
54. Beam splitting and switching magnet
55. A horizontal beam from 90 degree
56. Split and bent to right beam
57. Isodose of a horizontal proton beamlet from 90 degree
58. Split and bent to left beam
59. Combined isodose of vertical and horizontal proton beams and the elastic and inelastic reaction products
60. Right focusing magnet
61. Elastic and inelastic proton-proton collision reaction products
62. Left focusing magnet
64. Right 45 degree bending magnet
66. Right 45 degree bending magnet
68. Right focusing magnet
70. Left focusing magnet
70B. Beam transport system
70C. Beam transport system
72. Right 15 degree beam switching bipolar magnet
74. Left 15 degree beam switching bipolar magnet
76. 45-degree right bending magnet
78. 45-degree left bending magnet
80. Right quadrupole focusing magnet
82. Left quadrupole focusing magnet
84. Right 45-degree bending magnet
86. Left 45-degree bending magnet
88. Right 90-degree bent beam
90. Right entrance port for right split and bent beam
91. Right parallel beam generating system
92. Left entrance port for left split and bent beam
94. Left parallel beam generating system
96. Right beamline
98. Left beamline
100. Ion source
102. Compact nested high voltage DC accelerator (NHVDCA)
104A. Negatively charged ion beam from ion source
104B. Positively charged ion beam generated by NHVA
104C. Negatively charged ion beam Generated by the radiofrequency accelerator
106. Radiofrequency accelerator
108. RFQ accelerated negative polarity proton beam
110. Larger proton accelerator
112 Double lumen proton target tube-needle
114. Inner lumen
116. Outer lumen
118. Coolant
120. Coolant fluid inlet
120-b Fluid inlet
122. Air outlet
124. Coolant fluid inlet and outlet closure screw
124-b. Fluid inlet and outlet closure screw
126. Air outlet and inlet closure screw
128. Heat conducting tungsten wire
130. Outer wall of the inner lumen
131. Outer wall of the intermediate lumen
132. Outer wall of the outer lumen
134. Inner lumen holding and heat conducting tungsten wire
136. Outer lumen holding and heat conducting tungsten wire
138. Deuterium-titanium target1
140. RFQ output ion beam
142. Vacuum fitting
144. Vacuum flange
146. Vacuum fitting O-ring seal
148. Accelerator beam line fitting
150. Proton spray beam
152. Beam exit window
154. Sharp cone
156. Proton-proton beam spry
158. Intermediate lumen with coolant
158-b. Intermediate lumen with lithium compound
159. Nozzle-Taylor cone attached to intermediate lumen
160. Outer lumen holding chemotherapeutic
160-b. Outer lumen holding gadolinium compound
160-c. Outer lumen
161. Ionized coolant or chemotherapeutic spray from intermediate lumen
161-b vaporized lithium compound spray
162. Helium or nitrogen gas inlet or outlet
163. Nozzle-attached to outer lumen
164. Helium or nitrogen gas inlet and outlet closure screw
165. Ionized chemotherapeutic bound proton spray from outer lumen
166. Chemotherapeutics inlet
167. Gadolinium inlet
168. Chemotherapeutics inlet and outlet closure screw
169. Gadolinium inlet and outlet closure screw
170. Intermediate lumen holding and heat conducting tungsten wire
171. $^{10}$B inlet and outlet closure screw
172. Helium or nitrogen gas
174. Chemotherapeutic in the outer lumen
175. Outer lumen with Gadolinium
176. Vaporized chemotherapeutic
177. Outer lumen with $^{10}$B-compound
178. KeV electrode
180. Triple-lumen proton target tube-needle with chemotherapeutic
182. Coolant fluid and helium inlet and outlet
184. High voltage microelectrode
186. Ionized coolant or chemotherapeutic bound proton spray from outer lumen
188. Lithium compound
190. Gadolinium compound
191. Gadolinium compound inlet screw
192. Capillary inlet for reagent
194. Capillary inlet for pressurizing gas 196. Nozzle-Taylor cone attached to outer lumen
198. Gadolinium compound inlet and outlet closure screw
199. Ionized Gadolinium compound spray's interaction with neutron and proton spray
200. $^{10}$B-compound
202. $^{10}$B-compound inlet
204. Vaporized $^{10}$B compound
206. Ionized $^{10}$B-compound spray's interaction with neutron and proton spray
208. INRT needle
210. 17.4 MeV proton beam's Bragg-Peak
212. INRT needle guided 17.4 MeV proton's Brag-Peak at 10 cm depth
214. Simultaneous proton beam's collision product's and antiproton's Brag-Peak at 10 cm depth
216, Pencil proton beam
218. Passive scatterer
220. Nozzle
222 Spread out Bragg-peak
224. Tissue equivalent universal collimator
226. Patient specific collimator
228. Microfocus carbon tube's openings
230. Microfocus carbon tubes
232. Focusing anode
234. Focusing magnet
236. Focused micro/nanobeam in microfocus carbon tubes
238. Focused microbeam/nanobeam
240. Isocentric tumor
242. Conformal proton microbeam/nanobeam radiation to tumor
244. Scanning magnets
246. Scanned beam
247. Spot scanned focused microbeam/nanobeam
248. Scanned focused microbeam/nanobeam
250. Scanned focused micro/nanobeam in microfocus carbon tubes
252. Semi-patient specific carbon nanotube pre-collimator
254. Serial arrays of exposed vertically aligned MWCNT in a template
256. Scanning electron microscope image of sheets carbon nanotube
258. Single walled carbon nanotube (SWCNT)
260. Multiwalled carbon nanotube (MWCNT)
262. SWCNT in single aligned template
264 Single aligned templates
266. Interlacing beam source-1
268. Interlacing beam source-2
270. Interlacing beam source-3
272. Compact gantry mounted multiple simultaneous proton beam accelerator-1
274. Compact gantry mounted multiple simultaneous proton beam accelerator-2
276. Multi-beam proton accelerator with tissue equivalent universal collimator-1
278. Multi-beam proton accelerator with tissue equivalent universal collimator-2
280. Multi-beam proton accelerator with tissue equivalent universal collimator-3
282. Multi-beam proton accelerator with tissue equivalent universal collimator-4
284. Multi-beam proton accelerator with tissue equivalent universal collimator-5
286. Proton microbeam/nanobeam with peak and valley doses
288. Electron microbeam/nanobeam with peak and valley doses
290. Photon microbeam with peak and valley doses
292. Skin
294. Scattered radiation from electron in valley region tissue
296. Photon beam's scatter radiation in valley regions of normal tissue
298. Normal tissue valley
300. Proton peak dose in normal tissue
302. Electron peak dose in normal tissue
304. Photon peak dose in normal tissue
306. Microbeam/nanobeam proton spray
308. Single walled carbon nanotube (SWCNT)
310. Chemotherapeutic, lithium, boron, gadolinium adsorbed outside SWCNT
312. Chemotherapeutic, lithium, boron, gadolinium adsorbed inside SWCNT
314. Proton spray nuclear reaction, ionized chemotherapeutics, GdNCT, BNCT and ions
316. Target foil
318. Focused laser
320. Laser source
322. Mirror
324. Polyenergetic proton beams
326. Tissue equivalent collimator
328. Polyenergetic beam spatially separating magnet
330. Monoenergetic proton or carbon ion beam
332. Laser-RPA-proton or carbon ion accelerator-1
334. Laser-RPA-proton or carbon ion accelerator-2
336. Laser-RPA-proton or carbon ion accelerator-3
338. Laser-RPA-proton or carbon ion accelerator-4
340. Rotating circular gantry
342. Main ring laser source

39. DETAILED DESCRIPTION OF THE PREFERRED EMBODIMENTS

FIG. 1 is an illustration of generating numerous simultaneous parallel narrow proton beams by splitting the narrow proton beam from a radiofrequency accelerator combined with a drift tube accelerator for narrow proton beam radiation therapy with minimal or no long term toxicity to normal tissue. Lower energy proton beam is generated in the ion source 2. The beam transport 4 guides it into the radiofrequency accelerator RFQ 6 where it undergoes its first acceleration. The RFQ 6 accelerated multiple pulse negative polarity proton beam is then injected into the drift tube accelerator 8. The drift tube accelerator accelerated multiple pulse negative polarity proton beam 10 passes by a beam stopper 12 that serves as an emergency beam stopper when needed and a dose monitor 14 and the beam aperture collimating collimator 16 into a defocusing in one plane and focusing in another plane quadrupole magnet 18 which spreads out the proton beam in one plane and focuses it in another plane. The insert in FIG. 1 shows the quadrupole magnet with converging magnetic field in one plane 38 and the diverging magnetic field in another plane 40 as arranged symmetrically about the beam axis. The quadrupole magnet 18 with converging magnetic field in one plane 38 which focuses the proton beam and the diverging magnetic field in another plane 40 defocuses the proton beam. Thus the proton beam is spread out in one plane and focused in another plane. The one plane defocused and in another plane focused multiple pulse negatively charged proton beam 20 is injected into a defocusing, focusing and beam size controlling magnet 22. The split beam's size and spacing from each other is controlled with this magnet. This beam, deflected in one direction and focused in another is then passed through a stripper grid 24 that generates alternating positively and negatively charged beam segments 26. They are alternatively charged as positive and negative segments of the beam and they are passed through a deflection magnet with DC vertical dipole field 28. According to the Lawrence law of force, the positively charged proton beamlets deflects to the left 30 and the negatively charged proton beamlets deflects to the right 32. The separating distance between each of these beamlets is dependent on the strength of dipole field. It generates sets of numerous simultaneous parallel proton beams that covers the entire tumor volume but with beam separating spaces in between the beams. It generates peak and valley dose differentials in tissue. These beams are scanned as in proton spot scanning or raster scanning for proton beam radiation therapy but with a patient specific, secondary neutron absorbing capillary nozzle. The portion of the tissue that is radiated by the narrow parallel proton beam with peak dose 34 is the peak dose regions. The tissue that is separated between the two peak radiation regions in tissue is the low or no dose region, the valley dose 36 region in tissue. Alternatively, the proton beamlets are passed through capillary needles.

With interlaced narrow proton beams and simultaneously treating a tumor from different angles sterilize the tumor and its cancer stem cells without causing much long term toxicity to normal cells. It exposes the tumor antigens that induce personalized autoimmunity against a patient's cancer. When it is a high dose, 100 to 500 Gy single fraction radiosurgery, it does not induce adaptive resistance to radiation therapy as it can be with daily fractionated radiation therapy that lasts for eight to ten weeks. With single fraction, high dose radiation, it induces and enhances the cancer immunity. Thus it becomes as a method of radioimmunotherapy which minimizes or eliminates the need for protracted long term chemotherapy. As alternative to the RFQ, an alternating phase focusing channel accelerator is also used (119, 110). With 1 mm sized 10 simultaneous narrow proton beams and each separated by 4 mm and with interlaced beams from two or more proton accelerators treats a 5 cm sized tumor in a single exposure.

Figure 2A:
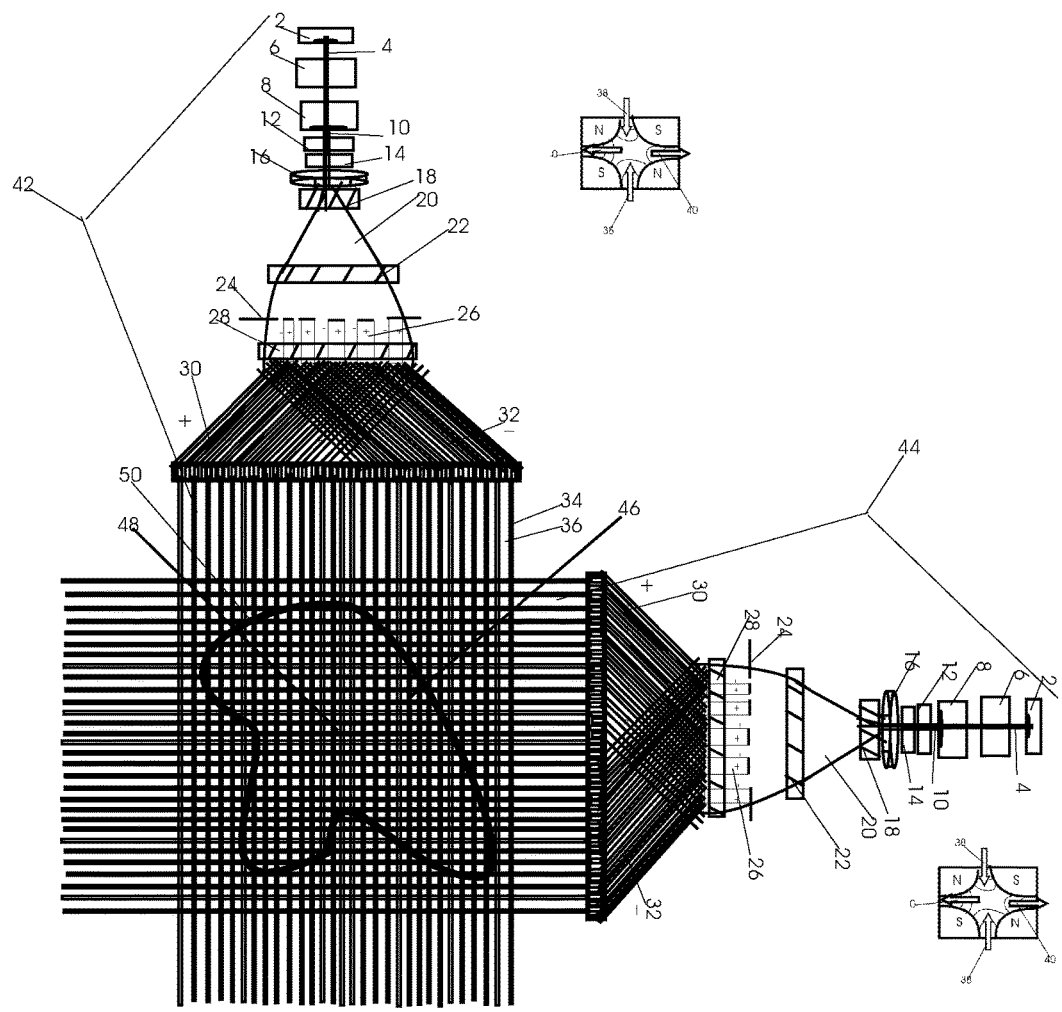
FIG. 2B is another illustration of interlacing proton parallel narrow beams that is shown in FIG. 2A but with the accelerators turned slightly to illustrate the interlacing beam-beam interaction as each beamlets of one accelerator hits the opposing beamlets of another accelerator.

FIG. 2A illustrates the interlacing beams from two sets of parallel narrow proton beams and proton beams from two sets of compact radiofrequency accelerators and a drift tube accelerators, one from 0 degree and another from 90 degrees and both converging at the isocenter that generates quasi proton-proton interaction and quasi antiproton for narrow proton beam radiation therapy with minimal or no long term toxicity to normal tissue. The proton accelerator-1, Number. 39 with segments of microbeam or nanobeams 42 from 0-degree is the same that is described in FIG. 1. Likewise, the proton accelerator system-2, (Number) 43 with segments of microbeam or nanobeams 44 from 90-degree is the same that is described in FIG. 1. Based on beam size adjusted with the DC vertical magnet 28, the split beams are made as narrow parallel beams. The parallel narrow beam peak dose 34 from both accelerators pass through the normal tissue towards the isocenter where they form high dose rate field with the interlaced beams 46. Each narrow beam segments from the split proton beam provides the parallel narrow beam peak dose 34 in the normal tissue. The tissue in between the two narrow parallel beams receives practically no significant dose. It is the valley dose 36. After the radiation to narrow segments of normal tissue through which the narrow proton beam passes through, the tissue damage caused in such narrow segment of normal tissue is repaired by proliferation of normal tissue from the valley region. By interlacing the parallel narrow beams at the isocenter 48 where the tumor is located, the peak and valley dose deferential of the parallel narrow is lost. The intensity and the size of each split segments of the proton beam are adjusted with DC vertical deflecting dipole magnet 28.

Interlaced, cross firing multiple simultaneous proton beam brought to the tumor site and its beam-beam elastic and none-elastic collision induced, higher secondary radiation including its positron and gamma radiation covering larger tumor volume even with lower energy proton as described here is a more efficient method of affordable parallel proton microbeam radiation therapy and radiosurgery that facilitates treating a tumor at high dose and dose rate in a few seconds without much toxicity to the normal tissue. With multiple simultaneous proton beams combined with bam-beam elastic interaction, the dose and dose rate of the β+-decay and γ emission increases significantly. With increased beam-beam inelastic collisions in tissue with multiple simultaneous proton beams, more and more nuclear disintegration in tissue is produced. It generates more locally absorbed nuclear fragments and antiprotons. Antiproton adds to the depth of the Brag peak; (109). With locally deposited γ emission energies in the range of 0.6 to 1 MeV is thus increased. It enables high dose and dose rate proton radiation therapy even with 7-30 MeV if its Brag peak depth can be brought close to the tumor site. The additive dose and dose rate of two simultaneous beams from two separate accelerators, both exposing the isocentric tumor simultaneously is twice the dose and dose rate from a single accelerator. Hence, in addition to all other radiobiological advantages of treating a tumor including those from the antiprotons from beam-on beam collision, the effective dose and dose rate of this interlaced two simultaneous beams reduces the time to treat a tumor to half than if the tumor were treated with one single accelerator. Proton beam has no exit dose. The peak and valley principles of the proton narrow beam radiation therapy also spare the normal tissue from radiation damages.

Figure 2B:
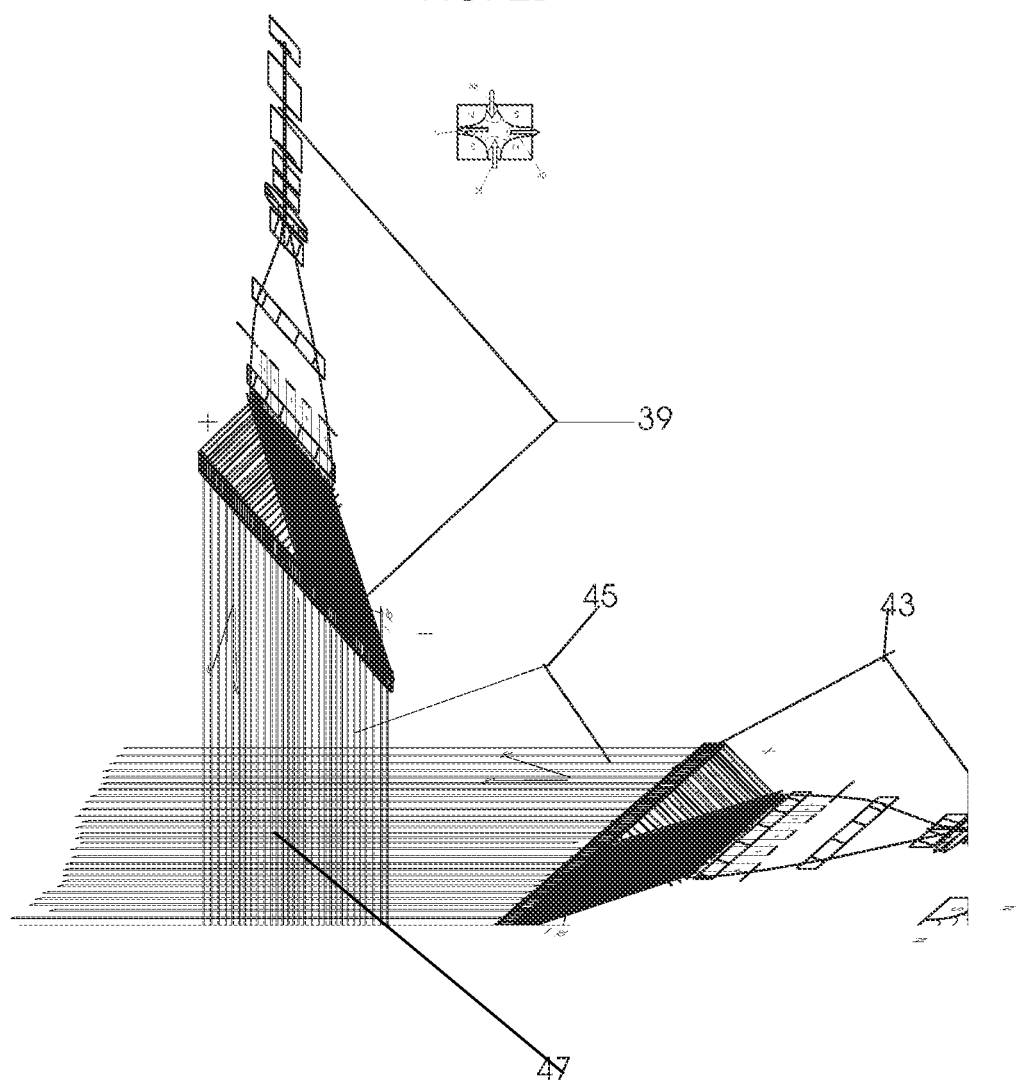

FIG. 2B is another illustration of interlacing proton parallel narrow beams that is shown in FIG. 2A but with the accelerators turned slightly to illustrate the interlacing beam-beam interaction as each beamlets of one accelerator hits the opposing beamlets of another accelerator. Otherwise, all the descriptions are the same as for those described under FIG. 2A. The narrow proton beam 45 from accelerator system 1, Reference number 39 interlaces with narrow proton beam 45 accelerator systems 2, Reference number 43 which forms the isocentric interlaced beams 47. In this FIG. 2B such slight turning of the accelerator systems is used to show the beam on beam interaction at the isocentric interlaced beams in a better perspective view than that is in FIG. 2A.

FIG. 3 Illustrates splitting and bending of a low μA proton beam to right (in FIG. 3 the bottom) and to left (in FIG. 3, the upper) and their transport to two numerous simultaneous parallel narrow proton beams generating systems. The proton beam exiting from the accelerator 8 is bent and split into two separate beams. The beam splitting quadruple magnet 52 and the beam splitting and switching magnet 54 are shown as switching the split and bent beams to right and to left. The split and bent to right beam 56 is focused by the right focusing magnet 60 and it travels through the beam transport system 70B. The split and bent to left beam 58 is focused by the left focusing magnet 62 and it travels through the beam transport system 70C. These beams are bent by right 45-degree bending magnet 64 and left 45-degree bending magnet 66. They are focused by the right focusing magnets 68 and the left focusing magnet 70. The right 15-degree beam switching bipolar magnet 72 switches the beam to a 15-degree angle divergence in the right side. The left 15-degree beam switching bipolar magnet 74 switches the beam to a 15-degree angle divergence in the left side. The split and bent to right beam 56 is made to make a 45° bend by bending the beam by the right 15-degree beam switching bipolar magnet 72. The split and bent to left beam 58 is made to make a 45° bend by bending the beam by the left 15-degree beam switching bipolar magnet 74. It is then made to travel towards the parallel beam generating systems by the beam steering system magnets consisting of 76, 80 and 84 on the right side and by, 78, 82 and 86 in the left side. The 45-degree right bending magnet 76 bends the beam to 45-degrees. The right split and bent beam 88 is thus made to travel towards the right entrance port 90 (in FIG. 4) of the right parallel beams generating system 91 (in FIG. 4). The 45-degree left bending magnet 78 bends the beam to 45-degrees towards the left entrance port 92 (in FIG. 4) of the left parallel beam generating system 94 (in FIG. 4). The right quadrupole focusing magnet 80 and the left quadrupole focusing magnet 82 and the right 45-degree bending magnet 84 and the left 45-degree bending magnet 86 bends the right and left split beam to 90-degrees. The right 90-degree bent beam 88 enters the right parallel beam generating system 91 through its right entrance port for right split and bent beam 90 (in FIG. 4). Also, as shown in FIG. 4, the split and bent to right beam 56 travels through the right beamline 96 towards the right parallel beam generating system 91 (in FIG. 4) and the split and bent to left beam 58 travels through the left beamline 98 towards the left parallel beam generating system 94 (in FIG. 4).

FIG. 4 illustrates a dual narrow proton beam system for radiation therapy as in FIG. 2 but with a single set of radiofrequency accelerator combined with a drift tube accelerator as the proton beam source and its proton beam as split into two and one of the multiple simultaneous parallel narrow proton beam generating system is placed at 0-degree and the other is paced at 90-degree and their parallel narrow beams interlacing at the isocenter that generates quasi proton-proton interaction and quasi antiproton for narrow proton beam radiation therapy with minimal or no long term toxicity to normal tissue. The proton beam exiting from the accelerator 8 and under control of the precautionary beam stop 12, dose monitor 14, collimator 16 and defocusing quadrupole magnet 18 is bent and split into two separate beams. The split beam's transport to right parallel beam generating system 91 and to left parallel beam generating system 94 by right beam transport systems 96 and left beam transport system 98 are described under FIG. 3. The split and bent beam from the defocusing quadrupole magnet 18 of the right parallel beam generating system 91 and the split and bent beam from the defocusing quadrupole magnet 18 of the right parallel beam generating system 94 are processed to generate multiple parallel micro or nanobeam with peak dose 34 and valley dose 36 as described under FIG. 1 and FIG. 2. The proton beam entering the defocusing quadrupole magnet 18 is checked and controlled by the precautionary beam stop 12, dose monitor 14, and collimator 16 and defocused by the defocusing quadrupole magnet 18. It is processed to generate multiple simultaneous parallel micro or nanobeam with peak dose 34 and valley dose 36 with right parallel beam generating system 91 and left parallel beam generating system 94. Their narrow parallel beams from 0-degree and 90-degree meets at the isocenter 48 as cross firing beams and forms a high dose rate field with the interlaced beams 46. The isocentric tumor 50 is treated with collimation to cover the treatment volume. The additive dose and dose rate of two simultaneous beams from two separate accelerators, both exposing the isocentric tumor simultaneously is twice the dose and dose rate from a single accelerator. Hence, in addition to all other radiobiological advantages of treating a tumor including those from the antiprotons from beam-on beam collision, the effective dose and dose rate of this interlaced two simultaneous beams reduces the time to treat a tumor to half than if the tumor were treated with one single accelerator. Proton beam has no exit dose. The peak and valley principles of the microbeam radiation therapy also spare the normal tissue from radiation damages.

FIG. 5 shows a nested high voltage accelerator combined with a radiofrequency accelerator as the proton beam source and generating numerous simultaneous parallel narrow proton beams for proton radiation therapy with minimal or no long term toxicity to normal tissue. In this instance, the lower energy proton beam is generated in the ion source 100 and injected into a compact nested high voltage DC accelerator (NHVDCA) system 102. As the negatively charged ions 104A from the ion source 100 passes through the first half of the NHVDCA 102 and a thin stripping foil 105, the negatively charged ion is converted into positively charged ions as is known with tandem accelerator technologies and that is incorporated into a nested high voltage DC accelerator (NHVDCA) system (120, 121). Size of such a 30 inch long and 12 inches wide tandem accelerator (128) can be further reduced to make smaller tandem accelerator incorporated nested high voltage accelerator for its use with a radiofrequency accelerator as the proton beam generating source in this invention. The positively charged and accelerated ions are injected into a radiofrequency accelerator 106 in which the positively charged ions are accelerated and are converted back to back to negatively charged ions 104C. The RFQ accelerated negative polarity proton beam 108 is then processed as the proton beam 10 processing shown in FIG. 1, FIG. 2 and FIG. 4. In this instance, the proton beam 108 passes by a beam stopper 12 that serves as an emergency beam stopper when needed and a dose monitor 14 and the beam aperture collimating collimator 16 into a defocusing in one plane and focusing in another plane quadrupole magnet 18 which spreads out the proton beam in one plane and focuses it in another plane. The insert shows the quadrupole magnet with converging magnetic field in one plane 38 and the diverging magnetic field in another plane 40 as arranged symmetrically about the beam axis. The quadrupole magnet 18 with converging magnetic field in one plane 38 which focuses the proton beam and the diverging magnetic field in another plane 40 defocuses the proton beam. Thus the proton beam is spread out in one plane and focused in another plane. The one plane defocused and in another plane focused multiple pulse negatively charged proton beam 20 is injected into a defocusing, focusing and after beam split beam size controlling magnet 22. The split beam's size controlling with this magnet is used to size the microbeam and nanobeam's size and spacing for peak and valley dose differential based microbeam and nanobeam, 100 to several thousands Gy flash radiation therapy without long term toxicity to normal tissue. This beam, deflected in one direction and focused in another is then passed through a stripper grid 24 that generates alternating positively and negatively charged beam segments 26. This proton beam with alternate positively and negatively a charge segment is passed through a deflection magnet with DC vertical dipole field 28. According to the Lawrence law of force, the positively charged proton beamlets deflects to the left 30 and the negatively charged proton beamlets deflects to the right 32 with amount of beamlets separation dependent on the strength of dipole field. It generates sets of numerous simultaneous parallel narrow proton beams segments. With interlaced narrow parallel proton beams and simultaneously treating a tumor from different angles sterilizes the tumor and its cancer stem cells without causing much long term toxicity to normal cells. It exposes the tumor antigens that induce tumor autoimmunity against a patient's cancer. Since it is a single fraction radiation therapy, it does not induce adaptive resistance to radiation therapy as it can be with daily fractionated radiation therapy that lasts for eight to ten weeks.

FIG. 6 illustrates interlacing beams from two sets of nested high voltage accelerator combined with a radiofrequency accelerator as the proton beam source and generating numerous simultaneous parallel narrow proton beams and one of the multiple simultaneous parallel narrow proton beam generating system is placed at 0-degree and the other is paced at 90-degree and their parallel narrow beams interlacing at the isocenter that generates quasi proton-proton interaction and quasi antiproton for narrow proton beam radiation therapy with minimal or no long term toxicity to normal tissue. Except for the difference in the proton beam generating systems, in this instance with two sets of compact nested high voltage DC accelerator (NHVDCA) system 102 combined with two sets of radiofrequency accelerators 106 than those shown in FIG. 2, in which the proton beams are generated with compact radiofrequency accelerators 6 and a drift tube accelerators 8 as the proton beam sources, all other construction features are the same as in FIG. 2. The additive dose and dose rate of two simultaneous beams from two separate accelerators, both exposing the isocentric tumor simultaneously is twice the dose and dose rate from a single accelerator. Hence, in addition to all other radiobiological advantages of treating a tumor including those from the antiprotons from beam-on beam collision, the effective dose and dose rate of this interlaced two simultaneous beams reduces the time to treat a tumor to half than if the tumor were treated with one single accelerator. Proton beam has no exit dose. The peak and alley dose difference between two parallel narrow beams also reduce radiation to normal tissue.

FIG. 7 shows a dual multiple simultaneous narrow proton beam system for radiation therapy as in FIG. 6 but with a single set of nested high voltage accelerator combined with a radiofrequency accelerator as the proton beam source and generating numerous simultaneous parallel narrow proton beams by splitting the accelerator generated proton beam and one such system is placed at 0-degree and the other at 90-degree and their parallel narrow proton beams interlacing at the isocentric tumor that generates quasi proton-proton interaction and quasi antiprotons and treats the tumor with minimal or no long term toxicity to normal tissue. Except for the difference in the proton beam generating systems, in this instance with two sets of compact nested high voltage DC accelerator (NHVDCA) system 102 combined with two sets of radiofrequency accelerators 106 than those shown in FIG. 4, in which the proton beams are generated with compact radiofrequency accelerators 6 and drift tube accelerators 8 as the proton beam sources, all other construction features and the beam handling are identical to those described under FIG. 4. The methods of transport of split beam 56 and split beam 58 are described under FIG. 3. The additive dose and dose rate of two simultaneous interlacing beams from two separate accelerators, both exposing the isocentric tumor simultaneously is twice the dose and dose rate from a single accelerator. Hence, in addition to all other radiobiological advantages of treating a tumor including those from the antiprotons from beam-on beam collision, the effective dose and dose rate of this interlaced two simultaneous beams reduces the time to treat a tumor to half than if the tumor were treated with one single accelerator. Proton beam has no exit dose. The peak and valley dose difference in between two narrow beams also spare the normal tissue from much radiation damages.

FIG. 8 illustrates a dual proton beam system for radiation therapy as in FIG. 7 but with proton beam from a synchrotron, cyclotron or synchro-cyclotron as the main proton beam source and splitting this proton beam into two and transporting them to two multiple parallel narrow proton beam generating systems and one such system is placed at 0-degree and the other at 90-degree and their interlaced parallel narrow beams exposing an isocenter tumor that generates quasi proton-proton interaction and quasi antiprotons for proton beam radiation therapy with minimal or no long term toxicity to normal tissue. Except for the difference in the proton beam generating systems, in this instance the proton beam source is the negatively charged proton beam from the beam line of a larger proton accelerator 110 than those shown in FIG. 4, in which the proton beams are generated with compact radiofrequency accelerators 6 and a drift tube accelerators 8 as the proton beam sources and also as in FIG. 7 in which the proton beams are generated with two sets of compact nested high voltage DC accelerator (NHVDCA) system 102 combined with two sets of radiofrequency accelerators 106, all other construction features and the beam handling systems are identical to those described under FIG. 4 and FIG. 7. The methods of transport of split beam 56 and split beam 58 are described under FIG. 3. The additive dose and dose rate of two simultaneous beams from two separate accelerators, both exposing the isocentric tumor simultaneously is twice the dose and dose rate from a single accelerator. Hence, in addition to all other radiobiological advantages of treating a tumor with interlaced beams including those from the antiprotons from beam-on beam collision, the effective dose and dose rate of these two interlaced simultaneous beams reduces the time to treat a tumor to half than if the tumor were treated with one single accelerator. Proton beam has no exit dose. The peak and valley principles of the narrow proton beam radiation therapy also spare the normal tissue from most of the radiation damages.

FIG. 9A-1 illustrates an enlarged view of a double lumen needle with titanium/D2 target that is used to generate higher MeV proton beam to transport the proton beam to a desired depth in tissue that is treated. The methods of proton beam generation at the end of a stainless steel tube-needle deposited with deuterated titanium (TiD2) target for ion induced nuclear radiation therapy (INRT)-(111) and in U.S. Pat. No. 5,547,454 (122). INRT with alternating phase focusing channel for low energy proton therapy was also proposed (112). Likewise fabrication of a double shell target was described in a DOE report by Steinman et al (123). However, they do not teach ion induced nuclear reaction proton radiation therapy with controlled temperature that is tolerable to a patient.

The double lumen proton target tube needle 112 (double lumen needle 112) has an inner lumen 114 and an outer lumen 116. The inner lumen 114 is a vacuum glass tube that has 200 µm diameters and 3 µm thick, the outer lumen 116 is also a glass capillary tube with 400 µm diameter and 3 µm thick. The outer lumen is filled with a coolant 118, like with ice cold water that is filled through the fluid inlet 120 while the air in the outer lumen is let to pass through the air outlet 122. After filling the outer lumen with coolant 118, the coolant fluid inlet 120 and air outlet 122 are closed with coolant fluid inlet and outlet closure screw 124 and air outlet and inlet closure screw 126. The inner lumen and the outer lumen are connected with 50 μm thick heat conducting tungsten wire 128 that is fixed on to the outer wall of the inner lumen 130 and the outer wall of the outer lumen 132 by inner lumen holding and heat conducting tungsten wire 134 and the outer lumen holding and heat conducting wire 136. The heat generated by the millisecond to a few seconds duration ion induced nuclear reaction in the deuterated titanium target 138 is conducted away to the coolant 118 so that the tissue that is radiated by the ion induced nuclear reaction is not over heated and it will not cause greater discomfort to the patient. The inner lumen 114 and the outer lumen 116 are constructed with glass or with stainless steel.

The methods of fabrication of needles with targets at its tip for d(3He,p)3He nuclear reaction was described before (111, 122). Lately in 2010, a 1 μm thick deuterium titanium target for neutron production was described (124). The collision of 650 keV, 1 microamp incident d(3He,p) beam from a RFQ accelerator on to a TiD2 target produces He and proton beams of varying energies ranging from 13.6 MeV to 17.4 MeV (125) with a dose rate of 1 Gy/s (126). This dose rate can be increased with higher than 1 microamp beam with good control of the temperature rise from the d(3He, p)3He nuclear reaction with the aid of a coolant 118 in the outer lumen 116 as in this invention. INRT with needle increases the temperature in normal tissue outside the treatment volume to about 12 degree centigrade when 70 Gy is administered in about 100 seconds at a dose rate of 1Gy/s (70% efficiency) with 1 microamp beam intensity (127). It brings the temperature to the normal tissue adjacent to the treatment area to about 49 degree centigrade. It damages the normal tissue outside the tumor permanently and or cause severe necrosis. With double shell proton target tube-needles 112 (double lumen needle 112), the heat generated by the d(3He,p)3He nuclear reaction is dissipated by the coolant 118 in the outer lumen 116. It brings the temperature to the normal tissue adjacent to the radiated tumor almost to normal body temperature of 37.5 digress. The base of the evacuated inner lumen 114 is fitted with a vacuum fitting 142 and to a vacuum flange 144 which is fitted with a vacuum fitting O-ring seal 146. When the needle is in use, the vacuum flange 144 is bolted onto the accelerator beam line fitting 148 equipped with a standard beam steering and alignment system that delivers the incoming ion beam to the respective needles as it is programmed for a particular treatment and with a select number of double shell proton target tube-needles 112 (double lumen needle 112). The collision of the $^3$H-ion beam with the TiD2 target and its interactions emits the proton-spray beam 150 in the energy range of 13.6 to 17.4 MeV (125). The proton-spray beam exits through the window 152 in front of the target 138. The double shell proton target tube-needle 112 is inserted into the tissue that is treated with the aid of the sharp cone 154 at the tip of the double shell proton target tube-needle 112.

Such double shell needles of varying lengths and with the target at the needle tip is inserted into a tumor as in an array of needles, adjusted according to the depth and location of the tumor and the site within the tumor that is radiated. Multiple simultaneous proton-spray beams emitted from the targets of this array of needles radiates multiple segments of a tumor simultaneously. With simultaneous parallel microbeam or nanobeams from an array of such a system facilitates curative radiosurgery as a single fraction treatment with minimal or no long term toxicity to normal tissue even at very high dose of 100 to 1,000 Gy. Such safe high, 100-700 Gy parallel microbeam radiation therapy using parallel microbeam from synchrotron is proven to be very efficient to cure even the most radioresistant glioblastoma multiforme with minimal or no long term toxicity to normal tissue. In this instance, such high dose is not needed. In this invention, the radiation therapy is based on proton-proton interaction with proton spray beams from opposing simultaneous beams from needles 112. It is further discussed in the LET and RBE section. Because of its Gray-equivalent factor compared to conventional radiation therapy with photon is even better than those for neutron, only about one third or less of the total dose is required for curative treatment of a tumor. Hence it does not need high dose of radiation even with broad beams as was described before (127). This is an entirely different, proton-proton interaction, proton-spray radiation therapy. In summary, highly efficient, proton-proton milliseconds to second duration radiation therapy is administered with this needle-needle proton spray radiation therapy system of this invention.

FIG. 9A-2 illustrates an enlarged view of a double lumen needle with titanium/D2 target that is used to generate higher MeV proton beam to transport the proton beam to a desired depth in tissue that is treated as in FIG. 9A-1 but with added coolant or chemotherapy ionization and protonspray. It is identical to the double lumen needle with titanium/D2 target that is used to generate higher MeV proton beam to transport the proton beam to a desired depth in tissue that is treated as in FIG. 9A-1 except the coolant or the chemotherapeutic is sprayed through the nozzle attached at the bottom of the needle is used to create sprays like sprays generated with Taylor cones. Through the nozzle-Taylor cone attached to the outer lumen 163, the evaporated cooler liquid or the chemotherapeutic is sprayed onto the proton spray 150. It generates the ionized coolant or ionized chemotherapeutic bound proton spray from outer lumen 186. The high pressure helium gas 172 pushes the chemotherapeutic and or the coolant down and brings them closer to the deuterium/titanium target which gets overheated by the d(3He,p)3He nuclear reaction. The helium compressed chemotherapeutics and or the coolant is heated and evaporated by the heat generated by the d(3He,p)3He nuclear reaction and sprayed onto the proton beam generating ionized chemotherapeutic and or coolant. The collision of the $^3$H-ion beam with the TiD2 target emits the proton-spray beam 150 in the energy range of 13.6 to 17.4 MeV (125). The proton-spray beam exits through the window 152 in front of the target 138. The double lumen proton target tube needle 112 is inserted into the tissue that is treated with the aid of the sharp cone 154 at the tip of the double lumen proton target tube-needle 112 for combined ionized chemotherapy and proton radiation therapy.

The collision reaction products of vaporized water molecule and proton includes transformation of the proton as an $H^+$ or as a neutral H after a single electron capture or as a $H^-$ after double electron capture (138). The collisional interaction of proton with vaporized water and uracil was investigated before (139). It is an important example for the proton spray radiation therapy and proton spray chemotherapy combined microbeam and nanobeam radiation therapy. The products of proton impact ionization of water includes mostly $H^+$, $H_2O^+_2$, and $OH^+$ and to a lesser amounts of $H^+_2$, $O^+_2$, $N^+$, $N^+_2$, $O^+_2$ (131). Similar ions at the same concentration are also produced by monochromatic electron collision with evaporated water molecules (132). There are uracil analogues containing chemotherapeutics. The uracil molecules ($C4H4N2O^+_2$) are fragmented by its collision with proton and monochromatic electron as ionized fragmented larger and smaller uracil molecules (C3H3NO+ and $CNO^+$) with varying energies are produced (133). In this invention proton spray or electron sprays chemotherapy described. In the case of electron spray, the monochromatic electron source for electron spray is much simpler to make (134). They ions add to the local cytotoxic effects of both radiation and chemotherapy.

The monochromatic electron spray (129) has similarities to electrospray (135). Electrosprayed bone marrow stem cells (BMSC) at 7.5 KeV retain its ability to survive and proliferate (136). However, it was also reported that at higher KeV electrospray, the BMSC become less viable (136). Still electrospray is not an efficient cytotoxic cancer treatment. Human lymphocytes electrosprayed at 1-30 KeV (maximum current 4 mA) did not show any cytogenetic or physiological changes (137, 139 139). In this study, the electrosprayed polydimethylsiloxane (140) did not show cytogenetic or physiological changes in the lymphocytes indicating electrospray with 1-30 KeV, up to 4 mA did not generate ionized fragments of compounds so electrosprayed. Hence there is no ionized radiation cytotoxicity to cells that are electrosprayed. On the contrary, proton sprayed uracil like molecules generates ionized fragments (133). Inelastic interaction of ionized particles causes nuclear fragmentation in the cells and high levels of cytotoxicity.

FIG. 9B shows three sets of varying lengths narrow double lumen needles with titanium/D2 target emitting proton-spray beams, in each sets, one from 0-degree and the other from 90 degrees that generates proton-proton-spray beams. Details of the proton beam generating needle with Ti/D2 target is described under FIG. 9A in which for the purpose of description, an enlarged figure of the needle was used. All the descriptions on the needle in FIG. 9A applies for the needles shown in this FIG. 9B. These sets of needles are illustrated as with varying lengths. In SET I the needles are longer than in SET II and III. In SET II, the needle at 90 degree is longer than the needle from 0 degree. Likewise in SET III, the needle from 0-degree is longer than the needle from 90 degree. By adjusting the length of the needles, their beam-beam proton spray interaction takes places within the intended region of the tumor. Thus it illustrates the adaptable, depth dose adjusted implant of the needles to achieve the desired isodose within the tumor. Also shown is the proton-spray beam-beam interaction. Beams from the needle at 0 degree and beams from the needle at 90 degrees collide and generate the proton-proton beam spray 156.

As described earlier, relatively low energy proton beam interaction in tissue generates low energy neutrons by nuclear reactions. These relatively low energy neutrons produce recoil protons by elastic collisions with hydrogen atoms. At the Brag peak region, the primary protons are slowed down and the recoil secondary protons become more dominant behind the distal end of the Brag peak (100). At about the Brag peak area, 80-90% of the absorbed dose is from the slowed down primary proton and about 5-20% absorbed dose is from secondary protons. Behind the distal endpoint of the Brag peak, the secondary proton production by $^1$H (n, p) reaction dominates. It contributes 70% of the absorbed dose at this point, behind the distal endpoint of the Brag peak (100). Non-elastic nuclear interactions of proton also produce positron in sufficient quantity that is used for proton dosimetry by positron emission tomography (PET) (101). Such positrons are produced from decay of $^{11}$C, $^{13}$N, and $^{15}$O mostly along the path of the proton beam. With increased beam-beam inelastic collisions in tissue with multiple simultaneous proton beams, more and more nuclear disintegration in tissue is produced. It generates more locally absorbed nuclear fragments and antiprotons. Antiproton adds to the depth of the Brag peak; (109).

FIG. 9C-1 illustrates an enlarged view of a triple lumen needle with titanium/D2 target that is used for combined ionized proton spay chemotherapy and microbeam-nanobeam proton beam radiation therapy. The triple lumen proton target tube needle 180 is identical to double lumen proton target needle 112 but with an added outside lumen 160 which makes the double lumen needle's 112 outside lumen 116 as the intermediate lumen in the triple lumen needle 180. Thus, its inner lumen 114, the intermediate lumen 158 and the outer lumen 160 makes it a triple lumen needle 180. The inner lumen 114 is a vacuum glass tube that has 200 μm diameter and 3 μm thick. The intermediate lumen 158 and the outer lumen 160 are also made of glass capillary tube with 400 μm diameter and 3 μm thick. The intermediate lumen is filled with a coolant 118, like with ice cold water which is filled through the fluid inlet 120 while the air in the outer lumen is let to pass through the air outlet 122. After filling the outer lumen with coolant 118, the coolant fluid inlet 120 and air outlet 122 are closed with coolant fluid inlet and outlet closure screw 124 and air outlet and inlet closure screw 126. The inner lumen 114, the intermediate lumen 158 and the outer lumen 160 are connected with 50 μm thick heat conducting tungsten wire 128 that is fixed on to the outer walls of the inner lumens 130, to the outer wall of the intermediate lumen 131 and to the outer wall of the outer lumen 132 by inner lumen holding and heat conducting tungsten wire 134, intermediate lumen holding and heat conducting tungsten wire 170 and the outer lumen holding and heat conducting wire 136. The heat generated by the millisecond to a few seconds duration ion induced nuclear reaction in the deuterated titanium target 138 is conducted away to the coolant 118 so that the tissue that is radiated by the ion induced nuclear reaction is not over heated and it will not cause greater discomfort to the patient. The inner lumen 114, the intermediate lumen 158 and the triple lumen needle's outer lumen 160 are constructed with glass or with stainless steel.

The intermediate lumen with coolant 158 moderates the higher temperature heat generated by the d(3He,p)3He nuclear reaction. The coolant 158 could be replaced with a chemotherapeutic for ionized chemotherapy and also could be placed under helium gas pressure. This coolant or the chemotherapeutic is sprayed through the nozzle to create a Taylor cone. Through this nozzle-Taylor cone attached to intermediate lumen 159 evaporated cooler liquid or the chemotherapeutic is sprayed onto the proton spray 150. It generates the ionized coolant or the ionized chemotherapeutic bound proton spray from intermediate lumen 161. Likewise, the chemotherapeutic in the outer lumen 174 is evaporated and sprayed through the nozzle-Taylor cone attached to outer lumen 163. It generates ionized chemotherapeutic bound proton spray from the outer lumen. The high pressure helium gas 172 pushes the chemotherapeutic and or the coolant down and brings them closer to the deuterium/titanium target which gets overheated by the d(3He,p)3He nuclear reaction. The helium compressed chemotherapeutics and or the coolant is heated and evaporated by the heat generated by the d(3He,p)3He nuclear reaction and sprayed onto the proton beam generating ionized chemotherapeutic and or coolant. The collision of the $^3$H-ion beam with the TiD2 target emits the proton-spray beam 150 in the energy range of 13.6 to 17.4 MeV (125). The proton-spray beam exits through the window 152 in front of the target 138. The triple lumen proton target tube needle 180 is inserted into the tissue that is treated with the aid of the sharp cone 154 at the tip of the triple lumen proton target tube-needle 180 for combined ionized chemotherapy and proton radiation therapy.

As described under FIG. 9A-2, the radiation therapy with collision reaction products of vaporized water molecule (138) and the collisional interaction of proton with vaporized uracil and its ionized nuclear fragments (139) is further improved with a triple lumen needle system as shown in this FIG.C-1.

FIG. 9C-2 illustrates an enlarged view of a triple lumen needle with titanium/D2 target that is used for combined ionized electrospray plus proton spay chemotherapy and microbeam-nanobeam proton beam radiation therapy. It is identical to the triple lumen needle with titanium/D2 target for combined ionized electrospray plus proton spay chemotherapy and microbeam-nanobeam proton radiation therapy described under FIG. 9C1 except its sharp cone 154 is equipped with microelectrodes for bioelectrospray of the vaporized-gas chemotherapeutics and or coolant for combined ionized electrospray plus proton spay chemotherapy and microbeam-nanobeam proton beam radiation therapy. As described in section 35, Proton Spray Ionization Radiation Therapy Compared with Electrospray, electrospray alone has no tumor cell killing capability. However, it enhances the ionization and cytotoxicity of proton spray microbeam and nanobeam radiation therapy.

FIG. 9C-3 illustrates an enlarged view of a triple lumen needle with titanium/D2 target that is used for proton spay neutron capture radiation therapy with gamma rays and Auger electrons from Gadolinium neutron-capture for Gadolinium neutron-capture therapy (Gd-NCT) and chemotherapy with ionized fragments of gadolinium by the proton spray. Neutron capture radiation therapy with gamma rays and Auger electrons from Gadolinium neutron-capture for Gadolinium neutron-capture therapy (Gd-NCT) was described before (141). The triple lumen needle 180 is identical to that is described under FIG. 9C-1. In this instance, it is used for proton spay neutron capture radiation therapy and ionized chemotherapy like in a modified version of boron neutron capture (BCNT) or Gadolinium neutron capture therapy (Gd NCT) but combined with ionized cytotoxic drug chemotherapy. The inner lumen 114 is a vacuum glass tube through which the RFQ accelerated beam pass through to the Ti/D2 target. The intermediate lumen 158-*b* is filled with a lithium compound like lithium chloride 188. The outer lumen 160-*b* is filled with a gadolinium compound 190. The lithium compound 158-*b* is filled through the fluid inlet 120-*b* or through the capillary inlet for reagent in intermediate lumen 192. The air in the intermediate lumen 158-*b* is let to pass through the air outlet 122. After filling the outer lumen with gadolinium compound 190, the fluid inlet 120-*b* and air outlet 122 are closed with fluid inlet and outlet and air outlet and inlet closure screw 126. Alternatively, the intermediate lumen is filled through the capillary inlet for reagent in intermediate lumen 192. The 50 µm thick heat conducting tungsten wire 128 that is fixed on to the outer walls of the inner lumens 130, to the outer wall of the intermediate lumen 131 and to the outer wall of the outer lumen 132 by inner lumen holding and heat conducting tungsten wire 134, intermediate lumen holding and heat conducting tungsten wire 170 and the outer lumen holding and heat conducting wire 136. The heat generated by the millisecond to a few seconds duration ion induced nuclear reaction in the deuterated titanium target 138 is conducted away to the liquid lithium compound 188 in the intermediate lumen 158-*b* and to the gadolinium compound 190 in the outer lumen 160-*b* so that the tissue that is radiated by the ion induced nuclear reaction is not over heated and it will not cause greater discomfort or burn to the patient. The inner lumen 114, the intermediate lumen 158 and the outer lumen 160-*b* of the triple lumen needle 180 are constructed with glass or with stainless steel.

The lithium compound 188 and the gadolinium compound 190 are sprayed through nozzles to create Taylor cones. Helium or nitrogen gas 172 is put into the intermediate lumen through the capillary inlet of the intermediate lumen 194. It pushes the liquid lithium compound 188 down. It brings the lithium compound closer to the deuterium/titanium target. The collision of the $^3$H-ion beam with the TiD2 target emits the proton-spray beam 150 with energy in the range of 13.6 to 17.4 MeV (125). The proton-spray beam exits through the window 152 in front of the target 138. The d(3He,p)3He nuclear reaction with the target T1/D2 generates heat that is conducted into the intermediate lumen with lithium compound 158-*b* by the heat conducting tungsten wires 128, 134 and 136. The heated, compressed and vaporized lithium compound is sprayed onto the proton spray 150 through the nozzle-Taylor cone attached to the intermediate lumen 159. This vaporized lithium compound spray 161-*b* interacts with proton spray 150 and generates the 7Li(p,n)7Be reaction. Ionized gadolinium compound spray's interaction with neutron and proton spray 199 generates gamma rays and Auger electrons for Gadolinium neutron-capture therapy (Gd-NCT).

The gadolinium compound 190 is filled through the gadolinium inlet 167 or through the capillary inlet for reagent in the outer lumen 194. The air in the outer lumen 160-*b* is let to pass through the helium or nitrogen gas inlet or outlet 162. After filling the outer lumen with gadolinium compound 190, through gadolinium inlet 167, the outer lumen with gadolinium 175 is closed with gadolinium inlet and outlet closure screw 169. The air outlet for the outer lumen 160-*b* is closed with the helium or nitrogen gas inlet and outlet closure screw 164. The gadolinium compound 190 in the outer lumen 160-*b* is sprayed through the nozzle attached to the outer lumen 196 that creates a Taylor cone. Helium or nitrogen gas 172 is put into the outer lumen holding gadolinium compound through the capillary inlet for the pressurizing gas 194 of the outer lumen 160-*b*. It pushes the liquid gadolinium compound 190 down. It brings the gadolinium compound 190 closer to the deuterium/titanium target. The d(3He,p)3He nuclear reaction with the target T1/D2 generates heat that is conducted into the intermediate lumen with lithium compound 158-*b* and the gadolinium compound 190 in the outer lumen 160-*b* by the heat conducting tungsten wires 128, 134 and 136. The heated, compressed and vaporized gadolinium compound 190 is sprayed onto the neutron generated by the proton-lithium interaction, 7Li(p,n)7Be, through the nozzle-Taylor cone attached to the outer lumen 196. The neutron reacts with gadolinium; $^{157}$Gd+nth (0.025 eV)→[$^{158}$Gd]→$^{158}$Gd+ γ+7.94 MeV. It thus releases gamma rays and Auger electrons for Gadolinium neutron-capture therapy (Gd-NCT). The proton spray onto the gadolinium compounds generates ionized fragments of gadolinium which serves as agents for ionized molecular chemotherapy.

FIG. 9C-4 is another illustration of an enlarged view of a triple lumen needle with titanium/D2 target that is used for proton spay boron neutron capture radiation therapy (psBNCT) with proton beam generated with a triple lumen capillary needle. The triple lumen structure and its working is identical to that described for the Gd NCT under FIG. 9C3. Here, the outer lumen is filled with a boron-10 containing compound instead a gadolinium compound. The interaction of proton spray with lithium as described under FIG. 9C-3 generates neutron which interacts with $^{10}$B that is sprayed onto it. The triple lumen needle is inserted into a tumor and this proton spray-boron neutron capture treatment is locally elicited which spares the normal tissue.

As described before, the inner lumen 114 is a vacuum glass tube through which the RFQ accelerated beam pass through to the Ti/D2 target. The intermediate lumen 158-$b$ is filled with a lithium compound like lithium chloride 188. The outer lumen 160-$c$ is filled with a $^{10}$B compound. The $^{10}$B compound 158-$b$ is filled through the fluid inlet 120-$b$ or through the capillary inlet for reagent in intermediate lumen 192. The air in the intermediate lumen 158-$b$ is let to pass through the air outlet 122. After filling the outer lumen with $^{10}$B compound 177, the fluid inlet 120-$b$ and air outlet 122 are closed with fluid inlet and outlet and air outlet and inlet closure screw 126. Alternatively, the intermediate lumen is filled through the capillary inlet for reagent in intermediate lumen 192. The 50 μm thick heat conducting tungsten wire 128 that is fixed on to the outer walls of the inner lumens 130, to the outer wall of the intermediate lumen 131 and to the outer wall of the outer lumen 132 by inner lumen holding and heat conducting tungsten wire 134, intermediate lumen holding and heat conducting tungsten wire 170 and the outer lumen holding and heat conducting wire 136. The heat generated by the millisecond to a few seconds duration ion induced nuclear reaction in the deuterated titanium target 138 is conducted away to the liquid lithium compound 188 in the intermediate lumen 158-$b$ and to the outer lumen with $^{10}$B compound 177 so that the tissue that is radiated by the ion induced nuclear reaction is not over heated and it will not cause greater discomfort or burn to the patient. The inner lumen 114, the intermediate lumen 158 and the outer lumen 160-$b$ of the triple lumen needle 180 are constructed with glass or with stainless steel.

The lithium compound 188 and the $^{10}$B compound 200 are sprayed through nozzles to create Taylor cone sprays. Helium or nitrogen gas 172 is put into the intermediate lumen through the capillary inlet of the intermediate lumen 194. It pushes the liquid lithium compound 188 down. It brings the lithium compound closer to the deuterium/titanium target. The collision of the $^3$H-ion beam with the TiD2 target emits the proton-spray beam 150 with energy in the range of 13.6 to 17.4 MeV (125). The proton-spray beam exits through the window 152 in front of the target 138. The d(3He,p)3He nuclear reaction with the target T1/D2 generates heat that is conducted into the intermediate lumen with lithium compound 158-$b$ by the heat conducting tungsten wires 128, 134 and 136. The heated, compressed and vaporized lithium compound is sprayed onto the proton spray 150 through the nozzle-Taylor cone attached to the intermediate lumen 159. It generates the 7Li(p,n)7Be reaction. Its neutron interacts with $^{10}$B.

The $^{10}$B compound 200 is filled through the $^{10}$B-compound inlet 202 or through the capillary inlet for reagent in the outer lumen 194. The air in the outer lumen 160-$c$ is let to pass through the helium or nitrogen gas inlet or outlet 162. After filling the outer lumen with $^{10}$B compound 200, through $^{10}$B inlet 202, the outer lumen with $^{10}$B compound 177 is closed with gadolinium inlet and outlet closure screw 171. The air outlet for the outer lumen 160-$c$ is closed with the helium or nitrogen gas inlet and outlet closure screw 164. The $^{10}$B compound 200 in the outer lumen 160-$c$ is sprayed through the nozzle attached to the outer lumen 196 that creates a Taylor cone spray. Helium or nitrogen gas 172 is put into the outer lumen holding $^{10}$B-compound 177 through the capillary inlet for the pressurizing gas 194 of the outer lumen 160-$c$. It pushes the $^{10}$B-compound 200 down. It brings the $^{10}$B-compound 190 closer to the deuterium/titanium target. The d(3He,p)3He nuclear reaction with the target T1/D2 generates heat that is conducted into the intermediate lumen with lithium compound 158-$b$ and the $^{10}$B-compound 200 in the outer lumen 160-$c$ by the heat conducting tungsten wires 128, 134 and 136. The heated, compressed and vaporized $^{10}$B-compound 204 is sprayed onto the neutron generated by the proton-lithium interaction, 7Li(p,n)7Be, through the nozzle-Taylor cone attached to the outer lumen 196. Ionized $^{10}$B-compound spray's interaction with neutron 206 generates a nuclear fission reaction. This classical nuclear fission reaction is used for clinical BNCT (142):

$^4$He+$^7$Li+2.79 MeV (6% of the interaction)

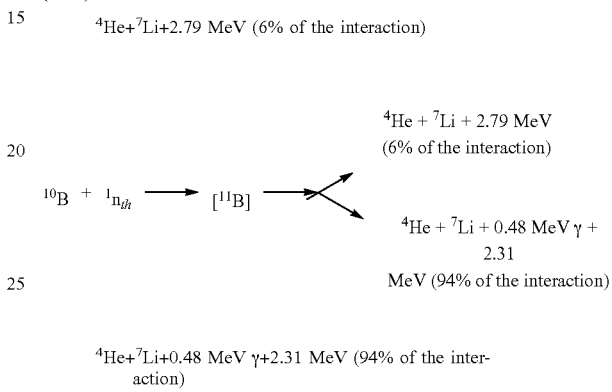

$^4$He+$^7$Li+0.48 MeV γ+2.31 MeV (94% of the interaction)

Here, both boron-neutron captures by thermal and epithermal neutrons take place. The epithermal neutron has higher depth dose characteristics. With proton spray BNCT (ppBNCT) with neutron source brought to the site of the tumor, the dose rate to the tumor at depth from all the components of this nuclear fission reaction, the $^{10}$B(n,α)$^7$Li, gamma radiation, $^{14}$N(n,p)$^{14}$C contributes to the tumor dose (142, FIGS. 66-2 and 3). These reaction products except for the gamma radiation have high LET. Hence, it has high RBE. Because of its Gray equivalent dose (GyEq) is much lower than the low LET radiation; about less than one third dose of a conventional low LET radiation, a much lower dose radiation is needed for tumor cure and control. One of the primary failures of the past BNCT in clinical practice was due to poor concentration of $^{10}$B at the tumor site. Intravenously or orally administered $^{10}$B do not reach in sufficient concentration at the tumor site. Hence the past BNCT were not very effective to cure or for long term control of a tumor. With the advantages of high LET ppBNCT and its GyEq of this invention by needle guided direct contact radiation to a tumor, minutes or seconds only duration radiosurgery without much toxicity to the normal tissue is made possible. It cures and controls more tumors. It was possible with past BNCT for cancer.

FIG. 9D illustrates an incoming vertical proton microbeam from 0-degree and an incoming horizontal microbeam from 90 degree with their respective isodose before and after beam-beam collision that generates elastic and inelastic proton-proton interaction producing neutron, secondary protons, gamma rays and antiprotons. The vertical beam 51 form 0 degree with its isodose 53 and the horizontal beam 55 from 90 degree with its isodose 57 collide. It generates elastic and inelastic proton-proton collision reaction products 61 and the combined isodose of vertical and horizontal proton beams 59.

When the relatively low energy single proton beam's interaction in tissue, either from 0-degree or from 90 degree as shown in this FIG. 9D occurs, it generates low energy neutrons by nuclear reactions. These relatively low energy neutrons produce recoil protons by elastic collisions with hydrogen atoms. At the Brag peak region, the primary protons are slowed down and the recoil secondary protons become more dominant behind the distal end of the Brag peak (100). At about the Brag peak area, 80-90% of the absorbed dose is from the slowed down primary proton and about 5-20% of the absorbed dose is from secondary protons. Behind the distal endpoint of the Brag peak, the secondary proton production by $^1$H (n, p) reaction dominates. It contributes 70% of the absorbed dose at this point, behind the distal endpoint of the Brag peak (100). Non-elastic nuclear interactions of proton also produce positron in sufficient quantity that is used for proton dosimetry by positron emission tomography (PET) (101). Such positrons are produced from decay of $^{11}$C, $^{13}$N, and $^{15}$O.

The low energy, single beam proton radiation therapy, the reaction product β+-decay and γ emission with energies ranging from 0.6 to 1 MeV is the most frequent reaction. The reaction product in tissue generated by lower energy, single proton beam radiation has only sparsely ionizing radiation and it reaches only a few millimeters away from its source. Hence its dose and dose rate is very low in tissue. However, with multiple simultaneous proton beams combined with bam-beam elastic interaction as shown in this FIG. 9D the dose and dose rate of this β+-decay and γ emission increases significantly. With increased beam-beam inelastic collisions in tissue with multiple simultaneous proton beams, more and more nuclear disintegration in tissue is produced. It generates more locally absorbed nuclear fragments and antiprotons. Antiproton adds to the depth of the Brag peak; (109) It enables high dose and dose rate proton radiation therapy even with 7-30 MeV if its Brag peak depth can be brought to correlate with the depth of the tumor site. It is accomplished with INRT-needles. Needle tip-µINRT is capable of delivering 15 Gy in 20 seconds to about 5 mm tumor volume (113, 114). In this invention, higher intensity of radiation and larger tumor volume coverage is achieved with interlaced, cross firing multiple simultaneous proton beam needle implant INRT as shown in FIG. 9E. Its beam-beam elastic and none-elastic collision induced, higher secondary radiation including its positron, neutron, secondary protons, nuclear fragments and ions, antiprotons, gamma radiation and ionization of water molecules is a far advanced conformal proton beam radiation therapy with minimal or no toxicities to normal tissue. These principles of interlaced multiple simultaneous proton beam radiation therapy is also adaptable for higher energy proton beam radiation therapy. Treating the entire treatment volume with interlaced multiple simultaneous proton beams as in this invention is an efficient method of conformal radiation therapy. It generates locally confined neutron, secondary protons, γ rays and positron that treat the entire tumor volume.

FIG. 9E shows parallel groups of selected microbeam or nanobeams from accelerator-1 at o-degree and with microbeam or nanobeams from accelerator-2 at 90-degree and their bam-beam collision generating ionization, neutron, secondary protons, gamma rays and antiprotons. It illustrates controlled beam-beam collision by beams from accelerator 42 at 0-degree and accelerator 44 at 90 degree shown in FIG. 2A. To illustrate the beams from 0-degree and 90 degrees, the accelerator 42 is slightly turned and shown as accelerator 39. Likewise, the accelerator 44 is slightly turned and shown as accelerator 43 in FIG. 2B. Their bam-beam collision within the isocentric tumor 50 generates combined isodose of vertical and horizontal proton beams and their elastic and inelastic reaction products 59. They generate neutrons, secondary protons, gamma rays and antiprotons. They are mostly confined within the tumor. This simultaneous beam's beam-beam collisional interaction within a tumor and their products facilitates high dose and dose rate conformal radiation therapy to the entire tumor volume. This beam-beam collisional interaction and their products are described in detail under FIG. 9D and in specification, section 33.

FIG. 9F shows the comparative depth dose and Brag-Peaks of the 17.4 MeV proton beam, its INRT needle guided depth dose and Brag-Peak and the combined Brag Peak of the INRT needle guided multiple simultaneous proton beams and proton spray beam's and their beam-on-beam collision's reaction products and antiprotons. The range of 17.4 MeV proton beam's Brag-Peak 210 in water is about 3.2 mm (143). It is not sufficient to treat a tumor at 10 cms depth. INRT needle guided proton beam's Brag-Peak can be brought to any clinically encountered location of a tumor and its depth from the skin. For example, as shown in this FIG. 9F, the 17.4 MeV proton beam's Brag Peak 210 is brought to 10 cm depth with the aid of the INRT needle 208. It is shown as the 17.4 MeV proton's INRT needle guided Brag-Peak at 10 cm depth 212.

The relatively low energy proton interaction in tissue generates low energy neutrons and recoil protons by its elastic collisions with hydrogen atoms. The non-elastic nuclear interactions of proton also produce $^{11}$C, $^{13}$N, $^{15}$O and positron (101). With multiple simultaneous proton beams' bam-on-beam collision's elastic interaction, in tissue generates more locally absorbed nuclear fragments and antiprotons. These antiprotons add to the depth of the Brag peak (109). It also generates locally deposited γ emission with energies in the range of 0.6 to 1 MeV. The simultaneous proton beam's collisions products and antiprotons Brag-Peak at 10 cm depth 214 also enhances the locally absorbed tumor dose. The multiple simultaneous beam's such radiation enables high dose and dose rate single fraction proton beam radiosurgery with 7-30 MeV. Intraoperatively transported ion beam brought through the INRT needle to a desired depth where the tumor is located, eliminates the need for higher energy proton beam to treat a tumor that is located several cms below the skin. The INRT needle guided proton-nuclear reaction is capable of delivering 15 Gy in 20 seconds (112) but to a limited volume of a larger tumor, in the case of µINRT only to about 5 mm of the tumor volume (114). With multiple simultaneous proton beams and their beam-on beam collision reaction product's wider range radiation, single fraction, intraoperative larger tumor volume coverage radiation therapy is made possible.

Single fraction intraoperative radiosurgery with interlaced, cross firing multiple simultaneous needle guided proton beam brought to a tumor site by the method of INRT needle guided proton beam radiation and the multiple simultaneous beam-beam elastic and none-elastic collision induced, secondary proton, antiprotons, neutrons, $^{11}$C, $^{13}$N, $^{15}$O ions and positrons and gamma radiations all taking place within the tumor while sparing the normal tissue from radiation toxicities and thereby inhibition of developing adaptive resistance to radiation and cancer treatments is a very powerful armamentarium to eradicate a tumor even when they are "radioresistant" and "chemotherapy resistant".

FIG. 10A illustrates proton microbeam and nanobeam generating and secondary neutron and proton absorbing cylindrical tissue equivalent collimator incorporated with a nozzle and a patient specific collimator through which the spread out proton beam's Bragg-peak travels towards an isocentric tumor in a patient. The pencil proton microbeam 216 is spread out by the passive scatterer 218 in the nozzle 220. The dose is monitored by the dose monitors 219. The spread out Bragg peak proton beam 222 is incident onto the patient specific collimator 226. The secondary neutrons generated by the interaction of incident proton on to the patient specific collimator 226 and the secondary protons are absorbed by the tissue equivalent universal collimator 224 which also contains microfocus carbon tubes 230. To maintain the peak and valley dose differential as in microbeam radiation therapy, the microfocus carbon tubes 230 are placed at a distance of one to four ratio of beam width and distance from each other in tissue equivalent universal collimator 224. If the beam width is say 75 micrometers then the distance from two adjacent microfocus carbon tubes 230 is kept as 300 micrometers. If the beam width were 10 micrometers, then the distance from two adjacent microfocus carbon tubes 230 is kept as 40 micrometers apart. Similar ratio of distance from microfocus carbon tubes 230 is also kept for nanobeams. If 500 nanometer width nanobeams were used for nanobeam radiation, then the distance from two adjacent microfocus carbon tubes 230 is kept as 2,000 nanometers that is 2 micrometers apart. The proton beam that enters into the microfocus carbon tubes 230 are focused by the focusing anode 232 and the focusing magnet 234. It is like electron beam and ion beam focused electron and ion beam microscopy (160 and 161). Such focusing of the proton beam traveling through the microtubes eliminates the disadvantages of widening of the proton beam when it travels through a long neutron absorbing tissue like neutron absorber (150). A 195 mm long plastic collimator absorbs almost all the secondary neutron produced by a 235 MeV proton beam (176). Similar to this, the length of the tissue equivalent universal collimator 224 for 235 MeV proton beam could be 20 cm or slightly higher, say 25 cm. It can be easily used with a patient specific brass collimator without much exposure to secondary neutron and proton. It allows using the microbeam and nanobeam generating tissue equivalent collimator as the tissue equivalent universal collimator 224. Different patients have different sized tumors. Patient specific collimators of varying size are placed upstream to the tissue equivalent universal collimator 224. The focused microbeam/nanobeam with hardly any penumbra leave the microfocus carbon tubes 232 as focused microbeam/nanobeam 238 and travels towards the isocentric tumor 240. Lateral penumbra is the most important reason why increased thickness patient specific collimator is not an ideal solution to minimize the secondary neutron exposure to the patient. (177). With microbeam and nanobeam radiation with hardly any penumbra as with tissue equivalent universal collimator 224 placed downstream to patient specific collimator is an ideal solution to eliminate or minimize the secondary neutron and proton reaching the patient. Insertion of an alternate pre-collimator, upstream to patient specific collimator to minimize and or eliminate the adverse effects of lateral penumbra (178) is also not needed when a tissue equivalent universal collimator 224 that generates microbeam and nanobeam with hardly any penumbra is used. With the tissue equivalent universal collimator 224 placed downstream to patient specific collimator 226, the proton beam is modulated in conformity with the shape and configuration of the tumor volume. Hence the microbeam/nanobeam arriving at the isocentric tumor 240 renders conformal proton microbeam/nanobeam radiation to tumor 242 with no or hardly any secondary neutron and proton exposure to the patient and hardly any adverse effects of lateral penumbra.

The most important elements in this system of microbeam/nanobeam generating tissue equivalent universal collimator 224 with specified width, focused micro/nanobeam in microfocus carbon tubes 236 is that it enables peak and valley principle, high dose, 100 to 1,000 Gy and higher with interlaced microbeam radiation therapy to a tumor without much toxicity to the normal tissue. It is described in more details in the Specification under Section 3, Microbeam Radiosurgery.

FIG. 10A-2 is another illustration of proton microbeam and nanobeam generating and secondary neutron and proton absorbing cylindrical tissue equivalent collimators incorporated with a nozzle and a patient specific collimator through which the spread out proton beam Bragg-peak travels towards an isocentric tumor in a patient as in FIG. 10A but with the proton beam first travels through a semi-patient specific carbon nanotube pre-collimator. Very high efficiency channeling of high energy particle beams with energies ranging from 3 MeV to 900 GeV through multi-wall nanotube (MWNT) is reported (179). Likewise motion of high energy, kilovolt ion beam through carbon nanotubes were studied in the past (180). A number of similar previous studies on energetic ion particles such protons and electrons channeling through hollow carbon nanotubes were also reported (181). Other rapidly developing studies on proton beam and heavy ion channeling through carbon nanotube include axial channeling of high energy protons in carbon nanotubes (182), nanotubes for particle channeling, radiation and electron sources (183) and many similar ones. Vertically aligned array of pillars of multi-walled carbon nanotubes (MWCNT) are manufactured on anodized aluminum oxide (AAO) as substrate and using chemical vapor deposition of MWCNT, thermocleaning and chemical etching to exposes the MWCNT (159). Commercially available vertically aligned MWCNT are also used to guide the proton beam exiting from the nozzle 220 and traveling through the semi-patient specific carbon nanotube pre-collimator 252. As the spread out Bragg-peak proton beam pass through the MWCNT in the semi-patient specific carbon nanotube pre-collimator 252, the proton beamlets are focused within the MWCNT by the induced magnetism by the incident proton beam (183). The spread out Bragg-peak proton beam enters into the MWCNT in the semi-patient specific carbon nanotube pre-collimator 252 per spot scanning In this instance, the spot scanning is at the MWCNT's upstream opening, not at the tumor as in conventional active spot scanning proton or ion radiation therapy. The proton beamlets in MWCNT is focused as nanobeams as they exit from the semi-patient specific carbon nanotube pre-collimator 252. These beams then pass through the patient specific collimator 226 and enter into the Microfocus carbon tube's openings 228 and travels through the microfocus carbon tubes 230 in the tissue equivalent universal collimator 224. The beam in the microfocus carbon tube 230 is focused by the focusing anode 232 and focusing magnet The focused microbeam/nanobeam continues to travel towards the isocenter after its exit from the microfocus carbon tubes 230 and radiates the isocentric tumor in 3-D conformity of the tumor as described under FIG. 10A.

FIG. 10B-1 shows active, pencil proton beam spot scanning with no scattering elements in the nozzle except for the beam monitors, no patient specific collimator and compensators and microbeam and nanobeam generating and secondary neutron and proton absorbing cylindrical tissue equivalent collimator for secondary neutron and proton absorbing proton microbeam and nanobeam radiation therapy. The basic principles of proton microbeam and nanobeam radiation therapy using a tissue equivalent universal collimator 224 are described under FIG. 10A. The pencil proton microbeam 216 is scanned with the scanning magnets 244. The scanned beam 246 exits from the nozzle 220 and enters into the microfocus carbon tubes 230 though the microfocus carbon tube's openings 228. The proton beamlets in microfocus carbon tubes 230 is focused with focusing anode 232 and focusing magnet 234. This scanned focused microbeam/nanobeam 248 pass through the microfocus carbon tubes 230. The canned focused micro/nanobeam in microfocus carbon tubes 250 is almost without any penumbra. The scanned focused microbeam/nanobeam 248 exits from the microfocus carbon tubes 230 and travels toward the isocentric tumor 240 without any significant lateral penumbra and renders conformal scanned spot beam or scanned raster beam radiation therapy as is known in the art.

To take advantages of peak and valley dose differentials as in microbeam/nanobeam radiation therapy, the beam width and distance of the carbon tubes 230 from each other is maintained at a ratio of 1:4 as described under FIG. 10A. Its significance for curative and tumor growth controlling microbeam/nanobeam radiosurgery with doses ranging fro 100 to 1,000 Gy single fraction radiation therapy under the principles of peak and valley dose differential and normal tissue regeneration is a very significant development for adaptive resistance inhibiting cancer treatment. It is described in more details in the Specification under Section 3, Microbeam Radiosurgery.

FIG. 10B-2 illustrates the active, pencil proton beam spot scanning with no scattering elements in the nozzle except for the beam monitors, no patient specific collimator and compensators and microbeam and nanobeam generating and secondary neutron and proton absorbing cylindrical tissue equivalent collimator for secondary neutron and proton absorbing proton microbeam and nanobeam radiation therapy as in FIG. 10B but with the proton beam first travels through a semi-patient specific carbon nanotube pre-collimator. Additional beam processing with a semi-patient specific carbon nanotube pre-collimator 252 as described under FIG. 10A-2 is used in this instance. The spread out Bragg-peak proton beam 222 enters into the MWCNT containing carbon nanotube pre-collimator 252 per spot scanning In this instance, the spot scanning is at the carbon nanotube's opening sites, not at the tumor as in conventional active spot scanning proton or ion radiation therapy. All the features described under FIG. 10B for active, pencil proton beam spot scanning are maintained.

The pencil proton microbeam 216 is scanned with the scanning magnets 244. The scanned beam 246 exits from the nozzle 220 and travels towards the semi-patient specific carbon nanotube pre-collimator 252 with MWCNT. The beam transport through the MWCNT improves the spot scanned microbeam/nanobeam as it becomes more focused and without any significant penumbra. This spot scanned focused microbeam/nanobeam 247 enters into the microfocus carbon tubes 230 though the microfocus carbon tube's openings 228. The proton beamlets in microfocus carbon tubes 230 is maintained as focused with focusing anode 232 and focusing magnet 234. This scanned focused microbeam/nanobeam 248 is almost without penumbra. It passes through the microfocus carbon tubes 230. The scanned focused micro/nanobeam in microfocus carbon tubes 250 travels towards the isocentric tumor 240. The scanned focused microbeam/nanobeam 248 exits from the microfocus carbon tubes 230 and travels toward the isocentric tumor 240. It is used for conformal scanned spot beam or scanned raster beam radiation therapy.

FIG. 10 B-3 shows serial arrays of exposed vertically aligned multi-wall carbon nanotubes that are used as semi-patient specific carbon nanotube pre-collimator to generate focused nanobeams in multi-walled carbon nanotubes and their fine structures. The semi-patient specific carbon nanotube pre-collimator 252 is composed of serial arrays of exposed vertically aligned MWCNT in a template 254 in an anodized aluminum oxide template (159). Scanning electron microscope image of sheets of carbon nanotubes 256 is shown to illustrate the nanostructures of these vertically aligned MWCNT. A single walled carbon nanotube (SW-CNT) 258 and a multi-walled carbon nanotube (MWCNT) 260 are shown beside a single aligned carbon nanotube in a single aligned template 262 and the single aligned template 264. Serial arrays of these aligned carbon nanotubes in serial arrays of templates constitutes the semi-patient specific carbon nanotube pre-collimator 252. Ion channeling through MWCNT is also used to make MWNT apertures for ion beam transport. Such aperture is produced by depositing the MWNT on a substrate and its strengthening and cutting their ends to open with an atomic force microscope. A metal shield round them is produced by etching and electron beam lithography (185).

FIG. 10 B-4 illustrates interlacing scanning beams from two sets of proton accelerators, one at 0-degree and the other at 90-degree and proton beam spot scanning radiation therapy with their cross firing perpendicular and horizontal simultaneous microbeam or nanobeam beam's elastic and none-elastic collisional interaction at the isocentric tumor as they interlace at the isocentric tumor and the nozzles without scattering elements and also without patient specific collimator and compensators and the microbeam and nanobeam generating and secondary neutron and proton absorbing cylindrical tissue equivalent collimator for secondary neutron and proton absorption. As described under FIG. 10B, the pencil proton microbeam 216 is scanned with the scanning magnets 244. The scanned beam 246 exits from the nozzle 220 and enters into the microfocus carbon tubes 230 though the microfocus carbon tube's openings 228. The proton beamlets in microfocus carbon tubes 230 is focused with focusing anode 232 and focusing magnet 234. This scanned focused microbeam/nanobeam 248 pass through the microfocus carbon tubes 230. The canned focused micro/nanobeam in microfocus carbon tubes 250 is almost without any penumbra. The scanned focused microbeam/nanobeam 248 exits from the microfocus carbon tubes 230 and travels toward the isocentric tumor 240 without any significant lateral penumbra. The perpendicular and horizontal microbeams and nanobeams from the accelerator at 0-degree and 90-degree are spot or raster scanned identically. To maintain the peak and valley dose differentials as in microbeam/nanobeam radiation therapy, the beam width and distance of the carbon tubes 230 from each other is maintained at a ratio of 1:4 as described under FIG. 10A. It is used for adaptive resistance inhibiting 100 to 1,000 Gy single fraction microbeam/nanobeam radiosurgery without much normal tissue toxicity. Regeneration of normal tissue in the peak reigns through which the proton beam travels to its Bragg-peak and the isocentric tumor occurs by migration of stem cells to peak regions in the normal tissue and by its healing proliferation.

Interlaced, cross firing multiple simultaneous vertical and horizontal beams' beam-beam elastic and none-elastic collision induced nuclear reaction produce $\beta+$-decay and $\gamma$ emission and locally deposited high energy in the tumor.

With increased beam-beam inelastic collisions in tissue by multiple simultaneous proton beams, more and more nuclear disintegration in tissue is produced. Multiple simultaneous beam-beam's elastic and none-elastic collision induced, secondary proton, antiprotons, neutrons, $^{11}$C, $^{13}$N, $^{15}$O ions and positrons and gamma radiations all taking place within the tumor while sparing the normal tissue from radiation toxicities. It thereby inhibits development of adaptive resistance to radiation and cancer treatments. It generates more locally absorbed nuclear fragments and antiprotons. The antiprotons produced by the beam-on-beam collisions increases the depth of the Brag peak (109). Locally deposited γ emission with energies in the range of 0.6 to 1 MeV is also produced. At the Brag peak region, the primary protons are slowed down and the recoil secondary protons become more dominant behind the distal end of the Brag peak (100). At about the Brag peak area, 80-90% of the absorbed dose is from the slowed down primary proton and about 5-20% of the absorbed dose is from secondary protons. Behind the distal endpoint of the Brag peak, the secondary proton production by $^1$H (n, p) reaction dominates. It contributes 70% of the absorbed dose at this point, behind the distal endpoint of the Brag peak (100). Non-elastic nuclear interactions of proton also produce positron in sufficient quantity that is used for positron emission tomography (PET) (101). Such positrons are produced from decay of $^{11}$C, $^{13}$N, and $^{15}$O. The beam-on beam collision of the interlaced proton beams enhances this depth and dose within the tumor. The additive dose and dose rate of two simultaneous beams from two separate accelerators, both exposing the isocentric tumor simultaneously is twice the dose and dose rate from a single accelerator. Hence, in addition to all other radiobiological advantages of treating a tumor including those from the antiprotons from beam-on beam collision, the effective dose and dose rate of this interlaced two simultaneous beams reduces the time to treat a tumor to half than if the tumor were treated with one single accelerator. Proton beam has no exit dose. The peak and valley principles of the microbeam radiation therapy also spare the normal tissue from radiation damages.

FIG. 10 B-5 shows 3 interlacing scanning beams from three sets of proton accelerators, one at 0-degree, one at 90-degree and other at 270 degree for three sources simultaneous proton beam spot scanning radiation therapy to an isocentric tumor by their cross firing perpendicular and horizontal microbeams or nanobeams as described under FIG. 10 B-4 but with 3 simultaneous beams. The perpendicular interlacing beam source-1, 266 from 0 degree, the horizontal interlacing beam source-2, 268 from 90 degree and the interlacing beam source-3, 270 from 270 degrees cross fires the isocentric tumor 240 that renders the conformal proton microbeam/nanobeam radiation to tumor 242. The additive dose and dose rate of three simultaneous beams from three separate accelerators, both exposing the isocentric tumor simultaneously is three times the dose and dose rate from a single accelerator. Hence, in addition to all other radiobiological advantages of treating a tumor including those from the antiprotons from beam-on beam collision, the effective dose and dose rate of this interlaced three simultaneous beams reduces the time to treat a tumor to one third if the tumor were treated with one single accelerator. Proton beam has no exit dose. The peak and valley principles of the microbeam radiation therapy also spare the normal tissue from radiation damages. Details of such beam sources are described under FIG. 10 B-4. Its proton-proton, beam on beam cross firing interactions are also described under FIG. 10 B-4. It is further enhanced with these three beam sources.

FIG. 11A is an illustration of generating multiple simultaneous sweeping proton parallel microbeams or nanobeams by splitting the proton beam from a gantry mounted compact proton accelerator equipped with microbeam and nanobeam generating and secondary neutron and proton absorbing cylindrical tissue equivalent collimator for secondary neutron and proton absorption. Basic principles for generation of multiple a multiple pulse negative polarity proton beam in one plane and focusing in another plane with quadrupole magnet that spreads out the proton beam in one plane and focuses it in another plane is described under Section 33 in specification and under FIG. 1. The accelerated multiple pulse negative polarity proton beam 10 passes through a beam stopper 12 that serves as an emergency beam stopper when needed and a dose monitor 14 and the beam aperture collimating collimator 16 into a quadrupole magnet with converging magnetic field in one field 38 and quadrupole magnet with diverging magnetic field in another plane 40. Thus the defocusing quadrupole magnet 18 spreads out the proton beam in one plane and focuses it in another plane. The insert shows the quadrupole magnet with converging magnetic field in one plane 38 and the diverging magnetic field in another plane 40 as arranged symmetrically about the beam axis. Thus the proton beam is spread out in one plane and focused in another plane. The one plane defocused and in another plane focused multiple pulse negatively charged proton beam 20 is injected into a defocusing, focusing and beam size controlling magnet 22. The split beam's size and spacing from each other is controlled with this magnet. This beam, deflected in one direction and focused in another is then passed through a stripper grid 24 that generates alternating positively and negatively charged beam segments 26. They are alternatively charged as positive and negative segments of the beam and they are passed through a deflection magnet with DC vertical dipole field 28. According to the Lawrence law of force, the positively charged proton beamlets deflects to the left 30 and the negatively charged proton beamlets deflects to the right 32. The separating distance between each of these beamlets is dependent on the strength of dipole field. It generates sets of numerous simultaneous parallel proton beams which enter into the tissue equivalent universal collimator 224 containing microfocus carbon tubes 230. To maintain the peak and valley dose differential as in microbeam radiation therapy, the microfocus carbon tubes 230 in tissue equivalent universal collimator 224 are placed at a distance of one to four ratio of beam width and distance from each other in tissue equivalent universal collimator 224. If the beam width is say 75 micrometers then the distance from two adjacent microfocus carbon tubes 230 is kept as 300 micrometers. If the beam width were 10 micrometers, then the distance from two adjacent microfocus carbon tubes 230 is kept as 40 micrometers apart. Similar ratio of distance from microfocus carbon tubes 230 is also kept for nanobeams. If 500 nanometer width nanobeams were used for nanobeam radiation, then the distance from two adjacent microfocus carbon tubes 230 is kept as 2,000 nanometers that is 2 micrometers apart. The proton beam that enters into the microfocus carbon tubes 230 are focused by the focusing anode 232 and the focusing magnet 234 like ion beam focusing in electron and ion beam microscopy (160, 161). Such focusing of the proton beam traveling through the microtubes eliminates the disadvantages of widening of the proton beam when it travels through a long neutron absorbing tissue like neutron absorber (150). A 195 mm long plastic collimator absorbs almost all the secondary neutron produced by a 235 MeV proton beam (176). Hence the length of the tissue equivalent universal collimator 224 is 20 cm. The focused microbeam/nanobeam with hardly any penumbra leave the microfocus carbon tubes 236 as focused microbeam/nanobeam 238 and travels towards the isocentric tumor 240. The tissue equivalent universal collimator 224 eliminates or minimizes the secondary neutron and proton reaching the patient. The beam passing through the microfocus carbon tubes 230 generates microbeam and nanobeam with hardly any penumbra. The multiple simultaneous sweeping proton parallel microbeams or nanobeams generated by splitting the proton beam from a gantry mounted compact proton accelerator equipped with microbeam and nanobeam generating and secondary neutron and proton absorbing cylindrical tissue equivalent collimator for secondary neutron and proton absorption treats the tumor 240 in a sweep and in conformity with the shape and configuration of the tumor volume. Alternatively, the sweeping multiple simultaneous beam is scanned with multi-leave magnets (not shown) in conformity with the tumor 240 to render conformal proton microbeam/nanobeam radiation to tumor 242 with no or hardly any secondary neutron and proton exposure to the patient.

FIG. 11 B illustrates interlaced, sweeping beam-on-beam collisional scanning with multiple simultaneous proton beams generated by splitting of the initial pencil beam of two gantry mounted compact proton accelerators and microbeam and nanobeam generating and secondary neutron and proton absorbing cylindrical tissue equivalent collimator for conformal microbeam and nanobeam radiation therapy to a tumor. Compact gantry mounted multiple simultaneous proton beam accelerator-1, 272 at 0-degree, and the compact gantry mounted multiple simultaneous proton beam accelerator-2, 274 at 90 degree are identical to the multiple simultaneous sweeping proton parallel microbeams or nanobeams generating proton accelerator described under FIG. 11A. The cross firing sweeping simultaneous proton beams sweeps the isocentric tumor in a single exposure. Their cross firing perpendicular and horizontal microbeams or nanobeams are like those described under FIG. 10-B-4 and FIG. 10 B-5 but in this instance the tumor is exposed with sweeping multiple simultaneous beams. The perpendicular beam from compact gantry mounted multiple simultaneous proton beam accelerator-1, 272 at 0-degree interlaces with the horizontal beam from the compact gantry mounted multiple simultaneous proton beam accelerator-2, 274 at 90 degree. The isocentric tumor 240 is exposed by these cross firing proton beams in conformity with the tumor volume and tumor contour with sparing of the normal tissue. Multiple simultaneous beam-beam's elastic and none-elastic cross firing collisional interaction induced, secondary proton, antiprotons, neutrons, $^{11}C$, $^{13}N$, $^{15}O$ ions and positrons and gamma radiations all taking place within the tumor while sparing the normal tissue from radiation toxicities. It thereby inhibits development of adaptive resistance to radiation and cancer treatments. It generates more locally absorbed nuclear fragments and antiprotons. The antiprotons produced by the beam-on-beam collisions increases the depth of the Brag peak (109). Locally deposited γ emission with energies in the range of 0.6 to 1 MeV is also produced. At the Brag peak region, the primary protons are slowed down and the recoil secondary protons become more dominant behind the distal end of the Brag peak (100). At about the Brag peak area, 80-90% of the absorbed dose is from the slowed down primary proton and about 5-20% of the absorbed dose is from secondary protons. Behind the distal endpoint of the Brag peak, the secondary proton production by $^1H$ (n, p) reaction dominates. It contributes 70% of the absorbed dose at this point, behind the distal endpoint of the Brag peak (100). Non-elastic nuclear interactions of proton also produce positron in sufficient quantity that is used for positron emission tomography (PET) (101). Such positrons are produced from decay of $^{11}C$, $^{13}N$, and $^{15}O$. The beam-on beam collision of the interlaced proton beams enhances this depth and dose within the tumor. The additive dose and dose rate of two simultaneous beams from two separate accelerators, both exposing the isocentric tumor simultaneously is twice the dose and dose rate from a single accelerator. Hence, in addition to all other radiobiological advantages of treating a tumor including those from the antiprotons from beam-on beam collision, the effective dose and dose rate of this interlaced two simultaneous beams reduces the time to treat a tumor to half than if the tumor were treated with one single accelerator. Proton beam has no exit dose. The peak and valley principles of the microbeam radiation therapy also spare the normal tissue from radiation damages. Its proton-proton, beam on beam cross firing interactions are also described under FIG. 10 B-4. Additional details of the compact gantry mounted multiple simultaneous proton beam accelerator are described under FIG. 11A.

FIG. 11 C shows interlaced, sweeping beam-on-beam collisional scanning with multiple simultaneous proton beams generated by splitting of the initial pencil beam as in FIG. 11B but with five gantry mounted compact proton accelerators and microbeam and nanobeam generating and secondary neutron and proton absorbing cylindrical tissue equivalent collimator for conformal microbeam and nanobeam radiation therapy to a tumor. Multi-beam proton accelerator with tissue equivalent universal collimator-1 276 at 0-degree, multi-beam proton accelerator with tissue equivalent universal collimator-2, 278, multi-beam proton accelerator with tissue equivalent universal collimator-3, 280, multi-beam proton accelerator with tissue equivalent universal collimator-4, 282, and multi-beam proton accelerator with tissue equivalent universal collimator-5, 284 are arranged circularly on to a gantry (gantry is not shown). The details of the multi-beam proton accelerator with tissue equivalent universal collimator is described under FIG. 11A. Their cross firing sweeping simultaneous proton beams sweeps the isocentric tumor in a single exposure as described under FIG. 11B. Their cross firing microbeams or nanobeams radiate the isocentric tumor 240. These multiple simultaneous beam-on-beam's elastic and none-elastic cross firing collisional interaction induced, secondary proton, antiprotons, neutrons, $^{11}C$, $^{13}N$, $^{15}O$ ions and positrons and gamma radiations all radiates the tumor simultaneously more effectively while sparing the normal tissue from most of the radiation toxicities. Thereby it inhibits development of adaptive resistance to radiation and cancer treatments more effectively. It generates more locally absorbed nuclear fragments and antiprotons. The antiprotons produced by the five beam-on-beam collisions increases the depth of the Brag peak (109). Locally deposited γ emission with energies in the range of 0.6 to 1 MeV is also produced. The five interlaced sweeping beams from five accelerators, all simultaneously cross firing the isocentric tumor in conformity with the contour of the tumor volume produce more antiprotons and nuclear fragments than those with a single accelerator or with two or three accelerators as in FIG. 11 B. The additive dose and dose rate of five simultaneous beams from five separate accelerators at the isocentric tumor is five times higher than the dose and dose rate from a single accelerator. Hence, in addition to all other radiobiological advantages of treating a tumor including those from the antiprotons from beam-on beam collision, the effective dose and dose rate of these interlaced five simultaneous beams reduces the time to treat a tumor to one fifth if the tumor were treated with one single accelerator. Its additive dose and dose rate is sufficient for 100 to 1,000 Gy single session, adaptive resistance inhibiting radiosurgery within a few seconds, within less than a breathing cycle. Proton beam has no exit dose. Hence the normal tissue is not exposed from the exit dose. The peak and valley principles of the microbeam radiation therapy also spare the normal tissue from radiation damages.

FIG. 11-D illustrates proton spray chemotherapy and neutron capture radiation therapy with lithium-boron and gadolinium absorbed in carbon nanotubes. Arrays of proton beams, the microbeam/nanobeam proton spray 306 is shown as radiating the single walled carbon nanotube (SWCNT) 312. The SWCNT is pretreated with substrates like any biologically active compounds that acts as the ionized chemotherapeutics when exposed to proton beam radiation. Single walled carbon nanotubes are used to attach biomolecules such as proteins, DNA, RNAi and thus for drug delivery, for example EGFR and cisplatin (190, 191). Polyethylene glycol (PEG)-coated SWNT is found to be an effective substrate for coating the EGFR on to SWCNT. EGFR is coated on to the outer wall of the SWCNT. EGFR coated SWCNT has tumor specific uptake. Thus, EGFR and cisplatin cogitated SWCNT is a tumor seeking cogitates. The EGFR is taken up by the outer surface of the SWCNT and the cisplatin is taken up in the interior of the SWCNT. Such SWCNT/cisplatin conjugate is effective in tumor growth inhibition. (191). EGFR acts as a receptor for the tumor which facilitates the tumor specific uptake of SWCNT-EGFR-cisplatin. Other examples include docetaxel in single walled carbon nanotubes used for combined chemotherapy and photothermal therapy in cancer treatments (192). Likewise, Paclitaxel conjugated to single walled carbon nanotubes had high efficacy in tumor growth suppression (193). The collisional interaction of proton with vaporized water and molecules like uracil (129) is an important link to proton spray chemotherapy combined with proton spray microbeam and nanobeam radiation therapy. The products of proton impact ionization of water includes mostly H+, H2O+2, and OH+ and to a lesser amounts of H+2, O+2, N+, N+2, O+2 (131). It ionizes the chemotherapeutic compounds in attached and absorbed in the carbon nanotubes. Thus when the carbon nanotubes containing the chemotherapeutics is radiated they are ionized. Such proton beam ionization of compounds and chemicals in the SWCNT and MWCNT provides effective chemotherapy even with SWNT absorbed non-toxic compounds. In other wards, these pro-drug compounds in the carbon nanotubes become cytotoxic agents as they are radiated with a spray of proton beams. Like in the example of EGFR/cisplatin, most biologically active compounds and elements adsorbed and absorbed by the SWCNT and the Multiwalled carbon nanotubes (MWCNT). In the case of EGFR/platinum, EGFR is adsorbed on to the outer wall of SWCNT and the cisplatin is absorbed to the interior of the SWNT.

Lithium diffuses into the interior of single walled carbon nanotubes through the opened ends and side wall defects (187). Multiwalled carbon nanotube interacts with boron and forms boron carbides on the surface of the MWCNT (188). Boron doped Multiwalled carbon nanotube has also superconductivity (189) which amplifies the proton spray chemotherapy and ionization in the CNT. Such lithium-boron carbon nanotubes are ideal for boron-neutron capture therapy.

Likewise, gadolinium is an ideal element for neutron capture therapy. It has the highest thermal neutron capture cross-section of any known element and hence it is a highly effective element for neutron capture therapy.

Just before, proton beam radiosurgery, SWCNT or MWCNT pretreated with bioactive compounds like the chemotherapeutic, lithium, gadolinium and boron is injected to the tumor. The single walled carbon nanotube (SWNT) 308 is shown both with chemotherapeutics, lithium, boron, gadolinium adsorbed outside SWCNT 310 and chemotherapeutic, lithium, boron, gadolinium adsorbed inside SWCNT 312. When it is exposed to microbeam/nanobeam proton spray 306, the proton-lithium interaction takes place, 7Li(p, n)7Be, which generates neutrons. The neutron interacts with gadolinium by the nuclear reaction $^{157}Gd+nth$ (0.025 eV)→ $[^{158}Gd]→^{158}Gd+\gamma+7.94$ MeV. It releases gamma rays and Auger electrons for Gadolinium neutron-capture therapy (Gd-NCT). Likewise, the proton beam generates the classical boron neutron capture nuclear reaction which facilitates the boron neutron capture therapy (BNCT). The bioactive compound absorbed into the carbon nanotube gives rise to ionized chemotherapy.

FIG. 12 is a comparative illustration of proton, electron and high energy photon microbeam and nanobeam's scattering as they travel through tissue and their relative abilities to maintain peak and valley dose differential without much scattered radiation in the valley regions from where the least radiated stem cell regenerates to heal the tissue damage caused by high radiation dose peak regions which is the fundamental principles of high dose, 100 to 1,000 Gy and higher, single fraction radiosurgery with least toxicity to normal tissue. As the proton microbeam/nanobeam 286, the electron microbeam/nanobeam 288 and the photon microbeam 296 enters the skin 292, they build up their relative scatter radiation in the surrounding normal tissue, the normal tissue valley 298 and it contributes the valley dose 36. In tissue, radiation from their parallel microbeam/nanobeam with peak dose 34 differs substantially. The proton peak dose in normal tissue 300 as it travels towards its Bragg-peak produce the least scatter radiation. The electron peak dose in normal tissue 302 is the least focused peak dose in tissue. It generates the greatest scatter radiation in the valley region tissue, 294. The photon peak dose in normal tissue 304 is better focused than the electron peak dose in normal tissue 302 but still very poorly focused peak dose as compared to proton peak dose in normal tissue 300. The photon beam's scatter radiation in valley regions of normal tissue 296 is almost like that of scattered radiation from electron in valley region tissue 294. Photon microbeam generated with synchrotron at single fraction doses of 100-750 Gy and higher was used as curative radiosurgery to treat experimental animals bearing incurable glioblastoma multiforme with almost no normal tissue toxicity (10, 11, 12, 13, 14, 15). Radiosurgery with compact gantry mounted proton accelerators and their focused proton beam with hardly any scatter as is shown here is a much superior method of 100 to 1,000 Gy and higher single fraction radiosurgery than the radiosurgery with photon microbeam generated with synchrotron at single fraction doses of 100-750 Gy and higher as was reported before (10, 11, 12, 13, 14, 15). In this instance, proton microbeam and nano beam radiosurgery with hardly any scattered radiation to normal tissue protects the patients from developing second primary tumors. Moreover, the radiosurgery with proton nanobeams further improves the curative single fraction radiosurgery. Its peak and valley principles of radiation with even lesser scattered radiation to normal tissue allows treating a tumor at super high single fraction doses of several thousand Gy with hardly any toxicities to normal tissue and almost complete freedom from developing second primary tumors. Its capabilities for superior imaging of the tissues that is treated and that for molecular investigations, proton spray chemotherapy and improved neutron capture therapy all allows adaptive resistance inhibiting cancer treatment with higher cure rate than it is possible at the present by other cancer treatment modalities.

FIG. 13 is an illustration of generating numerous simultaneous parallel narrow proton beams by splitting the narrow proton beam from a radiofrequency accelerator combined with a drift tube accelerator for narrow proton beam radiation therapy with no or minimal long term toxicity to normal tissue. Lower energy proton beam is generated in the ion source 2. The beam transport 4 guides it into the radiofrequency accelerator RFQ 6 where it undergoes its first acceleration. The RFQ 6 accelerated multiple pulse negative polarity proton beam is then injected into the drift tube accelerator 8. The drift tube accelerator accelerated multiple pulse negative polarity proton beam 10 passes by a beam stopper 12 that serves as an emergency beam stopper when needed and a dose monitor 14 and the beam aperture collimating collimator 16 into a defocusing in one plane and focusing in another plane quadrupole magnet 18 which spreads out the proton beam in one plane and focuses it in another plane. The insert in FIG. 1 shows the quadrupole magnet with converging magnetic field in one plane 38 and the diverging magnetic field in another plane 40 as arranged symmetrically about the beam axis. The quadrupole magnet 18 with converging magnetic field in one plane 38 which focuses the proton beam and the diverging magnetic field in another plane 40 defocuses the proton beam. Thus the proton beam is spread out in one plane and focused in another plane. The one plane defocused and in another plane focused multiple pulse negatively charged proton beam 20 is injected into a defocusing, focusing and beam size controlling magnet 22. The split beam's size and spacing from each other is controlled with this magnet. This beam, deflected in one direction and focused in another is then passed through a stripper grid 24 that generates alternating positively and negatively charged beam segments 26. They are alternatively charged as positive and negative segments of the beam and they are passed through a deflection magnet with DC vertical dipole field 28. According to the Lawrence law of force, the positively charged proton beamlets deflects to the left 30 and the negatively charged proton beamlets deflects to the right 32. The separating distance between each of these beamlets is dependent on the strength of dipole field. It generates sets of numerous simultaneous parallel proton beams. The proton pencil beam's half width maximum is 10 mm (1 cm). If there are 10 simultaneous proton pencil beams divided into microbeams or nanobeams, it will cover a 10×1 cm sized field by spot scanning. Likewise, if there are arrays of 20, 30 or 40 simultaneous proton pencil beams also divided into microbeam or nanobeam, it will cover 20×1, 30×1 and 40×1 cm sized field. It allows any sized treatment field's rapid spot scanning with pencil beams. This does not need the spread out Bragg-peak. It minimizes the secondary neutron, proton, ions and other radiations generated by the process of making spread out Bragg-peak that cause second primary tumors.

Down stream to the multiple simultaneous spot scanning proton pencil beam segments, a secondary neutron and proton absorbing cylindrical tissue equivalent universal collimator 224 is placed. The proton pencil beam 236 is incident onto a universal collimator 224 which also contains microfocus carbon tubes 230. To maintain the peak and valley dose differential as in microbeam radiation therapy, the microfocus carbon tubes 230 are placed at a distance of one to four ratio of beam width and distance from each other in tissue equivalent universal collimator 224. If the beam width is say 75 nanometers then the distance from two adjacent microfocus carbon tubes 230 is kept as 300 nanometers. With 266 scanning with 0.375 mm sized simultaneous spot scanning pencil beams, a 1 cm long and 1 cm wide field is spot scanned simultaneously. Thus 10×1,000 micrometer long and 10×1,000 micrometer wide field is spot scanned with 2,660 simultaneous 1 cm wide proton pencil beam. These beams are scanned as in proton spot scanning or raster scanning for proton beam radiation therapy but with split 2,660 simultaneous pencil proton beams from multiple simultaneous beams from multiple accelerators instead of just 1 single beam from a single accelerator as in conventional proton spot scanning or raster scanning.

The proton beam that enters into the microfocus carbon tubes 230 are focused by the focusing anode 232 and the focusing magnet 234. It is like electron beam and ion beam focused electron and ion beam microscopy (160 and 161). Such focusing of the proton beam traveling through the microtubes eliminates the disadvantages of widening of the proton beam when it travels through a long neutron absorbing tissue like neutron absorber (150). A 195 mm long plastic collimator absorbs almost all the secondary neutron produced by a 235 MeV proton beam (176). Similar to this, the length of the tissue equivalent universal collimator 224 for 235 MeV proton beam could be 20 cm or slightly higher, say 25 cm. It can be easily used with a patient specific brass collimator without much exposure to secondary neutron and proton. It allows using the microbeam and nanobeam generating tissue equivalent collimator as the tissue equivalent universal collimator 224. The focused microbeam/nanobeam with hardly any penumbra leave the microfocus carbon tubes 232 as focused microbeam/nanobeam 238 and travels towards the isocentric tumor 240. Lateral penumbra is the most important reason why increased thickness patient specific collimator is not an ideal solution to minimize the secondary neutron exposure to the patient. (177). Microbeam and nanobeam have hardly any penumbra. The tissue equivalent universal collimator 224 is an ideal solution to eliminate or minimize the secondary neutrons and protons reaching the patient. The proton pencil beam is scanned in conformity with the shape and configuration of the tumor volume. Hence the microbeam/nanobeam arriving at the isocentric tumor 240 renders conformal proton microbeam/nanobeam radiation to tumor 242 with no or hardly any secondary neutron and proton exposure to the patient and hardly any adverse effects of lateral penumbra.

FIG. 14 illustrates the interlacing beams from two sets of parallel narrow proton beams, one from 0 degree and another from 90 degrees and both converging at the isocenter that generates quasi proton-proton interaction and quasi antiproton for narrow proton beam radiation therapy with minimal or no long term toxicity to normal tissue. Details of the multiple simultaneous pencil beams producing accelerator, multiple simultaneous pencil beam spot scanning, microbeam and nanobeam generation in carbon tubes are described under FIG. 13. Based on beam size and intensity adjusted with the DC vertical magnet 28, the split beams are made as narrow parallel beams. The parallel narrow beam's peak dose 34 from both accelerators pass through the normal tissue towards the isocenter where they interlace with the vertical and horizontal beams from both accelerators, from accelerator at 0-degree and from the accelerator at 90 degree that creates the high dose interlaced beams 46. Each narrow beam segments from the split proton beam provides the parallel narrow beam peak dose 34 in the normal tissue. The tissue in between the two narrow parallel beams receives practically no significant dose. It is the valley dose 36. After radiation to the narrow segments of normal tissue through which the proton microbeams and nanobeams passes through, the tissue damage caused in such narrow segment of normal tissue is readily repaired by migration and proliferation of clonogenic normal cells from the valley region to the regions of peak dose.

Because of this micrometer and nanometer sized peak dose segments in normal tissue and no to very low dose to valley regions and migration of clonogenic cells from the valley regions to the peak dose regions, the damaged cells in the peak dose regions from high dose radiation is replaced with normal cells. It thus heals the radiation injury at the peak dose regions. Radiation sensitive functional subunits (FSUs) in an organ like a nephron in the kidney are of several nanometers and micrometers in size. It is also so for other FSUs in other organs. Because of the nanometer and micrometer sized peak dose regions to several hundreds of micrometer sized FSUs and its radiation damaged cells are replaced with normal cells by migration of clonogenic cells to the peak dose regions from the low or no dose regions in the valley, the past hypothesis on radiation effects on FSUs needs to be revised. In this case, the past descriptions of radiation effects in normal tissue based on parallel, serial or structurally undefined FSUs become insignificant. Those past descriptions were based on regeneration of radiation damaged cells by migration of clonogenic cells from unirradiated regions. The upper limit of tissue size for such healing process from radiation damage is considered as 1 cm. One microbeam is $10^4$ smaller and one nanobeam is $10^7$ times smaller than 1 cm. The past hypothesis of parallel, serial or structurally undefined FSUs based on smallest strip of radiated tissue having 1 cm size is insignificant in terms of clonogenic cell's crossing over to micrometer and nanometer sized radiated tissue in response to signals to its radiation damage. With nanometer and micrometer sized peak dose regions, the clonogenic cells readily migrates to this regions with radiation damaged cells and it readily replaces the cells that were damaged by the peak radiation dose. By interlacing the parallel microbeams or nanobeams at the isocenter 48 where the tumor is located, the peak and valley dose deferential of the parallel microbeam and nanobeam is lost. Hence safe single fraction radiosurgical doses of 100 Gy to 1,000 Gy and even as high as 4,000 Gy to 10,000 Gy without normal tissue damage is made possible. It thus makes the past definitions of tolerance doses to early responding and late responding normal tissue like the tolerance dose of spinal cord, kidney, intestine, lung etc insignificant.

High dose radiation to tumor cells not only damages its DNA but also it cause oxidative damage to DNA damage repairing enzymes and proteins. Intrinsic apoptotic pathway can be triggered either by damage to DNA or by damage to the plasma membrane. The fractionated daily radiation in the dose range of 1.8 to 3 Gy primarily cause DNA damage which is rapidly repaired by activation of various DNA repairing proteins; for example the ATM which phosphorylates DNA repairing proteins like H2AX, p53, BRCA1, Artemis etc. Megarads radiation is required to inactivate enzymes like glutamate dehydrogenase (201). Radiation target analysis of RNA also demonstrates the need for Megarads range of radiation to inactivate the RNA (202). The DNA damage caused by the daily fractionated, 1.8 to 3 Gy radiation is mostly repaired by the DNA repairing proteins like the ATM which is not inactivated by low dose radiation. Safe single fraction microbeam and nanobeam radiation to doses as high as 100 to 1,000 Gy and even higher as high as 4,000 to 10,000 Gy on the other hand inactivates DNA damage repairing enzymes in a tumor. Inactivation of these enzymes leads to inhibition of DNA damage repair by these enzymes. Thus, microbeam and nanobeam radiosurgery at doses as high as 100 to 1,000 Gy and 4,000 to 10,000 Gy without any lasting normal tissue damage is an effective, curative cancer treatment that inhibits the adaptive radioresistance and tumor growth both by DNA damage and oxidative damage to cellular proteins. It was not possible before.

Targeted, localized enzymes and protein damage within a tumor by 100 to 1,000 Gy and 4,000 to 10,000 Gy single fraction radiosurgery also elicits localized cytotoxic effects like those caused by chemotherapy which interferes with the functions of specific enzymes and proteins but without the systemic toxicity as with the chemotherapy. Adaptive resistance to chemotherapy is one of the major reasons why the initially very effective chemotherapy becomes ineffective for sustained tumor control. Immediately after the initial administration of a chemotherapeutic agent, the tumor cell synthesizes increased levels of proteins like p-glycoprotein and glutathione. It renders the tumor cells as multi-drug resistant. 100 to 1,000 Gy and 4,000 to 10,000 Gy single fraction radiosurgery inhibits the activities of such proteins. It thus reverses the acquired multi-drug resistance in the tumor cells. Presently, a number of chemotherapeutic agents are used to interfere with the cellular enzymes that regulate the tumor growth. To name a few, 5-flurouracil inhibits thymidylate synthase, Gemcitabine inhibits ribonucleotide reductase, Celecoxib inhibits prostaglandins, Curcumin and Genistein inhibit NFkB, Erlotinib inhibits EGFR small molecule tyrosine kinase, Bortezomib inhibits the chymotrypsin-like activity of the 26S proteasome, Irinotecan inhibits complex formation between topoisomerase I and DNA and cause DNA single strand breaks and inhibits DNA replication, the small molecule multi-kinase inhibitor Sorafinib targets RAF1, KIT, FLT3, VEGFR (KDR) and PDGFR, the small molecule tyrosine kinase inhibitor Imatinib inhibits BCR/ABL kinase, Tipifarnib inhibits farnesyl transferase, Cetuximab inhibits EGFR, Gefitinib inhibits small molecule tyrosine kinase and Amsacrine inhibits topoisomerase II. Since 100 to 1,000 Gy and 4,000 to 10,000 Gy single fraction radiosurgery destroys activities of these enzymes and proteins, such localized super high dose, enzyme activity inactivating radiosurgery is superior to any one of these chemotherapeutic agents alone or all of them combined to inhibit the tumor cell from proliferation and growth. There will be prohibitive systemic toxicity if chemotherapy is administered with all these drugs combined. Localized, interlaced beam, 100 to 1,000 Gy and 4,000 to 10,000 Gy single fraction radiosurgery with minimal or no long term toxicity as described here on the other hand is superior to suppress all these tumor growth simulating enzymes without systemic toxicity.

FIG. 15 shows polyenergetic laser-target interaction's proton or monoenergetic carbon ions generation and separation of proton beam's highest energy beam as a monochromatic beam with a tissue equivalent collimator containing microfocus carbon tubes and transport of proton or carbon ion beam for microbeam and nanobeam generation. The methods for laser target normal sheath acceleration (TSNA) and radiation pressure acceleration (RPA) are used to generate proton beam from laser-thin target foil interaction. Micrometer thick metal foils or diamond like carbon (DLC) foils 316 is radiated with focused laser 318 from a laser source 320 that is reflected by the mirror 322 at intensities over $10^{18}$ W/cm². The laser-target-TSNA method produce polyenergetic proton beams of energies of 60 MeV and higher. The RPA method produces therapeutic range, higher energy, and quasimonochromatic proton beam. The laser-RPA-target interaction much more thinly, micrometer and nanometer thick target foil 316 is used. In TSNA methods of proton beam production, laser-target interaction produces relativistic electron at the radiated surface. This electron spreads through the target foil 316 and builds up an intense electrostatic filed at the rear surface of the target foil 316. Its intense electrostatic field accelerates surface ions, mostly hydrogen contaminants that produce dense polyenergetic proton beams 324 which are spatially separated with polyenergetic beam spatially separating magnet 328. Theoretically, therapeutic range proton beams of 200-250 MeV could be generated with laser beam intensities of $10^{22}$ Watt by TSNA methods but the highest proton beam energy produced by TSNA is about 60 MeV (196). Its highest energy beam is separated as centrally located monochromatic beam 330. To select the higher energy proton beam from the lower energy proton beam without producing much neutron, secondary proton and gamma radiation from the interactions of the polyenergetic proton with secondary magnet and collimators, a tissue equivalent collimator 326 containing microfocus carbon tubes 230 is positioned in the path of laser generated polyenergetic proton beam. It is in contrast to the methods of polyenergetic beam's spatial separation and rejoining with the aid of superconducting magnets described by Ma C. M. et al (200) that produce significant amounts of neutrons secondary protons, gamma radiations and ions which contribute to the development of secondary tumors. The spatially separated lower energy beams from the polyenergetic proton beams are either absorbed by the tissue equivalent collimator 326 or they travel through the microfocus carbon tubes 230 in the tissue equivalent collimator 326 to the end of their depth of penetration without exiting out of the microfocus carbon tubes 230. The lower energy proton absorbing carbon tubes has no lumen through which the proton beam can pass through. The depth of penetration of the lower energy proton beam varies based on their energy. A 10 to 30 mm (1 cm to 3 cm) long tissue equivalent plastic collimator with microfocus carbon tubes 230 absorbs almost all the lower energy beams from the polyenergetic proton beam leaving suitable higher energy proton beam for injection into a RF accelerator for its further acceleration. As ion source for acceleration in the RF accelerator, 20 MeV proton generated by the laser target interaction is usually selected. Hence the length of its tissue equivalent collimator 326 is selected as 1.5 cm when 20 MeV protons is generated by the TSNA method for injection into a RF accelerator. In this instance, the spatially separated and centrally located highest energy proton beam travels far beyond the 1.5 cm length of tissue equivalent collimator 326 through the open microfocus carbon tube 230 and exits from it as monoenergetic proton beam 330. The laterally located lower energy proton beams are absorbed by the tissue equivalent collimator 326 and the carbon nanotubes 230. In the embodiment with hybrid laser generated proton beam and RF accelerator, 10 to 20 MeV monoenergetic proton beams 330 generated with a desktop laser system and the tissue equivalent collimator 326 is injected into the RF accelerator for its further acceleration to a therapeutic level proton energies of about 200 to 250 MeV.

In the embodiment of direct therapeutic range, 50 to 250 MeV range quasimonochromatic proton beam or 85-430 MeV/u carbon ion generation without a hybrid laser-proton-RF system, the RPA methods of proton or carbon ion beam generation is elected (208). In RPA methods of higher energy laser-protons and carbon ions generation, nanometer to few micrometer thick target foil 316 is used as compared with the thicker, still micrometer thick, target used in TSNA methods of proton and ion generation. Diamond like carbon (DLC) target foils mostly generates pure carbon ions. In RPA the pressure from the accelerated ions at the front side of the target pushes the electrons inwards relative to the ions. This radiation pressure compresses the electron in the inside of the target until it balances with the charge separation electric field. At this point, the linear and circular polarization differs and the linear polarization acquires twice the laser frequency. It cause the electron to heat up and to oscillate in longitudinal direction in large amplitudes while the circular polarization produce mostly stationary radiation pressure that pushes the electron in the direction of the laser without heating it. The circular acceleration's phase is stable in terms of longitudinal acceleration. The ions initially stays as coupled with electron in the electrostatic filed and then it accelerates as quasimonochromatic ion beam with ballistic speed and with high laser-to-ion energy conversion efficiency (197). With stable circular acceleration and with laser intensities of about $10^{21}$ W/cm², proton energies of 200 MeV and higher is generated (198). In US patent application US 2011/0273115 A1 such a RPA based proton accelerator is claimed to generate 50 to 350 protons (199-B). In this instance a longer tissue equivalent collimator that absorbs neutrons, secondary protons, gamma radiations and ions is used. Its length is adjusted to coincide with the Brag-peak of the 50 to 250 MeV proton beams and 85-430 MeV/u carbon ions. A 195 mm long plastic collimator absorbs almost all the secondary neutron produced by the 235 MeV proton beams (176). Hence the length of this tissue equivalent collimator 326 for generating 200 to 250 MeV monochromatic proton beam is selected as 20 cm. The higher energy monoenergetic proton or carbon ion beam 330 emerges from the hollow carbon tube 230 as magnetically focused beam. Because of the narrow beam profiles of the carbon ion than that of proton beam, it is more suitable to implement the principles of peak and valley dose differentials associated normal tissue sparing microbeam and nanobeam radiosurgery as described in this invention. Because of its high LET, it is far superior to photons and protons for adaptive resistance inhibiting microbeam and nanobeam radiosurgery which is the main focus of this invention.

FIG. 16 illustrates an hybrid laser proton or carbon ion-radiofrequency accelerator in which laser generated proton or carbon ion beam's post acceleration is conducted in the hybrid radio frequency accelerator and generating numerous simultaneous parallel narrow proton or carbon ion beams by splitting the accelerated high energy proton or carbon ion beam into microbeams or nanobeams for proton microbeam or nanobeam radiation therapy with no or minimal long term toxicity to normal tissue. Methods of isolation of highest energy proton beam from the polyenergetic proton or carbon ion beams generated by the laser-target TSNA methods are described under FIG. 15. So generated lower energy proton or carbon ion beam of about 20 MeV range is used as the ion source for the hybrid laser generated proton beams acceleration in a RF accelerator. When needed, the charge of the accelerated beam is modified with a charge stripper foil before injecting the beam into the RF accelerator. Except for this laser generated proton or carbon ion beam as the ion source for acceleration, the methods of microbeam or nanobeam generation for microbeam or nanobeam radiation therapy are identical as those described under FIG. 13. In this instance, the spatially separated higher energy monoenergetic proton or carbon ion beam 330 is injected in to the RF accelerator for its acceleration to 200-250 MeV. Micrometer thick metal or DLC target foil 316 is radiated with focused laser 318 from a laser source 320 that is reflected by the mirror 322 at intensities over $10^{18}$ W/cm$^2$. It produces polyenergetic proton beams which are spatially separated with a magnet. The centrally located high monoenergetic proton or carbon ion beam 330 is isolated from the lower energy proton beam with a tissue equivalent collimator 326 as described under FIG. 15. Such isolated, lower MeV, monoenergetic proton or carbon ion beam 330 is injected into the RF accelerator. Such accelerated proton or carbon ion beam is split into several beams from which microbeams or nanobeams are generated as described under FIG. 13 for microbeam or nanobeam radiation therapy. Because of the narrow beam profiles of the carbon ion than that of proton beam, it is more suitable to implement the principles of peak and valley dose differentials associated normal tissue sparing microbeam and nanobeam radiosurgery as described in this invention. Because of its high LET, it is far superior to photons and protons for adaptive resistance inhibiting microbeam and nanobeam radiosurgery which is the main focus of this invention.

FIG. 17 is another illustration of interlacing beams from two sets of parallel narrow proton or carbon ion beams, one from 0 degree and another from 90 degrees and both converging at the isocenter for narrow proton or carbon ion beam radiation therapy with minimal or no long term toxicity to normal tissue as in FIG. 14 but with two hybrid laser-proton or carbon ion-RF accelerators. Post acceleration of the laser produced proton or carbon ion in a radiofrequency accelerator generates high energy proton beam in the range of 50 to 250 MeV or carbon ion beam of 85 to 430 MeV. As described under FIG. 13, such accelerated high energy proton (or in this instance also carbon ion) beam is split into numerous simultaneous parallel narrow proton beams. Subsequently, they are modulated into parallel microbeam or nanobeam with a tissue equivalent universal collimator 224 as described under FIG. 13 for proton or carbon ion microbeam or nanobeam radiation therapy with no or minimal long term toxicity to normal tissue, also as described under FIG. 13. Because of the narrow beam profiles of the carbon ion than that of proton beam, it is more suitable to implement the principles of peak and valley dose differentials associated normal tissue sparing microbeam and nanobeam radiosurgery as described in this invention. Because of its high LET, it is far superior to photons and protons for adaptive resistance inhibiting microbeam and nanobeam radiosurgery which is the main focus of this invention. As previously described, because of the micrometer and nanometer sized peak dose segments in normal tissue and no to very low dose to valley regions and migration of clonogenic cells from the valley regions to the peak dose regions, the damaged cells in the peak dose regions from high dose radiation is replaced with normal cells. It thus heals the radiation injury at the peak dose regions in the normal tissue. By interlacing the parallel microbeams or nanobeams at the isocenter 48 where the tumor is located, the peak and valley dose deferential of the parallel microbeam and nanobeam is lost. Safe single fraction radiosurgical doses of 100 Gy to 1,000 Gy and even as high as 4,000 Gy to 10,000 Gy without normal tissue damage is made possible. It is thus a curative cancer treatment that inhibits the adaptive radioresistance and tumor growth both by cancer cell's DNA damage and oxidative damage to its cellular proteins. It was not possible before.

FIG. 18 shows a laser proton or carbon ion generating accelerator in which high 50 to 250 MeV quasimonochromatic proton beam or 85-430 MeV/u carbon ion is generated by the laser-target-radiation pressure acceleration (RPA) methods and also generating numerous simultaneous parallel narrow proton or carbon ion beams by splitting the accelerated high energy proton or carbon ion beam into microbeams or nanobeams for proton or carbon ion microbeam or nanobeam radiation therapy with no or minimal long term toxicity to normal tissue. As described before, the laser-target-RPA methods of proton or carbon ion produces therapeutic range, higher energy, and quasimonochromatic proton or carbon ion beam. Its contaminating polyenergetic protons, neutrons, gamma and ions radiations from its interactions with surrounding elements and collimations are removed with tissue equivalent collimator 326 containing microfocus carbon tubes 230. It is positioned in the path of laser generated quasimonochromatic proton or carbon ion beam. The length of the tissue equivalent collimator 236 is adjusted to coincide with the Brag-peak of the 200 to 250 MeV proton beams. A 195 mm long plastic collimator absorbs almost all the secondary neutron produced by the 235 MeV proton beams (176). Hence the length of this tissue equivalent collimator 326 for generating 200 to 250 MeV monochromatic proton or carbon ion beam is selected as 20 cm. The higher energy monoenergetic proton beam 330 emerges from the hollow carbon tube 230 as magnetically focused beam and passes by an emergency beam stopper 12 and a dose monitor 14. This beam is collimated by a collimator 16. This collimated beam is defocused in one plane and focused in another plane with the quadrupole magnet 18 which spreads out the proton beam in one plane and focuses it in another plane. The proton beam is spread out in one plane and focused in another plane. The one plane defocused and in another plane focused multiple pulse negatively charged proton beam 20 is injected into a defocusing, focusing and beam size controlling magnet 22. The split beam's size and spacing from each other is controlled with this magnet. This beam, deflected in one direction and focused in another is then passed through a stripper grid 24 that generates alternating positively and negatively charged beam segments 26. They are alternatively charged as positive and negative segments of the beam and they are passed through a deflection magnet with DC vertical dipole field 28. According to the Lawrence law of force, the positively charged proton beamlets deflects to the left 30 and the negatively charged proton beamlets deflects to the right 32. The separating distance between each of these beamlets is dependent on the strength of dipole field. It generates numerous simultaneous parallel proton beams. These beams are subsequently processed as microbeams or nanobeams with a tissue equivalent universal collimator 224 as described under FIG. 13, FIG. 14, FIG. 16 and FIG. 17.

FIG. 19 illustrates two sets of interlacing parallel proton or carbon ion microbeams or nanobeams, one set from 0 degree and another set from 90 degrees and both converging at the isocenter for narrow proton or carbon ion beam radiation therapy with proton or carbon ion accelerator. Its details are described under FIG. 18. High energy 50 to 250 MeV quasimonochromatic proton beam or carbon ion beam is generated by laser-RPA method as described earlier. All the elements for proton or carbon ion microbeam or nanobeam generation shown in this FIG. 19 are identical to those described under FIG. 18. It is also identical to those described under FIG. 17 except for the high energy proton or carbon ion beam is generated by the laser-RPA method and it has no hybrid laser-proton-RF accelerator. Microbeam or nanobeam from two such accelerators, one from 0-degree and another from 90-degree are made to interlace at the isocentric tumor 240. The principles of peak and valley dose differential associated sparing of the normal tissue from radiation damage is lost at the isocentric tumor 240 as these two beams interlace at the isocentric tumor 240 and the whole tumor is radiated with peak dose.

FIG. 20 shows four sets of interlacing parallel proton microbeams or nanobeams generated from a main ring laser from which four split beams are taken for RPA method of high energy proton or carbon ion generation and their interlacing beams. Carbon ion is generated with DLC as the target. It consists of one set from 0 degree, 332, one set from 90 degrees 334, one set from 180 degrees 336 and one set from 270 digress 338 and all the four sets are arranged in a circular rotating gantry 340. Their simultaneous beams are shown as interlacing at the isocentric tumor 240. Details of the laser-RPA high energy proton or carbon ion beam generation and creation of peak dose at the interlacing beam at the isocentric tumor 240 are described in FIG. 18 and FIG. 19. The proton and carbon ion beams have no exit dose. Hence the parallel opposed proton or carbon ion microbeam or nanobeam do not add any added radiation damage to normal tissue. The split laser source 320 from the main ring laser source 342 is focused by the mirror 322 as the focused laser 318. It interacts with the nanometer to micrometer sized target foil 316 by laser-RPA methods of ion acceleration. It produces therapeutic range high energy proton or carbon ion beam. It is then split into several microbeam or nanobeams and interlaced at the isocenter as described under FIG. 18 and FIG. 19.

37. METHODS OF OPERATION

Figure 11C:
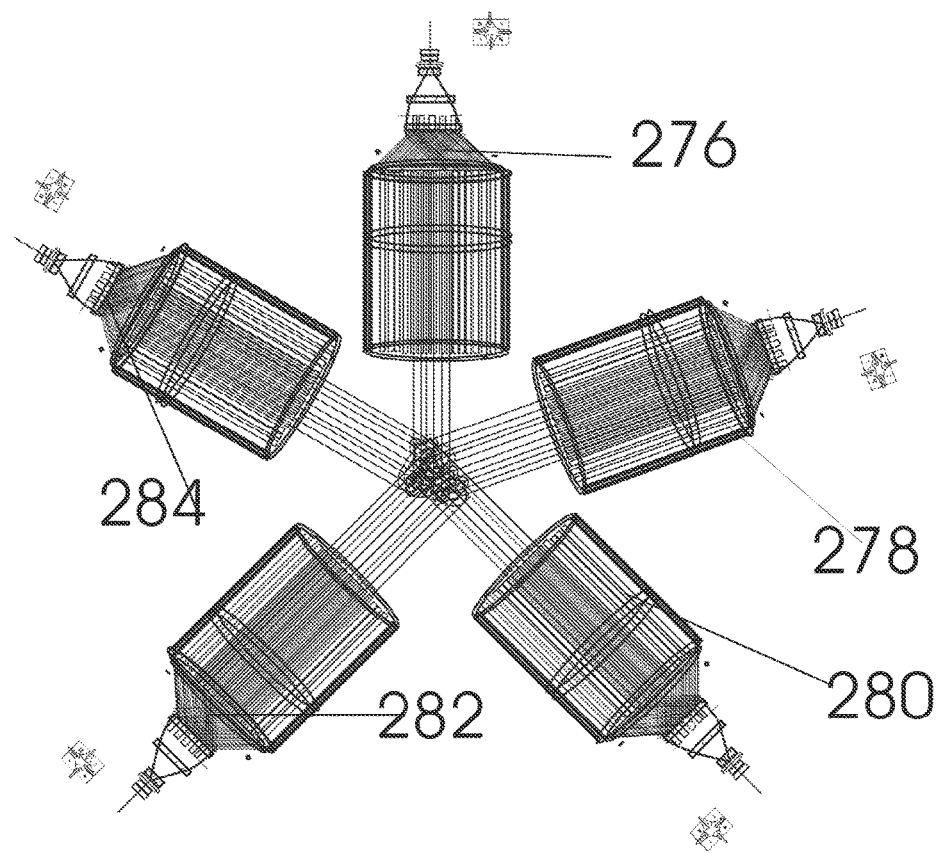

High Dose and Dose Rate, Adaptive Resistance Inhibiting Radiosurgery with Interlaced Parallel Microbeam or Nanobeam Interlaced parallel microbeam or nanobeam are generated with RFQ and drift tube accelerators or with nested high voltage DC accelerator combined with RFQ accelerator or with compact gantry mounted proton accelerators is described under FIG. 1 through FIG. 8 and FIG. 10-A through FIG. 11C and in FIGS. 13 and 14. In FIG. 15, generation of laser-target-proton or carbon ion and spatial separation of low and high energy proton or carbon ion with tissue equivalent collimator is described. In FIG. 16, the methods of laser generated proton or carbon ion's post acceleration in hybrid RF accelerators to generate 50 to 250 MeV protons or 85 to 430 MeV/u carbon ions, the beam splitting into several sub-beams and their subsequent treatment in a tissue equivalent collimator and generating microbeam and nanobeam is described. Treating a tumor with 50 to 250 MeV protons or 85 to 430 MeV/u carbon ion microbeam or nanobeam generated by the hybrid proton-RF accelerators and treating an isocentric tumor with interlaced microbeam and nanobeam is described in FIG. 17. The methods of higher energy carbon ion or proton generation by laser-target interaction by RPA methods and such accelerated beam's splitting into several sub-beams and its further treatment in a tissue equivalent collimator and generating microbeam and nanobeams is described in FIG. 18. The methods of treating a tumor with interlaced 85 to 430 MeV/u carbon ion beam or 50 to 350 MEV proton beam generated by laser-target- by RPA methods is described in FIG. 19. For sets of RPA methods of 85 to 430 MeV/u carbon ion beam or 50 to 350 MEV proton beam generating accelerators mounted on to a rotating gantry and treating a tumor with four sets of simultaneously interlacing beams at the isocentric tumor is described in FIG. 20. The isocentric tumor is treated with interlaced parallel microbeam or nanobeam at high dose and dose rate, 100 to 1,000 Gy and 4,000 to 10,000 Gy with least toxicity to normal tissue by treating the tumor with the dose differential between the peak dose and the valley region created by two adjacent beams in tissue. Radiosurgery at doses of 100-1,000 Gy or 4,000 to 10,000 Gy with interlaced, cross firing multiple simultaneous proton or carbon ion beam and with beam-on-beam elastic and none-elastic collision induced, locally absorbed radiation is given in a few seconds, within a respiratory cycle. The normal tissue outside the tumor is spared from toxic effects of radiation by the microbeam and nanobeam and their spacing between them, by the peak and valley dose differential and by migration of clonogenic cells to the radiation damaged peak dose regions. The radiation toxicities to the peak radiation regions in the normal tissue is healed by proliferation of the migrating stem cells from the unirradiated and or least radiated tissue in the valley regions. Because of the micrometer and nanometer wide peak dose regions, all the tissues with parallel, serial or undefined FSUs have the same radiation effects and tolerance. Radiation effects for all organs becomes the same.

With 100 to 10,000 Gy multiple simultaneous proton or carbon ion beams radiation and its combined bam-on-beam elastic interaction, the dose and dose rate of the β+-decay and γ emission increases. With increased beam-on-beam inelastic collisions in tissue with multiple simultaneous proton and carbon ion beams, more and more nuclear disintegration in tissue is produced. It generates more locally absorbed nuclear fragments and antiprotons. Antiproton adds to the depth of the Brag peak; (109). This method of radiation inactivates a host of DNA repairing enzymes and acts as both DNA strand breaking and oxidative protein damaging radiation therapy. Conventional daily 2 Gy fractions radiotherapy do not damage cellular enzymes and proteins much. It is a superior method of enzyme inactivating cancer therapy than all of the more toxic and expensive enzyme inactivating chemotherapy.

The methods of radiosurgery are well established. Patients who are able to follow instructions of the clinical staffs are placed onto the treatment table as immobilized in radiosurgical position and radiosurgery is done in less than one breathing cycle duration that is in seconds so that the organ movements associated with breathing is avoided. These patients do not need treatment under anesthesia. Those patients who cannot be kept as immobilized and treated with instructions to hold the breath or for other clinical reasons are treated under short anesthesia.

The conventional methods of proton or carbon ion beam radiation therapy with spread out Bragg-peak and patient specific collimator are modified to remove the secondary neutron and proton from beam shaping devices and they not to reach the patient. Unwanted laser generating neutrons, gamma rays and secondary ions are absorbed with a tissue equivalent collimator that also absorbs the spatially separated lower energy proton beams. It minimizes secondary radiation to the patient. A cylindrical, tissue equivalent universal collimator is placed downstream to patient specific collimator. It absorbs the secondary neutrons, protons and other nuclear products generated by the interaction of spread out Bragg-peak with patient specific collimator that shapes the beam's conformity with the tumor volume and configuration. The tissue equivalent universal collimator also equipped with microfocus carbon tubes that modulates incoming proton beam into microbeam or nanobeam. The proton beam in microfocus carbon tubes are focused with anode and focusing magnet. Such focused microbeam/nanobeam hardly has any penumbra. Carbon ion with still narrower microbeam and nanobeam is far superior for generating peak and valley dose differential and protecting the normal tissue from radiation damage. Radiosurgery with such focused microbeam/nanobeam and its treatment field shaped by patient specific collimator is a far advanced cancer treatment. Different patients have different sized tumors. Patient specific collimators of varying size are placed upstream to the tissue equivalent universal collimator. Only those beams shaped by the patient specific collimator passes through the wider tissue equivalent universal collimator placed downstream to the patient specific collimator. The focused microbeam/nanobeam with hardly any penumbra leave the microfocus carbon tubes as focused microbeam/nanobeam and travels towards the isocentric tumor. The interlaced microbeam/nanobeam arriving at the isocentric tumor renders conformal proton microbeam/nanobeam radiation to the tumor.

In an alternative method of generating fine focused nanobeam, the spread out proton beam from the nozzle of a proton accelerator first travels through a semi-patient specific multi walled carbon nanotube pre-collimator. The fine focused nanobeam exiting from the semi-patient specific multi walled carbon nanotube pre-collimator enters into the microfocus carbon tubes in the tissue equivalent universal collimator. It is maintained as focused with the anode and focusing magnet. Such fine focused microbeam/nanobeam travels towards the isocentric tumor and radiates the tumor in 3-D conformity of the tumor.

Alternative to conventional proton beam radiation therapy with field defining patient specific collimator combined with the secondary neutron and proton and ions absorbing tissue equivalent universal collimator as above a newer system for proton and carbon ion radiation therapy with proton or carbon ion beam spot scanning and raster scanning is used. In this instance, active, pencil proton beam spot scanning with no scattering elements in the nozzle and without any patient specific collimator and compensators are used for conformal proton or carbon ion beam radiation therapy. The secondary neutron and proton absorbing cylindrical tissue equivalent collimator are used in combination with the spot scanned proton microbeam/nanobeam. The accelerator generated pencil proton or carbon ion microbeam or nanobeam is scanned into the microfocus carbon nanotube with preliminary scanning magnets. The proton beamlets in microfocus carbon tube is focused with focusing anode and focusing magnet. This scanned focused microbeam/nanobeam in microfocus carbon tubes exits from it almost without any penumbra. It travels toward the isocentric tumor as spot scanned beam and radiates the tumor as in active spot scanned proton beam radiation therapy known in the art. To take advantages of peak and valley dose differentials as in high dose and dose rate microbeam radiation therapy, the beam width and distance of the carbon tubes from each other is maintained at a ratio of 1:4.

Additional beam processing with a semi-patient specific carbon nanotube pre-collimator containing MWCNT pre-collimator as shown in FIG. 10-B2 and FIG. 10-B-3 further improves the active spot scanned and raster scanned proton radiotherapy. In this instance, the spot or raster scanning is at the carbon nanotube's opening sites, not at the tumor as in conventional active spot scanning or raster scanning proton or ion radiation therapy. The spot scanned microbeam/nanobeam becomes more focused and without any significant penumbra. The proton beamlets in microfocus carbon tubes is maintained as focused with focusing anode and focusing magnet. The scanned focused microbeam/nanobeam in microfocus carbon tubes travels towards the isocentric tumor and exits from the microfocus carbon tubes. After exiting from the microfocus carbon tubes, they travels toward the isocentric tumor and radiates the tumor as in conventional proton beam spot scanning or raster scanning methods but with multiple simultaneous spot scanned or raster scanned microbeam/nanobeam within the tumor. Instead of the single beam generating proton or carbon ion accelerators as with cyclotron, synchrotron or compact proton accelerators, the accelerated main beam is first split into multiple sub-beams which are subsequently processed as microbeam or nanobeam.

Adaptive Resistance inhibiting high dose and dose rate radiosurgery with conventional and spot or raster scanned multiple simultaneous proton parallel microbeam or nanobeam with compact proton accelerators Interlaced proton beams from compact proton accelerators shown in FIG. 10A-1, FIG. 10A-2, FIG. 10B-1, FIG. 10B-2, FIG. 10B-4, FIG. 10B-5 are used for spot or raster scanned proton parallel microbeam or nanobeam conformal radiation therapy. The vertical and horizontal beam from separate compact proton accelerators radiates the tumor as interlaced beams. The beam-on beam collisional interactions of interlaced beams coming from two or three compact accelerators (FIG. 10-B-4 and FIG. 10 B-5) creates several nuclear reaction products. Multiple simultaneous beam-on-beams elastic and none-elastic collision produces locally absorbed, secondary proton, antiprotons, neutrons, $^{11}C$, $^{13}N$, $^{15}O$ ions and gamma radiations. The antiprotons produced by the beam-on-beam collisions increases the depth of the Brag peak (109). Multiple simultaneous beam-beam's elastic and none-elastic collision induced, secondary proton, antiprotons, neutrons, $^{11}C$, $^{13}N$, $^{15}O$ ions and gamma radiations are produced within the tumor while it spares the normal tissue from radiation toxicities. It generates more locally absorbed nuclear fragments and antiprotons. The antiprotons produced by the beam-on-beam collisions increases the depth of the Brag peak (109). At the Bragg peak region, the primary protons are slowed down and the recoil secondary protons become more dominant behind the distal end of the Bragg peak (100). At about the Bragg peak area, 80-90% of the absorbed dose is from the slowed down primary proton and about 5-20% of the absorbed dose is from secondary protons. Behind the distal endpoint of the Brag peak, the secondary proton production by $^{1}H$ (n, p) reaction dominates. It contributes 70% of the absorbed dose at this point, behind the distal endpoint of the Bragg peak (100). Non-elastic nuclear interactions of proton also produce positron that is used for positron emission tomography (PET) (101). Such positrons are produced from decay of $^{11}C$, $^{13}N$, and $^{15}O$. The additive dose and dose rate of two or three or more simultaneous beams dose and dose rate is the sum of each of the accelerator beams dose and dose rate, the additive dose and dose rate. Proton beam has no exit dose; it also spares the normal tissue from radiation. The peak and valley principles of the microbeam radiation therapy also spare the normal tissue from radiation damages.

Adaptive Resistance inhibiting high dose and dose rate radiosurgery with sweeping spot scanned or raster scanned multiple simultaneous proton or carbon ion parallel microbeam or nanobeam generating accelerators.

Sweeping multiple simultaneous proton parallel microbeams or nanobeams by splitting the proton or carbon ion beam from a gantry mounted compact proton or laser based carbon ion generating accelerator is also used as an alternative method of proton beam spot scanning and raster scanning. The split multiple simultaneous sub-beams are further processed in microbeam and nanobeam generating and secondary neutron and proton absorbing cylindrical tissue equivalent collimator for secondary neutron and proton and photon radiation's absorption. The accelerated multiple pulse negative polarity proton beams is injected into a quadrupole magnet with converging magnetic field in one field and quadrupole magnet with diverging magnetic field in another plane. Thus the defocusing quadrupole magnet spreads out the proton beam in one plane and focuses it in another plane. The one plane defocused and in another plane focused multiple pulse negatively charged proton beam is injected into a defocusing, focusing and beam size controlling magnet. The split beam's size and spacing from each other is controlled with this magnet. It then passes through a stripper grid that generates alternating positively and negatively charged beam segments. They are alternatively charged as positive and negative segments of the beam and they are passed through a deflection magnet with DC vertical dipole field. The positively charged proton beamlets deflects to the left and the negatively charged proton beamlets deflects to the right. The separating distance between each of these beamlets is dependent on the strength of dipole field. It generates sets of numerous simultaneous parallel proton beams which enter into the tissue equivalent universal collimator containing microfocus carbon tubes. To maintain the peak and valley dose differential as in microbeam radiation therapy, the microfocus carbon tubes in tissue equivalent universal collimator are placed at a distance of one to four ratio of beam width and distance from each other in tissue equivalent universal collimator. The proton beam that enters into the microfocus carbon tubes are focused by the focusing anode and the focusing magnet like ion beam focusing in electron and ion beam microscopy (160, 161). Such focusing of the proton beam traveling through the microtubes eliminates the disadvantages of widening of the proton beam when it travels through a long neutron absorbing tissue like neutron absorber (150). The focused microbeam/nanobeam with hardly any penumbra leaves the microfocus carbon tubes and travels towards the isocentric tumor. The multiple simultaneous sweeping proton parallel microbeams or nanobeams generated by splitting the proton beam from a gantry mounted compact proton accelerator is equipped with microbeam and nanobeam generating and secondary neutron and proton absorbing cylindrical tissue equivalent collimator for secondary neutron and proton absorption. The tumor is treated with interlaced sweeping multiple simultaneous microbeams/nanobeams from multiple accelerators. Such simultaneous scanned beams treat the tumor in conformity with its shape and volume in a single sweep.

Multiple simultaneous beam-on-beam's elastic and noneelastic cross firing collisional interaction induced, secondary proton, antiprotons, neutrons, $^{11}C$, $^{13}N$, $^{15}O$ ions and positrons and gamma radiations all are taking place within the tumor while sparing the normal tissue from radiation toxicities. It generates more locally absorbed nuclear fragments and antiprotons. The antiprotons produced by the beam-on-beam collisions increases the depth of the Brag peak (109). Locally deposited γ emission with energies in the range of 0.6 to 1 MeV is also produced. At the Brag peak region, the primary protons are slowed down and the recoil secondary protons become more dominant behind the distal end of the Brag peak (100). At about the Brag peak area, 80-90% of the absorbed dose is from the slowed down primary proton and about 5-20% of the absorbed dose is from secondary protons. Behind the distal endpoint of the Brag peak, the secondary proton production by $^{1}H$ (n, p) reaction dominates. It contributes 70% of the absorbed dose at this point, behind the distal endpoint of the Brag peak (100). Nonelastic nuclear interactions of proton also produce positron in sufficient quantity that is used for positron emission tomography (PET) (101). Such positrons are produced from decay of $^{11}C$, $^{13}N$, and $^{15}O$. The beam-on beam collision of the interlaced proton beams enhances this depth and dose within the tumor. The additive dose and dose rate of two simultaneous beams from two separate accelerators, both exposing the isocentric tumor simultaneously is twice the dose and dose rate from a single accelerator. The additive dose and dose rate of five simultaneous beams from five separate accelerators at the isocentric tumor is five times higher than the dose and dose rate from a single accelerator. Hence, in addition to all other radiobiological advantages of treating a tumor including those from the antiprotons from beam-on beam collision, the effective dose and dose rate of these interlaced simultaneous beams reduces the time to treat a tumor to one half than if the tumor were treated with one single accelerator or to one fifth if the tumor were treated with one single accelerator. Its additive dose and dose rate is sufficient for 100 to 1,000 Gy single session, adaptive resistance inhibiting radiosurgery within a few seconds, within less than a breathing cycle. Proton beam has no exit dose. The peak and valley principles of the microbeam radiation therapy also spare the normal tissue from radiation damages.

Methods of adaptive resistance inhibiting high dose and dose rate radiosurgery with ion induced nuclear reaction radiation therapy (INRT) and proton spray chemotherapy The various methods of ion induced nuclear reaction proton radiation therapy (INRT) with controlled temperature alone or in combination with proton spray chemotherapy, Gadolinium neutron-capture therapy (Gd-NCT) and proton spay boron neutron capture radiation therapy (psBNCT) are described under FIG. 9A-1, FIG. 9A-2, FIG. 9B, FIG. 9C-1, FIG. 9C-2, FIG. 9C-3, FIG. 9C-4, FIG. 9D, FIG. 9E and in FIG. 9F. The ion induced nuclear reaction's temperature is controlled with ice cold water that is filled into one of the lumen surrounding the lumen with RFQ output ion beam. The heat generated by the ion induced nuclear reaction is removed by the heat conducting tungsten wire that connects in between the lumens in the needle. The collision of 650 keV, 1 microamp incident d(3He,p) beam from a RFQ accelerator on to a TiD2 target produces He and proton beams of varying energies ranging from 13.6 MeV to 17.4 MeV (125) with a dose rate of 1 Gy/s (126). This dose rate can be increased with higher than 1 microamp beam with good control of the temperature rise from the d(3He,p)3He nuclear reaction with the aid of a coolant. With coolant, the temperature is brought down to about 37.5 degrees. With a standard beam steering and alignment system that delivers the incoming ion beam from the multibeam accelerator to the respective needles as it is programmed for a particular treatment and with a select number of double shell proton target tube-needles. The proton spray exits through a window in front of the TiD2 target. The INRT double shell needles of varying lengths and with the target at the needle tip is inserted into a tumor as in an array of needles, adjusted according to the depth and location of the tumor and the site within the tumor that is radiated. Multiple simultaneous proton-spray beams emitted from the targets of this array of needles radiates multiple segments of a tumor simultaneously. With simultaneous parallel microbeam or nanobeams from an array of such a system facilitates curative radiosurgery as a single fraction treatment with minimal or no long term toxicity to normal tissue even at very high dose of 100 to 1,000 Gy.

The coolant could be a fluid containing chemotherapeutics. It is sprayed through the nozzle attached at the bottom of the needle that creates sprays like that generated with Taylor cones. Through such nozzle-Taylor cone the evaporated cooler liquid or the chemotherapeutic is sprayed onto the proton spray. It generates the ionized coolant or ionized chemotherapeutic bound proton spray. The high pressure helium gas is used to push the chemotherapeutic and or the coolant down to bring it closer to the deuterium/titanium target which gets overheated by the d(3He,p)3He nuclear reaction. The helium compressed chemotherapeutics and or the coolant is heated and evaporated by the heat generated by the d(3He,p)3He nuclear reaction and sprayed onto the proton beam generating ionized chemotherapeutic and or coolant. The collision of the $^3$H-ion beam with the TiD2 target emits the proton-spray beam. These double lumen proton target tube needles are inserted into the tissue that is treated with the aid of the sharp cone at the tip of the double lumen proton target tube-needle for combined ionized chemotherapy and proton radiation therapy.

The collision reaction products of vaporized water molecule and proton includes transformation of the proton as an H$^+$ or as a neutral H after a single electron capture or as a H$^-$ after double electron capture (128). The collisional interaction of proton with vaporized water and uracil was investigated before (129). It is an important example for the proton spray radiation therapy and proton spray chemotherapy combined microbeam and nanobeam radiation therapy. The products of proton impact ionization of water includes mostly H$^+$, H$_2$O$^+_2$, and OH$^+$ and to a lesser amounts of H$^+_2$, O$^+_2$, N$^+$, N$^+_2$, O$^+_2$ (131). Similar ions at the same concentration are also produced by monochromatic electron collision with evaporated water molecules (132). There are uracil analogues containing chemotherapeutics. The uracil molecules (C4H4N2O$^+_2$) are fragmented by its collision with proton and monochromatic electron as ionized fragmented larger and smaller uracil molecules (C3H3NO+ and CNO$^+$) with varying energies (133). In this invention, proton spray or electron sprays chemotherapy is described. In the case of electron spray, the monochromatic electron source is much simpler to make (134). Such ion produced by proton spray or electron spray adds to the local cytotoxic effects of both radiation and chemotherapy.

Needle guided adaptive resistance inhibiting high dose and dose rate radiosurgery combined with ionized proton spay chemotherapy Alternatively, combined ionized proton spay chemotherapy and needle guided radiation therapy is administered with a triple lumen needle with titanium/D2 target. The triple lumen proton target tube needle with an added outside lumen makes the double lumen needle as a triple lumen needle with an intermediate lumen. The inner lumen is a vacuum glass tube. The intermediate lumen and the outer lumen are also glass capillary tubes. The intermediate lumen is filled with a coolant like with ice cold water. The inner lumen, the intermediate lumen and the outer lumen are connected with heat conducting tungsten wire. The heat generated by the millisecond to a few seconds duration ion induced nuclear reaction in the deuterated titanium target is conducted away to the coolant.

The intermediate lumen with coolant moderates the higher temperature heat generated by the d(3He,p)3He nuclear reaction. The coolant in the intermediate lumen could be replaced with a chemotherapeutic for ionized chemotherapy. The coolant or the chemotherapeutic is sprayed through the nozzle to create a Taylor cone. Through this nozzle-Taylor cone attached to intermediate lumen, evaporated cooler liquid or the chemotherapeutic is sprayed onto the proton spray. It generates the ionized coolant or the ionized chemotherapeutic bound proton spray from intermediate lumen. Likewise, the outer lumen could be filled with a chemotherapeutic. The chemotherapeutic in the outer lumen is also evaporated and sprayed through the nozzle-Taylor cone attached to outer lumen. It generates ionized chemotherapeutic bound proton spray from the outer lumen. A high pressure helium gas pushes the chemotherapeutic and or the coolant down and brings them closer to the deuterium/titanium target which gets overheated by the d(3He,p)3He nuclear reaction. The helium compressed chemotherapeutics and or the coolant is heated and evaporated by the heat generated by the d(3He,p)3He nuclear reaction and sprayed onto the proton beam generating ionized chemotherapeutic and or coolant. The collision of the $^3$H-ion beam with the TiD2 target emits the proton-spray beam. The proton-spray beam exits through the window in front of the target. The triple lumen proton target tube needle is inserted into the tissue that is treated with the aid of the sharp cone at the tip of the triple lumen proton target tube-needle for combined ionized chemotherapy and proton radiation therapy. The collision reaction products of vaporized water molecule alone or with chemotherapeutics and the collisional interaction of proton with vaporized molecules like the uracil and or other molecules and their ionized nuclear fragments is used as the chemotherapeutics. Alternatively, a sharp cone is attached with microelectrodes for bioelectrospray of the vaporized-gas chemotherapeutics and or coolant for combined ionized electrospray plus proton spays chemotherapy and microbeam-nanobeam proton beam radiation therapy.

Needle guided, adaptive resistance inhibiting high dose and dose rate gadolinium neutron-capture therapy (Gd-NCT) and chemotherapy with ionized fragments of gadolinium A triple lumen needle with titanium/D2 target is also used for proton spays neutron capture radiation therapy with gamma rays and Auger electrons from Gadolinium neutron-capture the Gadolinium neutron-capture therapy (Gd-NCT) and chemotherapy. In this instance, the triple lumen needle is used for proton spay neutron capture radiation therapy and ionized chemotherapy like in a modified version of boron neutron capture (BCNT) or Gadolinium neutron capture therapy (Gd NCT) but it is combined with ionized cytotoxic drug chemotherapy. The inner lumen of the triple lumen needle is a vacuum glass tube through which accelerated proton beam pass through to the Ti/D2 target. Its intermediate lumen is filled with a lithium compound like lithium chloride. The outer lumen is filled with a gadolinium compound. The heat generated by the millisecond to a few seconds duration ion induced nuclear reaction in the deuterated titanium target is conducted away to the liquid lithium compound in the intermediate lumen and to the gadolinium compound in the outer lumen so that the tissue that is radiated by the ion induced nuclear reaction is not over heated and it will not cause greater discomfort or burn to the patient.

The lithium compound and the gadolinium compound are sprayed through nozzles to create Taylor cones. Helium or nitrogen gas pushes the liquid lithium compound. It brings the lithium compound closer to the deuterium/titanium target. The collision of the $^3$H-ion beam with the TiD2 target emits the proton-spray beam. The proton-spray beam exits through the window in front of the target. The d(3He,p)3He nuclear reaction with the target T1/D2 generates heat that is conducted into the intermediate lumen with lithium compound by the heat conducting tungsten wires. The heated, compressed and vaporized lithium compound is sprayed onto the proton spray through the nozzle-Taylor cone attached to the intermediate lumen. This vaporized lithium compound spray interacts with proton spray and generates the 7Li(p,n)7Be reaction. The heated, compressed and vaporized gadolinium compound is sprayed onto the neutron generated by the proton-lithium interaction, 7Li(p,n)7Be, through the nozzle-Taylor cone attached to the outer lumen. The neutron reacts with gadolinium; $^{157}$Gd+nth (0.025 eV)→[$^{158}$Gd]→$^{158}$Gd+γ+7.94 MeV. It thus releases gamma rays and Auger electrons for Gadolinium neutron-capture therapy (Gd-NCT). The proton spray onto the gadolinium compounds generates ionized fragments of gadolinium which serves as agents for ionized molecular chemotherapy.

Needle guided, adaptive resistance inhibiting high dose and dose rate proton spay boron neutron capture radiation therapy (psBNCT)

Proton spay boron neutron capture radiation therapy (psBNCT) with proton beam generally uses the same methods as described for Gadolinium neutron-capture therapy (Gd-NCT) and chemotherapy with ionized fragments of gadolinium above. In this case, the outer lumen is filled with a boron-10 containing compound instead a gadolinium compound. The interaction of proton spray with lithium as described under Gadolinium neutron-capture therapy generates neutron which interacts with $^{10}$B that is sprayed onto it. The triple lumen needle is inserted into a tumor and this proton spray-boron neutron capture treatment is locally elicited which spares the normal tissue.

The lithium compound and the $^{10}$B compound are sprayed through nozzles to create Taylor cone sprays. Helium or nitrogen gas pushes the liquid lithium compound closer to the deuterium/titanium target. The collision of the $^3$H-ion beam with the TiD2 target emits the proton-spray beam. The proton-spray beam exits through the window in front of the target. The d(3He,p)3He nuclear reaction with the target T1/D2 generates heat that is conducted into the intermediate lumen with lithium compound by the heat conducting tungsten wires. The heated, compressed and vaporized lithium compound is sprayed onto the proton spray through the nozzle-Taylor cone attached to the intermediate lumen. It generates the 7Li(p,n)7Be reaction. Its neutron interacts with $^{10}$B.

The $^{10}$B compound in the outer lumen is sprayed through the nozzle attached to the outer lumen that creates a Taylor cone spray. Helium or nitrogen gas pushes the $^{10}$B-compound down. It brings the $^{10}$B-compound closer to the deuterium/titanium target. The d(3He,p)3He nuclear reaction with the target T1/D2 generates heat that is conducted into the intermediate lumen with lithium compound and the $^{10}$B-compound in the outer lumen by the heat conducting tungsten wires. The heated, compressed and vaporized $^{10}$B-compound is sprayed onto the neutron generated by the proton-lithium interaction, 7Li(p,n)7Be, through the nozzle-Taylor cone attached to the outer lumen. Ionized $^{10}$B-compound spray's interaction with neutron 206 generates a nuclear fission reaction.

This classical nuclear fission reaction shown below is used for clinical BNCT (142):

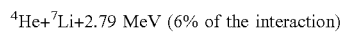
$^4$He+$^7$Li+2.79 MeV (6% of the interaction)

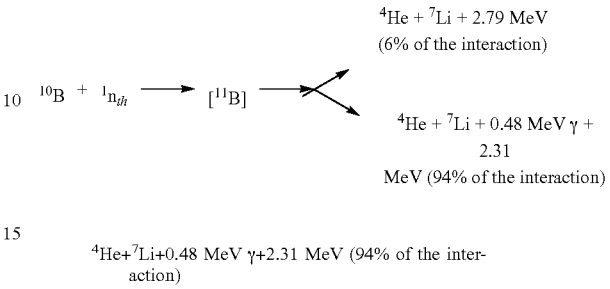

$^4$He+$^7$Li+0.48 MeV γ+2.31 MeV (94% of the interaction)

Here, both boron-neutron captures by thermal and epithermal neutrons take place. The epithermal neutron has higher depth dose characteristics. With proton spray BNCT (ppBNCT) with neutron source brought to the site of the tumor, the dose rate to the tumor at depth from all the components of this nuclear fission reaction, the $^{10}$B(n,α)$^7$Li, gamma radiation and the $^{14}$N(n,p)$^{14}$C contributes to the tumor dose. These reaction products except for the gamma radiation have high LET. Hence, it has high RBE.

Low energy needle implant guided ion induced nuclear reaction radiation therapy

For needle guided ion induced nuclear reaction proton radiation therapy lower energy proton beam like 17.4 MeV proton is sufficient. The range of 17.4 MeV protons beam's Brag-Peak in water is about 3.2 mm (143). It is not sufficient to treat a tumor at 10 cms depth, however the INRT needle guided proton beam's Bragg-Peak is brought to any clinically encountered tumor site with needle guided INRT.

The relatively low energy proton interaction in tissue generates low energy neutrons and recoil protons by its elastic collisions with hydrogen atoms. The non-elastic nuclear interactions of proton also produce $^{11}$C, $^{13}$N, $^{15}$O and positron (101). The multiple simultaneous proton beams' bam-on-beam collision's elastic interaction; in tissue generates more locally absorbed nuclear fragments and antiprotons. These antiprotons add to the depth of the Brag peak (109). The simultaneous proton beam's collisions products and antiprotons Brag-Peak at 10 cm depth also enhances the locally absorbed tumor dose. The multiple simultaneous beam's such radiation enables high dose and dose rate single fraction proton beam radiosurgery with 7-30 MeV. Intraoperatively transported ion beam brought through the INRT needle to a desired depth where the tumor is located, eliminates the need for higher energy proton beam to treat a tumor that is located several cms below the skin. The INRT needle guided proton-nuclear reaction is capable of delivering 15 Gy in 20 seconds (112) but to a limited volume of a larger tumor, in the case of μINRT only to about 5 mm of the tumor volume (114). With multiple simultaneous proton beams and their beam-on beam collision reaction product's larger volume tumor is radiated in its entirety in one treatment setup.

High energy, proton accelerators generated proton microbeam/nanobeam spray, ionized chemotherapy and neutron capture therapy with lithium, gadolinium and born absorbed in carbon nanotubes.

The SWCNT is pretreated with substrates like any biologically active compounds that acts as the ionized chemotherapeutics when exposed to proton beam radiation. Carbon nanotube conjugated tumor seeking EGFR/cisplatin is injected intravenously. Other biological compounds are absorbed and adsorbed into the SWCNT and injected directly into the tumor. They include SWCNT or MWCNT absorbed bioactive compounds for chemotherapy, lithium, boron, gadolinium for neutron capture therapy.

Collisional interaction of proton with vaporized water and molecules and organic compounds makes the proton spray chemotherapy combined with proton spray microbeam and nanobeam radiation therapy. The products of proton impact ionization of water, mostly H+, H2O+2, and OH+ and to a lesser amounts of H+2, O+2, N+, N+2, O+2 (131) generates the local ionization and ionized chemotherapy. The organic compounds in carbon nanotubes serves as the pro-drug compounds. They become cytotoxic agents as they are radiated with a spray of proton microbeam and nanobeams.

Just before, proton beam radiosurgery, SWCNT or MWCNT pretreated with bioactive compounds like the chemotherapeutic, lithium, gadolinium and boron is injected into the tumor. The single walled carbon nanotube (SWNT) absorbed with chemotherapeutics, lithium, boron and gadolinium interacts with the proton microbeam and nanobeam. The proton-lithium interaction, 7Li(p,n)7Be, generates neutrons. The neutron interacts with gadolinium by the nuclear reaction $^{157}Gd+nth$ (0.025 eV)$\rightarrow[^{158}Gd]\rightarrow{}^{158}Gd+\gamma+7.94$ MeV. It releases gamma rays and Auger electrons for Gadolinium neutron-capture therapy (Gd-NCT). Likewise, the proton beam generates the classical boron neutron capture nuclear reaction which facilitates the boron neutron capture therapy (BNCT). The bioactive compound absorbed into the carbon nanotube gives rise to ionized chemotherapy.

The present preferred embodiments of this invention are described here; however other modifications could be made without departing from the scope of this invention. The apparatus, methods, procedures and treatments are exemplary and are not intended as limitations on the scope of the invention. Other variations will appear to those skilled in the art and are contemplated to be within the scope of the appended claims.

What is claimed is:

1. Apparatus for proton and carbon ion microbeam and nanobeam radiosurgery comprising:
   a first unit comprising isocentric microbeam and nanobeam generating proton accelerators, wherein the accelerators are configured to accelerate a low energy proton beam to a high energy proton beam with a radiofrequency accelerator combined with a drift tube accelerator;
   a second unit comprising:
      an emergency beam stopper,
      a dose monitor,
      a primary beam collimator,
      a first focusing and defocusing quadrupole magnet having a converging magnetic field in one plane and a diverging magnetic field in another plane,
      a focusing and beam size controlling magnet,
      a stripper grid,
      alternatively positively and negatively charged beam segments,
      a deflection magnet with DC vertical dipole field,
      a proton beam focusing magnet,
      a tissue equivalent primary collimator,
      a tissue equivalent universal collimator,
      microfocus carbon tubes,
      a focusing anode, and
      a focusing magnet configured to create a focused microbeam and focused nanobeam;
   a third unit comprising a second focusing and defocusing quadrupole magnet configured to generate a magnetic field configured for defocusing the high energy proton beam in one plane and focusing the high energy proton beam in another plane;
   a fourth unit comprising an isocentric microbeam and nanobeam processing nested high voltage proton accelerators;
   a fifth unit comprising:
      a double lumen target tube-needle with inner and outer lumens,
      a coolant fluid inlet and a coolant fluid outlet,
      an air outlet,
      fluid inlet and outlet closure screws,
      air outlet screws,
      a heat conducting tungsten wire,
      a deuterium-titanium target,
      a vacuum fitting radiofrequency accelerator,
      a vacuum flange,
      a vacuum fitting O-ring seal,
      an accelerator beam line fitting,
      a proton spray beam exit,
      a needle Taylor cone,
      a radiofrequency ion beam conduit inner lumen,
      an inner lumen tungsten wire, and
      an outer lumen tungsten wire;
   a sixth unit comprising a second double lumen target tube-needle with a deuterium-titanium target;
   a seventh unit comprising an orthogonal two proton beam generating double lumen target tube-needle;
   an eighth unit comprising:
      a triple lumen target tube-needle with inner, intermediate, and outer lumens, wherein said intermediate lumen contains a coolant and said outer lumen contains chemotherapeutics, helium or nitrogen gas;
      a coolant inlet and outlet;
      an air outlet;
      a fluid inlet and a fluid outlet;
      closure screws;
      air outlet screws;
      a tungsten wire;
      a deuterium-titanium target;
      a vacuum fitting radiofrequency accelerator;
      a vacuum flange;
      a vacuum fitting o-ring seal;
      an accelerator beam line fitting;
      a proton spray beam exit;
      a Taylor cone needle;
      a radiofrequency ion beam conduit inner lumen;
      an inner lumen tungsten wire;
      an outer lumen tungsten wire;
   a ninth unit comprising:
      a neutron spray processing triple lumen target tube-needle, with inner intermediate and outer lumens, wherein said intermediate lumen contains lithium chloride and said outer lumen contains chemotherapeutics,
      helium or nitrogen gas inlet and outlets,
      a nozzle-Taylor cone, and
      high voltage microelectrodes;
   a tenth unit comprising:
      a proton spray boron neutron capture beam processing triple lumen target tube-needle with a deuterium inner lumen vacuum glass tube, an intermediate lumen containing lithium chloride, and an outer lumen containing gadolinium-boron-10;
      an outlet closure screw and an inlet closure screw;

capillary inlets;
an inner lumen holding and heat conducting tungsten wire;
an intermediate lumen holding and heat conducting tungsten wire;
an outer lumen holding and heat conducting wire; and
a nozzle-Taylor cone for proton spray boron neutron capture therapy;
an eleventh unit comprising:
a microbeam and nanobeam generating proton accelerator and corresponding nozzle;
a microbeam configured with a passive scatterer to have a spread out proton Bragg peak;
dosimeters;
patient specific collimators; and
a tissue equivalent universal collimator wherein the proton accelerator is configured to emit proton parallel microbeam and nanobeam by the tissue equivalent universal collimator;
a twelfth unit comprising:
orthogonal dual proton and carbon ion accelerators configured to emit an isocentric additive high dose and dose rate microbeam and nanobeam wherein the orthogonal accelerators are configured to apply additive high dose and dose rate radiation therapy to an isocentric tumor;
a thirteenth unit comprising:
gantry mounted compact proton accelerators configured to emit an isocentric additive high dose and dose_rate microbeam and nanobeam wherein said gantry mounted accelerators are configured to apply additive high dose and dose rate radiation therapy to an isocentric tumor;
a fourteenth unit comprising:
gantry mounted compact proton accelerators configured to emit an isocentric additive high dose and dose rate microbeam and nanobeam wherein said gantry mounted accelerators are configured for microbeam and nanobeam processing and application of additive high dose and dose rate radiation therapy to an isocentric tumor;
a fifteenth unit comprising:
a universal collimator with microfocus carbon tubes;
a secondary neutron and a proton absorbing cylindrical tissue equivalent collimators;
a focusing anode;
a focusing magnet; and
a parallel micro focus carbon tubes;
a sixteenth unit comprising:
isocentric proton and carbon ion microbeam and nanobeam generating accelerators mounted on a rotating gantry and corresponding radiation pressure proton and carbon ion accelerators;
a main ring laser source; and
a split laser source;
a seventeenth unit comprising a semi-patient specific carbon nanotube pre-collimator configured to process a pencil proton beam with a Bragg peak into microbeams and nanobeams;
an eighteenth unit comprising a microbeam and nanobeam processing proton accelerator with spot scanning magnets;
a nineteenth unit comprising isocentric proton microbeam and nanobeam processing dual proton accelerators with pencil proton microbeam scanning magnets;
a twentieth unit comprising:
orthogonally placed, dual nested high voltage proton accelerators configured for isocentric proton microbeam and nanobeam processing;
a twenty-first unit comprising beam splitting and focusing magnets configured for pencil beam splitting and focusing into main split focused beams;
a twenty-second unit comprising a nested high voltage accelerator configured to split a beam into two as isocentric cross firing microbeams and nanobeams;
a twenty-third unit comprising orthogonally placed proton accelerators, said accelerators being a compact radiofrequency accelerator and a drift tube accelerator, wherein the accelerators have split dual beams;
a twenty-fourth unit comprising two sets of orthogonal laser radiation pressure accelerators with parallel proton beams interlacing at an isocenter;
a twenty fifth unit comprising two sets of orthogonal laser radiation pressure accelerators with parallel carbon ion beams interlacing at an isocenter;
a twenty sixth unit comprising sets of gantry mounted laser radiation pressure proton accelerators;
a twenty seventh unit comprising sets of gantry mounted laser radiation pressure carbon ion accelerators, wherein isocentric microbeams and nanobeams are generated from a synchrotron, a cyclotron, or a synchro-cyclotron's split proton beam;
a twenty eighth unit comprising accelerators mounted on a rotating gantry and corresponding radiation pressure proton and carbon ion accelerators configured to generate an isocentric proton and carbon ion microbeam and nanobeam, a main ring laser source, and a split laser source; and
a twenty ninth unit comprising an isocentric microbeam and nanobeam processing tandem proton accelerator incorporated with a nested high voltage DC accelerator.

2. The apparatus as in claim 1, wherein in said first unit, the isocentric microbeam and nanobeam generating proton accelerators comprise an ion source, a beam transport, the radiofrequency accelerator, the drift tube accelerator, a beam stop, dose monitors, a beam aperture collimating collimator, a defocusing quadrupole magnet, a defocusing and beam size controlling magnet, a stripper grid, a DC vertical deflecting dipole magnet, and accelerator beam line fittings wherein a proton ion source accelerator is configured to emit a proton microbeam and nanobeam.

3. Apparatus of claim 1, wherein said second unit further comprises an isocentric proton microbeam and nanobeam generating accelerator and corresponding laser target normal sheath acceleration source, mirror, micrometer and nanometer thick target foil, a polyenergetic beam spatially separating magnet, neutrons and secondary protons and gamma radiations absorbing one and a half cm long tissue equivalent collimator, microfocus carbon tubes, a beam transport, a radiofrequency accelerator, a drift tube accelerator, a beam stop, dose monitors, a beam aperture collimating collimator, a defocusing quadrupole magnet, a defocusing and beam size controlling magnet, a stripper grid, a DC vertical deflecting dipole magnet and accelerator beam line fittings wherein a proton ion source accelerator is configured to emit proton microbeams and nanobeams.

4. Apparatus of claim 1, wherein in said sixteenth unit, the accelerators mounted on the rotating gantry and corresponding radiation pressure accelerators configured to generate isocentric proton microbeams and nanobeams further comprise:
an ion source;
a mirror;

a micrometer and nanometer thick target foil; a polyenergetic beam spatially separating magnet;
a one and a half cm long tissue equivalent collimator configured to absorb neutrons, secondary protons, and gamma radiation;
microfocus carbon tubes;
a beam transport;
a beam stop;
dose monitors;
a beam aperture collimating collimator;
a defocusing quadrupole magnet;
a defocusing and beam size controlling magnet;
a stripper grid;
a DC vertical deflecting dipole magnet; and
accelerator beam line fittings wherein the ion source accelerator is configured to emit a proton microbeam and nanobeam.

5. Apparatus of claim 1, wherein in the twenty eighth unit, the isocentric carbon ion microbeam and nanobeam generating accelerators, the ring laser source, and the split laser source further comprise:
a mirror;
a micrometer and nanometer thick target foil; a magnet configured to spatially separating a polyenergetic beam;
a target foil;
a one and a half cm long tissue equivalent collimator configured to absorb neutrons, secondary protons, and gamma radiation;
microfocus carbon tubes;
a beam transport;
a radiofrequency accelerator;
a drift tube accelerator;
a beam stop;
dose monitors;
a beam aperture;
a collimating collimator;
a defocusing quadrupole magnet;
a defocusing and beam size controlling magnet;
a stripper grid;
a DC vertical deflecting dipole magnet; and
accelerator beam line fittings,
wherein the carbon ion accelerators are configured to emit carbon microbeams and nanobeams.

6. Apparatus of claim 1, wherein in said twenty seventh unit, the synchrotron, cyclotron or synchro-cyclotron are configured to orthogonally split beams and are configured to emit multiple simultaneous parallel microbeams and nanobeams interlacing with additive high dose and dose rate causing antiproton nuclear interactions at an isocentric tumor.

7. Apparatus of claim 1, wherein in the thirteenth unit, the proton ion generating gantry mounted compact proton accelerator systems consist of:
an accelerated negative polarity proton beam;
a beam stopper;
dose monitors;
a beam aperture collimating collimator;
a defocusing quadrupole magnet;
a defocusing and beam size controlling magnet;
a stripper grid;
a DC vertical deflecting dipole magnet;
a beam shaping patient specific collimator; and
a tissue equivalent universal collimator,
wherein said accelerator systems are mounted on a compact gantry at 0-degree, 45 degree, 135 degree, 225 degree and 315 degrees for five simultaneous proton microbeam or nanobeam interlaced sweeping beam-on beam collisional scanning radiation.

8. Apparatus of claim 1, wherein in said eleventh unit, the isocentric microbeam and nanobeam generating proton accelerator and the corresponding nozzle further comprise:
a passive scatterer,
a proton beam configured to have a spread out Bragg peak,
microfocus carbon tubes;
focusing anode and focusing magnet; and
a secondary neutron and proton absorbing twenty cm long tissue equivalent universal collimator configured to emit a proton microbeam and nanobeam.

9. Apparatus of claim 1, wherein in the twenty third unit, the orthogonal proton accelerators are configured to emit proton or carbon microbeams and nanobeams and their multiple simultaneous parallel microbeams and nanobeams are configured to have an additive high dose and dose rate to cause antiproton nuclear interactions at an isocentric tumor.

10. Apparatus of claim 1, wherein the tenth unit, further comprises a proton, neutron and electron spray and lithium-boron proton spray double and triple lumen target Taylor cone needles.

11. Apparatus of claim 1, wherein said fourteenth unit is further configured to emit multiple simultaneous parallel proton microbeams and nanobeams that interlace with antiproton nuclear interactions which produce an additive high dose and dose rate at an isocentric tumor.

12. Apparatus of claim 1, wherein the seventeenth unit, further comprises:
an isocentric microbeam and nanobeam generating proton accelerator with a nozzle;
a passive scatterer;
dose monitors;
a proton beam configured to have a spread out Bragg peak;
a patient specific collimator;
microfocus carbon tubes;
a focusing anode;
a focusing magnet; and
a secondary neutron and proton absorbing twenty cm long tissue equivalent universal collimator configured to emit proton microbeams and nanobeams.

13. Apparatus of claim 1, wherein in said eighteenth unit, the isocentric microbeam and nanobeam processing proton accelerator comprises a nozzle and further comprises:
pencil proton microbeam scanning magnets;
a scanned proton beam;
a semi-patient specific carbon nanotube pre-collimator;
microfocus carbon tubes;
a focusing anode and focusing magnet;
a secondary neutron and proton absorbing twenty cm long tissue equivalent universal collimator configured to emit a spot scanned proton microbeam and nanobeam.

14. Apparatus of claim 1, wherein in said nineteenth unit, the isocentric proton microbeam and nanobeam processing proton accelerators comprises a nozzle and further comprises:
pencil proton microbeam scanning magnets;
a scanned proton beam;
microfocus carbon tubes;
a focusing anode and focusing magnet; and
a secondary neutron and proton absorbing twenty cm long tissue equivalent universal collimator; and
said accelerators are configured to emit a spot scanned interlaced proton microbeam and nanobeam at an iso- 15. Apparatus of claim 1, wherein said twenty ninth unit further comprises:
isocentric microbeam and nanobeam generating proton accelerators;
an ion source;
a tandem accelerator;
incorporated nested high voltage DC accelerator with thin stripping foil;
a radiofrequency accelerator;
a beam stop;
dose monitors;
a beam aperture collimating collimator;
defocusing quadrupole magnet;
defocusing and beam size controlling magnet;
a stripper grid; and
a DC vertical deflecting dipole magnet;
wherein each proton accelerator is configured to emit proton microbeams and nanobeams with peak and valley doses.

16. Apparatus of claim 1, wherein said fourth unit, further comprises:
orthogonally placed proton accelerators with a corresponding ion source;
a compact nested high voltage accelerator;
a radiofrequency accelerator;
a drift tube accelerator;
a beam stopper dose monitors;
a beam aperture collimating collimator;
a defocusing quadrupole magnet;
a beam splitter;
bending and focusing magnets;
a defocusing and beam size controlling magnet;
a stripper grid; and
a DC vertical deflecting dipole magnet,
wherein said accelerators are configured to emit proton microbeams and nanobeams and multiple simultaneous parallel microbeams and nanobeams that interlace resulting in an additive high dose and dose rate and antiproton nuclear interactions at an isocentric tumor.

17. Apparatus of claim 1, wherein the twenty-first unit further comprises:
a beam steering and splitting corresponding beam splitting quadrupole magnet;
a beam splitting and switching magnet;
right and left focusing magnets;
right and left 45 degree bending magnets;
a beam transport;
right and left focusing magnets;
right and left 15 degree beam switching bipolar magnets;
right and left 45 degree bending magnet;
right and left quadrupole focusing magnets; and
right and left 45 degree bending magnets.

18. Apparatus of claim 1, wherein the twentieth unit, further comprises:
orthogonally placed split beam accelerators corresponding to an ion source;
a compact nested high voltage accelerator;
a radiofrequency accelerator;
a beam stopper;
dose monitors;
a beam aperture collimating collimator;
a defocusing quadrupole magnet;
beam splitter;
bending and focusing magnets;
defocusing and beam size controlling magnet;
a stripper grid; and
a DC vertical deflecting dipole magnet;
wherein said accelerators are configured to emit interlacing proton simultaneous parallel microbeams and nanobeams with additive high doses and dose rates and cause antiproton nuclear interactions at an isocentric tumor.

19. Apparatus of claim 1, wherein said twenty third unit, further comprises:
orthogonally placed split beam accelerators with a corresponding ion source;
a compact radiofrequency accelerator;
a beam stopper;
dose monitors;
a beam aperture collimating collimator;
a defocusing quadrupole magnet;
a beam splitter;
bending and focusing magnets;
a defocusing and beam size controlling magnet;
a stripper grid; and
a DC vertical deflecting dipole magnet;
wherein said accelerators are configured to emit proton microbeams and nanobeams and multiple simultaneous parallel interlacing microbeams and nanobeams with additive high doses and dose rates and cause antiproton nuclear interactions at an isocentric tumor.

20. Apparatus of claim 1, wherein said twenty fourth unit, further comprises:
orthogonally placed two laser-proton accelerators with a corresponding laser source;
a mirror;
a micrometer and nanometer thick target foil;
a polyenergetic beam spatially separating magnet;
a one and a half cm long tissue equivalent collimator configured to absorb neutrons, secondary protons, and gamma radiation;
microfocus carbon tubes;
a beam transport;
a radiofrequency accelerator;
a drift tube accelerator;
a beam stopper;
dose monitors;
a beam aperture collimating collimator;
a defocusing quadrupole magnet;
a beam splitter;
bending and focusing magnets;
a defocusing and beam size controlling magnet;
a stripper grid;
DC vertical deflecting dipole magnet; and
a tissue equivalent universal collimator;
wherein and said accelerators are configured to emit proton microbeams and nanobeams and multiple simultaneous parallel interlacing microbeams and nanobeams with additive high doses and dose rates that cause antiproton nuclear interactions at an isocentric tumor.

21. Apparatus of claim 1, wherein said twenty sixth unit further comprises isocentric proton microbeam and nanobeam generating accelerators mounted on a rotating gantry, wherein said isocentric proton microbeam and nanobeam generating accelerators and corresponding radiation pressure proton accelerators comprises:
a main ring laser source;
a split laser source;
a mirror;
a micrometer and nanometer thick target foil;
a polyenergetic beam spatially separating magnet;

a one and a half cm long tissue equivalent collimator configured to absorb neutrons, secondary protons, and gamma radiation;
  microfocus carbon tubes;
  a beam transport;
  a beam stop;
  dose monitors;
  a beam aperture collimating collimator;
  a defocusing quadrupole magnet;
  a defocusing and beam size controlling magnet;
  a stripper grid;
  a DC vertical deflecting dipole magnet; and
  accelerator beam line fittings;
  wherein said gantry mounted proton accelerators are configured to emit interlacing proton microbeam and nanobeams simultaneously with an additive high dose and dose rate at an isocentric tumor.

22. Apparatus of claim 1, wherein in said twenty seventh unit, said radiation pressure carbon ion accelerators comprise:
  a main ring laser source;
  a split laser source;
  a mirror;
  a micrometer and nanometer thick target foil;
  a polyenergetic beam spatially separating magnet;
  a one and a half cm long tissue equivalent collimator configured to absorb neutrons, secondary protons, and gamma radiation;
  microfocus carbon tubes;
  a beam transport;
  a beam stop;
  dose monitors;
  a beam aperture collimating collimator;
  a defocusing quadrupole magnet;
  a defocusing and beam size controlling magnet;
  a stripper grid;
  a DC vertical deflecting dipole magnet; and
  accelerator beam line fittings;
  wherein said gantry mounted carbon ion accelerators are configured to emit interlacing carbon ion microbeams and nanobeams simultaneously which produces an additive high dose and dose rate at an isocentric tumor.

\* \* \* \* \*